United States Patent
Honda et al.

(10) Patent No.: US 7,544,703 B2
(45) Date of Patent: Jun. 9, 2009

(54) CYCLIC COMPOUND HAVING 4-PYRIDYLALKYLTHIO GROUP HAVING SUBSTITUTED OR UNSUBSTITUTED AMINO GROUP INTRODUCED THEREIN

(75) Inventors: Takahiro Honda, Ikoma (JP); Hisashi Tajima, Ikoma (JP); Kenji Kawashima, Ikoma (JP); Kazuyoshi Okamoto, Ikoma (JP); Minoru Yamamoto, Ikoma (JP); Takaaki Inaba, Ikoma (JP); Yuriko Takeno, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/587,410

(22) PCT Filed: Feb. 17, 2005

(86) PCT No.: PCT/JP2005/002971

§ 371 (c)(1),
(2), (4) Date: Jul. 27, 2006

(87) PCT Pub. No.: WO2005/085201

PCT Pub. Date: Sep. 15, 2005

(65) Prior Publication Data

US 2007/0149574 A1 Jun. 28, 2007

(30) Foreign Application Priority Data

Feb. 17, 2004 (JP) .............................. 2004-039862
Sep. 6, 2004 (JP) .............................. 2004-294347

(51) Int. Cl.
*A61K 31/4436* (2006.01)
*C07D 213/89* (2006.01)

(52) U.S. Cl. ..................................... 514/335; 546/261
(58) Field of Classification Search ................ 514/335; 546/261

See application file for complete search history.

(56) References Cited

U.S. PATENT DOCUMENTS

| | | | |
|---|---|---|---|
| 6,329,372 B1 * | 12/2001 | Head et al. | .................. 514/241 |
| 6,380,214 B1 | 4/2002 | Gant et al. | |
| 2006/0194836 A1 | 8/2006 | Honda et al. | |

FOREIGN PATENT DOCUMENTS

| CA | 2350208 A1 | 5/2000 |
|---|---|---|
| EP | 0 422 369 A2 | 4/1991 |
| JP | 02-129173 A | 5/1990 |
| JP | 02-501051 A | 1/2002 |
| WO | WO 97/30035 A1 | 8/1997 |
| WO | WO 98/35958 A1 | 8/1998 |
| WO | WO 98/50356 A1 | 11/1998 |
| WO | WO 00/27819 A2 | 5/2000 |
| WO | WO 01/55114 A1 | 8/2001 |
| WO | WO 02/066470 A1 | 8/2002 |
| WO | WO 03/040096 A2 | 5/2003 |
| WO | WO 2004/018414 A2 | 3/2004 |
| WO | WO 2004/018428 A1 | 3/2004 |
| WO | WO 2004/078723 A1 | 9/2004 |

OTHER PUBLICATIONS

King, Med Chem: Principle and Practice (1994), p. 206-208.*
Nakayama Shoten, *Molecular Medicine*, vol. 35, special issue, "Molecular Mechanism of Symptoms and Pathologic conditions," pp. 73-74, (1998), (Abstract).
Kyoritsu Shuppan, *Protein, Nucleic Acid, Enzyme*, extra number, "The Most Advanced Development of New Drugs," pp. 1182-1187, (2000), (Abstract).
R. Ponci et al., *Il Farmaco-Ed. Sc.*, "Derivati Piridinici Dell'Acido 2-Mercaptobenzoico Ad Attivita' Antifungina," vol. 18, pp. 288-304, (1963), (Abstract).

* cited by examiner

*Primary Examiner*—Taofiq A Solola
(74) *Attorney, Agent, or Firm*—Frishauf, Holtz, Goodman & Chick, P.C.

(57) ABSTRACT

A novel cyclic compound having a 4-pyridylalkylthio group having an (un)substituted amino group introduced therein or a salt thereof. They are useful as a medicine. The cyclic compound is a compound represented by the following formula (1), which is useful for the treatment of diseases in which angiogenesis participates. In the following formula (1), ring A represents a benzene ring or a 5- or 6-membered aromatic heterocycle optionally fused with a cycloalkane ring; B represents alkylene; $R^1$ and $R^2$ each represents H, (substituted) aryl, (substituted) heterocyclic group, etc.; $R^3$ and $R^4$ each represents H, (substituted) alkyl, (substituted) cycloalkyl, $-Z-R^5$, etc.; $R^5$ represents (substituted) alkyl, (substituted) aryl, (substituted) heterocyclic group, etc.; X and Y each represents H, etc.; Z represents $-CO-$, $-COO-$, $-CONR^6-$, $-SO_2-$, etc.; $R^6$ represents H, etc.; p is 0, 1, or 2; and q is 0 or 1.

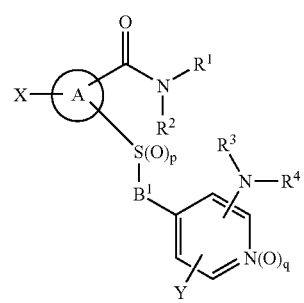

(1)

22 Claims, No Drawings

CYCLIC COMPOUND HAVING 4-PYRIDYLALKYLTHIO GROUP HAVING SUBSTITUTED OR UNSUBSTITUTED AMINO GROUP INTRODUCED THEREIN

This application is the United States national phase application of International Application PCT/JP2005/002971 filed Feb. 17, 2005.

1. Technical Field

The present invention relates to a novel cyclic compound having a 4-pyridylalkylthio group having a substituted or unsubstituted amino group introduced therein or a salt thereof which is useful as a pharmaceutical. Such a compound is useful as a therapeutic agent for a disease in which angiogenesis or vascular hyperpermeability is involved, particularly as a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

2. Background Art

Angiogenesis is a phenomenon in which a new vascular network is formed from an existing blood vessel and is observed mainly in a microvessel. Angiogenesis is originally a physiological phenomenon and is essential for blood vessel formation at embryogenesis, but it is usually observed only at a limited site such as endometrium or follicle or at a limited period such as a wound healing process in adults. However, pathologic angiogenesis is observed in a disease such as cancer, rheumatoid arthritis, age-related macular degeneration, diabetic retinopathy, retinopathy of prematurity, retinal vein occlusion, polypoid choroidal angiopathy, diabetic macular degeneration, psoriasis vulgaris and atherosclerosis, and closely relates to the progress of pathema of these diseases. It is considered that angiogenesis or vascular hyperpermeability is regulated by balance between its promotive factor and inhibitory factor, and angiogenesis or vascular hyperpermeability is caused by disruption of the balance (Molecular Medicine vol. 35, special issue, "Molecular Mechanism of Symptoms and Pathologic conditions", Nakayama Shoten, 73-74 (1998), and Protein, Nucleic Acid, Enzyme, extra number, "The Most Advanced Development of New Drugs", Kyoritsu Shuppan, 1182-1187 (2000)).

A vascular endothelial growth factor (hereinafter abbreviated as "VEGF") is a factor which specifically acts on a receptor (Flt-1, KDR/Flk-1 or the like) present on the surface of vascular endothelial cells, thereby proliferation and migration of the vascular endothelial cells, construction of a capillary vessel network due to vasculogenesis. VEGF plays a very important role in occurrence of angiogenesis and vascular hyperpermeability. Accordingly, there have been many reports on attempts to treat a disease in which angiogenesis or the vascular hyperpermeability is involved by inhibiting VEGF to control angiogenesis and vascular hyperpermeability. Examples of drugs to be used for the treatment include 2-indolinone derivatives (WO 98/50356), phthalazine derivatives (WO 98/35958), quinazoline derivatives (WO 97/30035), anthranyl amide derivatives (WO 00/27819), 2-aminonicotinic acid derivatives (WO 01/55114) and the like.

However, there is no description on cyclic compounds having a 4-pyridylalkylthio group in these patent documents. Still less, there is no description on compounds having a substituted or unsubstituted amino group introduced in the pyridine ring of a 4-pyridylalkylthio group.

On the other hand, Il Farmaco-Ed. Sc., 18, 288 (1963) and WO 02/066470 reported compounds having a chemical structures relatively close to those of the cyclic compounds having a 4-pyridylalkylthio group having a substituted or unsubstituted amino group introduced therein. The compound disclosed in Il Farmaco-Ed. Sc., 18, 288 (1963) is a benzoic acid amide derivative having a 3-pyridylalkylthio group, and an antibacterial action is recited as its use. WO 02/066470 relates to substituted alkylamine derivatives and their pharmaceutical use, and discloses compounds having enormous combinations of chemical structures. WO 02/066470 just discloses a derivative having a 4-pyridylalkylamino group as one example among those compounds, and does not describe a cyclic compound having a 4-pyridylalkylthio group having a substituted or unsubstituted amino group introduced therein at all.

DISCLOSURE OF THE INVENTION

It is a very interesting subject to study synthesis of novel cyclic compounds having a 4-pyridylalkylthio group having a substituted or unsubstituted amino group introduced therein and to find a pharmacological action of the compounds.

The present inventors have studied synthesis of novel cyclic compounds having a 4-pyridylalkylthio group having a substituted or unsubstituted amino group introduced therein and succeeded in producing a number of novel compounds.

Further, they studied pharmacological actions of these compounds widely, and found that the compounds have a cell proliferation inhibitory effect, a tumor growth inhibitory effect, a paw edema inhibitory effect and/or a choroidal neovascularization inhibitory effect, and are useful as a therapeutic agent for a disease in which angiogenesis and/or vascular hyperpermeability are/is involved, particularly as a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like, thus completed the present invention.

The present invention provides a novel cyclic compound having a 4-pyridylalkylthio group having a substituted or unsubstituted amino group introduced therein or a salt thereof which is useful as a pharmaceutical. The novel cyclic compound according to the present invention has an excellent cell proliferation inhibitory effect, a tumor growth inhibitory effect, a paw edema inhibitory effect and/or a choroidal neovascularization inhibitory effect, and is useful as a therapeutic agent for a disease in which angiogenesis and/or vascular hyperpermeability are/is involved, for example, cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

The present invention relates to a compound represented by the general formula (1) or a salt thereof (hereinafter referred to as "the compound of the present invention" unless otherwise specified) and a pharmaceutical composition containing the compound of the present invention. The compound of the present invention has a chemical structural feature in which a substituted or unsubstituted amino group has been introduced into the pyridine ring moiety of the 4-pyridylalkylthio group.

To describe a pharmaceutical application of the compound of the present invention in more detail, it relates to a therapeutic agent containing the compound of the present invention as an active ingredient for a disease in which angiogenesis and/or vascular hyperpermeability are/is involved, for example, it relates to a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

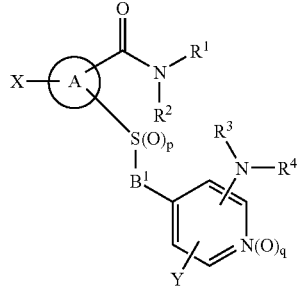

(1)

(In the formula, the ring A represents a benzene ring, or an aromatic five-membered heterocyclic ring or an aromatic six-membered heterocyclic ring which may be fused with a cycloalkane ring;

$R^1$ and $R^2$, which are same or different, represent a hydrogen atom, a hydroxy group, a substituted or unsubstituted alkoxy group, a substituted or unsubstituted aryloxy group, a substituted or unsubstituted alkyl group, a substituted or unsubstituted cycloalkyl group, a substituted or unsubstituted aryl group, a substituted or unsubstituted heterocyclic ring, an amino group, a substituted or unsubstituted alkylamino group, a substituted or unsubstituted arylamino group, or a substituted or unsubstituted acyl group;

$R^1$ and $R^2$ may join together to form a substituted or unsubstituted heterocyclic ring;

$R^3$ and $R^4$, which are same or different, represent a hydrogen atom, a substituted or unsubstituted alkyl group, a substituted or unsubstituted cycloalkyl group, a substituted or unsubstituted aryl group, a substituted or unsubstituted heterocyclic ring, a hydrocarbonyl group, a substituted or unsubstituted alkylcarbonyl group, a substituted or unsubstituted arylcarbonyl group, or $Z-R^5$;

$R^3$ and $R^4$ may join together to form a substituted or unsubstituted heterocyclic ring;

Z represents CO, CS, $COB^2O$, $CSB^2O$, $CONB^2R^6$, $CSB^2NR^6$, $CONB^2R^6SO_2$, $CSB^2NR^6SO_2$ or $SO_2$;

$R^5$ represents a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted aryl group, a substituted or unsubstituted heterocyclic ring, a carboxy group or an ester thereof or an amide thereof, a hydrocarbonyl group, a substituted or unsubstituted alkylcarbonyl group, a substituted or unsubstituted arylcarbonyl group, or a substituted or unsubstituted heterocyclic carbonyl group;

$R^5$ and $R^6$ may join together to form a substituted or unsubstituted heterocyclic ring;

$R^6$ represents a hydrogen atom, a substituted or unsubstituted alkyl group, or a substituted or unsubstituted aryl group;

X and Y, which are same or different, represent one or plural groups selected from a hydrogen atom, a halogen atom, a hydroxy group, a substituted or unsubstituted alkoxy group, a substituted or unsubstituted aryloxy group, a substituted or unsubstituted alkyl group, a substituted or unsubstituted cycloalkyl group, a substituted or unsubstituted aryl group, a substituted or unsubstituted alkylamino group, a substituted or unsubstituted arylamino group, a mercapto group, a substituted or unsubstituted alkylthio group, a substituted or unsubstituted arylthio group, a carboxy group or an ester thereof or an amide thereof, a cyano group, and a nitro group;

$B^1$ represents an alkylene group;

$B^2$ represents a single bond or an alkylene group;

p represents 0, 1 or 2; and q represents 0 or 1. The same definitions are applied hereinafter.)

The respective atoms, rings or groups defined above are defined to have the following meanings throughout this specification.

The "cycloalkane ring" refers to a cycloalkane ring having 3 to 8 carbon atoms. Specific examples thereof include a cyclopropane ring, a cyclobutane ring, a cyclopentane ring, a cyclohexane ring, a cycloheptane ring, a cyclooctane ring and the like.

The "aromatic five-membered heterocyclic ring" refers to a monocyclic aromatic five-membered heterocyclic ring having one or plural heteroatoms selected from a nitrogen atom, an oxygen atom and a sulfur atom in the ring. Specific examples thereof include a pyrrole ring, a pyrazole ring, an imidazole ring and a [1,2,3]triazole ring, each of which has a nitrogen atom in the ring; a furan ring, which has an oxygen atom in the ring; a thiophene ring, which has a sulfur atom in the ring; an oxazole ring and an isoxazole ring, each of which has a nitrogen atom and an oxygen atom in the ring; and a thiazole ring and an isothiazole ring, each of which has a nitrogen atom and a sulfur atom in the ring. Preferred is a pyrazole ring, a furan ring or a thiophene ring, and particularly preferred is a thiophene ring.

The "aromatic five-membered heterocyclic ring fused with a cycloalkane ring" refers to a bicyclic ring in which an aromatic five-membered heterocyclic ring is fused with a cycloalkane ring.

The "aromatic six-membered heterocyclic ring" refers to a monocyclic aromatic six-membered heterocyclic ring having one or plural nitrogen atoms in the ring. Specific examples thereof include a pyridine ring, a pyridazine ring, a pyrimidine ring, a pyrazine ring, a [1,2,3]triazine ring, a [1,2,4]triazine ring and a [1,2,3,4]tetrazine ring. Preferred is a pyridine ring or a pyrazine ring, and particularly preferred is a pyridine ring.

The "aromatic six-membered heterocyclic ring fused with a cycloalkane ring" refers to a bicyclic ring in which an aromatic six-membered heterocyclic ring is fused with a cycloalkane ring.

The "alkylene" refers to straight-chain or branched alkylene having 1 to 8 carbon atoms. Specific examples thereof include methylene, ethylene, trimethylene, tetramethylene, pentamethylene, hexamethylene, heptamethylene, octamethylene, methylmethylene, dimethylmethylene, propylene, 2-methyltrimethylene and the like.

The "alkoxy" refers to straight-chain or branched alkoxy having 1 to 6 carbon atoms. Specific examples thereof include methoxy, ethoxy, n-propoxy, n-butoxy, n-pentoxy, n-hexyloxy, isopropoxy, isobutoxy, sec-butoxy, tert-butoxy, isopentoxy and the like.

The "alkyl" refers to straight-chain or branched alkyl having 1 to 6 carbon atoms. Specific examples thereof include methyl, ethyl, n-propyl, n-butyl, n-pentyl, n-hexyl, isopropyl, isobutyl, sec-butyl, tert-butyl, isopentyl and the like.

The "cycloalkyl" refers to cycloalkyl having 3 to 8 carbon atoms. Further, a saturated polycyclic hydrocarbon formed by fusion of 2 or 3 cycloalkane rings is also included in the "cycloalkyl" of the present invention. Specific examples of the cycloalkyl include cyclopropyl, cyclobutyl, cyclopentyl, cyclohexyl, cycloheptyl, cyclooctyl and the like. Specific examples of the saturated polycyclic hydrocarbon include adamantyl and the like.

The "aryl" refers to a monocyclic aromatic hydrocarbon or a bicyclic or tricyclic fused polycyclic aromatic hydrocarbon having 6 to 14 carbon atoms. Further, a fused polycyclic hydrocarbon formed by fusion thereof with a cycloalkane ring is also included in the "aryl" of the present invention. A specific example of the monocyclic aromatic hydrocarbon is phenyl, specific examples of the fused polycyclic aromatic hydrocarbon include naphthyl, anthryl, phenanthryl and the like, and specific examples of the fused polycyclic hydrocarbon include indanyl, tetrahydronaphthyl, tetrahydroanthranyl and the like.

The "aryloxy" refers to a monocyclic aromatic hydrocarbonoxy or a fused polycyclic aromatic hydrocarbonoxy having 6 to 14 carbon atoms, or a fused polycyclic hydrocarbonoxy formed by fusion thereof with a cycloalkane ring. A specific example of the monocyclic aromatic hydrocarbonoxy is phenoxy, specific examples of the fused polycyclic aromatic hydrocarbonoxy include naphthyloxy, anthryloxy, phenanthryloxy and the like, and specific examples of the fused polycyclic hydrocarbonoxy include indanyloxy, tetrahydronaphthyloxy, tetrahydroanthranyloxy and the like.

The "heterocyclic ring" refers to a saturated or unsaturated monocyclic heterocyclic ring, or bicyclic or tricyclic fused polycyclic heterocyclic ring having one or plural heteroatoms selected from a nitrogen atom, an oxygen atom and a sulfur atom in the ring.

Specific examples of the saturated monocyclic heterocyclic ring include aziridine, azetidine, pyrrolidine, pyrazolidine, imidazolidine, triazolidine, piperidine, hexahydropyridazine, hexahydropyrimidine, piperazine, homopiperidine, homopiperazine and the like, each of which has a nitrogen atom in the ring; oxirane, tetrahydrofuran, tetrahydropyran and the like, each of which has an oxygen atom in the ring; tetrahydrothiophene, tetrahydrothiopyran and the like, each of which has a sulfur atom in the ring; oxazolidine, isoxazolidine, morpholine and the like, each of which has a nitrogen atom and an oxygen atom in the ring; and thiazolidine, isothiazolidine, thiomorpholine and the like, each of which has a nitrogen atom and a sulfur atom in the ring.

Further, such a saturated monocyclic heterocyclic ring may be fused with a benzene ring or the like to form a fused polycyclic heterocyclic ring such as dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chroman, isochroman, dihydrobenzothiophene, dihydroisobenzothiophene, thiochroman, isothiochroman, dihydrobenzoxazole, dihydrobenzisoxazole, dihydrobenzoxazine, dihydrobenzothiazole, dihydrobenzoisothiazole, dihydrobenzothiazine, xanthene, 4a-carbazole or perimidine.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine, pyrazine and the like, each of which has a nitrogen atom in the ring; dihydrofuran, furan, dihydropyran, pyran and the like, each of which has an oxygen atom in the ring; dihydrothiophene, thiophene, dihydrothiopyran, thiopyran and the like, each of which has a sulfur atom in the ring; dihydrooxazole, oxazole, dihydroisoxazole, isoxazole, dihydrooxazine, oxazine and the like, each of which has a nitrogen atom and an oxygen atom in the ring; dihydrothiazole, thiazole, dihydroisothiazole, isothiazole, dihydrothiazine, thiazine and the like, each of which has a nitrogen atom and a sulfur atom in the ring.

Further, such an unsaturated monocyclic heterocyclic ring may be fused with a benzene ring or the like to form a fused polycyclic heterocyclic ring such as indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromen, isochromen, benzothiophene, isobenzothiophene, thiochromen, isothiochromen, benzoxazole, benzisoxazole, benzoxazine, benzothiazole, benzoisothiazole, benzothiazine, phenoxanthine, carbazole, β-carboline, phenanthridine, acridine, phenanthroline, phenazine, phenothiazine or phenoxazine.

The "alkylamino" refers to monoalkylamino having 1 to 6 carbon atoms or dialkylamino having 2 to 12 carbon atoms. Specific examples of the monoalkylamino include methylamino, ethylamino, hexylamino and the like, and specific examples of the dialkylamino include ethylmethylamino, dimethylamino, diethylamino, dihexylamino and the like.

The "arylamino" refers to monoarylamino having 6 to 20 carbon atoms or diarylamino having 12 to 28 carbon atoms. Specific examples of the monoarylamino include phenylamino, naphthylamino, ethylphenylamino and the like, and specific examples of the diarylamino include diphenylamino, dianthrylamino and the like.

The "acyl" refers to hydrocarbonyl, alkylcarbonyl, cycloalkylcarbonyl, arylcarbonyl or heterocyclic carbonyl. Specific examples of the hydrocarbonyl include formyl, specific examples of the alkylcarbonyl include acetyl, propionyl, butyryl, isobutyryl, valeryl, isovaleryl, pivaloyl, monochloroacetyl, trifluoroacetyl and the like, specific examples of the cycloalkylcarbonyl include cyclopentanecarbonyl, cyclohexanecarbonyl and the like, specific examples of the arylcarbonyl include benzoyl, naphthoyl, toluoyl and the like, and specific examples of the heterocyclic carbonyl include furoyl, thenoyl, picolinoyl, nicotinoyl, isonicotinoyl and the like.

The "alkenyl" refers to straight-chain or branched alkenyl having 2 to 8 carbon atoms. Specific examples thereof include vinyl, allyl, 1-propenyl, 3-butenyl, 3-pentenyl, 4-hexenyl, 5-heptenyl, 7-octenyl, 1-methylvinyl and the like.

The "alkynyl" refers to straight-chain or branched alkynyl having 2 to 8 carbon atoms. Specific examples thereof include ethynyl, 2-propynyl, 2-butynyl, 3-pentynyl, 4-hexynyl, 5-heptynyl, 7-octynyl, 2-methylbutyl and the like.

The "halogen" refers to fluorine atom, chlorine atom, bromine atom or iodine atom.

The "ester of a carboxy group" refers to an ester with an alkyl alcohol, an aryl alcohol or the like. Specific examples of the alkyl alcohol include methanol, ethanol, propanol, butanol, benzylalcohol, phenethylalcohol and the like. Specific examples of the aryl alcohol include phenol, naphthol, anthrol, cresol, xylenol and the like.

The "amide of a carboxy group" refers to an amide with alkylamine, cycloalkylamine, arylamine, heterocyclic amine or the like. Specific examples of the alkylamine include methylamine, ethylamine, ethylmethylamine, dimethylamine, diethylamine, benzylamine and the like, specific examples of the cycloalkylamine include cyclopentylamine, cyclohexylamine, cyclohexylmethylamine and the like, specific examples of the arylamine include aniline, naphthylamine, diphenylamine, ethylphenylamine, anisidine, toluidine and the like, and specific examples of the heterocyclic amine include benzofuranamine, quinolylamine and the like.

The "alkylcarbonyl" refers to straight-chain or branched alkylcarbonyl having 2 to 7 carbon atoms. Specific examples thereof include methylcarbonyl, ethylcarbonyl, n-propylcarbonyl, n-butylcarbonyl, n-pentylcarbonyl, n-hexylcarbonyl, isopropylcarbonyl, isobutylcarbonyl, sec-butylcarbonyl, tert-butylcarbonyl, isopentyl carbonyl and the like.

The "arylcarbonyl" refers to monocyclic aromatic hydrocarbon carbonyl or fused polycyclic aromatic hydrocarbon carbonyl having 7 to 15 carbon atoms, or fused polycyclic hydrocarbon carbonyl formed by fusion thereof with a cycloalkane ring. A specific example of the monocyclic aromatic hydrocarboncarbonyl is phenylcarbonyl, specific examples of the fused polycyclic aromatic hydrocarboncarbonyl include naphthylcarbonyl, anthrylcarbonyl, phenanthrylcarbonyl and the like, and specific examples of the fused polycyclic hydrocarboncarbonyl include indanyl carbonyl, tetrahydronaphthyl carbonyl, tetrahydroanthryl carbonyl and the like.

The "heterocyclic carbonyl" refers to saturated or unsaturated monocyclic heterocyclic carbonyl, or bicyclic or tricyclic fused polycyclic heterocyclic carbonyl, each of which has one or plural heteroatoms selected from a nitrogen atom, an oxygen atom and a sulfur atom in the ring.

The "alkylsulfonyl" refers to straight-chain or branched alkylsulfonyl having 1 to 6 carbon atoms. Specific examples thereof include methylsulfonyl, ethylsulfonyl, n-propylsulfonyl, n-butylsulfonyl, n-pentylsulfonyl, n-hexylsulfonyl, isopropylsulfonyl, isobutylsulfonyl, sec-butylsulfonyl, tert-butylsulfonyl, isopentylsulfonyl and the like.

The "arylsulfonyl" refers to monocyclic aromatic hydrocarbon sulfonyl or fused polycyclic aromatic hydrocarbon sulfonyl having 6 to 14 carbon atoms, or fused polycyclic hydrocarbon sulfonyl formed by fusion thereof with a cycloalkane ring. A specific example of the monocyclic aromatic hydrocarbonsulfonyl is phenylsulfonyl, specific examples of the fused polycyclic aromatic hydrocarbonsulfonyl include naphthylsulfonyl, anthrylsulfonyl, phenanthrylsulfonyl and the like, and specific examples of the fused polycyclic hydrocarbonsulfonyl include indanyl sulfonyl, tetrahydronaphthyl sulfonyl, tetrahydroanthryl sulfonyl and the like.

The "alkylthio" refers to straight-chain or branched alkylthio having 1 to 6 carbon atoms. Specific examples thereof include methylthio, ethylthio, n-propylthio, n-butylthio, n-pentylthio, n-hexylthio, isopropylthio, isobutylthio, sec-butylthio, tert-butylthio, isopentylthio and the like.

The "arylthio" refers to monocyclic aromatic hydrocarbonthio, or bicyclic or tricyclic fused polycyclic aromatic hydrocarbonthio having 6 to 14 carbon atoms. Further, it refers to a bicyclic to tetracyclic fused polycyclic hydrocarbonthio formed by fusion thereof with a cycloalkane ring. A specific example of the monocyclic aromatic hydrocarbonthio is phenylthio, specific examples of the fused polycyclic aromatic hydrocarbonthio include naphthylthio, anthrylthio, phenanthrylthio and the like, and specific examples of the fused polycyclic hydrocarbonthio include indanylthio, tetrahydronaphthylthio, tetrahydroanthrylthio and the like.

The "halogenoalkoxy" refers to an alkoxy group having one or plural same or different halogen atoms as substituents.

The "hydroxyalkoxy" refers to an alkoxy group having one or plural hydroxy groups as substituents.

The "alkoxyalkoxy" refers to an alkoxy group having one or plural same or different alkoxy groups as substituents.

The "aryloxyalkoxy" refers to an alkoxy group having one or plural same or different aryloxy groups as substituents.

The "halogenoalkyl" refers to an alkyl group having one or plural same or different halogen atoms as substituents.

The "hydroxyalkyl" refers to an alkyl group having one or plural hydroxy groups as substituents.

The "alkoxyalkyl" refers to an alkyl group having one or plural same or different alkoxy groups as substituents.

The "aryloxyalkyl" refers to an alkyl group having one or plural same or different aryloxy groups as substituents.

The "hydroxyaryl" refers to an aryl group having one or plural hydroxy groups as substituents.

The "alkoxyaryl" refers to an aryl group having one or plural same or different alkoxy groups as substituents.

The "substituted alkoxy group" refers to an alkoxy group having one or plural groups as substituents selected from a halogen atom, a hydroxy group, an alkoxy group, an alkoxy group substituted with an aryl group, an aryloxy group, a cycloalkyl group, an aryl group, an aryl group substituted with an alkoxy group, a heterocyclic group, an amino group, an alkylamino group, an arylamino group, a mercapto group, an alkylthio group, an arylthio group, a carboxy group or an ester thereof or an amide thereof, a cyano group and a nitro group.

The "substituted aryloxy group" refers to an aryloxy group having one or plural groups as substituents selected from a halogen atom, a hydroxy group, an alkoxy group, an aryloxy group, an alkyl group, a cycloalkyl group, an aryl group, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group.

The "substituted alkyl group" refers to an alkyl group having one or plural groups as substituents selected from a halogen atom, a hydroxy group, an alkoxy group, an aryloxy group, a cycloalkyl group, an alkenyl group, an aryl group, an aryl group substituted with a halogen atom, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group.

The "substituted cycloalkyl group" refers to a cycloalkyl group having one or plural groups as substituents selected from a halogen atom, a hydroxy group, an alkoxy group, an aryloxy group, an alkyl group, a cycloalkyl group, an aryl group, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group.

The "substituted aryl group" refers to an aryl group having one or plural groups as substituents selected from a halogen atom, a hydroxy group, an alkoxy group, an alkoxy group substituted with a halogen atom, an aryloxy group, an alkyl group, an alkyl group substituted with a halogen atom, a cycloalkyl group, an aryl group, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group, or an aryl group having one or plural carbonyl groups or thiocarbonyl groups in the ring.

The "substituted heterocyclic ring" refers to a heterocyclic ring having one or plural groups as substituents selected from a halogen atom, a hydroxy group, an alkoxy group, an alkoxy group substituted with a halogen atom, an aryloxy group, an alkyl group, an alkyl group substituted with a halogen atom, a cycloalkyl group, an aryl group, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group, or a heterocyclic ring having one or plural carbonyl groups or thiocarbonyl groups in the ring.

The "substituted alkylamino group" refers to an alkylamino group having one or plural groups in its alkyl moiety as substituents selected from a halogen atom, a hydroxy group, an alkoxy group, an aryloxy group, a cycloalkyl group, an aryl group, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group.

The "substituted arylamino group" refers to an arylamino group having one or plural groups in its aryl moiety as substituents selected from a halogen atom, a hydroxy group, an alkoxy group, an aryloxy group, an alkyl group, a cycloalkyl group, an aryl group, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group, or an arylamino group having one or plural carbonyl groups or thiocarbonyl groups in the ring.

The "substituted acyl group" refers to an acyl group having one or plural groups as substituents selected from a halogen atom, a hydroxy group, an alkoxy group, an aryloxy group, a cycloalkyl group, an aryl group, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group.

The "substituted alkenyl group" refers to an alkenyl group having one or plural groups as substituents selected from a halogen atom, a hydroxy group, an alkoxy group, an aryloxy group, a cycloalkyl group, an aryl group, a heterocyclic group, an amino group, an alkylamino group, an arylamino group, a carboxy group or an ester thereof or an amide thereof, a formyl group, an alkylcarbonyl group, an arylcarbonyl group, a cyano group and a nitro group.

The "substituted alkynyl group" refers to an alkynyl group having one or plural groups as substituents selected from a halogen atom, a hydroxy group, an alkoxy group, an aryloxy group, a cycloalkyl group, an aryl group, a heterocyclic group, an amino group, an alkylamino group, an arylamino group, a carboxy group or an ester thereof or an amide thereof, a formyl group, an alkylcarbonyl group, an arylcarbonyl group, a cyano group and a nitro group.

The "substituted alkylcarbonyl group" refers to an alkylcarbonyl group having one or plural groups as substituents selected from a halogen atom, a hydroxy group, an alkoxy group, an aryloxy group, a cycloalkyl group, an alkenyl group, an aryl group, an aryl group substituted with a halogen atom, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group.

The "substituted arylcarbonyl group" refers to an arylcarbonyl group having one or plural groups as substituents selected from a halogen atom, a hydroxy group, an alkoxy group, an alkoxy group substituted with a halogen atom, an aryloxy group, an alkyl group, an alkyl group substituted with a halogen atom, a cycloalkyl group, an aryl group, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group, or an arylcarbonyl group having one or plural carbonyl groups or thiocarbonyl groups in the ring.

The "substituted heterocyclic carbonyl group" refers to a heterocyclic carbonyl group having one or plural groups as substituents selected from a halogen atom, a hydroxy group, an alkoxy group, an alkoxy group substituted with a halogen atom, an aryloxy group, an alkyl group, an alkyl group substituted with a halogen atom, a cycloalkyl group, an aryl group, a heterocyclic group, an amino group, an alkylamino group, an arylamino group, a mercapto group, an alkylthio group, an arylthio group, a carboxy group or an ester thereof or an amide thereof, a formyl group, an alkylcarbonyl group, an arylcarbonyl group, a cyano group and a nitro group, or a heterocyclic carbonyl group having one or plural carbonyl groups or thiocarbonyl groups in the ring.

The "substituted alkylthio group" refers to an alkylthio group having one or plural groups as substituents selected from a halogen atom, a hydroxy group, an alkoxy group, an alkoxy group substituted with an aryl group, an aryloxy group, a cycloalkyl group, an aryl group, an aryl group substituted with an alkoxy group, a heterocyclic group, an amino group, an alkylamino group, an arylamino group, a carboxy group or an ester thereof or an amide thereof, a formyl group, an alkylcarbonyl group, an arylcarbonyl group, a cyano group and a nitro group.

The "substituted arylthio group" refers to an arylthio group having one or plural groups as substituents selected from a halogen atom, a hydroxy group, an alkoxy group, an aryloxy group, an alkyl group, a cycloalkyl group, an aryl group, a heterocyclic group, an amino group, an alkylamino group, an arylamino group, a carboxy group or an ester thereof or an amide thereof, a formyl group, an alkylcarbonyl group, an arylcarbonyl group, a cyano group and a nitro group, or an arylthio group having one or plural carbonyl groups or thiocarbonyl groups in the ring.

When the compound of the present invention has a free hydroxy group, a free amino group, a free alkylamino group, a free arylamino group or a free mercapto group as a substituent, these substituents may be protected with a protecting group. When the heterocyclic group has a free nitrogen atom, the nitrogen atom may also be protected with a protecting group.

The "protecting group for the free hydroxy group" refers to one widely-used as a protecting group such as a substituted or unsubstituted alkyl group, or an unsubstituted alkenyl group such as a methyl group, a methoxymethyl group, a benzyl group, a 4-methoxyphenylmethyl group or an allyl group; a substituted or unsubstituted heterocyclic group such as 3-bromotetrahydropyranyl group, a tetrahydropyranyl group or a tetrahydrofuranyl group; a substituted or unsubstituted alkylcarbonyl group or a substituted or unsubstituted arylcarbonyl group such as an acetyl group, a trifluoroacetyl group, a benzoyl group or a 4-chlorobenzoyl group; a substituted or unsubstituted alkyloxycarbonyl group, an unsubstituted alkenyloxycarbonyl group, or a substituted or unsubstituted aryloxycarbonyl group such as a methoxycarbonyl group, an ethoxycarbonyl group, an isobutoxycarbonyl group, a tert-butoxycarbonyl group, a benzyloxycarbonyl group, a p-methoxybenzyloxycarbonyl group, 9-fluorenylmethoxycarbonyl group, a vinyloxycarbonyl group, an aryloxycarbonyl group, a phenyloxycarbonyl group or a p-nitrophenyloxycarbonyl group; or a substituted silyl group such as a trimethylsilyl group, a triethylsilyl group, a triisopropylsilyl group, a tert-butyldimethylsilyl group or a tert-butyldiphenylsilyl group.

The "protecting group for the free amino group, the free alkylamino group, the free arylamino group, or the free nitrogen atom in the case where the heterocyclic group has a nitrogen atom in its ring" refers to one widely-used as a protecting group such as an unsubstituted alkenyl group such as an allyl group; a hydrocarbonyl group such as a formyl group; a substituted or unsubstituted alkylcarbonyl group, a substituted or unsubstituted arylcarbonyl group, or an unsubstituted heterocyclic carbonyl group such as an acetyl group, a trichloroacetyl group, a trifluoroacetyl group, a benzoyl group, a 4-chlorobenzoyl group or a picolinoyl group; a substituted or unsubstituted alkyloxycarbonyl group, or a substituted or unsubstituted aryloxycarbonyl group such as a methoxycarbonyl group, an isobutoxycarbonyl group, a tert-butoxycarbonyl group, a 2,2,2-trichloroethoxycarbonyl group, a benzyloxycarbonyl group, a diphenylmethoxycarbonyl group, a phenoxycarbonyl group or a m-nitrophenoxycarbonyl group; or a substituted or unsubstituted alkylsulfonyl group, or a substituted or unsubstituted arylsulfonyl group such as a methylsulfonyl group, a benzylsulfonyl group, a phenylsulfonyl group, 4-chlorophenylsulfonyl group, a tolylsulfonyl group or 2,4,6-trimethylphenylsulfonyl group.

The "protecting group for the free mercapto group" refers to one widely-used as a protecting group such as a substituted or unsubstituted alkyl group, or an unsubstituted alkenyl group such as a methyl group, a methoxymethyl group, a benzyl group, a 4-methoxyphenylmethyl group or an allyl group; a substituted or unsubstituted heterocyclic group such as 3-bromotetrahydropyranyl group, a tetrahydropyranyl group or a tetrahydrofuranyl group; a substituted or unsubstituted alkylcarbonyl group, or a substituted or unsubstituted arylcarbonyl group such as an acetyl group, a trifluoroacetyl group, a benzoyl group or a 4-chlorobenzoyl group; or a substituted or unsubstituted alkyloxycarbonyl group, an unsubstituted alkenyloxycarbonyl group, or a substituted or unsubstituted aryloxycarbonyl group such as a methoxycarbonyl group, an ethoxycarbonyl group, an isobutoxycarbonyl group, a tert-butoxycarbonyl group, a benzyloxycarbonyl group, a p-methoxybenzyloxycarbonyl group, 9-fluorenylmethoxycarbonyl group, a vinyloxycarbonyl group, an aryloxycarbonyl group, a phenyloxycarbonyl group or a p-nitrophenyloxycarbonyl group.

The "plural groups" as used herein may be either same or different, respectively.

Further, in the "group" as used herein, respective atoms and rings are also included.

The "salt" in the compound of the present invention is not particularly limited as long as it is a pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumalic acid, maleic acid, succinic acid, citric acid, tartaric acid, adipic acid, lactic acid, methanesulfonic acid, trifluoromethanesulfonic acid or p-toluenesulfonic acid; salts with an alkali metal such as lithium, sodium or potassium; salts with an alkaline earth metal such as calcium or magnesium; and quaternary salts with ammonia, methyl iodide and the like.

In the case where there are geometrical isomers or optical isomers in the compound of the present invention, these isomers are also included in the scope of the present invention.

Further, the compound of the present invention may be in the form of a hydrate or a solvate.

Further, in the case where there is proton tautomerism in the compound of the present invention, the tautomeric isomers thereof are also included in the scope of the present invention.

(a) Preferred examples of the compound of the present invention include compounds that satisfy the following definitions and salts thereof.

In the general formula (1), (a1) the ring A represents a benzene ring, a thiophene ring or a pyridine ring; and/or (a2) $R^1$ represents an alkyl group, a cycloalkyl group, an aryl group or a heterocyclic ring; and/or (a3) in the case where $R^1$ is an alkyl group, the alkyl group may have one or plural substituents selected from an aryl group, a hydroxyaryl group and an alkoxyaryl group; and/or (a4) in the case where $R^1$ is an aryl group, the aryl group may have one or plural substituents selected from a halogen atom, a hydroxy group, an alkoxy group, a halogenoalkoxy group, a hydrocarbonyloxy group, an alkylcarbonyloxy group, an arylcarbonyloxy group, an alkyl group, a halogenoalkyl group and an aryl group; and/or (a5) $R^2$ represents a hydrogen atom, an alkyl group or an aryl group; and/or (a6) in the case where $R^2$ is an alkyl group, the alkyl group may have one or plural substituents selected from a carboxy group, an alkoxycarbonyl group and an aryloxycarbonyl group; and/or (a7) $R^3$ represents a hydrogen atom, an alkyl group, a cycloalkyl group, an aryl group, a heterocyclic ring or $Z\text{-}R^5$; and/or (a8) in the case where $R^3$ is an alkyl group, the alkyl group may have one or plural substituents selected from a hydroxy group, an alkoxy group, an aryloxy group, an amino group, an alkylamino group and an arylamino group; and/or (a9) in the case where $R^3$ is a heterocyclic ring, the heterocyclic ring may have one or plural cyano groups as substituents; and/or (a10) $R^3$ and $R^4$ may join together to form a heterocyclic ring; and/or (a11) in the case where $R^3$ and $R^4$ join together to form a heterocyclic ring, the heterocyclic ring may have one or plural substituents selected from a hydroxy group, an alkoxy group, an aryloxy group, an alkyl group, a hydroxyalkyl group, an alkoxyalkyl group, an aryloxyalkyl group, an aryl group, an amino group, an alkylamino group, an arylamino group, a carboxy group, an alkoxycarbonyl group, an aryloxycarbonyl group, a hydrocarbonyl group, an alkylcarbonyl group, an arylcarbonyl group, an aminocarbonyl group, an alkylaminocarbonyl group and an arylaminocarbonyl group, further, the heterocyclic ring may have a carbonyl group in the ring; and/or (a12) $R^4$ represents a hydrogen atom, an alkyl group, an aryl group, a hydrocarbonyl group, an alkylcarbonyl group or an arylcarbonyl group; and/or (a13) in the case where $R^4$ is an alkylcarbonyl group, the alkylcarbonyl group may have one or plural alkylcarbonyloxy groups as substituents; and/or (a14) Z represents CO, CS, CO—$B^2$—O, CS—$B^2$—O, CO—$B^2$—$NR^6$, CS—$B^2$—$NR^6$, CO—$B^2$—$NR^6SO_2$, CS—$B^2$—$NR^6SO_2$ or $SO_2$; and/or (a15) $R^5$ represents a hydrogen atom, an alkyl group, an alkenyl group, an alkynyl group, a cycloalkyl group, an aryl group, a heterocyclic ring, a carboxy group, an alkoxycarbonyl group, an aryloxycarbonyl group, a hydrocarbonyl group, an alkylcarbonyl group, an arylcarbonyl group, a heterocyclic carbonyl group, an aminocarbonyl group, an alkylaminocarbonyl group, or an arylaminocarbonyl group; and/or (a16) in the case where $R^5$ is an alkyl group, the alkyl group may have one or plural substituents selected from a halogen atom, a hydroxy group, an alkoxy group, a hydroxyalkoxy group, alkoxyalkoxy group, an aryloxyalkoxy group, a cycloalkyl group, an aryl group, a heterocyclic ring, a carboxy group, an alkoxycarbonyl group, an aryloxycarbonyl group, a hydrocarbonyl group, an alkylcarbonyl group, an arylcarbonyl group, an amino group, an alkylamino group, an arylamino group, an alkoxycarbonylamino group, an aryloxycarbonylamino group, a hydrocarbonylamino group, an alkylcarbonylamino group, an arylcarbonylamino group, a mercapto group, an alkylthio group, an arylthio group and a cyano group; and/or (a17) in the case where $R^5$ is an aryl group, the aryl group may have one or plural halogen atoms as substituents; and/or (a18) in the case where $R^5$ is a heterocyclic ring, the heterocyclic ring may have one or plural substituents selected from an alkyl group and an aryl group; and/or (a19) in the case where $R^5$ is an alkylcarbonyl group, the alkylcarbonyl group may have one or plural substituents selected from a carboxy group, a hydrocarbonyloxy group, an alkylcarbonyloxy group, an arylcarbonyloxy group, an amino group, an alkylamino group and an arylamino group; and/or (a20) $R^5$ and $R^6$ may join together to form a heterocyclic ring; and/or (a21) in the case where $R^5$ and $R^6$ join together to form a heterocyclic ring, the heterocyclic ring may have one or plural substituents selected from a hydroxy group, an alkoxy group, an aryloxy group, an alkyl group, a hydroxyalkyl group, an alkoxyalkyl group, an aryloxyalkyl group, a carboxy group, an alkoxycarbonyl group, an aryloxycarbonyl group, a carbonyl group, a hydrocarbonyl group, an alkylcarbonyl group and an arylcarbonyl group, further, the heterocyclic ring may have a carbonyl group in the ring; and/or (a22) $R^6$ represents a hydrogen atom, an alkyl group or an aryl group; and/or (a23) X and Y, which are same or different, represent one or plural groups selected from a hydrogen atom, a halogen atom and alkyl group; and/or (a24) $B^1$ represents an alkylene group; and/or (a25) $B^2$ represents a single bond or an alkylene group; and/or (a26) p represents 0, 1 or 2; and/or (a27) q represents 0 or 1.

That is, preferred examples thereof include in the compounds represented by the general formula (1), compounds that satisfy one or a combination of two or more selected from the above (a1), (a2), (a3), (a4), (a5), (a6), (a7), (a8), (a9), (a10), (a11), (a12), (a13), (a14), (a15), (a16), (a17), (a18), (a19), (a20), (a21), (a22), (a23), (a24), (a25), (a26) and (a27) and salts thereof.

(b) More preferred examples of the compound of the present invention include compounds that satisfy the following definitions and salts thereof.

In the general formula (1), (b1) the ring A represents a benzene ring, a thiophene ring or a pyridine ring; and/or (b2) $R^1$ represents an alkyl group, a cycloalkyl group, an aryl group or a heterocyclic ring; and/or (b3) in the case where $R^1$ is an alkyl group, the alkyl group may have one or plural alkoxyaryl groups as substituents; and/or (b4) in the case where $R^1$ is an aryl group, the aryl group may have one or plural substituents selected from a halogen atom, a hydroxy group, an alkoxy group, a halogenoalkoxy group, an alkylcarbonyloxy group, an alkyl group and a halogenoalkyl group; and/or (b5) $R^2$ represents a hydrogen atom or an alkyl group; and/or (b6) in the case where $R^2$ is an alkyl group, the alkyl group may have one or plural substituents selected from a carboxy group and an alkoxycarbonyl group; and/or (b7) $R^3$ represents a hydrogen atom, an alkyl group, a cycloalkyl group, an aryl group, a heterocyclic ring or Z-$R^5$; and/or (b8) in the case where $R^3$ is an alkyl group, the alkyl group may have one or plural substituents selected from a hydroxy group and an alkylamino group; and/or (b9) in the case where $R^3$ is a heterocyclic ring, the heterocyclic ring may have one or plural cyano groups as substituents; and/or (b10) $R^3$ and $R^4$ may join together to form a heterocyclic ring; and/or (b11) in the case where $R^3$ and $R^4$ join together to form a heterocyclic ring, the heterocyclic ring may have one or plural substituents selected from a hydroxy group, an alkyl group, a hydroxyalkyl group, an alkylamino group, an alkoxycarbonyl group, an alkylcarbonyl group and an alkylaminocarbonyl group, further, the heterocyclic ring may have a carbonyl group in the ring; and/or (b12) $R^4$ represents a hydrogen atom, an alkyl group or an alkylcarbonyl group; and/or (b13) in the case where $R^4$ is an alkylcarbonyl group, the alkylcarbonyl group may have one or plural alkylcarbonyloxy groups as substituents; and/or (b14) Z represents CO, CO—$B^2$—O, CO—$B^2$—$NR^6$, CS—$B^2$—$NR^6$, CO—$B^2$—$NR^6SO_2$ or $SO_2$; and/or (b15) $R^5$ represents a hydrogen atom, an alkyl group, an alkenyl group, an alkynyl group, a cycloalkyl group, an aryl group, a heterocyclic ring, an alkoxycarbonyl group, an alkylcarbonyl group, a heterocyclic carbonyl group or an alkylaminocarbonyl group; and/or (b16) in the case where $R^5$ is an alkyl group, the alkyl group may have one or plural substituents selected from a halogen atom, a hydroxy group, an alkoxy group, a hydroxyalkoxy group, an alkoxyalkoxy group, a cycloalkyl group, a heterocyclic ring, a carboxy group, an alkoxycarbonyl group, an amino group, an alkylamino group, an alkoxycarbonylamino group, an alkylcarbonylamino group, an alkylthio group and a cyano group; and/or (b17) in the case where $R^5$ is an aryl group, the aryl group may have one or plural halogen atoms as substituents; and/or (b18) in the case where $R^5$ is a heterocyclic ring, the heterocyclic ring may have one or plural alkyl groups as substituents; and/or (b19) in the case where $R^5$ is an alkylcarbonyl group, the alkylcarbonyl group may have one or plural substituents selected from a carboxy group, an alkylcarbonyloxy group and an alkylamino group; and/or (b20) $R^5$ and $R^6$ may join together to form a heterocyclic ring; and/or (b21) in the case where $R^5$ and $R^6$ join together to form a heterocyclic ring, the heterocyclic ring may have one or plural substituents selected from a hydroxy group, an alkyl group, a hydroxyalkyl group, an alkoxycarbonyl group and an alkylcarbonyl group, further, the heterocyclic ring may have a carbonyl group in the ring; and/or (b22) $R^6$ represents a hydrogen atom or an alkyl group; and/or (b23) X and Y represent a hydrogen atom; and/or (b24) $B^1$ represents an alkylene group; and/or (b25) $B^2$ represents a single bond or an alkylene group; and/or (b26) p represents 0 or 1; and/or (b27) q represents 0.

That is, more preferred examples thereof include in the compounds represented by the general formula (1), compounds that satisfy one or a combination of two or more selected from the above (b1), (b2), (b3), (b4), (b5), (b6), (b7), (b8), (b9), (b10), (b11), (b12), (b13), (b14), (b15), (b16), (b17), (b18), (b19), (b20), (b21), (b22), (b23), (b24), (b25), (b26) and (b27) and salts thereof.

(c) Further more preferred examples of the compound of the present invention include compounds that satisfy the following definitions and salts thereof.

In the general formula (1), (c1) the ring A represents a benzene ring, a thiophene ring or a pyridine ring; and/or (c2) $R^1$ represents an aryl group or a heterocyclic ring; and/or (c3) in the case where $R^1$ is an aryl group, the aryl group may have one or plural substituents selected from a halogen atom, a halogenoalkoxy group, an alkyl group and a halogenoalkyl group; and/or (c4) $R^2$ represents a hydrogen atom; and/or (c5) $R^3$ represents a hydrogen atom, an alkyl group, a cycloalkyl group, an aryl group, a heterocyclic ring or $Z-R^5$; and/or (c6) in the case where $R^3$ is an alkyl group, the alkyl group may have one or plural alkylamino groups as substituents; and/or (c7) in the case where $R^3$ is a heterocyclic ring, the heterocyclic ring may have one or plural cyano groups as substituents; and/or (c8) $R^3$ and $R^4$ may join together to form a heterocyclic ring; and/or (c9) in the case where $R^3$ and $R^4$ join together to form a heterocyclic ring, the heterocyclic ring may have one or plural substituents selected from an alkyl group and an alkylcarbonyl group; and/or (c10) $R^4$ represents a hydrogen atom or an alkyl group; and/or (c11) Z represents CO, $CO-B^2-O$, $CO-B^2-NR^6$, $CO-B^2-NR^6SO_2$ or $SO_2$; and/or (c12) $R^5$ represents a hydrogen atom, an alkyl group, an aryl group, an alkylcarbonyl group or an alkylaminocarbonyl group; and/or (c13) in the case where $R^5$ is an alkyl group, the alkyl group may have one or plural substituents selected from a halogen atom, a hydroxy group, a heterocyclic ring, an alkylamino group and an alkylcarbonylamino group; and/or (c14) in the case where $R^5$ is an aryl group, the aryl group may have one or plural halogen atoms as substituents; and/or (c15) in the case where $R^5$ is an alkylcarbonyl group, the alkylcarbonyl group may have one or plural carboxy groups as substituents; and/or (c16) $R^5$ and $R^6$ may join together to form a heterocyclic ring; and/or (c17) in the case where $R^5$ and $R^6$ join together to form a heterocyclic ring, the heterocyclic ring may have one or plural hydroxyalkyl groups as substituents; and/or (c18) $R^6$ represents a hydrogen atom or an alkyl group; and/or (c19) X and Y represent a hydrogen atom; and/or (c20) $B^1$ represents an alkylene group; and/or (c21) $B^2$ represents a single bond or an alkylene group; and/or (c22) p represents 0; and/or (c23) q represents 0.

That is, further more preferred examples thereof include in the compounds represented by the general formula (1), compounds that satisfy one or a combination of two or more selected from the above (c1), (c2), (c3), (c4), (c5), (c6), (c7), (c8), (c9), (c10), (c11), (c12), (c13), (c14), (c15), (c16), (c17), (c18), (c19), (c20), (c21), (c22) and (c23), and salts thereof.

(d) Preferred examples of the compound of the present invention in terms of pharmacological activity include compounds that satisfy the definitions described in any one of the above (a) to (c) and in which in the general formula (1), the ring A is a pyridine ring or a thiophene ring or salts thereof, and particularly preferred are compounds in which the ring A is a pyridine ring and salts thereof.

(e) More preferred examples of the compound of the present invention in terms of pharmacological activity include compounds that satisfy the definitions described in any one of the above (a) to (d) and in which in the general formula (1), a partial structure (C):

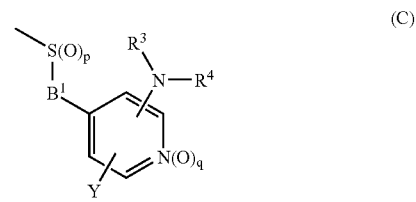

and a partial structure (D):

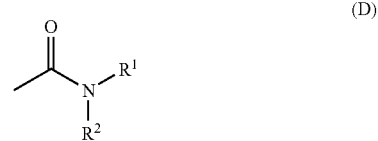

are bonded to adjacent carbon atoms on the ring A, and salts thereof.

(f) Further more preferred examples of the compound of the present invention in terms of pharmacological activity include compounds that satisfy the definition described in the above (d) and the definition described in the above (e) and in which the partial structure (C) or (D) is bonded to the carbon atom located at the α-position to a heteroatom on the ring A and salts thereof.

(g) Particularly preferred examples of the compound of the present invention include compounds that satisfy the definitions described in any one of the above (a) to (f) and also satisfy the definitions described below and salts thereof.

In the general formula (1), (g1) $R^3$ represents $Z-R^5$; and/or (g2) Z represents CO, $CO-B^2-O$, $CO-B^2-NR^6$ or $CO-B^2-NR^6SO_2$; and/or (g3) $R^5$ represents a hydrogen atom, an alkyl group, an aryl group, an alkylcarbonyl group or an alkylaminocarbonyl group; and/or (g4) in the case where $R^5$ is an alkyl group, the alkyl group may have one or plural substituents selected from a halogen atom, a hydroxy group, a heterocyclic ring, an alkylamino group and an alkylcarbonylamino group; and/or (g5) in the case where $R^5$ is an aryl group, the aryl group may have one or plural halogen atoms as substituents; and/or (g6) in the case where $R^5$ is an alkylcarbonyl group, the alkylcarbonyl group may have one or plural carboxy groups as substituents; and/or (g7) $R^5$ and $R^6$ may join together to form a heterocyclic ring; and/or (g8) in the case where $R^5$ and $R^6$ join together to form a heterocyclic ring, the heterocyclic ring may have one or plural hydroxyalkyl groups as substituents; and/or (g9) $R^6$ represents a hydrogen atom or an alkyl group; and/or (g10) $B^2$ represents a single bond or an alkylene group.

That is, particularly preferred examples thereof include in the compounds that satisfy the definitions described in any one of the above (a) to (f) and are represented by the general formula (1), compounds that satisfy one or a combination of two or more selected from the above (g1), (g2), (g3), (g4), (g5), (g6), (g7), (g8), (g9) and (g10), and salts thereof.

Particularly preferred specific examples of the compound of the present invention are shown below.

N-(3,5-Dimethylphenyl)-2-[2-(4-methylpiperazin-1-yl)pyridin-4-ylmethylthio]pyridine-3-carboxamide
2-(2-Cyclopropylaminopyridin-4-ylmethylthio)-N-(3,5-dimethylphenyl)pyridine-3-carboxamide
2-[2-(N-(2-Dimethylaminoethyl)-N-methylamino)pyridin-4-ylmethylthio]-N-(3,5-dimethylphenyl)pyridine-3-carboxamide
N-(3,5-Dimethylphenyl)-2-(2-morpholinopyridin-4-ylmethylthio)pyridine-3-carboxamide
N-(3,5-Dimethylphenyl)-2-[2-(piperidin-1-yl)pyridin-4-ylmethylthio]pyridine-3-carboxamide
2-[2-(4-Acetylpiperazin-1-yl)pyridin-4-ylmethylthio]-N-(3,5-dimethylphenyl)pyridine-3-carboxamide
N-(Indan-5-yl)-2-(2-morpholinopyridin-4-ylmethylthio)pyridine-3-carboxamide
2-[2-(4-Acetylpiperazin-1-yl)pyridin-4-ylmethylthio]-N-(indan-5-yl)pyridine-3-carboxamide
N-(3,5-Dimethylphenyl)-2-(2-n-pentylaminopyridin-4-ylmethylthio)pyridine-3-carboxamide
2-(2-tert-Butoxycarbonylaminopyridin-4-ylmethylthio)-N-(3,5-dimethylphenyl)pyridine-3-carboxamide
2-(2-tert-Butoxycarbonylaminopyridin-4-ylmethylthio)-N-(3-isopropylphenyl)pyridine-3-carboxamide
2-(2-tert-Butoxycarbonylaminopyridin-4-ylmethylthio)-N-(indan-5-yl)pyridine-3-carboxamide
2-(2-tert-Butoxycarbonylaminopyridin-4-ylmethylthio)-N-(4-trifluoromethoxyphenyl)pyridine-3-carboxamide
2-(2-tert-Butoxycarbonylaminopyridin-4-ylmethylthio)-N-(4-tert-butylphenyl)pyridine-3-carboxamide
2-(2-tert-Butoxycarbonylaminopyridin-4-ylmethylthio)-N-(1H-indazol-6-yl)pyridine-3-carboxamide
2-[2-(N-tert-Butoxycarbonyl-N-methylamino)pyridin-4-ylmethylthio]-N-(3,5-dimethylphenyl)pyridine-3-carboxamide
2-[2-(5-Cyanothiazol-2-ylamino)pyridin-4-ylmethylthio]-N-(3,5-dimethylphenyl)pyridine-3-carboxamide
2-(2-Aminopyridin-4-ylmethylthio)-N-(3,5-dimethylphenyl)pyridine-3-carboxamide
2-(2-Aminopyridin-4-ylmethylthio)-N-(3-isopropylphenyl)pyridine-3-carboxamide
2-(2-Aminopyridin-4-ylmethylthio)-N-(indan-5-yl)pyridine-3-carboxamide
2-(2-Aminopyridin-4-ylmethylthio)-N-(4-tert-butylphenyl)pyridine-3-carboxamide
2-(2-Aminopyridin-4-ylmethylthio)-N-(1H-indazol-6-yl)pyridine-3-carboxamide
N-(3,5-Dimethylphenyl)-2-(2-methylaminopyridin-4-ylmethylthio)pyridine-3-carboxamide
N-(Indan-5-yl)-2-(2-methylaminopyridin-4-ylmethylthio)pyridine-3-carboxamide
2-(2-Methylaminopyridin-4-ylmethylthio)-N-(4-trifluoromethoxyphenyl)pyridine-3-carboxamide
2-(2-Aminopyridin-4-ylmethylthio)-N-(4-chlorophenyl)pyridine-3-carboxamide
2-(2-Aminopyridin-4-ylmethylthio)-N-(4-trifluoromethoxyphenyl)pyridine-3-carboxamide
2-(2-Aminopyridin-4-ylmethylthio)-N-(isoquinolin-3-yl)pyridine-3-carboxamide
2-(2-Aminopyridin-4-ylmethylthio)-N-(3,5-dimethylphenyl)benzamide
2-(2-Aminopyridin-4-ylmethylthio)-N-(4-chlorophenyl)benzamide
3-(2-Aminopyridin-4-ylmethylthio)-N-(3,5-dimethylphenyl)thiophene-2-carboxamide
2-(2-Acetylaminopyridin-4-ylmethylthio)-N-(3,5-dimethylphenyl)pyridine-3-carboxamide
N-(3,5-Dimethylphenyl)-2-(2-propionylaminopyridin-4-ylmethylthio)pyridine-3-carboxamide
N-(3,5-Dimethylphenyl)-2-(2-trifluoroacetylaminopyridin-4-ylmethylthio)pyridine-3-carboxamide
N-(3,5-Dimethylphenyl)-2-(2-isobutyrylaminopyridin-4-ylmethylthio)pyridine-3-carboxamide
N-(3,5-Dimethylphenyl)-2-(2-pivaloylaminopyridin-4-ylmethylthio)pyridine-3-carboxamide
N-(3,5-Dimethylphenyl)-2-(2-trifluoromethanesulfonylaminopyridin-4-ylmethylthio)pyridine-3-carboxamide
2-(2-Acetylaminopyridin-4-ylmethylthio)-N-(4-chlorophenyl)pyridine-3-carboxamide
2-(2-Acetylaminopyridin-4-ylmethylthio)-N-(4-trifluoromethoxyphenyl)pyridine-3-carboxamide
2-[2-(N-Acetyl-N-methylamino)pyridin-4-ylmethylthio]-N-(3,5-dimethylphenyl)pyridine-3-carboxamide
2-(2-Acetylaminopyridin-4-ylmethylthio)-N-(1H-indazol-6-yl)pyridine-3-carboxamide
2-(2-Acetylaminopyridin-4-ylmethylthio)-N-(3,5-dimethyl-4-hydroxyphenyl)pyridine-3-carboxamide
2-(2-Acetylaminopyridin-4-ylmethylthio)-N-(4-chlorophenyl)benzamide
2-(2-Acetylaminopyridin-4-ylmethylthio)-N-(4-tert-butylphenyl)benzamide
3-(2-Acetylaminopyridin-4-ylmethylthio)-N-(3,5-dimethylphenyl)thiophene-2-carboxamide
3-(2-Acetylaminopyridin-4-ylmethylthio)-N-(4-chlorophenyl)thiophene-2-carboxamide
N-(3,5-Dimethylphenyl)-2-[2-(N'-n-propylureido)pyridin-4-ylmethylthio]-pyridine-3-carboxamide
2-[2-(N'-tert-Butylureido)pyridin-4-ylmethylthio]-N-(3,5-dimethylphenyl)-pyridine-3-carboxamide
2-[2-(N'-4-Chlorophenylureido)pyridin-4-ylmethylthio]-N-(3,5-dimethylphenyl)pyridine-3-carboxamide
N-(3,5-Dimethylphenyl)-2-(2-formylaminopyridin-4-ylmethylthio)pyridine-3-carboxamide
N-(3,5-Dimethylphenyl)-2-(2-phenylaminopyridin-4-ylmethylthio)pyridine-3-carboxamide
N-(3,5-Dimethylphenyl)-2-[2-(N'-methylureido)pyridin-4-ylmethylthio]pyridine-3-carboxamide
2-[2-(N'-Methylureido)pyridin-4-ylmethylthio]-N-(4-trifluoromethoxyphenyl)pyridine-3-carboxamide
N-(4-Chlorophenyl)-2-[2-(N'-methylureido)pyridin-4-ylmethylthio]pyridine-3-carboxamide
N-(4-Difluoromethoxyphenyl)-2-[2-(N'-methylureido)pyridin-4-ylmethylthio]pyridine-3-carboxamide
2-(2-Acetoxyacetylaminopyridin-4-ylmethylthio)-N-(3,5-dim ethylphenyl)pyridine-3-carboxamide
2-(2-Acetoxyacetylaminopyridin-4-ylmethylthio)-N-(4-trifluoromethoxyphenyl)pyridine-3-carboxamide 2-(2-Aminoacetylaminopyridin-4-ylmethylthio)-N-(3,5-dimethylphenyl)pyridine-3-carboxamide
2-(2-Hydroxyacetylaminopyridin-4-ylmethylthio)-N-(4-trifluoromethoxyphenyl)pyridine-3-carboxamide
N-(3,5-Dimethylphenyl)-2-(2-hydroxyacetylaminopyridin-4-ylmethylthio)pyridine-3-carboxamide
N-(4-Chlorophenyl)-2-(2-hydroxyacetylaminopyridin-4-ylmethylthio)pyridine-3-carboxamide
N-(3,5-Dimethyl-4-hydroxyphenyl)-2-(2-hydroxyacetylaminopyridin-4-ylmethylthio)pyridine-3-carboxamide
2-(2-Hydroxyacetylaminopyridin-4-ylmethylthio)-N-(3-methylphenyl)pyridine-3-carboxamide
2-(2-Hydroxyacetylaminopyridin-4-ylmethylthio)-N-(4-trifluoromethylphenyl)pyridine-3-carboxamide
2-(2-Hydroxyacetylaminopyridin-4-ylmethylthio)-N-(isoquinolin-3-yl)pyridine-3-carboxamide
N-(3-Chlorophenyl)-2-(2-hydroxyacetylaminopyridin-4-ylmethylthio)pyridine-3-carboxamide
2-(2-Hydroxyacetylaminopyridin-4-ylmethylthio)-N-(indan-5-yl)pyridine-3-carboxamide
N-(3-Chloro-4-trifluoromethoxyphenyl)-2-(2-hydroxyacetylaminopyridin-4-ylmethylthio)pyridine-3-carboxamide
2-(2-Hydroxyacetylaminopyridin-4-ylmethylthio)-N-(3-isopropylphenyl)pyridine-3-carboxamide
N-(4-Difluoromethoxyphenyl)-2-(2-hydroxyacetylaminopyridin-4-ylmethylthio)pyridine-3-carboxamide
2-(2-Hydroxyacetylaminopyridin-4-ylmethylthio)-N-(3-trifluoromethylphenyl)pyridine-3-carboxamide
2-[2-(3-Hydroxycarbonylpropionyloxy)acetylaminopyridin-4-ylmethylthio]-N-(4-trifluoromethoxyphenyl)pyridine-3-carboxamide
N-(3,5-Dimethylphenyl)-2-(2-methanesulfonylaminoacetylaminopyridin-4-ylmethylthio)pyridine-3-carboxamide
2-(2-Dimethylaminocarbonyloxyacetylaminopyridin-4-ylmethylthio)-N-(4-trifluoromethoxyphenyl)pyridine-3-carboxamide
2-(2-Isopropylaminoacetylaminopyridin-4-ylmethylthio)-N-(4-trifluoromethoxyphenyl)pyridine-3-carboxamide
2-(2-Dimethylaminoacetylaminopyridin-4-ylmethylthio)-N-(3,5-dimethyl-phenyl)pyridine-3-carboxamide
2-(2-Dimethylaminoacetylaminopyridin-4-ylmethylthio)-N-(4-trifluoromethoxyphenyl)pyridine-3-carboxamide
2-(2-Morpholinoacetylaminopyridin-4-ylmethylthio)-N-(4-trifluoromethoxyphenyl)pyridine-3-carboxamide
2-[2-(2-Dimethylaminoethyl)aminoacetylaminopyridin-4-ylmethylthio]-N-(4-trifluoromethoxyphenyl)pyridine-3-carboxamide
2-[2-(2-Morpholinoethyl)aminoacetylaminopyridin-4-ylmethylthio]-N-(4-trifluoromethoxyphenyl)pyridine-3-carboxamide
2-[2-(3-Hydroxypropyl)aminoacetylaminopyridin-4-ylmethylthio]-N-(4-trifluoromethoxyphenyl)pyridine-3-carboxamide
N-(4-Chlorophenyl)-2-[2-(2-dimethylaminoethyl)aminoacetylaminopyridin-4-ylmetylthio]pyridine-3-carboxamide
2-(2-Aminoacetylaminopyridin-4-ylmethylthio)-N-(4-trifluoromethoxyphenyl)pyridine-3-carboxamide
2-[2-(N-(2-Dimethylaminoethyl)-N-methylamino)acetylaminopyridin-4-ylmethylthio]-N-(4-trifluoromethoxyphenyl)pyridine-3-carboxamide
2-[2-(2-Hydroxyethyl)aminoacetylaminopyridin-4-ylmethylthio]-N-(4-trifluoromethoxyphenyl)pyridine-3-carboxamide
2-[2-(Piperazin-1-yl)acetylaminopyridin-4-ylmethylthio]-N-(4-trifluoromethoxyphenyl)pyridine-3-carboxamide
N-(4-Difluoromethoxyphenyl)-2-(2-dimethylaminoacetylaminopyridin-4-ylmethylthio)pyridine-3-carboxamide
2-[2-(2-Acetylaminoethyl)aminoacetylaminopyridin-4-ylmethylthio]-N-(4-trifluoromethoxyphenyl)pyridine-3-carboxamide
N-(4-Chlorophenyl)-2-[2-(piperazin-1-yl)acetylaminopyridin-4-ylmethyl-thio]pyridine-3-carboxamide
2-[2-(2-Hydroxyethyl)aminoacetylaminopyridin-4-ylmethylthio]-N-(3-methylphenyl)pyridine-3-carboxamide
N-(4-Difluoromethoxyphenyl)-2-[2-(2-dimethylaminoethyl)aminoacetylaminopyridin-4-ylmethylthio]pyridine-3-carboxamide
N-(4-Difluoromethoxyphenyl)-2-[2-(2-hydroxyethyl)aminoacetylaminopyridin-4-ylmethylthio]pyridine-3-carboxamide
2-[2-(2-Acetylaminoethyl)aminoacetylaminopyridin-4-ylmethylthio]-N-(4-difluoromethoxyphenyl)pyridine-3-carboxamide
N-(4-Difluoromethoxyphenyl)-2-[2-(N-(2-dimethylaminoethyl)-N-methyl-amino)acetylaminopyridin-4-ylmethylthio]pyridine-3-carboxamide
2-[2-(2-Dimethylaminoethyl)aminoacetylaminopyridin-4-ylmethylthio]-N-(4-trifluoromethylphenyl)pyridine-3-carboxamide
2-[2-(4-(2-Hydroxyethyl)piperazin-1-yl)acetylaminopyridin-4-ylmethylthio]-N-(4-trifluoromethoxyphenyl)pyridine-3-carboxamide
N-(4-Difluoromethoxyphenyl)-2-[2-(piperazin-1-yl)acetylaminopyridin-4-ylmethylthio]pyridine-3-carboxamide
N-(4-Difluoromethoxyphenyl)-2-(2-isopropylaminoacetylaminopyridin-4-ylmethylthio)pyridine-3-carboxamide
2-[2-(2-Dimethylaminoethyl)aminoacetylaminopyridin-4-ylmethylthio]-N-(3,5-dimethylphenyl)pyridine-3-carboxamide
N-(3,5-Dimethylphenyl)-2-(2-isopropylaminoacetylaminopyridin-4-ylmethylthio)pyridine-3-carboxamide
N-(3,5-Dimethylphenyl)-2-[2-(3-hydroxypropyl)aminoacetylaminopyridin-4-ylmethylthio]pyridine-3-carboxamide
N-(3,5-Dimethylphenyl)-2-[2-(2-morpholinoethyl)aminoacetylaminopyridin-4-ylmethylthio]pyridine-3-carboxamide
2-(2-Ethylaminoacetylaminopyridin-4-ylmethylthio)-N-(4-trifluoromethoxyphenyl)pyridine-3-carboxamide
2-(2-Aminoacetylaminopyridin-4-ylmethylthio)-N-(4-difluoromethoxyphenyl)pyridine-3-carboxamide
2-(3-Aminopyridin-4-ylmethylthio)-N-(3,5-dimethylphenyl)pyridine-3-carboxamide
2-(3-Acetylaminopyridin-4-ylmethylthio)-N-(3,5-dimethylphenyl)pyridine-3-carboxamide
N-(3,5-Dimethylphenyl)-2-(2-morpholinoacetylaminopyridin-4-ylmethylthio)pyridine-3-carboxamide
2-[2-(3-Dimethylaminopropyl)aminoacetylamino]pyridin-4-ylmethylthio]-N-(4-trifluoromethoxyphenyl)pyridine-3-carboxamide
2-(2-Dimethylaminoacetylaminopyridin-4-ylmethylthio)-N-(3-methylphenyl)pyridine-3-carboxamide
2-[2-(2-Dimethylaminoethyl)aminoacetylaminopyridin-4-ylmethylthio]-N-(3-methylphenyl)pyridine-3-carboxamide
N-(3-Methylphenyl)-2-[2-(piperazin-1-yl)acetylaminopyridin-4-ylmethylthio]pyridine-3-carboxamide
2-[2-(Piperazin-1-yl)acetylaminopyridin-4-ylmethylthio]-N-(4-trifluoromethylphenyl)pyridine-3-carboxamide
N-(4-Difluoromethoxyphenyl)-2-[2-(N-(2-hydroxyethyl)-N-methylamino)acetylaminopyridin-4-ylmethylthio]pyridine-3-carboxamide The compounds of the present invention can be prepared by the following methods. Each specific process for preparing the present compounds will be described in detail in the following Examples (under the item of preparation examples). The term "Hal" used in the following synthetic routes represents a halogen atom, the term "Boc" represents a tert-butoxycarbonyl group, and the term "TBS" represents a tert-butyldimethylsilyl group. When an oxygen atom, a nitrogen atom, a sulfur atom or the like are included in $R^1$, $R^2$, $R^3$, $R^4$, $R^5$ or $R^6$ of the following formulas, the protection and the deprotection can be conducted according to methods widely used.

The processes to prepare the compounds of the present invention are divided roughly into the methods described below, and the suitable method can be chosen according to the kind of substituent.

1) The compound of the present invention (Ia) ($R^3$, $R^4$; alkyl, aryl, hydrogen or the like) can be synthesized according to Synthetic route 1. Namely, the compound of the present invention (Ia) can be given by the reaction of compound (IIa) with amine (III) without solvent or in an organic solvent such as tributylamine at 100° C. to 200° C. for 1 hour to 12 hours.

Synthetic Route 1

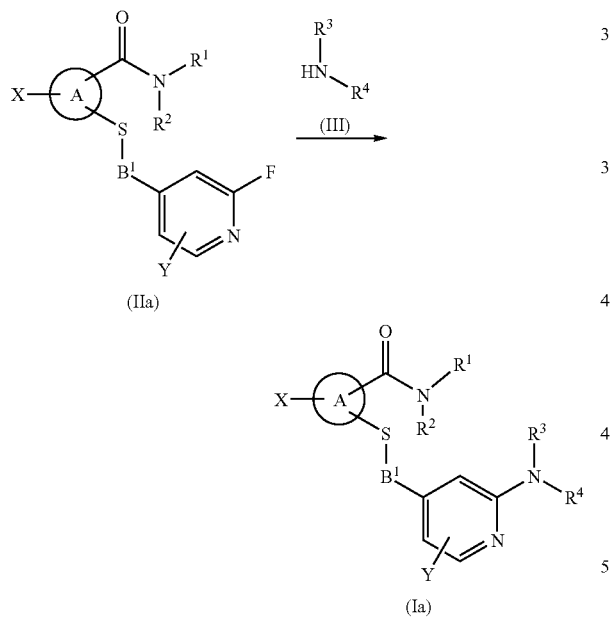

Compound (II) (Hal; F, Cl, Br) including compound (IIa) can be synthesized according to Synthetic route 1-1. Namely, compound (II) can be given by the reaction of compound (IV) with amine (V) in an organic solvent such as dichloromethane or N,N-dimethylformamide (hereinafter referred to as DMF) in the presence of a condensing agent such as N,N'-dicyclohexylcarbodiimide (hereinafter referred to as DCC), O-(7-azabenzotriazol-1-yl)-1,1,3,3-tetramethyluronium hexafluorophosphate (hereinafter referred to as HATU) or N-benzyl-N'-cyclohexylcarbodiimide polymer-bound and in the presence of a base such as N,N-diisopropylethylamine at room temperature to 50° C. for 1 hour to 24 hours.

Synthetic Route 1-1

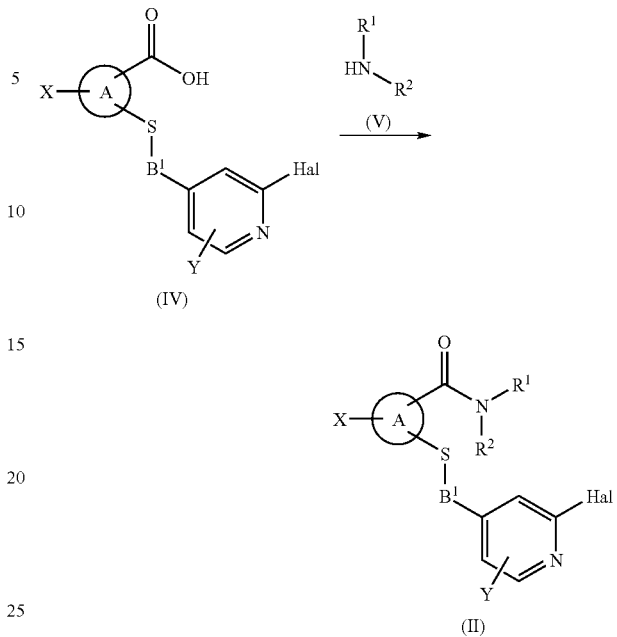

Compound (IV) can be synthesized according to Synthetic route 1-2. Namely, compound (IV) can be given by the reaction of compound (VI) with compound (VII) in an organic solvent such as DMF in the presence of a base such as triethylamine at 0° C. to room temperature for 1 hour to 12 hours.

Synthetic Route 1-2

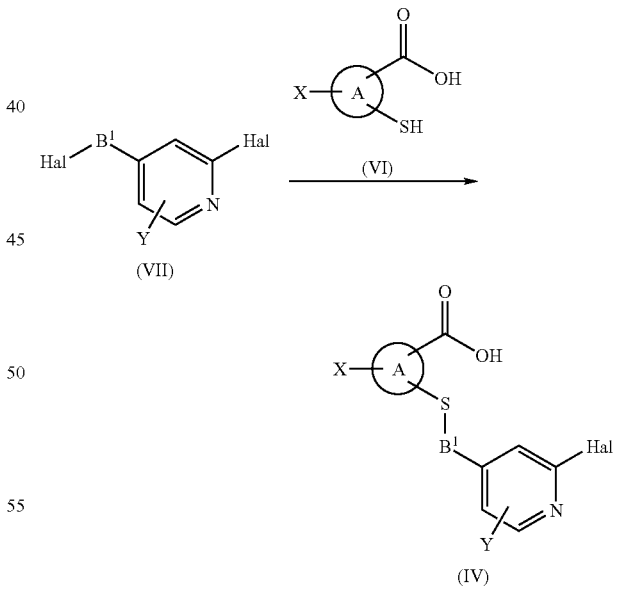

Compound (VII) can be synthesized according to Synthetic route 1-3. Namely, compound (VII) can be given by the treatment of compound (VIII) in an organic solvent such as acetonitrile and in the presence of a radical initiator such as benzoyl peroxide and a halogenating agent such as N-chlorosuccinimide or N-bromosuccinimide under reflux for 1 hour to 12 hours. $R^7$ and $R^8$ used in the following synthetic route represents a hydrogen atom, an alkyl group or the like.

Synthetic Route 1-3

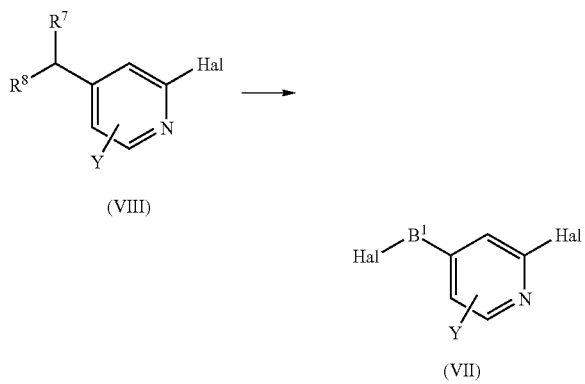

(R⁷, R⁸=H or alkyl etc.)

2) The compound of the present invention (Ib) (R³; alkyl, aryl, hydrogen atom: R⁴; alkyl, aryl, hydrogen atom, COR⁵, CONR⁵R⁶ or the like) can be synthesized according to Synthetic route 2. Namely, it can be given by the reaction of compound (IIb), obtained according to Synthetic route 1-1, with compound (III) (amine, amide or urea) in the presence of a transition metal catalyst such as palladium acetate or tris(dibenzylideneacetone)dipalladium(0), in the presence of a base such as cesium carbonate, in the presence of a catalytic ligand such as 4,5-bis(diphenylphosphino)-9,9-dimethylxanthene and in an organic solvent such as 1,4-dioxane at 80° C. to 150° C. for 1 hour to 12 hours.

Synthetic Route 2

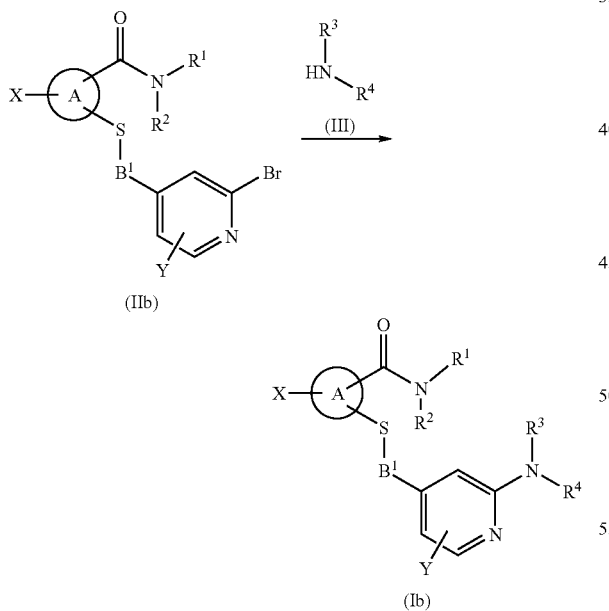

3) The compound of the present invention (Ic) (Z; CO, SO₂ or the like) can be synthesized according to Synthetic route 3. Namely, the compound of the present invention (Ic) can be given by the reaction of the compound of the present invention (Id) with acid anhydride (IX) such as acetic anhydride or acid halide (X) such as pivaloyl chloride in the presence of an organic solvent such as pyridine at 0° C. to 80° C. for 1 hour to 12 hours.

Synthetic Route 3

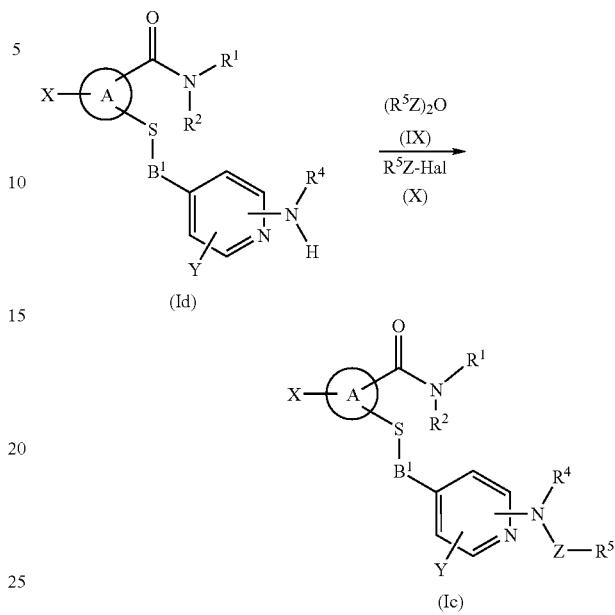

4) The compound of the present invention (Ie) (Z; CO, CS or the like) can be synthesized according to Synthetic route 4. Namely, the compound of the present invention (Ie) can be given by the reaction of the compound of the present invention (Id) with isocyanate (XI) such as n-propyl isocyanate or isothiocyanate (XII) such as methyl isothiocyanate in an organic solvent such as DMF at room temperature to 100° C. for 1 hour to 12 hours.

Synthetic Route 4

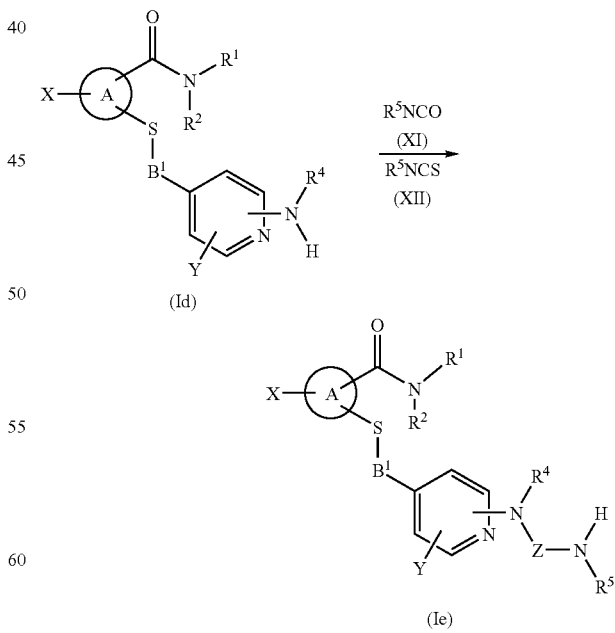

5) The compound of the present invention (Ib) (R³; alkyl, aryl, hydrogen atom: R⁴; alkyl, aryl, hydrogen atom, COR⁵, CONR⁵R⁶ or the like) can be synthesized according to Synthetic route 5. Namely, the compound of the present invention (Ib) can be given by the reaction of compound (XIII) with amine (V) in an organic solvent such as methylene chloride or DMF in the presence of a condensing agent such as DCC, HATU or N-benzyl-N'-cyclohexylcarbodiimide polymer-bound and in the presence of a base such as N,N-diisopropylethylamine at room temperature to 50° C. for 1 hour to 12 hours.

Synthetic Route 5

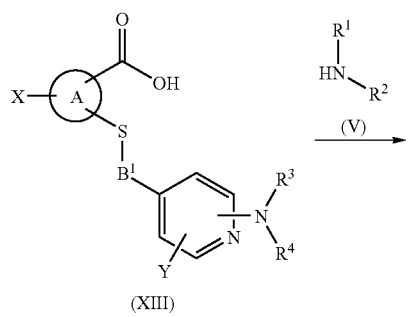

(XIII)

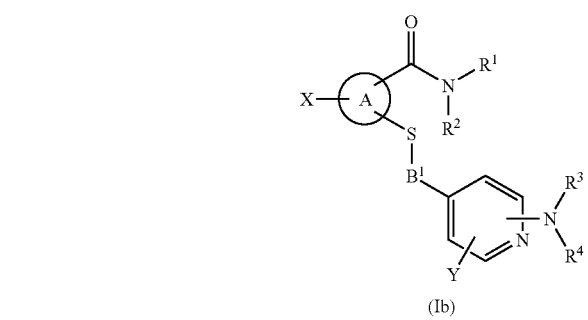

(Ib)

Compound (XIII) can be synthesized according to Synthetic route 5-1. Namely, compound (XIII) can be given by the reaction of compound (VI) with compound (XIV) (W; a leaving group such as a halogen atom, a methanesulfonyloxy group, a toluenesulfonyloxy group or the like) in an organic solvent such as DMF and in the presence of a base such as triethylamine at 0° C. to room temperature for 1 hour to 12 hours.

Synthetic Route 5-1

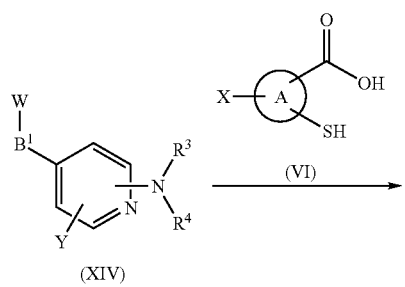

-continued

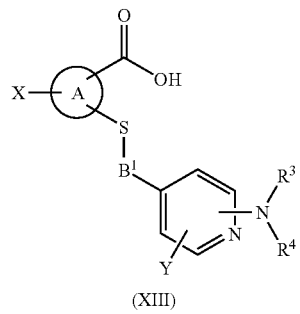

(XIII)

Compound (XIVa) can be synthesized according to Synthetic route 5-2. Namely, compound (XIVa) can be given by the reaction of compound (XV) with a halogenating agent such as carbon tetrabromide-triphenylphosphine in an organic solvent such as methylene chloride at 0° C. to room temperature for 1 hour to 4 hours.

Synthetic Route 5-2

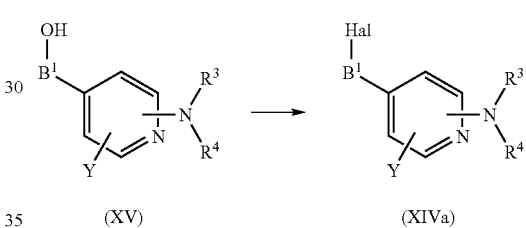

(XV)                            (XIVa)

Compound (XIVb) can be synthesized according to Synthetic route 5-3. Namely, compound (XIVb) can be given by the reaction of compound (XV) with methanesulfonyl chloride in an organic solvent such as methylene chloride and in the presence of a base such as N,N-diisopropylethylamine at 0° C. to room temperature for 30 minutes to 3 hours.

Synthetic Route 5-3

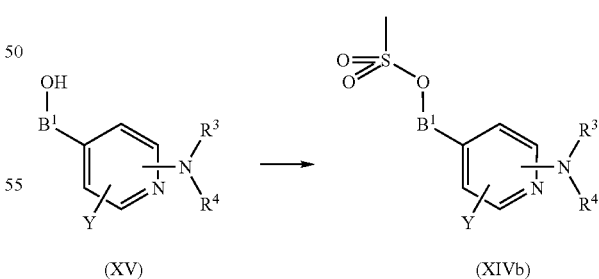

(XV)                            (XIVb)

6) The compound of the present invention (If) can be synthesized according to Synthetic route 6. Namely, the compound of the present invention (If) can be given by the reaction of the compound of the present invention (Id) with a formylating agent such as N-formylbenzotriazole in an organic solvent such as tetrahydrofuran under reflux for 3 hours to 24 hours.

Synthetic Route 6

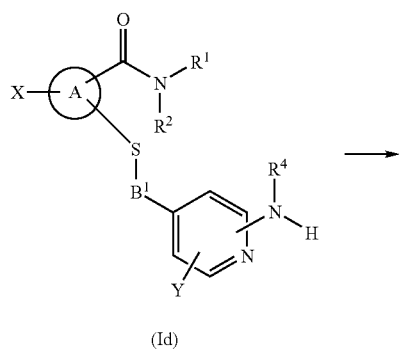

(Id)

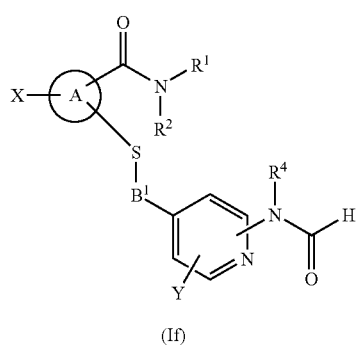

(If)

7) The compound of the present invention (Ig) (R²; alkyl or the like) can be synthesized according to Synthetic route 7. Namely, the compound of the present invention (Ig) can be given by the reaction of the compound of the present invention (Ih) with R²-halide (XVI) (R²; alkyl or the like) in an organic solvent such as tetrahydrofuran or DMF and in the presence of a base such as sodium hydride at 0° C. to room temperature for 30 minutes to 3 hours.

Synthetic Route 7

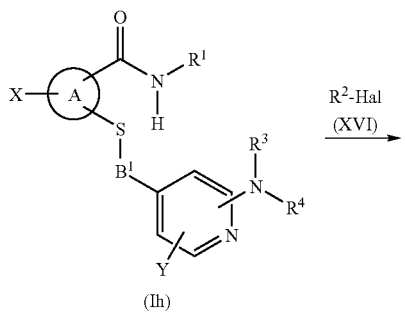

(Ih)

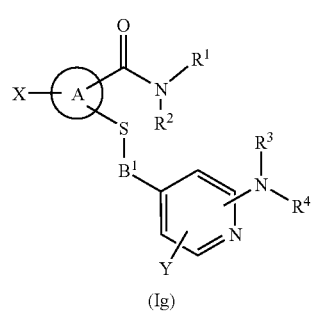

(Ig)

8) The compound of the present invention (Ii) can be synthesized according to Synthetic route 8. Namely, the compound of the present invention (Ii) can be given by the reaction of the compound of the present invention (Id) with R³-halide (XVII) (R³; substituted or unsubstituted aryl and the like) in an organic solvent such as tetrahydrofuran or 1,4-dioxane, in the presence of a transition metal catalyst such as palladium acetate or tris(dibenzylideneacetone)dipalladium(0), in the presence of a catalytic ligand such as triphenylphosphine, 1,4-bis(diphenylphosphino)butane or 4,5-bis(diphenylphosphino)-9,9-dimethylxanthene and in the presence of a base such as cesium carbonate at 50° C. to 120° C. for 3 hours to 24 hours.

Synthetic Route 8

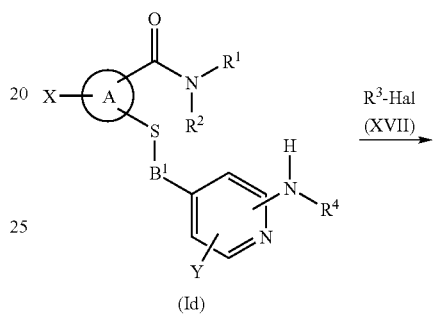

(Ii)

9) The compound of the present invention (Ij) (p=0, 1 or 2, q=0 or 1) can be synthesized according to Synthetic route 9. Namely, the compound of the present invention (Ij), wherein the sulfur atom or the nitrogen atom of compound (Ib) (R³; alkyl, aryl or hydrogen atom: R⁴; alkyl, aryl, hydrogen atom, COR⁵, CONR⁵R⁶ or the like) is oxidized, can be given by the treatment of compound (Ib) in an organic solvent such as chloroform and in the presence of an oxidizing agent such as m-chloroperbenzoic acid or hydrogen peroxide at 0° C. to room temperature for 1 hour to 12 hours.

Synthetic Route 9

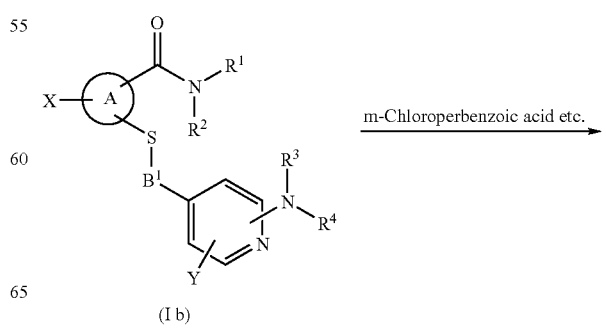

(Ib)

Synthetic Route 11

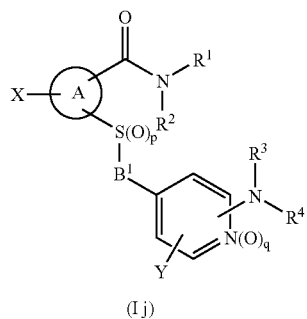
(Ij)

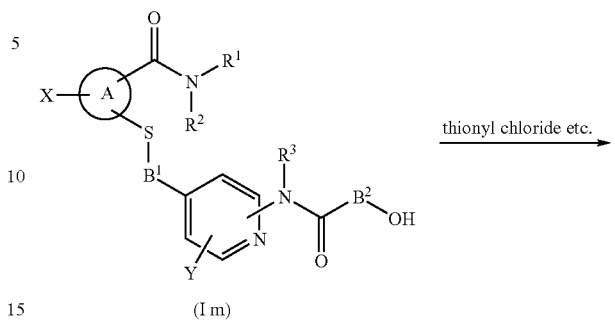
(Im)

thionyl chloride etc.

10) The compound of the present invention (Ik) (B²; alkylene or the like: R⁷, R⁸; alkyl, hydrogen atom or the like) can be synthesized according to Synthetic route 10. Namely, the compound of the present invention (Ik) can be given by the reaction of the compound of the present invention (Il) (B²; alkylene or the like: W; halogen atom or the like) with amine (XVIII) without solvent or in an organic solvent such as DMF or methanol at room temperature to 100° C. for 10 minutes to 12 hours.

Synthetic Route 10

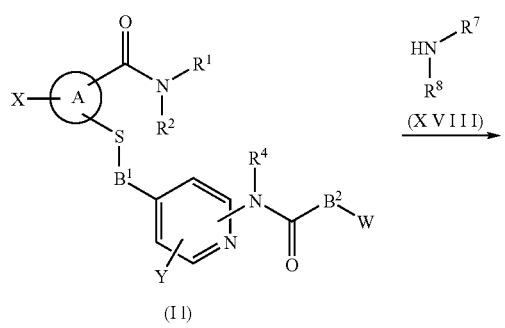
(Il)

(Ik)

11) The compound of the present invention (Il) (B²; alkylene or the like) can be synthesized according to Synthetic route 11. Namely, the compound of the present invention (Il) can be given by the reaction of the compound of the present invention (Im) with a halogenating agent such as thionyl chloride in an organic solvent such as methylene chloride at 0° C. to 50° C. for 10 minutes to 12 hours.

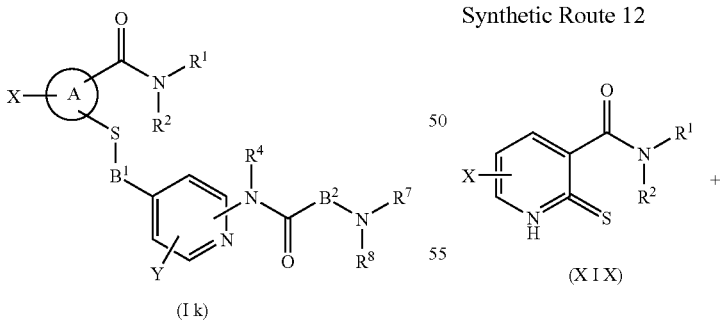
(Il)

12) The compound of the present invention (In) (R³; alkyl, aryl, hydrogen atom or the like: R⁴; alkyl, aryl, hydrogen atom, COR⁵, CONR⁵R⁶ or the like) can be synthesized according to Synthetic route 12. Namely, the compound of the present invention (In) can be given by the reaction of compound (XIX) with compound (XIV) (W; a leaving group such as a bromine atom or a methanesulfonyloxy group) in an organic solvent such as DMF and in the presence of a base such as triethylamine at 0° C. to 50° C. for 30 minutes to 24 hours.

Synthetic Route 12

(XIX)

+

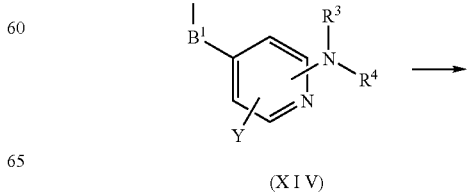
(XIV)

-continued

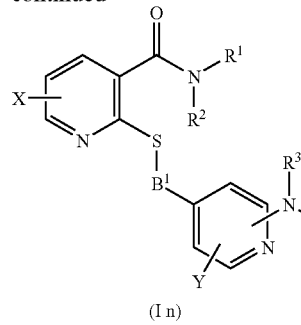

(In)

Compound (XIX) can be synthesized according to Synthetic route 12-1. Namely, compound (XIX) can be given by the reaction of amine (V) with compound (VIa) in an organic solvent such as DMF and in the presence of a condensing agent such as DCC, HATU or carbonyldiimidazole and in the presence of a base such as N,N-diisopropylethylamine at 0° C. to 50° C. for 1 hour to 12 hours.

Synthetic Route 12-1

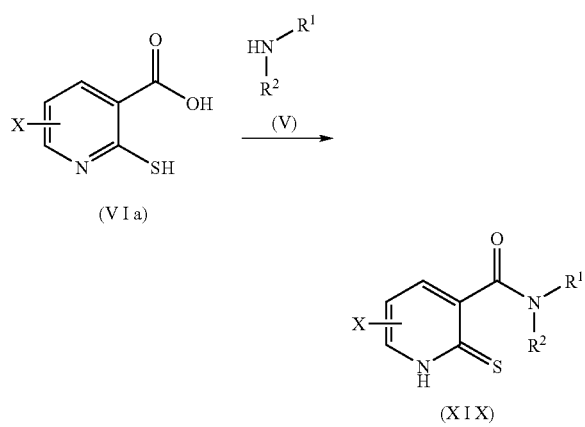

Compound (XIVc) can be synthesized according to Synthetic route 12-2. Namely, compound (XIVc) can be given by the reaction of compound (XV) with a halogenating agent such as an aqueous solution of hydrobromide in water or an organic solvent such as methylene chloride or DMF at 0° C. to 100° C. for 3 hours to 12 hours.

Synthetic Route 12-2

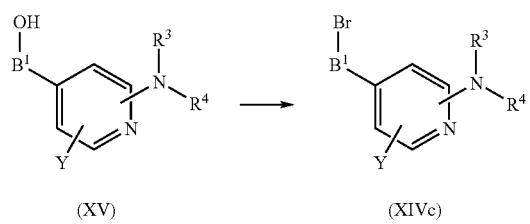

13) The compound of the present invention (Io) ($B^2$; alkylene or the like) can be synthesized according to Synthetic route 13. Namely, the compound of the present invention (Io) can be given by the treatment of the compound of the present invention (Ip) in the presence of a base such as hydrazine monohydrate or an aqueous solution of sodium hydroxide and in an organic solvent such as methanol or 1,4-dioxane at room temperature to 100° C. for 1 hour to 24 hours.

Synthetic Route 13

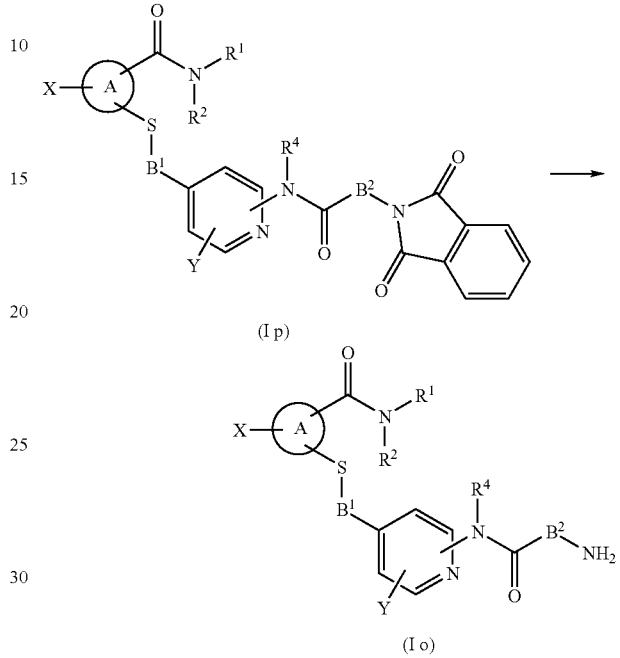

In order to find the usefulness of the compounds of the present invention, the following pharmacological tests 1 to 4 were performed, and the pharmacological effects of the compounds of the present invention were evaluated. The details will be described in the following Examples (under the item of pharmacological tests). In the pharmacological test 1 (in vitro), the compounds of the present invention exhibited an excellent cell proliferation inhibitory action, and an angiogenesis inhibitory effect was found, and then vascular hyperpermeability inhibitory effect was suggested. Further, the compounds of the present invention exhibited an excellent tumor growth inhibitory action, a paw edema inhibitory action and a choroidal neovascularization inhibitory effect in the pharmacological tests 2 to 4 (in vivo) using specific disease model animals, and it was found that the compounds of the present invention are useful as a therapeutic agent for a specific disease in which angiogenesis or vascular hyperpermeability is involved.

1. Evaluation Test of Angiogenesis Inhibitory Effect

A cell proliferation inhibitory action test of the compounds of the present invention was performed using a VEGF-induced HUVEC proliferation evaluation system (HUVEC stands for normal human umbilical vein endothelial cells), which is one of the widely-used methods of evaluating in vitro angiogenesis inhibitory effects of drugs.

2. Evaluation Test of Anticancer Effect

A tumor growth inhibitory action test of the compounds of the present invention was performed using a tumor growth model in mice, which is one of the widely-used methods of evaluating in vivo anticancer effects of drugs.

3. Evaluation Test of Antiarthritis Effect

A paw edema inhibitory action test of the compounds of the present invention was performed using an adjuvant arthritis model in rats, which is one of the widely-used methods of evaluating in vivo antiarthritis effects of drugs.

4. Evaluation Test of Choroidal Neovascularization Inhibitory Effect

A neovascularization incidence test of the compounds of the present invention was performed using a choroidal neovascularization model in rats, which is one of the widely-used methods of evaluating in vivo choroidal neovascularization inhibitory effects of drugs.

As shown in the tests 1 to 4, the compounds of the present invention are useful as a therapeutic agent for a disease in which angiogenesis and/or vascular hyperpermeability are/is involved, specifically they are very useful as a therapeutic agent for cancer, rheumatoid arthritis, age-related macular degeneration, diabetic retinopathy, retinopathy of prematurity, retinal vein occlusion, polypoid choroidal angiopathy, diabetic macular edema, psoriasis vulgaris or atherosclerosis.

The compound of the present invention can be administered orally or parenterally. Examples of the dosage form for administration include a tablet, a capsule, a granule, a powder, an injection, an ophthalmic solution and the like. Such a preparation can be prepared by a widely-used technique.

For example, oral preparations such as a tablet, a capsule, a granule and a powder can be prepared by optionally adding an excipient such as lactose, mannitol, starch, crystalline cellulose, light silicic anhydride, calcium carbonate or calcium hydrogenphosphate, a lubricant such as stearic acid, magnesium stearate or talc, a binder such as starch, hydroxypropyl cellulose, hydroxypropylmethyl cellulose or polyvinylpyrrolidone, a disintegrator such as carboxymethyl cellulose, low-substituted hydroxypropylmethyl cellulose or calcium citrate, a coating agent such as hydroxypropylmethyl cellulose, macrogol or a silicone resin, a stabilizer such as ethyl p-hydroxybenzoate or benzyl alcohol, a corrigent such as a sweetener, a sour agent or a flavor, or the like.

Parenteral preparations such as an injection and an ophthalmic solution can be prepared by optionally adding a tonicity agent such as sodium chloride, concentrated glycerin, propylene glycol, polyethylene glycol, potassium chloride, sorbitol or mannitol, a buffer such as sodium phosphate, sodium hydrogenphosphate, sodium acetate, citric acid, glacial acetic acid or trometamol, a surfactant such as polyoxyethylene sorbitan monoolate, polyoxyl 40 stearate or polyoxyethylene hydrogenated castor oil, a stabilizer such as sodium citrate or disodium edetate, a preservative such as benzalkonium chloride, paraben, benzethonium chloride, p-hydroxybenzoate, sodium benzoate or chlorobutanol, a pH adjusting agent such as hydrochloric acid, citric acid, phosphoric acid, glacial acetic acid, sodium hydroxide, sodium carbonate or sodium hydrogen carbonate, a soothing agent such as benzyl alcohol, or the like.

The dosage of the compound of the present invention can be appropriately selected depending on symptoms, age of patients, dosage form and the like. For example, in the case of an oral preparation, the compound of the present invention can be administered in an amount of generally 0.01 to 1,000 mg, preferably 1 to 100 mg per day, which can be given in a single dose or several divided doses. Further, in the case of an ophthalmic solution, one containing the compound of the present invention at a concentration of 0.0001 to 10% (w/v), preferably 0.01 to 5% (w/v) can be administered once to several times per day.

BEST MODE FOR CARRYING OUT THE INVENTION

Hereinafter, preparation examples, formulation examples, and the results of pharmacological tests of the compounds of the present invention will be shown. These examples are intended to make the present invention more clearly understandable, and do not limit the scope of the present invention.

PREPARATION EXAMPLES

Reference Example 1

4-Chloromethyl-2-fluoropyridine (Reference Compound No. 1-1)

N-Chlorosuccinimide (8.8 g, 66 mmol), acetic acid (0.15 mL) and benzoyl peroxide (220 mg, 0.91 mmol) were added to a solution of 2-fluoro-4-picoline (5.0 g, 45 mmol) in acetonitrile (25 mL) at room temperature, and the mixture was refluxed for 2 hours. The reaction mixture was cooled to room temperature, water (200 mL) was added thereto, and then the mixture was extracted with ethyl acetate (300 mL). The organic layer was washed with brine (200 mL) and dried over anhydrous magnesium sulfate. The organic layer was evaporated under reduced pressure, hexane/ethyl acetate (1:1) was added to the resulting residue, and then the insoluble matter was filtered out. The filtrate was evaporated under reduced pressure to give 6.5 g of the title reference compound as a crude product.

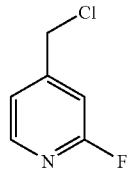

$^1$H-NMR(500 MHz, DMSO-$d_6$)

δ 4.83(s,2H), 7.26(s,1H), 7.43(d,J=5.2 Hz,1H), 8.27(d, J=5.2 Hz,1H)

As described below, Reference compounds (No. 1-2) were obtained using the corresponding compounds selected from commercially available compounds or known compounds according to the synthetic method of Reference compound (No. 1-1).

2-Bromo-4-chloromethylpyridine (Reference Compound No. 1-2)

$^1$H-NMR(500 MHz, DMSO-$d_6$)

δ 4.51(s,2H), 7.28(s,1H), 7.52(d,J=5.2 Hz,1H), 8.36(d, J=5.2 Hz,1H)

Reference Example 2

2-(2-Fluoropyridin-4-ylmethylthio)pyridine-3-carboxylic acid (Reference Compound No. 2-1)

A solution of triethylamine (7.0 mL, 50 mmol) in N,N-dimethylformamide (20 mL) was added to a solution of 4-chloromethyl-2-fluoropyridine (Reference compound No. 1-1, 5.5 g, 38 mmol) and 2-mercaptonicotinic acid (6.2 g, 40 mmol) in N,N-dimethylformamide (40 mL) under ice-cooling, then the mixture was stirred for 12 hours at room temperature. Ethyl acetate (50 mL) was added to the reaction mixture, the whole was extracted with 0.1 N aqueous sodium hydroxide solution (100 mL). 1 N hydrochloric acid was added to the aqueous layer to adjust to pH 5, and the precipitated crystal was filtered off. The crystal was dried at 80° C. under reduced pressure to give 5.3 g of the title reference compound as a brown solid. (Yield 53%)

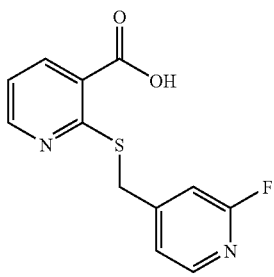

$^1$H-NMR(500 MHz, DMSO-$d_6$)

δ 4.43(s,2H), 7.20(s,1H), 7.23(dd,J=7.9,4.9 Hz,1H), 7.39 (d,J=5.2 Hz,1H), 8.13(d,J=5.2 Hz,1H), 8.24(dd,J=7.9,1.8 Hz,1H), 8.64(dd,J=4.9,1.8 Hz,1H), 14.60(br s,1H)

As described below, Reference compound (No. 2-2) was obtained using the corresponding compounds selected from Reference compound (No. 1-2), commercially available compounds or known compounds according to the synthetic method of Reference compound (No. 2-1).

2-(2-Bromopyridin-4-ylmethylthio)pyridine-3-carboxylic acid (Reference Compound No. 2-2)

$^1$H-NMR(500 MHz, DMSO-$d_6$)

δ 4.37(s,2H), 7.28(dd,J=7.8,4.7 Hz,1H), 7.48(dd,J=4.9,1.4 Hz,1H), 7.69(dd,J=1.4,0.4 Hz,1H), 8.23(dd,J=7.8,1.7 Hz,1H), 8.27(dd,J=4.9,0.4 Hz,1H), 8.63(dd, J=4.7,1.7 Hz,1H), 13.55(s,1H)

Reference Example 3

N-(3,5-Dimethylphenyl)-2-(2-fluoropyridin-4-ylmethylthio)pyridine-3-carboxamide (Reference Compound No. 3-1)

O-(7-Azabenzotriazol-1-yl)-N,N,N',N'-tetramethyluronium hexafluorophosphate (3.0 g, 7.9 mmol) was added to a solution of 2-(2-fluoropyridin-4-ylmethylthio)pyridine-3-carboxylic acid (Reference compound No. 2-1, 1.5 g, 5.7 mmol), 3,5-xylidine (0.90 g, 7.4 mmol) and N,N-diisopropylethylamine (2.0 mL, 11 mmol) in N,N-dimethylformamide (20 mL) at room temperature, and the mixture was stirred for 12 hours. Ethyl acetate (30 mL) was added to the reaction mixture, the whole was washed with brine (50 mL), and then the organic layer was dried over anhydrous magnesium sulfate. The organic layer was evaporated under reduced pressure, and the resulting residue was purified by silica gel column chromatography to give 0.91 g of the title reference compound as a colorless solid. (Yield 44%)

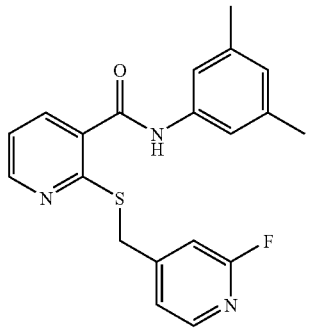

$^1$H-NMR(500 MHz, DMSO-$d_6$)

δ 2.26(s,6H), 4.46(s,2H), 6.76(s,1H), 7.18(s,1H), 7.29(dd, J=7.3,4.6 Hz,1H), 7.32(s,2H), 7.38(d,J=5.2 Hz,1H), 7.94(dd, J=7.3,1.5 Hz,1H), 8.13(d,J=5.2 Hz,1H), 8.58(dd,J=4.6,1.5 Hz,1H), 10.32(s,1H)

As described below, Reference compounds (No. 3-2~7) were obtained using the corresponding compounds selected from Reference compound (No. 2-1), Reference compound (No. 2-2), commercially available compounds or known compounds according to the synthetic method of Reference compound (No. 3-1).

2-(2-Fluoropyridin-4-ylmethylthio)-N-(indan-5-yl) pyridine-3-carboxamide (Reference Compound No. 3-2)

$^1$H-NMR(500 MHz, DMSO-$d_6$)

δ 1.98-2.06(m,2H), 2.79-2.90(m,4H), 4.46(s,2H), 7.16-7.20(m,2H), 7.29(dd,J=7.3,4.9 Hz,1H), 7.38(dd,J=4.6,1.5 Hz,2H), 7.61(s,1H), 7.95(dd,J=7.3,1.5 Hz, 1H), 8.13(d,J=5.2 Hz,1H), 8.58(dd,J=4.9,1.5 Hz,1H), 10.35(s,1H)

2-(2-Fluoropyridin-4-ylmethylthio)-N-(4-trifluoromethoxyphenyl)pyridine-3-carboxamide (Reference Compound No. 3-3)

$^1$H-NMR(500 MHz, DMSO-$d_6$)

δ 4.47(s,2H), 7.18(s,1H), 7.32(dd,J=7.6,4.9 Hz,1H), 7.35-7.40(m,3H), 7.81(d,J=8.2 Hz,2H), 8.00(dd,J=7.6,1.8 Hz,1H), 8.13(d,J=5.2 Hz,1H), 8.61(dd,J=4.9,1.8 Hz,1H), 10.67(s,1H)

2-(2-Bromopyridin-4-ylmethylthio)-N-(3,5-dimethylphenyl)pyridine-3-carboxamide (Reference Compound No. 3-4)

$^1$H-NMR(400 MHz, DMSO-$d_6$)

δ 2.26(s,6H), 4.41(s,2H), 6.76(s,1H), 7.29(dd,J=7.6,4.9 Hz,1H), 7.32(s,2H), 7.47(dd,J=5.1,1.5 Hz,1H), 7.67(d,J=0.7 Hz,1H), 7.94(dd,J=7.6,1.7 Hz,1H), 8.27(dd,J=5.1,0.7 Hz,1H), 8.58(dd,J=4.9,1.7 Hz,1H), 10.32(s,1H)

2-(2-Bromopyridin-4-ylmethylthio)-N-(4-trifluoromethoxyphenyl)pyridine-3-carboxamide (Reference Compound No. 3-5)

$^1$H-NMR(500 MHz, DMSO-$d_6$)

δ 4.42(s,2H), 7.32(dd,J=7.6,4.9 Hz,1H), 7.38(d,J=8.7 Hz,2H), 7.47(d,J=5.1 Hz,1H), 7.67(s,1H), 7.80(d,J=8.7 Hz,2H), 8.00(dd,J=7.6,1.7 Hz,1H), 8.27(dd,J=5.1 Hz,1H), 8.60(dd,J=4.9,1.7 Hz,1H), 10.68(s,1H)

2-(2-Bromopyridin-4-ylmethylthio)-N-(4-chlorophenyl)pyridine-3-carboxamide (Reference Compound No. 3-6)

$^1$H-NMR(400 MHz, DMSO-$d_6$)

δ 4.41(s,2H), 7.31(dd,J=7.6,4.9 Hz,1H), 7.42(d,J=9.0 Hz,2H), 7.47(dd,J=5.0,1.5 Hz,1H), 7.67(d,J=0.7 Hz,1H), 7.73(d,J=9.0 Hz,2H), 8.00(dd,J=7.6,1.7 Hz,1H), 8.27(dd, J=5.0,0.7 Hz,1H), 8.60(dd,J=4.9,1.7 Hz,1H), 10.61(s,1H)

2-(2-Bromopyridin-4-ylmethylthio)-N-(4-difluoromethoxyphenyl)pyridine-3-carboxamide (Reference Compound No. 3-7)

$^1$H-NMR(400 MHz, DMSO-$d_6$)

δ 4.41(s,2H), 7.16(t,J=74.2 Hz,1H), 7.19(d,J=8.8 Hz,2H), 7.31(dd,J=7.6,4.9 Hz,1H), 7.47(dd,J=5.1,1.5 Hz,1H), 7.67(s, 1H), 7.73(d,J=8.8 Hz,2H), 7.99(dd,J=7.6,1.7 Hz,1H), 8.27(d, J=5.1 Hz,1H), 8.59(dd,J=4.9,1.7 Hz,1H), 10.56(s,1H)

Reference Example 4

(2-tert-Butoxycarbonylaminopyridin-4-yl)methanol (Reference Compound No. 4-1)

Di-tert-butyl dicarbonate (7.1 g, 32 mmol) was added to a solution of (2-aminopyridin-4-yl)methanol (3.0 g, 24 mmol) in tert-butanol (60 mL) at room temperature, and the mixture was stirred for 12 hours. The reaction mixture was evaporated under reduced pressure, ethyl acetate (20 mL) was added to the resulting residue, and then the insoluble matter was filtered out. The filtrate was evaporated under reduced pressure, and the resulting residue was purified by silica gel column chromatography to give 3.6 g of the title reference compound as a colorless crystal. (Yield 60%)

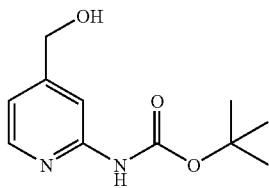

$^1$H-NMR(500 MHz, CDCl$_3$)

δ 1.56(s,9H), 1.86(t,J=6.1 Hz,1H), 4.73(d,J=6.1 Hz,2H), 7.00(d,J=5.2 Hz,1H), 7.53(br s,1H), 7.92(s,1H), 8.21(d,J=5.2 Hz,1H)

Reference Example 5

2-tert-Butoxycarbonylamino-4-(tert-butyldimethylsilyloxymethyl)pyridine (Reference Compound No. 5-1)

Imidazole (2.1 g, 31 mmol) and tert-butyldimethylsilyl chloride (4.4 g, 29 mmol) were added to a solution of (2-tert-butoxycarbonylaminopyridin-4-yl)methanol (Reference compound No. 4-1, 6.2 g, 28 mmol) in N,N-dimethylformamide (120 mL) at room temperature, and the mixture was stirred for 2 hours. Ethyl acetate (300 mL) was added to the reaction mixture, then the mixture was washed with water (750 mL) and brine (200 mL), and then the mixture was dried over anhydrous magnesium sulfate. The organic layer was evaporated under reduced pressure to give 9.0 g of the title reference compound as a colorless solid. (Yield 96%)

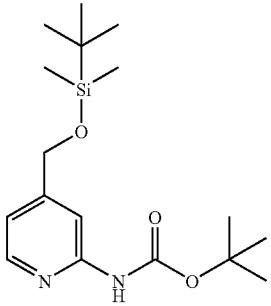

$^1$H-NMR(400 MHz, DMSO-$d_6$)

δ 0.09(s,6H), 0.92(s,9H), 1.46(s,9H), 4.72(s,2H), 6.93(dd, J=4.9,0.9 Hz,1H), 7.78(s,1H), 8.16(d,J=4.9 Hz,1H), 9.67(s, 1H)

Reference Example 6

2-(N-tert-Butoxycarbonyl-N-methylamino)-4-(tert-butyldimethylsilyloxymethyl)pyridine (Reference Compound No. 6-1)

60% Sodium hydride (310 mg, 7.6 mmol) was washed with hexane (5.0 mL), and the residue was suspended in N,N-dimethylformamide (20 mL). 2-tert-Butoxycarbonylamino-4-(tert-butyldimethylsilyloxymethyl)pyridine (Reference compound No. 5-1, 1.3 g, 3.7 mmol) was added dropwise to the suspension for 15 minutes under ice-cooling, and methyl iodide (2.4 mL, 39 mmol) was added thereto, and then the mixture was stirred overnight at room temperature. Water (70 mL) was added to the reaction suspension, and the whole was extracted with ethyl acetate (100 mL). The organic layer was washed with saturated aqueous sodium hydrogen carbonate solution (50 mL) and brine (100 mL), and dried over anhydrous magnesium sulfate. The organic layer was evaporated under reduced pressure to give 1.4 g of the mixture including the title reference compound as an orange-red oil.

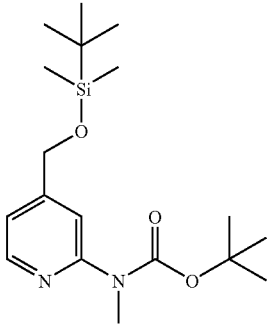

$^1$H-NMR(500 MHz, CDCl$_3$)

δ 0.11(s,6H), 0.95(s,9H), 1.51(s,9H), 3.39(s,3H), 4.73(s, 2H), 7.01(d,J=5.2 Hz,1H), 7.57(s,1H), 8.31(d,J=5.2 Hz,1H)

Reference Example 7

[2-(N-tert-Butoxycarbonyl-N-methylamino)pyridin-4-yl]methanol (Reference Compound No. 7-1)

A solution of tetra-n-butylammonium fluoride trihydrate (1.3 g, 4.2 mmol) in tetrahydrofuran (20 mL) was added to a solution of 2-(N-tert-butoxycarbonyl-N-methylamino)-4-(tert-butyldimethylsilyloxymethyl)pyridine (Reference compound No. 6-1, 1.4 g, 3.7 mmol) in tetrahydrofuran (20 mL) for 5 minutes at room temperature, and the mixture was stirred for 15 minutes. Ethyl acetate (50 mL) and water (100 mL) were added to the reaction mixture, the whole was separated, and then the aqueous layer was extracted with ethyl acetate (50 mL). These organic layers were combined, then it was washed with brine (100 mL) and dried over anhydrous magnesium sulfate. The organic layer was evaporated under reduced pressure, then the resulting residue was purified by silica gel column chromatography to give 450 mg of the title reference compound as a reddish brown oil. (Yield 50%)

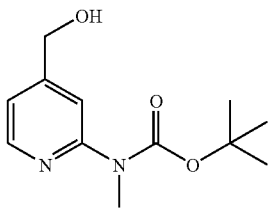

$^1$H-NMR(500 MHz, CDCl$_3$)
δ 1.53(s,9H), 1.93(t,J=5.6 Hz,1H), 3.40(s,3H), 4.73(d, J=5.6 Hz,2H), 7.02(d,J=5.1 Hz,1H), 7.70(s,1H), 8.34(d,J=5.1 Hz,1H)

Reference Example 8

4-Bromomethyl-2-tert-butoxycarbonylaminopyridine (Reference Compound No. 8-1)

Triphenylphosphine (970 mg, 3.7 mmol) and carbon tetrabromide (1.5 g, 4.6 mmol) were added to a solution of (2-tert-butoxycarbonylaminopyridin-4-yl)methanol (Reference compound No. 4-1, 690 mg, 3.1 mmol) in methylene chloride (20 mL) under ice-cooling, and the mixture was stirred for 2 hours at room temperature. Ethyl acetate (30 mL) was added to the reaction mixture, the whole was washed with saturated aqueous sodium hydrogen carbonate solution (20 mL) and brine (20 mL), and then dried over anhydrous magnesium sulfate. The organic layer was evaporated under reduced pressure, and the resulting solid was filtered off with ethyl acetate to give 550 mg of the title reference compound as a colorless solid. (Yield 62%)

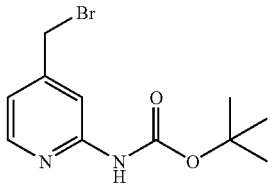

$^1$H-NMR(400 MHz, CDCl$_3$)
δ 1.54(s,9H), 4.38(s,2H), 6.99(d,J=5.1 Hz,1H), 7.61(br s,1H), 7.98(s,1H), 8.22(d,J=5.1 Hz,1H)

As described below, Reference compounds (No. 8-2~3) were obtained using the corresponding compounds selected from Reference compound (No. 7-1), commercially available compounds or known compounds according to the synthetic method of Reference compound (No. 8-1).

4-Bromomethyl-2-(N-tert-butoxycarbonyl-N-methylamino)pyridine (Reference Compound No. 8-2)

$^1$H-NMR(500 MHz, DMSO-d$_6$)
δ 1.48(s,9H), 3.29(s,3H), 4.67(s,2H), 7.17(d,J=5.1 Hz,1H), 7.70(s,1H), 8.35(d,J=5.1 Hz,1H)

4-Bromomethyl-2-phthaloylaminopyridine (Reference Compound No. 8-3)

$^1$H-NMR(500 MHz, CDCl$_3$)
δ 4.48(s,2H), 7.39(dd,J=5.2,1.5 Hz,1H), 7.48(s,1H), 7.80-7.84(m,2H), 7.96-8.00(m,2H), 8.67(d,J=5.2 Hz,1H)

Reference Example 9

2-(2-tert-Butoxycarbonylaminopyridin-4-ylmethylthio)pyridine-3-carboxylic acid (Reference Compound No. 9-1)

A solution of triethylamine (0.75 mL, 5.4 mmol) in N,N-dimethylformamide (2.0 mL) was added to a solution of 4-bromomethyl-2-tert-butoxycarbonylaminopyridine (Reference compound No. 8-1, 500 mg, 1.7 mmol) and 2-mercaptonicotinic acid (270 mg, 1.7 mmol) in N,N-dimethylformamide (3.0 mL) under ice-cooling, and the mixture was stirred for 12 hours at room temperature. Ethyl acetate (20 mL) was added to the reaction mixture, and the whole was extracted with 0.1N aqueous sodium hydroxide solution (50 mL). 1N Hydrochloric acid was added to the aqueous layer to adjust to pH 5, and the precipitated crystal was filtered off. The crystal was dried under reduced pressure at 60° C. to give 560 mg of the title reference compound as a colorless crystal. (Yield 88%)

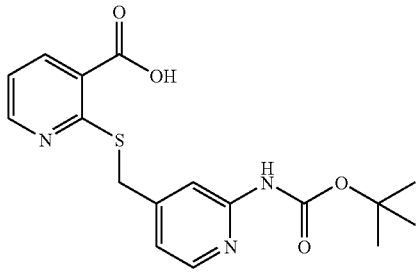

$^1$H-NMR(500 MHz, DMSO-d$_6$)
δ 1.46(s,9H), 4.35(s,2H), 7.05(d,J=5.2 Hz,1H), 7.26(dd, J=7.9,4.9 Hz,1H), 7.87(s,1H), 8.12(d,J=5.2 Hz,1H), 8.23(dd, J=7.9,1.8 Hz,1H), 8.63(dd,J=4.9,1.8 Hz,1H), 9.67(s,1H), 13.50(br s,1H)

As described below, Reference compounds (No. 9-2~6) were obtained using the corresponding compound selected from Reference compound (No. 8-2), Reference compound (No. 8-3), commercially available compounds or known compounds according to the synthetic method of Reference compound (No. 9-1).

2-[2-(N-tert-Butoxycarbonyl-N-methylamino)pyridin-4-ylmethylthio]pyridine-3-carboxylic acid (Reference Compound No. 9-2)

$^1$H-NMR(500 MHz, DMSO-d$_6$)
δ 1.40(s,9H), 3.25(s,3H), 4.38(s,2H), 7.17(dd,J=5.2,1.5 Hz,1H), 7.27(dd,J=7.6,4.9 Hz,1H), 7.61(s,1H), 8.21-8.26(m, 2H), 8.63(dd,J=4.9,1.8 Hz,1H), 13.49(br s,1H)

2-(2-Phthaloylaminopyridin-4-ylmethylthio)pyridine-3-carboxylic acid (Reference Compound No. 9-3)

¹H-NMR(400 MHz, DMSO-d$_6$)

δ 4.46(s,2H), 7.27(dd,J=7.7,4.8 Hz,1H), 7.56(d,J=5.1 Hz,1H), 7.61(s,1H), 7.91-8.00(m,4H), 8.23(dd,J=7.7,1.8 Hz,1H), 8.52(d,J=5.1 Hz,1H), 8.63(dd,J=4.8,1.8 Hz,1H), 13.55(br s,1H)

2-[2-(5-Cyanothiazol-2-ylamino)pyridin-4-ylmethylthio]pyridine-3-carboxylic acid (Reference Compound No. 9-4)

¹H-NMR(400 MHz, DMSO-d$_6$)

δ 4.39(s,2H), 7.12(d,J=5.1 Hz,1H), 7.21(s,1H), 7.27(dd, J=7.8,4.6 Hz,1H), 8.23(dd,J=7.8,1.7 Hz,1H), 8.25(s,1H), 8.29(d,J=5.1 Hz,1H), 8.62(dd,J=4.6,1.7 Hz,1H), 12.19(s, 1H), 13.52(br s,1H)

2-(2-tert-Butoxycarbonylaminopyridin-4-ylmethylthio)benzoic acid (Reference Compound No. 9-5)

¹H-NMR(500 MHz, DMSO-d$_6$)

δ 1.47(s,9H), 4.22(s,2H), 7.09(d,J=5.2 Hz,1H), 7.22(t, J=7.6 Hz,1H), 7.42(d,J=7.6 Hz,1H), 7.47(t,J=7.6 Hz,1H), 7.88(s,1H), 7.89(d,J=7.6 Hz,1H), 8.16(d,J=5.2 Hz,1H), 9.74 (s,1H), 13.10(br s,1H)

3-(2-tert-Butoxycarbonylaminopyridin-4-ylmethylthio)thiophene-2-carboxylic acid (Reference Compound No. 9-6)

¹H-NMR(400 MHz, DMSO-d$_6$)

δ 1.47(s,9H), 4.33(s,2H), 7.09(d,J=5.1 Hz,1H), 7.17(d, J=5.1 Hz,1H), 7.85(d,J=5.1 Hz,1H), 7.90(s,1H), 8.17(d,J=5.1 Hz,1H), 9.76(s,1H), 13.04(br s,1H)

Reference Example 10

N-(3,5-Dimethylphenyl)-2-thioxo-1,2-dihydropyridine-3-carboxamide (Reference Compound No. 10-1)

2-Mercaptonicotinic acid (90 g, 0.58 mol) was suspended in N,N-dimethylformamide (660 mL), and carbonyldiimidazole (110 g, 0.70 mol) was added thereto under ice-cooling, and then the mixture was stirred at room temperature for 2 hours. Water (5.4 mL) was added thereto, the whole was stirred for 40 minutes. 3,5-Xylidine (76 mL, 0.61 mol) was added thereto, and the mixture was stirred for 16 hours at 60° C. The mixture was allowed to stand, water (1.3 L) was added thereto, and then the precipitated solid was filtered off. The solid was dried under reduced pressure at 45° C. to give 130 g of the title reference compound as a yellow solid. (Yield 89%)

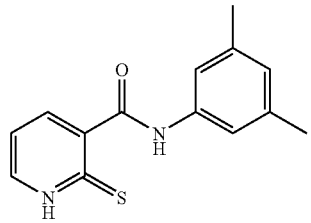

¹H-NMR(500 MHz, DMSO-d$_6$)

δ 2.27(s,6H), 6.77(s,1H), 7.10(dd,J=7.6,6.0 Hz,1H), 7.34 (s,2H), 8.03(dd,J=6.0, 1.8 Hz,1H), 8.55(dd,J=7.6,1.8 Hz,1H), 12.90(s,1H), 14.18(s,1H)

As described below, Reference compounds (No. 10-2~10) were obtained using the corresponding compounds selected from commercially available compounds or known compounds according to the synthetic method of Reference compound (No. 10-1).

2-Thioxo-N-(4-trifluoromethoxyphenyl)-1,2-dihydropyridine-3-carboxamide (Reference Compound No. 10-2)

¹H-NMR(500 MHz, DMSO-d$_6$)

δ 7.08(dd,J=7.5,5.8 Hz,1H), 7.39(d,J=8.8 Hz,2H), 7.82(d, J=8.8 Hz,2H), 8.03(dd,J=5.8,1.8 Hz,1H), 8.48(dd,J=7.5,1.8 Hz,1H), 12.91(s,1H), 14.19(s,1H)

N-(4-Chlorophenyl)-2-thioxo-1,2-dihydropyridine-3-carboxamide (Reference Compound No. 10-3)

¹H-NMR(400 MHz, DMSO-d$_6$)

δ 7.08(dd,J=7.6,6.1 Hz,1H), 7.43(d,J=8.7 Hz,2H), 7.74(d, J=8.7 Hz,2H), 8.03(dd,J=6.1,1.8 Hz,1H), 8.48(dd,J=7.6,1.8 Hz,1H), 12.90(s,1H), 14.19(s,1H)

N-(Indan-5-yl)-2-thioxo-1,2-dihydropyridine-3-carboxamide (Reference Compound 10-4)

¹H-NMR(400 MHz, DMSO-d$_6$)

δ 1.98-2.06(m,2H), 2.81-2.89(m,4H), 7.09(dd,J=7.6,4.8 Hz,1H), 7.20(d,J=8.1 Hz,1H), 7.43(dd,J=8.1,2.0 Hz,1H), 7.62(s,1H), 8.03(dd,J=4.8,1.7 Hz,1H), 8.55(dd,J=7.6,1.7 Hz,1H), 12.93(s,1H), 14.18(s,1H)

N-(4-tert-Butylphenyl)-2-thioxo-1,2-dihydropyridine-3-carboxamide (Reference Compound No. 10-5)

¹H-NMR(400 MHz, DMSO-d$_6$)

δ 1.28(s,9H), 7.09(dd,J=7.6,5.9 Hz,1H), 7.39(d,J=8.8 Hz,2H), 7.62(d,J=8.8 Hz,2H), 8.03(dd,J=5.9,1.9 Hz,1H), 8.55(dd,J=7.6,1.9 Hz,1H), 12.90(s,1H), 14.19(s,1H)

N-(3-Methylphenyl)-2-thioxo-1,2-dihydropyridine-3-carboxamide (Reference Compound No. 10-6)

¹H-NMR(400 MHz, DMSO-d$_6$)

δ 2.32(s,3H), 6.95(d,J=7.6 Hz,1H), 7.10(dd,J=7.6,5.9 Hz,1H), 7.25(t,J=7.6 Hz,1H), 7.52-7.55(m,2H), 8.03(dd, J=5.9,2.0 Hz,1H), 8.54(dd,J=7.6,2.0 Hz, 1H), 12.91(s,1H), 14.19(s,1H)

2-Thioxo-N-(4-trifluoromethylphenyl)-1,2-dihydro-pyridine-3-carboxamide (Reference Compound No. 10-7)

¹H-NMR(500 MHz, DMSO-d₆)
δ 7.09(dd,J=7.6,5.8 Hz,1H), 7.74(d,J=8.4 Hz,2H), 7.92(d, J=8.4 Hz,2H), 8.04(dd,J=5.8,1.8 Hz,1H), 8.47(dd,J=7.6,1.8 Hz,1H), 13.04(s,1H), 14.20(br s,1H)

N-(3-Chlorophenyl)-2-thioxo-1,2-dihydropyridine-3-carboxamide (Reference Compound No. 10-8)

¹H-NMR(500 MHz, DMSO-d₆)
δ 7.08(dd,J=7.6,5.8 Hz,1H), 7.19(d,J=7.9 Hz,1H), 7.40(t, J=7.9 Hz,1H), 7.52(d,J=7.9 Hz,1H), 7.96(t,J=2.0 Hz,1H), 8.03(dd,J=5.8,1.8 Hz,1H), 8.46(dd,J=7.6,1.8 Hz,1H), 12.90(s,1H), 14.19(br s,1H)

N-(4-Difluoromethoxyphenyl)-2-thioxo-1,2-dihydro-pyridine-3-carboxamide (Reference Compound No. 10-9)

¹H-NMR(500 MHz, DMSO-d₆)
δ 7.09(dd,J=7.5,4.8 Hz,1H), 7.18(t,J=74.6 Hz,1H), 7.20(d, J=9.1 Hz,2H), 7.75(d,J=9.1 Hz,2H), 8.03(dd,J=4.8,1.9 Hz,1H), 8.51(dd,J=7.5,1.9 Hz,1H), 12.90(s,1H), 14.18(s,1H)

N-(Isoquinolin-3-yl)-2-thioxo-1,2-dihydropyridine-3-carboxamide (Reference Compound No. 10-10)

¹H-NMR(400 MHz, DMSO-d₆)
δ 7.15(dd,J=7.8,6.1 Hz,1H), 7.58(t,J=7.5 Hz,1H), 7.75(t, J=7.0 Hz,1H), 7.97(d,J=8.1 Hz,1H), 8.08-8.10(m,2H), 8.69-8.72(m,2H), 9.19(s,1H), 13.71(s,1H), 14.24(s,1H)

Reference Example 11

4-Acetoxymethyl-2-acetylaminopyridine (Reference Compound No. 11-1)

(2-Aminopyridin-4-yl)methanol (5.0 g, 40 mmol) was suspended in pyridine (20 mL), acetic anhydride (11 mL, 120 mmol) was added thereto under ice-cooling, and the mixture was stirred for 5 hours at room temperature. Ethyl acetate (150 mL) was added to the reaction mixture, and then the mixture was washed with water (150 mL), saturated aqueous sodium hydrogen carbonate solution (150 mL) and brine (150 mL) successively. The organic layer was dried over anhydrous magnesium sulfate, and the solvent was evaporated under reduced pressure. The resulting solid was filtered off with hexane, then dried under reduced pressure at 40° C. to give 6.7 g of the title reference compound as a colorless solid. (Yield 79%)

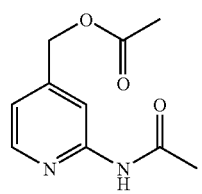

¹H-NMR(500 MHz, DMSO-d₆)
δ 2.09(s,3H), 2.11(s,3H), 5.11(s,2H), 7.04(d,J=5.2 Hz,1H), 8.05(s,1H), 8.27(d,J=5.2 Hz,1H), 10.51(s,1H)

Reference Compound No. 12

(2-Acetylaminopyridin-4-yl)methanol (Reference Compound No. 12-1)

4-Acetoxymethyl-2-acetylaminopyridine (Reference compound No. 11-1, 6.6 g, 32 mmol) was dissolved in tetrahydrofuran (20 mL), and 2N aqueous sodium hydroxide solution (19 mL, 38 mmol) was added dropwise thereto under ice-cooling. The mixture was stirred for 40 minutes at room temperature, and water (100 mL) was added thereto. The whole was extracted with ethyl acetate (80 mL) six times, and then the organic layer was dried over anhydrous magnesium sulfate. The solvent was evaporated under reduced pressure, and the resulting solid was filtered off with the mixed solvent of ethyl acetate and hexane, and then the solid was dried under reduced pressure at 40° C. to give 4.5 g of the title reference compound as a colorless solid. (Yield 86%)

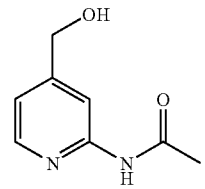

¹H-NMR(400 MHz, DMSO-d₆)
δ 2.08(s,3H), 4.50(d,J=5.9 Hz,2H), 5.40(t,J=5.9 Hz,1H), 7.01(d,J=4.9 Hz,1H), 8.05(s,1H), 8. 20(d,J=4.9 Hz,1H), 10.38(s,1H)

Reference Example 13

2-Acetylamino-4-methanesulfonyloxymethylpyridine (Reference Compound No. 13-1)

A solution of triethylamine (1.7 mL, 12 mmol) and methanesulfonyl chloride (0.70 mL, 9.0 mmol) in anhydrous tetrahydrofuran (3.0 mL) was added to a solution of (2-acetylaminopyridin-4-yl)methanol (Reference compound No. 12-1, 1.0 g, 6.0 mmol) in anhydrous tetrahydrofuran (9.0 mL) under ice-cooling, and the mixture was stirred for 20 minutes. Water (30 mL) was added to the reaction mixture, the whole was extracted with ethyl acetate (40 mL) three times, and then the organic layer was dried over anhydrous magnesium sulfate. The solvent was evaporated under reduced pressure, and the resulting solid was filtered off with hexane. The solid was dried under reduced pressure at 40° C. to give 1.3 g of the title reference compound as a pale yellow solid. (Yield 87%)

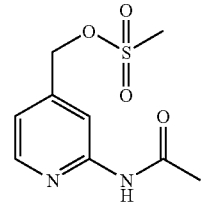

¹H-NMR(400 MHz, CDCl₃)
δ 2.22(s,3H), 3.08(s,3H), 5.25(s,2H), 7.10(dd,J=5.2,1.8 Hz,1H), 8.18(s,1H), 8.23(s,1H), 8.30(d,J=5.2 Hz,1H)

Reference Example 14

2-Amino-4-bromomethylpyridine hydrobromide (Reference Compound No. 14-1)

(2-Aminopyridin-4-yl)methanol (15 g, 12 mmol) was suspended in a 47% aqueous hydrobromic acid solution (120 mL, 72 mmol) at room temperature, and the mixture was stirred for 6 hours at outer temperature 120° C. The mixture was stirred for 15 hours at room temperature, then the precipitated solid was filtered off and washed with ethyl acetate. The solid was dried under reduced pressure to give 23 g of the title reference compound as a gray solid. (Yield 71%)

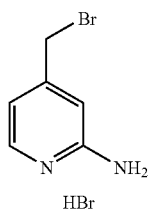

$^1$H-NMR(400 MHz, DMSO-$d_6$)
δ 4.69(s,2H), 6.88(dd,J=6.8,1.7 Hz,1H), 7.04(s,1H), 7.94 (d,J=6.8 Hz,1H), 8.13 (br s,2H), 13.28(br s,1H)

Example 1

N-(3,5-Dimethylphenyl)-2-[2-(4-methylpiperazin-1-yl)pyridin-4-ylmethylthio]pyridine-3-carboxamide (Compound No. 1-1)

N-Methylpiperazine (2.0 mL) was added to N-(3,5-dimethylphenyl)-2-(2-fluoropyridin-4-ylmethylthio)pyridine-3-carboxamide (Reference compound No. 3-1, 100 mg, 0.27 mmol) at room temperature, then the vessel was sealed and the reaction mixture was stirred for 3 hours at 150° C. The mixture was cooled to room temperature, ethyl acetate (20 mL) was added to the reaction mixture, and then the whole was washed with brine (20 mL) and dried over anhydrous magnesium sulfate. The organic layer was evaporated under reduced pressure, and the resulting solid was filtered off with ethyl acetate to give 39 mg of the target compound as a colorless crystal. (Yield 32%)

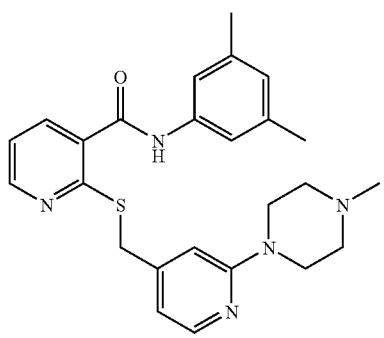

$^1$H-NMR(500 MHz, DMSO-$d_6$)
δ 2.19(s,3H), 2.25(s,6H), 2.35(t,J=5.0 Hz,4H), 3.42(t,J=5.0 Hz,4H), 4.31(s, 2H), 6.64(dd,J=5.2,1.2 Hz,1H), 6.76(s,1H), 6.84(s,1H), 7.28(dd,J=7.5,4.9 Hz, 1H), 7.32(s,2H), 7.91 (dd,J=7.5,1.8 Hz,1H), 7.99(d,J=5.2 Hz,1H), 8.59(dd,J=4.9, 1.8 Hz,1H), 10.30(s,1H)

As described below, Compounds (No. 1-2~21) were obtained using the corresponding compounds selected from Reference compounds (No. 3-1~3), commercially available compounds or known compounds according to the synthetic method of Compound (No. 1-1).

2-(2-Cyclopropylaminopyridin-4-ylmethylthio)-N-(3,5-dimethylphenyl)pyridine-3-carboxamide (Compound No. 1-2)

$^1$H-NMR(500 MHz, CDCl$_3$)
δ 0.48-0.53(m,2H), 0.73-0.77(m,2H), 2.32(s,6H), 2.46(m, 1H), 4.41(s,2H), 5.20(br s,1H), 6.67(d,J=5.2 Hz,1H), 6.79(s, 1H), 6.81(s,1H), 7.13(dd,J=7.6,4.9 Hz,1H), 7.24(s,2H), 7.88-7.91(m,2H), 7.93(d,J=5.2 Hz,1H), 8.91(dd,J=4.9,1.8 Hz,1H)

2-[2-(N-(2-Dimethylaminoethyl)-N-methylamino)pyridin-4-ylmethylthio]-N-(3,5-dimethylphenyl)pyridine-3-carboxamide (Compound No. 1-3)

$^1$H-NMR(500 MHz, DMSO-$d_6$)
δ 2.13(s,6H), 2.25(s,6H), 2.33(t,J=7.0 Hz,2H), 2.94(s,3H), 3.56(t,J=7.0 Hz,2H), 4.30(s,2H), 6.53(d,J=5.2 Hz,1H), 6.60 (s,1H), 6.76(s,1H), 7.28(dd,J=7.6,4.9 Hz, 1H), 7.31(s,2H), 7.90(dd,J=7.6,1.5 Hz,1H), 7.93(d,J=5.2 Hz,1H), 8.59(dd, J=4.9,1.5 Hz,1H), 10.30(s,1H)

N-(3,5-Dimethylphenyl)-2-(2-morpholinopyridin-4-ylmethylthio)pyridine-3-carboxamide (Compound No. 1-4)

$^1$H-NMR(500 MHz, CDCl$_3$)
δ 2.32(s,6H), 3.47(t,J=4.9 Hz,4H), 3.80(t,J=4.9 Hz,4H), 4.40(s,2H), 6.70(s, 1H), 6.72(d,J=5.2 Hz,1H), 6.82(s,1H), 7.15(dd,J=7.6,4.8 Hz,1H), 7.24(s,2H), 7.76(s,1H), 7.90(dd, J=7.6,1.5 Hz,1H), 8.10(d,J=5.2 Hz,1H), 8.54(dd,J=4.8, 1.5 Hz,1H)

N-(3,5-Dimethylphenyl)-2-[2-(piperidin-1-yl)pyridin-4-ylmethylthio]pyridine-3-carboxamide (Compound No. 1-5)

$^1$H-NMR(500 MHz, DMSO-$d_6$)
δ 1.46-1.60(m,6H), 2.25(s,6H), 3.46(t,J=5.2 Hz,4H), 4.30 (s,2H), 6.58(d,J=6.1 Hz,1H), 6.76(s,1H), 6.82(s,1H), 7.28 (dd,J=7.6,4.9 Hz,1H), 7.32(s,2H), 7.91(m,1H), 7.96(m,1H), 8.58(dd,J=4.9,1.8 Hz,1H), 10.30(s,1H)

2-[2-(4-Acetylpiperazin-1-yl)pyridin-4-ylmethylthio]-N-(3,5-dimethylphenyl)pyridine-3-carboxamide (Compound No. 1-6)

$^1$H-NMR(500 MHz, CDCl$_3$)
δ 2.13(s,3H), 2.32(s,6H), 3.46-3.49(m,2H), 3.54-3.56(m, 2H), 3.59-3.61(m,2H), 3.70-3.73(m,2H), 4.39(s,2H), 6.72 (m,1H), 6.82(s,1H), 7.00(s,1H), 7.15(dd,J=7.6,4.8 Hz,1H), 7.24(s,2H), 7.75(s,1H), 7.89(dd,J=7.6,1.7 Hz,1H), 8.09(dd, J=4.6,1.2 Hz,1H), 8.54(dd,J=4.8,1.7 Hz,1H)

2-[2-(4-tert-Butoxycarbonylpiperazin-1-yl)pyridin-4-ylmethylthio]-N-(3,5-dimethylphenyl)pyridine-3-carboxamide (Compound No. 1-7)

$^1$H-NMR(400 MHz, CDCl$_3$)
δ 1.47(s,9H), 2.29(s,6H), 3.49(br s,8H), 4.36(s,2H), 6.68 (d,J=5.3 Hz,1H), 6.70(s,1H), 6.80(s,1H), 7.08(dd,J=7.6,4.9 Hz,1H), 7.29(s,2H), 7.85(dd,J=7.6,1.7 Hz, 1H), 8.05(s,1H), 8.07(d,J=5.3 Hz,1H), 8.51(dd,J=4.9,1.7 Hz,1H)

N-(3,5-Dimethylphenyl)-2-[2-(N-(2-hydroxyethyl)-N-methylamino)pyridin-4-ylmethylthio]pyridine-3-carboxamide (Compound No. 1-8)

$^1$H-NMR(500 MHz, CDCl$_3$)

δ 2.17(s,1H), 2.32(s,6H), 3.02(s,3H), 3.66(t,J=5.0 Hz,2H), 3.79(t,J=5.0 Hz,2H), 4.38(s,2H), 6.59(s,1H), 6.63(dd,J=5.2, 1.8 Hz,1H), 6.81(s,1H), 7,13(dd,J=7.6, 4.9 Hz,1H), 7.24(s, 2H), 7.87(s,1H), 7.89(dd,J=7.6,1.5 Hz,1H), 7.94(d,J=5.2 Hz,1H), 8.53(dd,J=4.9,1.5 Hz,1H)

N-(3,5-Dimethylphenyl)-2-[2-(4-hydroxypiperidin-1-yl)pyridin-4-ylmethylthio]pyridine-3-carboxamide (Compound No. 1-9)

$^1$H-NMR(500 MHz, CDCl$_3$)

δ 1.43(s,1H), 1.48-1.61(m,2H), 1.92-1.98(m,2H), 2.32(s, 6H), 3.09-3.14(m,2H), 3.90(m,1H), 4.01-4.06(m,2H), 4.38 (s,2H), 6.64(dd,J=5.1,1.1 Hz,1H), 6.73(s, 1H), 6.82(s,1H), 7.14(dd,J=7.6,4.8 Hz,1H), 7.24(s,2H), 7.79(s,1H), 7.90(d, J=4.8 Hz,1H), 8.08(d,J=5.1 Hz,1H), 8.55(dd,J=4.8,1.8 Hz,1H)

N-(Indan-5-yl)-2-(2-morpholinopyridin-4-ylmethylthio)pyridine-3-carboxamide (Compound No. 1-10)

$^1$H-NMR(500 MHz, CDCl$_3$)

δ 2.03-2.13(m,2H), 2.85-2.94(m,4H), 3.47(t,J=4.9 Hz,4H), 3.80(t,J=4.9 Hz, 4H), 4.39(s,2H), 6.68-6.72(m,2H), 7.15(dd,J=7.6,4.8 Hz,1H), 7.19(d,J=8.3 Hz, 1H), 7.24(s,1H), 7.58(s,1H), 7.81(s,1H), 7.91(d,J=7.6 Hz,1H), 8.10(d,J=5.2 Hz,1H), 8.54(dd,J=4.8,1.8 Hz,1H)

2-[2-(4-Acetylpiperazin-1-yl)pyridin-4-ylmethylthio]-N-(indan-5-yl)-pyridine-3-carboxamide (Compound No. 1-11)

$^1$H-NMR(500 MHz, CDCl$_3$)

δ 2.09(t,J=7.3 Hz,2H), 2.13(s,3H), 2.87-2.94(m,4H), 3.47 (t,J=5.2 Hz,2H), 3.53-3.58(m,2H), 3.59-3.62(m,2H), 3.72(t, J=5.2 Hz,2H), 4.39(s,2H), 6.72(m,2H), 7.15(dd,J=7.6,4.8 Hz,1H), 7.19(d,J=8.9 Hz,1H), 7.24(s,1H), 7.58(s,1H), 7.80 (s,1H), 7.91(d,J=6.7 Hz,1H), 8.09(m,1H), 8.54(dd,J=4.8,1.8 Hz,1H)

2-(2-Morpholinopyridin-4-ylmethylthio)-N-(4-trifluoromethoxyphenyl)pyridine-3-carboxamide (Compound No. 1-12)

$^1$H-NMR(500 MHz, DMSO-d$_6$)

δ 3.38(t,J=4.8 Hz,4H), 3.66(t,J=4.8 Hz,4H), 4.33(s,2H), 6.70(dd,J=5.2,1.2 Hz,1H), 6.86(s,1H), 7.31(dd,J=7.6,4.9 Hz,1H), 7.37(d,J=8.6 Hz,2H), 7.80(d,J=8.6 Hz,2H), 7.97(dd, J=7.6,1.8 Hz,1H), 8.01(d,J=5.2 Hz,1H), 8.62(dd,J=4.9,1.8 Hz,1H), 10.66(s,1H)

2-[2-(4-Acetylpiperazin-1-yl)pyridin-4-ylmethylthio]-N-(4-trifluoromethoxyphenyl)pyridine-3-carboxamide (Compound No. 1-13)

$^1$H-NMR(400 MHz, CDCl$_3$)

δ 2.05(s,3H), 3.44-3.49(m,2H), 3.52-3.57(m,2H), 3.59-3.63(m,2H), 3.68-3.73(m,4H), 4.40(s,2H), 6.70-6.73(m,2H), 7.17(dd,J=7.6,4.9 Hz,1H), 7.23(d,J=8.3 Hz,2H), 7.64(d, J=8.3 Hz,2H), 7.92(dd,J=7.6,1.7 Hz,1H), 7.98(s,1H), 8.10 (dd,J=5.1,0.7 Hz,1H), 8.57(dd,J=4.9,1.7 Hz,1H)

N-(3,5-Dimethylphenyl)-2-[2-(4-ethoxycarbonylpiperazin-1-yl)pyridin-4-ylmethylthio]pyridine-3-carboxamide (Compound No. 1-14)

$^1$H-NMR(400 MHz, DMSO-d$_6$)

δ 1.15-1.21(m,3H), 2.25(s,6H), 3.18-3.40(m,2H), 3.41-3.48(m,6H), 4.03-4.09(m,2H), 4.32(s,2H), 6.68(d,J=5.0 Hz,1H), 6.76(s,1H), 6.88(s,1H), 7.28(dd,J=7.6, 4.9 Hz,1H), 7.32(s,2H), 7.91(dd,J=7.6,1.7 Hz,1H), 8.00(d,J=5.0 Hz,1H), 8.59(dd,J=4.9,1.7 Hz,1H), 10.31(s,1H)

N-(3,5-Dimethylphenyl)-2-(2-thiomorpholinopyridin-4-ylmethylthio)pyridine-3-carboxamide (Compound No. 1-15)

$^1$H-NMR(400 MHz, DMSO-d$_6$)

δ 2.25(s,6H), 2.49-2.56(m,4H), 3.84-3.87(m,4H), 4.30(s, 2H), 6.62(d,J=5.3 Hz,1H), 6.76(s,1H), 6.86(s,1H), 7.28(dd, J=7.6,4.9 Hz,1H), 7.32(s,2H), 7.91(dd,J=7.6,1.7 Hz,1H), 7.98(d,J=5.3 Hz,1H), 8.59(dd,J=4.9,1.7 Hz,1H), 10.31(s,1H)

N-(3,5-Dimethylphenyl)-2-[2-(3-hydroxymethylpiperidin-1-yl)pyridin-4-ylmethylthio]pyridine-3-carboxamide (Compound No. 1-16)

$^1$H-NMR(500 MHz, DMSO-d$_6$)

δ 1.14(m,1H), 1.37-1.74(m,4H), 2.25(s,6H), 2.71-2.77(m, 2H), 3.24-3.35(m,2H), 4.12(d,J=13.1 Hz,1H), 4.24(d,J=13.1 Hz,1H), 4.29(s,2H), 4.54(t,J=5.2 Hz, 1H), 6.58(d,J=5.2 Hz,1H), 6.76(s,1H), 6.82(s,1H), 7.27(dd,J=7.6,4.9 Hz,1H), 7.32(s,2H), 7.91(dd,J=7.6,1.6 Hz,1H), 7.95(d,J=5.2 Hz,1H), 8.59(dd,J=4.9, 1.6 Hz,1H), 10.30(s,1H)

2-[2-((2S)-Dimethylaminocarbonylpyrrolidin-1-yl)pyridin-4-ylmethylthio]-N-(3,5-dimethylphenyl)pyridine-3-carboxamide (Compound No. 1-17)

$^1$H-NMR(400 MHz, DMSO-d$_6$)

δ 1.90-2.00(m,2H), 2.25(s,6H), 2.76(s,3H), 3.08(s,3H), 3.20-3.45(m,4H), 4.27(d,J=13.6 Hz,1H), 4.33(d,J=13.6 Hz,1H), 4.87(m,1H), 6.41(s,1H), 6.53(dd,J=5.4, 1.3 Hz,1H), 6.75(s,1H), 7.27(dd,J=7.5,4.9 Hz,1H), 7.32(s,2H), 7.87(d, J=5.4 Hz,1H), 7.89(dd,J=7.5,1.7 Hz,1H), 8.59(dd,J=4.9,1.7 Hz,1H), 10.32(s,1H)

2-[2-(3-Dimethylaminopyrrolidin-1-yl)pyridin-4-ylmethylthio]-N-(3,5-dimethylphenyl)pyridine-3-carboxamide (Compound No. 1-18)

$^1$H-NMR(400 MHz, DMSO-d$_6$)

δ 1.75(m,1H), 2.11(m,1H), 2.17(s,6H), 2.25(s,6H), 2.74 (m,1H), 3.04(m,1H), 3.28(m,1H), 3.50(t,J=8.5 Hz,1H), 3.60 (dd,J=9.8,7.1 Hz,1H), 4.30(s,2H), 6.48(s,1H), 6.54(dd,J=5.1, 1.2 Hz,1H), 6.76(s,1H), 7.27(dd,J=7.8,5.0 Hz,1H), 7.32(s, 2H), 7.89-7.93(m,2H), 8.59(dd,J=5.0,1.7 Hz,1H), 10.30(s, 1H)

N-(3,5-Dimethylphenyl)-2-[2-(2-hydroxyethylamino)pyridin-4-ylmethylthio]pyridine-3-carboxamide (Compound No. 1-19)

$^1$H-NMR(400 MHz, CDCl$_3$)

δ 2.32(s,6H), 2.88(s,1H), 3.43(t,J=4.6 Hz,2H), 3.74(t, J=4.6 Hz,2H), 4.34(s,2H), 5.08(s,1H), 6.52(s,1H), 6.63(dd, J=5.4,1.2 Hz,1H), 6.81(d,J=0.8 Hz,1H), 7.11(dd,J=7.8,4.8 Hz,1H), 7.24(s,2H), 7.83-7.93(m,3H), 8.51(dd,J=4.8,1.7 Hz,1H)

N-(3,5-Dimethylphenyl)-2-(2-n-pentylaminopyridin-4-ylmethylthio)pyridine-3-carboxamide (Compound No. 1-20)

$^1$H-NMR(500 MHz, CDCl$_3$)
δ 0.86-0.92(m,3H), 1.20-1.38(m,4H), 1.55-1.60(m,2H), 2.31(s,6H), 3.18-3.20(m,2H), 4.35(s,2H), 4.57(s,1H), 6.41(s,1H), 6.58(dd,J=5.2,1.5 Hz,1H), 6.80(s,1H), 7.09(dd,J=7.6,4.9 Hz,1H), 7.24(s,2H), 7.86(dd,J=7.6,1.7 Hz,1H), 7.94(d,J=5.2 Hz,1H), 8.02(s,1H), 8.51(dd,J=4.9,1.7 Hz,1H)

N-(3,5-Dimethylphenyl)-2-[2-(4-ethoxycarbonylpiperidin-1-yl)pyridin-4-ylmethylthio]pyridine-3-carboxamide (Compound No. 1-21)

$^1$H-NMR(500 MHz, DMSO-d$_6$)
δ 1.18(t,J=7.0 Hz,3H), 1.48-1.51(m,2H), 1.82-1.86(m,2H), 2.25(s,6H), 2.57(m,1H), 2.86-2.93(m,2H), 4.06(q,J=7.0 Hz,2H), 4.13-4.16(m,2H), 4.30(s,2H), 6.62(dd,J=5.2,1.1 Hz,1H), 6.76(s,1H), 6.87(s,1H), 7.28(dd,J=7.6,4.9 Hz,1H), 7.32(s,2H), 7.91(dd,J=7.6,1.7 Hz,1H), 7.98(d,J=5.2 Hz,1H), 8.59(dd,J=4.9,1.7 Hz,1H), 10.31(s,1H)

Example 2

2-(2-tert-Butoxycarbonylaminopyridin-4-ylmethylthio)-N-(3,5-dimethylphenyl)pyridine-3-carboxamide (Compound No. 2-1)

O-(7-Azabenzotriazol-1-yl)-N,N,N',N'-tetramethyluronium hexafluorophosphate (630 mg, 1.7 mmol) was added to a solution of 2-(2-tert-butoxycarbonylaminopyridin-4-ylmethylthio)pyridine-3-carboxylic acid (Reference compound No. 9-1, 500 mg, 1.4 mmol), 3,5-xylidine (180 mg, 1.5 mmol) and N,N-diisopropylethylamine (0.72 mL, 4.1 mmol) in N,N-dimethylformamide (7 mL) at room temperature, and the mixture was stirred for 12 hours. Ethyl acetate (30 mL) was added to the reaction mixture, then the whole was washed with brine (50 mL) and dried over anhydrous magnesium sulfate. The organic layer was evaporated under reduced pressure, then the resulting residue was purified by silica gel column chromatography to give 670 mg of the target compound quantitatively as a colorless solid.

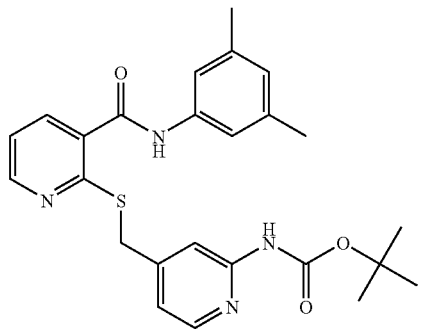

$^1$H-NMR(500 MHz, DMSO-d$_6$)
δ 1.45(s,9H), 2.25(s,6H), 4.38(s,2H), 6.76(s,1H), 7.03(d,J=5.2 Hz,1H), 7.28(dd,J=7.6,4.9 Hz,1H), 7.32(s,2H), 7.87(s,1H), 7.92(dd,J=7.6,1.8 Hz,1H), 8.11(d,J=5.2 Hz,1H), 8.57(dd,J=4.9,1.8 Hz,1H), 9.66(s,1H), 10.30(br s,1H)

As described below, Compounds (No. 2-2~36) were obtained using the corresponding compounds selected from Reference compounds (No. 9-1~6), commercially available compounds or known compounds according to the synthetic method of Compound (No. 2-1).

2-(2-tert-Butoxycarbonylaminopyridin-4-ylmethylthio)-N-(3-isopropylphenyl)pyridine-3-carboxamide (Compound No. 2-2)

$^1$H-NMR(500 MHz, DMSO-d$_6$)
δ 1.20(d,J=7.0 Hz,6H), 1.45(s,9H), 2.86(m,1H), 4.39(s,2H), 7.00(d,J=7.6 Hz,1H), 7.04(dd,J=4.9,1.5 Hz,1H), 7.24-7.30(m,2H), 7.51(d,J=7.6 Hz,1H), 7.59(s,1H), 7.87(s,1H), 7.96(dd,J=7.6,1.5 Hz,1H), 8.11(m,1H), 8.58(dd,J=4.9,1.5 Hz,1H), 9.66(s,1H), 10.39(s,1H)

2-(2-tert-Butoxycarbonylaminopyridin-4-ylmethylthio)-N-(indan-5-yl)pyridine-3-carboxamide (Compound No. 2-3)

$^1$H-NMR(500 MHz, DMSO-d$_6$)
δ 1.45(s,9H), 1.98-2.04(m,2H), 2.80-2.89(m,4H), 4.38(s,2H), 7.03(dd,J=4.9,1.5 Hz,1H), 7.17(d,J=8.2 Hz,1H), 7.28(dd,J=7.6,4.9 Hz,1H), 7.38(d,J=8.2 Hz,1H), 7.61(s,1H), 7.87(s,1H), 7.93(dd,J=7.6,1.5 Hz,1H), 8.11(d,J=4.9 Hz,1H), 8.57(dd,J=4.9,1.5 Hz,1H), 9.67(s,1H), 10.33(s,1H)

2-(2-tert-Butoxycarbonylaminopyridin-4-ylmethylthio)-N-(4-trifluoromethoxyphenyl)pyridine-3-carboxamide (Compound No. 2-4)

$^1$H-NMR(500 MHz, DMSO-d$_6$)
δ 1.45(s,9H), 4.39(s,2H), 7.03(d,J=5.2 Hz,1H), 7.30(dd,J=7.6,4.9 Hz,1H), 7.37(d,J=8.2 Hz,2H), 7.81(d,J=8.2 Hz,2H), 7.87(s,1H), 7.98(dd,J=7.6,1.8 Hz,1H), 8.11(d,J=5.2 Hz,1H), 8.60(dd,J=4.9,1.8 Hz,1H), 9.67(s,1H), 10.66(s,1H)

2-(2-tert-Butoxycarbonylaminopyridin-4-ylmethylthio)-N-(4-tert-butylphenyl)pyridine-3-carboxamide (Compound No. 2-5)

$^1$H-NMR(500 MHz, DMSO-d$_6$)
δ 1.27(s,9H), 1.45(s,9H), 4.38(s,2H), 7.03(d,J=5.2 Hz,1H), 7.28(dd,J=7.6,4.9 Hz,1H), 7.36(d,J=8.8 Hz,2H), 7.60(d,J=8.8 Hz,2H), 7.87(s,1H), 7.94(dd,J=7.6,1.5 Hz,1H), 8.11(d,J=5.2 Hz,1H), 8.58(dd,J=4.9,1.5 Hz,1H), 9.67(s,1H), 10.39(s,1H)

2-(2-tert-Butoxycarbonylaminopyridin-4-ylmethylthio)-N-(1H-indazol-6-yl)pyridine-3-carboxamide (Compound No. 2-6)

$^1$H-NMR(500 MHz, DMSO-d$_6$)
δ 1.45(s,9H), 4.40(s,2H), 7.04(d,J=5.2 Hz,1H), 7.24(d,J=8.3 Hz,1H), 7.31(dd,J=7.6,4.9 Hz,1H), 7.69(d,J=8.3 Hz,1H), 7.87(s,1H), 7.97-8.00(m,2H), 8.11(d,J=5.2 Hz,1H), 8.21(s,1H), 8.60(dd,J=4.9,1.6 Hz,1H), 9.68(s,1H), 10.60(s,1H), 12.95(s,1H)

2-[2-(N-tert-Butoxycarbonyl-N-methylamino)pyridin-4-ylmethylthio]-N-(3,5-dimethylphenyl)pyridine-3-carboxamide (Compound No. 2-7)

$^1$H-NMR(500 MHz, DMSO-d$_6$)
δ 1.41(s,9H), 2.25(s,6H), 3.24(s,3H), 4.41(s,2H), 6.76(s,1H), 7.15(d,J=5.2 Hz,1H), 7.28(dd,J=7.6,4.9 Hz,1H), 7.31(s,2H), 7.64(s,1H), 7.93(dd,J=7.6,1.5 Hz,1H), 8.25(d,J=5.2 Hz,1H), 8.58(dd,J=4.9,1.5 Hz,1H), 10.29(s,1H)

2-[2-(N-tert-Butoxycarbonyl-N-methylamino)pyridin-4-ylmethylthio]-N-(indan-5-yl)pyridine-3-carboxamide (Compound No. 2-8)

$^1$H-NMR(500 MHz, DMSO-d$_6$)

δ 1.41(s,9H), 2.01(t,J=7.3 Hz,2H), 2.80-2.86(m,4H), 3.24(s,3H), 4.41(s,2H), 7.14-7.18(m,2H), 7.28(dd,J=7.6,4.9 Hz,1H), 7.38(d,J=8.6 Hz,1H), 7.61(s,1H), 7.64(s,1H), 7.92(dd,J=7.6,1.8 Hz,1H), 8.24(d,J=4.9 Hz,1H), 8.58(dd,J=4.9,1.8 Hz,1H), 10.33(s,1H)

2-[2-(N-tert-Butoxycarbonyl-N-methylamino)pyridin-4-ylmethylthio]-N-(4-trifluoromethoxyphenyl)pyridine-3-carboxamide (Compound No. 2-9)

$^1$H-NMR(500 MHz, DMSO-d$_6$)

δ 1.40(s,9H), 3.24(s,3H), 4.43(s,2H), 7.15(dd,J=5.2,1.5 Hz,1H), 7.31(dd,J=7.6, 4.9 Hz,1H), 7.37(d,J=8.6 Hz,2H), 7.63(s,1H), 7.80(d,J=9.2 Hz,2H), 7.99(dd,J=7.6,1.8 Hz,1H), 8.23(d,J=5.2 Hz,1H), 8.60(dd,J=4.9,1.8 Hz,1H), 10.65(s,1H)

2-(2-tert-Butoxycarbonylaminopyridin-4-ylmethylthio)-N-(4-chlorophenyl)pyridine-3-carboxamide (Compound No. 2-10)

$^1$H-NMR(500 MHz, DMSO-d$_6$)

δ 1.45(s,9H), 4.39(s,2H), 7.03(d,J=5.2 Hz,1H), 7.29(dd,J=7.6,4.9 Hz,1H), 7.41(d,J=8.9 Hz,2H), 7.72(d,J=8.9 Hz,2H), 7.87(s,1H), 7.98(dd,J=7.6,1.5 Hz,1H), 8.10(d,J=5.2 Hz,1H), 8.59(dd,J=4.9,1.5 Hz,1H), 9.66(s,1H), 10.60(s,1H)

2-[2-(N-tert-Butoxycarbonyl-N-ethylamino)pyridin-4-ylmethylthio]-N-(3,5-dimethylphenyl)pyridine-3-carboxamide (Compound No. 2-11)

$^1$H-NMR(400 MHz, CDCl$_3$)

δ 1.19(t,J=6.9 Hz,3H), 1.47(s,9H), 2.31(s,6H), 3.94(q,J=6.9 Hz,2H), 4.45(s,2H), 6.79(s,1H), 7.04(dd,J=5.1,1.4 Hz,1H), 7.14(dd,J=7.6,4.9 Hz,1H), 7.22(s,2H), 7.56(s,1H), 7.86(dd,J=7.6,1.8 Hz,1H), 7.97(s,1H), 8.25(d,J=5.1 Hz,1H), 8.55(dd,J=4.9,1.8 Hz,1H)

2-(2-tert-Butoxycarbonylaminopyridin-4-ylmethylthio)-N-(3-chlorophenyl)pyridine-3-carboxamide (Compound No. 2-12)

$^1$H-NMR(500 MHz, DMSO-d$_6$)

δ 1.45(s,9H), 4.39(s,2H), 7.03(d,J=5.2 Hz,1H), 7.19(d,J=8.2 Hz,1H), 7.30(dd,J=7.6,4.9 Hz,1H), 7.38(t,J=8.1 Hz,1H), 7.59(d,J=8.2 Hz,1H), 7.87(s,1H), 7.89(s,1H), 7.99(dd,J=7.6,1.8 Hz,1H), 8.11(d,J=5.2 Hz,1H), 8.60(dd,J=4.9, 1.8 Hz,1H), 9.67(s,1H), 10.64(s,1H)

2-(2-tert-Butoxycarbonylaminopyridin-4-ylmethylthio)-N-(isoquinolin-3-yl)pyridine-3-carboxamide (Compound No. 2-13)

$^1$H-NMR(400 MHz, DMSO-d$_6$)

δ 1.45(s,9H), 4.40(s,2H), 7.05(dd,J=5.2,1.5 Hz,1H), 7.28(dd,J=7.6,4.9 Hz,1H), 7.58(ddd,J=7.1,6.8,1.0 Hz,1H), 7.75(ddd,J=7.1,6.8,1.0 Hz,1H), 7.88(br s,1H), 7.98(d,J=7.1 Hz,1H), 8.06(dd,J=7.6,1.7 Hz,1H), 8.08(br s,1H), 8.11(d,J=5.2 Hz,1H), 8.59(dd,J=4.9,1.7 Hz,1H), 8.59(d,J=1.0 Hz,1H), 9.19(s,1H), 9.68(s,1H), 11.16(s,1H)

2-[2-(N-tert-Butoxycarbonyl-N-methylamino)pyridin-4-ylmethylthio]-N-(4-chlorophenyl)pyridine-3-carboxamide (Compound No. 2-14)

$^1$H-NMR(400 MHz, DMSO-d$_6$)

δ 1.40(s,9H), 3.24(s,3H), 4.42(s,2H), 7.15(dd,J=5.2,1.7 Hz,1H), 7.30(dd,J=7.6, 4.9 Hz,1H), 7.41(d,J=8.9 Hz,2H), 7.63(s,1H), 7.72(d,J=8.9 Hz,2H), 7.98(dd,J=7.6,1.7 Hz,1H), 8.24(d,J=5.2 Hz,1H), 8.60(dd,J=4.9,1.7 Hz,1H), 10.58(s,1H)

2-[2-(N-tert-Butoxycarbonyl-N-methylamino)pyridin-4-ylmethylthio]-N-(3-chlorophenyl)pyridine-3-carboxamide (Compound No. 2-15)

$^1$H-NMR(400 MHz, DMSO-d$_6$)

δ 1.40(s,9H), 3.24(s,3H), 4.43(s,2H), 7.16-7.18(m,2H), 7.31(dd,J=7.6,4.9 Hz,1H), 7.38(t,J=8.1 Hz,1H), 7.58(d,J=9.3 Hz,1H), 7.63(s,1H), 7.88(t,J=2.0 Hz,1H), 7.99(dd,J=7.6,1.7 Hz,1H), 8.24(dd,J=5.0,0.6 Hz,1H), 8.60(dd,J=4.9,1.7 Hz,1H), 10.63(s,1H)

2-[2-(N-tert-Butoxycarbonyl-N-methylamino)pyridin-4-ylmethylthio]-N-(4-tert-butylphenyl)pyridine-3-carboxamide (Compound No. 2-16)

$^1$H-NMR(400 MHz, DMSO-d$_6$)

δ 1.27(s,9H), 1.40(s,9H), 3.24(s,3H), 4.41(s,2H), 7.15(dd,J=5.2,1.6 Hz,1H), 7.29(dd,J=7.6,4.9 Hz,1H), 7.36(d,J=8.8 Hz,2H), 7.60(d,J=8.8 Hz,2H), 7.63(s,1H), 7.94(dd,J=7.6,1.7 Hz,1H), 8.24(d,J=5.1 Hz,1H), 8.58(dd,J=4.9,1.7 Hz,1H), 10.37(s,1H)

2-[2-(N-tert-Butoxycarbonyl-N-methylamino)pyridin-4-ylmethylthio]-N-(isoquinolin-3-yl)pyridine-3-carboxamide (Compound No. 2-17)

$^1$H-NMR(500 MHz, DMSO-d$_6$)

δ 1.39(s,9H), 3.24(s,3H), 4.43(s,2H), 7.16(dd,J=5.2,1.5 Hz,1H), 7.28(dd,J=7.6, 4.9 Hz,1H), 7.58(t,J=7.6 Hz,1H), 7.64(s,1H), 7.75(t,J=8.1 Hz,1H), 7.97(d,J=8.1 Hz,1H), 8.05-8.10(m,2H), 8.25(d,J=5.2 Hz,1H), 8.59-8.60(m,2H), 9.19(s,1H), 11.15(s,1H)

2-(2-tert-Butoxycarbonylaminopyridin-4-ylmethylthio)-N-[2-(4-methoxyphenyl)ethyl]pyridine-3-carboxamide (Compound No. 2-18)

$^1$H-NMR(500 MHz, DMSO-d$_6$)

δ 1.46(s,9H), 2.75(t,J=7.3 Hz,2H), 3.35-3.41(m,2H), 3.71(s,3H), 4.33(s,2H), 6.83(d,J=8.5 Hz,2H), 7.02(dd,J=4.9,1.2 Hz,1H), 7.15(d,J=8.5 Hz,2H), 7.21(dd,J=7.6,4.9 Hz,1H), 7.73(dd,J=7.6,1.7 Hz,1H), 7.87(br s,1H), 8.11(d,J=4.9 Hz,1H), 8.52(dd,J=4.9,1.7 Hz,1H), 8.58(t,J=5.4 Hz,1H), 9.68(s,1H)

N-(Adamantan-1-yl)-2-(2-tert-butoxycarbonylaminopyridin-4-ylmethylthio)pyridine-3-carboxamide (Compound No. 2-19)

$^1$H-NMR(400 MHz, DMSO-d$_6$)

δ 1.47(s,9H), 1.64(br s,6H), 2.03(br s,9H), 4.35(s,2H), 7.03(dd,J=5.4,1.5 Hz,1H), 7.17(dd,J=7.6,4.9 Hz,1H), 7.67(dd,J=7.6,1.7 Hz,1H), 7.85-7.92(m,2H), 8.11(d,J=5.4 Hz,1H), 8.48(dd,J=4.9,1.7 Hz,1H), 9.68(s,1H)

2-[2-(N-tert-Butoxycarbonyl-N-methylamino)pyridin-4-ylmethylthio]-N-(3,5-dimethylphenyl)-N-methylpyridine-3-carboxamide (Compound No. 2-20)

¹H-NMR(400 MHz, DMSO-d₆)
δ 1.44(s,9H), 2.04(s,6H), 3.25(s,3H), 3.32(s,3H), 4.43(s,2H), 6.73-6.78(m,3H), 6.98(m,1H), 7.10(d,J=5.1 Hz,1H), 7.41(m,1H), 7.67(s,1H), 8.25(d,J=5.1 Hz,1H), 8.33(m,1H)

N-(3,5-Dimethylphenyl)-2-(2-phthaloylaminopyridin-4-ylmethylthio)pyridine-3-carboxamide (Compound No. 2-21)

¹H-NMR(400 MHz, DMSO-d₆)
δ 2.25(s,6H), 4.50(s,2H), 6.76(s,1H), 7.29(dd,J=7.6,4.9 Hz,1H), 7.32(s,2H), 7.56(d,J=5.1 Hz,1H), 7.61(s,1H), 7.94-8.00(m,5H), 8.52(d,J=5.1 Hz,1H), 8.59(dd,J=4.9,1.7 Hz,1H), 10.32(s,1H)

N-(4-Chlorophenyl)-2-[2-(5-cyanothiazol-2-ylamino)pyridin-4-ylmethylthio]pyridine-3-carboxamide (Compound No. 2-22)

¹H-NMR(400 MHz, DMSO-d₆)
δ 4.43(s,2H), 7.11(d,J=5.1 Hz,1H), 7.21(s,1H), 7.31(dd,J=7.6,4.9 Hz,1H), 7.42(d,J=8.8 Hz,2H), 7.73(d,J=8.8 Hz,2H), 7.99(dd,J=7.6,1.7 Hz,1H), 8.25(s,1H), 8.28(d,J=5.1 Hz,1H), 8.60(dd,J=4.9,1.7 Hz,1H), 10.60(s,1H), 12.20(s,1H)

2-[2-(5-Cyanothiazol-2-ylamino)pyridin-4-ylmethylthio]-N-(4-trifluoromethoxyphenyl)pyridine-3-carboxamide (Compound No. 2-23)

¹H-NMR(400 MHz, DMSO-d₆)
δ 4.43(s,2H), 7.11(d,J=5.1 Hz,1H), 7.22(s,1H), 7.32(dd,J=7.6,4.9 Hz,1H), 7.38 (d,J=8.3 Hz,2H), 7.81(d,J=8.3 Hz,2H), 8.00(dd,J=7.6,1.7 Hz,1H), 8.25(s,1H), 8.28(d,J=5.1 Hz,1H), 8.61(dd,J=4.9,1.7 Hz,1H), 10.67(s,1H), 12.21(s,1H)

2-[2-(5-Cyanothiazol-2-ylamino)pyridin-4-ylmethylthio]-N-(3,5-dimethylphenyl)pyridine-3-carboxamide (Compound No. 2-24)

¹H-NMR(500 MHz, DMSO-d₆)
δ 2.25(s,6H), 4.42(s,2H), 6.76(s,1H), 7.11(d,J=5.2 Hz,1H), 7.21(s,1H), 7.29(dd,J=7.6,4.9 Hz,1H), 7.32(s,2H), 7.94(dd,J=7.6,1.5 Hz,1H), 8.25(s,1H), 8.28(d,J=5.2 Hz,1H), 8.58(dd,J=4.9,1.5 Hz,1H), 10.31(s,1H), 12.21(s,1H)

2-(2-tert-Butoxycarbonylaminopyridin-4-ylmethylthio)-N-(4-chlorophenyl)benzamide (Compound No. 2-25)

¹H-NMR(500 MHz, DMSO-d₆)
δ 1.45(s,9H), 4.22(s,2H), 6.99(d,J=5.2 Hz,1H), 7.30(t,J=7.6 Hz,1H), 7.40(d,J=8.6 Hz,2H), 7.42(t,J=7.6 Hz,1H), 7.48(d,J=7.6 Hz,1H), 7.52(d,J=7.6 Hz,1H), 7.75(d,J=8.6 Hz,2H), 7.83(s,1H), 8.11(d,J=5.2 Hz,1H), 9.68(s,1H), 10.48(s,1H)

2-(2-tert-Butoxycarbonylaminopyridin-4-ylmethylthio)-N-(4-tert-butylphenyl)benzamide (Compound No. 2-26)

¹H-NMR(500 MHz, DMSO-d₆)
δ 1.27(s,9H), 1.45(s,9H), 4.22(s,2H), 7.00(d,J=5.2 Hz,1H), 7.28(t,J=7.6 Hz,1H), 7.34(d,J=8.6 Hz,2H), 7.40(t,J=7.6 Hz,1H), 7.46(d,J=7.6 Hz,1H), 7.49(d,J=7.6 Hz,1H), 7.62(d,J=8.6 Hz,2H), 7.84(s,1H), 8.11(d,J=5.2 Hz,1H), 9.70(s,1H), 10.27(s,1H)

2-(2-tert-Butoxycarbonylaminopyridin-4-ylmethylthio)-N-(4-trifluoromethoxyphenyl)benzamide (Compound No. 2-27)

¹H-NMR(500 MHz, DMSO-d₆)
δ 1.45(s,9H), 4.23(s,2H), 6.99(d,J=5.2 Hz,1H), 7.30(t,J=7.6 Hz,1H), 7.35(d,J=8.6 Hz,2H), 7.43(t,J=7.6 Hz,1H), 7.49(d,J=7.6 Hz,1H), 7.53(d,J=7.6 Hz,1H), 7.83(d,J=8.6 Hz,2H), 7.84(s,1H), 8.11(d,J=5.2 Hz,1H), 9.68(s,1H), 10.55(s,1H)

2-(2-tert-Butoxycarbonylaminopyridin-4-ylmethylthio)-N-(isoquinolin-3-yl)benzamide (Compound No. 2-28)

¹H-NMR(400 MHz, DMSO-d₆)
δ 1.44(s,9H), 4.24(s,2H), 7.01(d,J=5.1 Hz,1H), 7.30(d,J=7.3 Hz,1H), 7.43(t,J=8.3 Hz,1H), 7.47(d,J=7.1 Hz,1H), 7.57(t,J=8.3 Hz,1H), 7.61(d,J=7.3 Hz,1H), 7.74(t,J=8.3 Hz,1H), 7.84(br s,1H), 7.97(d,J=8.3 Hz,1H), 8.08(d,J=8.3 Hz,1H), 8.11(d,J=5.1 Hz,1H), 8.60(s,1H), 9.18(s,1H), 9.71(s,1H), 10.96(s,1H)

2-(2-tert-Butoxycarbonylaminopyridin-4-ylmethylthio)-N-(3-isopropylphenyl)benzamide (Compound No. 2-29)

¹H-NMR(500 MHz, DMSO-d₆)
δ 1.20(d,J=6.7 Hz,6H), 1.45(s,9H), 2.86(m,1H), 4.23(s,2H), 6.98(d,J=7.6 Hz,1H), 7.01(d,J=5.2 Hz,1H), 7.24(t,J=7.6 Hz,1H), 7.28(t,J=7.6 Hz,1H), 7.41(t,J=7.6 Hz,1H), 7.46(d,J=7.6 Hz,1H), 7.50-7.55(m,2H), 7.62(br s,1H), 7.84(s,1H), 8.12(d,J=5.2 Hz,1H), 9.70(s,1H), 10.28(s,1H)

2-(2-tert-Butoxycarbonylaminopyridin-4-ylmethylthio)-N-(4-chloro-3-methylphenyl)benzamide (Compound No. 2-30)

¹H-NMR(500 MHz, DMSO-d₆)
δ 1.45(s,9H), 2.32(s,3H), 4.25(s,2H), 6.99(d,J=5.2 Hz,1H), 7.29(t,J=7.3 Hz,1H), 7.36(t,J=8.6 Hz,1H), 7.45(m,1H), 7.51(d,J=7.3 Hz,1H), 7.54(d,J=8.6 Hz,1H), 7.72-7.80(m,2H), 7.84(br s,1H), 8.11(d,J=5.2 Hz,1H), 9.70(s,1H), 10.41(s,1H)

2-(2-tert-Butoxycarbonylaminopyridin-4-ylmethylthio)-N-(1H-indazol-6-yl)benzamide (Compound No. 2-31)

¹H-NMR(500 MHz, DMSO-d₆)
δ 1.44(s,9H), 4.24(s,2H), 7.00(d,J=5.2 Hz,1H), 7.26(d,J=8.6 Hz,1H), 7.30(t,J=8.6 Hz,1H), 7.43(t,J=8.6 Hz,1H), 7.48(d,J=7.3 Hz,1H), 7.54(d,J=7.3 Hz,1H), 7.68(d,J=8.6 Hz,1H), 7.84(s,1H), 7.99(br s,1H), 8.11(d,J=5.2 Hz,1H), 8.25(s,1H), 9.69(s,1H), 10.49(s,1H), 12.93(s,1H)

2-(2-tert-Butoxycarbonylaminopyridin-4-ylmethylthio)-N-(3,5-dimethylphenyl)benzamide (Compound No. 2-32)

¹H-NMR(500 MHz, DMSO-d₆)
δ 1.45(s,9H), 2.25(s,6H), 4.22(s,2H), 6.74(s,1H), 7.00(dd,J=4.9 1.2 Hz,1H), 7.28(t,J=7.3 Hz,1H), 7.35(s,2H), 7.41(m,

1H), 7.45(s,1H), 7.48(t,J=7.3 Hz,1H), 7.84(s,1H), 8.12(d, J=4,9 Hz,1H), 9.69(s,1H), 10.18(s,1H)

3-(2-tert-Butoxycarbonylaminopyridin-4-ylmethylthio)-N-(3,5-dimethylphenyl)thiophene-2-carboxamide (Compound No. 2-33)

¹H-NMR(400 MHz, DMSO-d₆)
δ 1.45(s,9H), 2.25(s,6H), 4.26(s,2H), 6.74(s,1H), 6.95(d, J=5.1 Hz,1H), 7.24(s,2H), 7.24(d,J=5.1 Hz,1H), 7.82(s,1H), 7.83(s,1H), 8.11(d,J=5.1 Hz,1H), 9.71(s,1H), 9.82(s,1H)

2-(2-tert-Butoxycarbonylaminopyridin-4-ylmethylthio)-N-(3,5-dimethyl-4-hydroxyphenyl)pyridine-3-carboxamide (Compound No. 2-34)

¹H-NMR(400 MHz, DMSO-d₆)
δ 1.46(s,9H), 2.15(s,6H), 4.37(s,2H), 7.03(dd,J=5.0,1.3 Hz,1H), 7.23(s,2H), 7.26(dd,J=7.6,4.9 Hz,1H), 7.87(s,1H), 7.90(dd,J=7.6,1.6 Hz,1H), 8.10-8.12(m,2H), 8.56(dd,J=4.9, 1.6 Hz,1H), 9.68(s,1H), 10.09(s,1H)

2-(2-tert-Butoxycarbonylaminopyridin-4-ylmethylthio)-N-(3-chloro-4-trifluoromethoxyphenyl)pyridine-3-carboxamide (Compound No. 2-35)

¹H-NMR(500 MHz, DMSO-d₆)
δ 1.45(s,9H), 4.40(s,2H), 7.03(dd,J=5.2,1.5 Hz,1H), 7.32 (dd,J=7.6,4.9 Hz,1H), 7.58(dd,J=8.9,1.2 Hz,1H), 7.71(dd, J=8.9,2.4 Hz,1H), 7.87(s,1H), 8.01(dd,J=7.6,1.8 Hz,1H), 8.08(d,J=2.4 Hz,1H), 8.10(d,J=5.2 Hz,1H), 8.61(dd,J=4.9, 1.8 Hz,1H), 9.67(s,1H), 10.81(s,1H)

2-(2-tert-Butoxycarbonylaminopyridin-4-ylmethylthio)-N-(3-trifluoromethylphenyl)pyridine-3-carboxamide (Compound No. 2-36)

¹H-NMR(500 MHz, DMSO-d₆)
δ 1.45(s,9H), 4.40(s,2H), 7.04(d,J=5.2 Hz,1H), 7.32(dd, J=7.6,4.9 Hz,1H), 7.48(d,J=7.9 Hz,1H), 7.60(t,J=7.9 Hz,1H), 7.88(s,1H), 7.91(d,J=7.9 Hz,1H), 8.03(dd,J=7.6,1.8 Hz,1H), 8.11(d,J=5.2 Hz,1H), 8.18(s,1H), 8.61(dd,J=4.9,1.8 Hz,1H), 9.67(s,1H), 10.79(s,1H)

Example 3

2-(2-Aminopyridin-4-ylmethylthio)-N-(3,5-dimethylphenyl)pyridine-3-carboxamide monohydrochloride (Compound No. 3-1)

A solution of 4 N hydrochloric acid in 1,4-dioxane (5.0 mL) was added to a solution of 2-(2-tert-butoxycarbonylaminopyridin-4-ylmethylthio)-N-(3,5-dimethylphenyl)pyridine-3-carboxamide (Compound No. 2-1, 420 mg, 0.90 mmol) in 1,4-dioxane (5.0 mL) at room temperature, and the mixture was stirred for 12 hours. Ethanol (6.0 mL) was added to the reaction mixture, and the precipitated solid was filtered off. The solid was dried under reduced pressure at 60° C. to give 320 mg of the target compound as a colorless crystal. (Yield 88%)

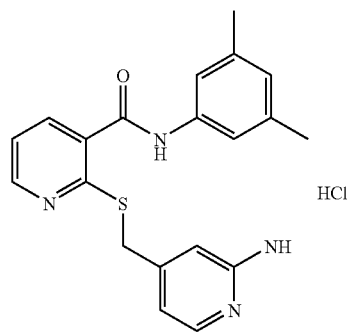

Or as described below, a free base of Compound No. 3-1 was synthesized.

N-(3,5-Dimethylphenyl)-2-thioxo-1,2-dihydropyridine-3-carboxamide (Reference compound No. 10-1, 100 g, 0.39 mol) and 2-amino-4-bromomethylpyridine hydrobromide (Reference compound No. 14-1, 110 g, 0.40 mol) were dissolved in N,N-dimethylformamide (840 mL) under ice-cooling, then triethylamine (160 mL, 1.2 mol) was added dropwise thereto, and the mixture was stirred for 6 hours at room temperature. The reaction mixture was poured into water (2.5 L), and then the precipitated solid was filtered off and dried under reduced pressure at 45° C. to give 140 g of the free base of the target compound quantitatively as a pale yellow solid.

¹H-NMR(500 MHz, DMSO-d₆)
δ 2.26(s,6H), 4.44(s,2H), 6.77(s,1H), 6.89(d,J=6.7 Hz,1H), 7.03(s,1H), 7.32(dd,J=7.6, 4.9 Hz,1H), 7.34(s,2H), 7.84(d,J=6.7 Hz,1H), 7.97(br s,2H), 8.00(dd,J=7.6, 1.8 Hz,1H), 8.56(dd,J=4.9,1.8 Hz,1H), 10.35(s,1H), 13.40(br s,1H)

As described below, Compounds (No. 3-2~37) were obtained using the corresponding compounds selected from Reference compounds (No. 2-1~36), commercially available compounds or known compounds according to the synthetic method of Compound (No. 3-1).

2-(2-Aminopyridin-4-ylmethylthio)-N-(3-isopropylphenyl)pyridine-3-carboxamide monohydrochloride (Compound No. 3-2)

¹H-NMR(500 MHz, DMSO-d₆)
δ 1.21(d,J=6.7 Hz,6H), 2.87(m,1H), 4.41(s,2H), 6.89(d, J=6.7 Hz,1H), 7.00-7.03(m,2H), 7.27(m,1H), 7.32(dd,J=7.6, 4.9 Hz,1H), 7.53(d,J=7.3 Hz,1H), 7.60(s,1H), 7.84(d,J=6.7 Hz,1H), 7.95(s,2H), 8.04(d,J=7.6 Hz,1H), 8.56(d,J=4.9 Hz,1H), 10.44(s,1H), 13.33(br s,1H)

2-(2-Aminopyridin-4-ylmethylthio)-N-(indan-5-yl)pyridine-3-carboxamide monohydrochloride (Compound No. 3-3)

¹H-NMR(500 MHz, DMSO-d₆)
δ 1.91-2.05(m,2H), 2.81-2.90(m,4H), 4.40(s,2H), 6.89(m, 1H), 7.03(s,1H), 7.19(d,J=7.6 Hz,1H), 7.31(dd,J=7.6,4.9 Hz,1H), 7.41(d,J=7.6 Hz,1H), 7.63(s,1H), 7.84(d,J=6.7 Hz,1H), 8.00-8.05(m,3H), 8.56(dd,J=4.9,1.5 Hz,1H), 10.40 (s,1H), 13.50(br s,1H)

2-(2-Aminopyridin-4-ylmethylthio)-N-(4-tert-butylphenyl)pyridine-3-carboxamide monohydrochloride (Compound No. 3-4)

¹H-NMR(500 MHz, DMSO-d₆)
δ 1.28(s,9H), 4.40(s,2H), 6.89(dd,J=7.7,1.5 Hz,1H), 7.03 (s,1H), 7.32(dd,J=7.7,4.9 Hz,1H), 7.37(d,J=8.8 Hz,2H), 7.62

(d,J=8.8 Hz,2H), 7.84(d,J=6.4 Hz,1H), 7.97(s,2H), 8.02(dd, J=7.7,1.5 Hz,1H), 8.56(dd,J=4.9,1.5 Hz,1H), 10.44(s,1H), 13.42(br s,1H)

2-(2-Aminopyridin-4-ylmethylthio)-N-(1H-indazol-6-yl)pyridine-3-carboxamide monohydrochloride (Compound No. 3-5)

¹H-NMR(500 MHz, DMSO-d₆)

δ 4.42(s,2H), 6.39(br s,1H), 6.89(d,J=6.4 Hz,1H), 7.06(s,1H), 7.29-7.36(m,2H), 7.70(d,J=8.5 Hz,1H), 7.85(d,J=6.4 Hz,1H), 8.02(s,1H), 8.02-8.16(m,3H), 8.23(s,1H), 8.58(dd, J=4.9,1.5 Hz,1H), 10.70(s,1H), 13.71(br s,1H)

N-(3,5-Dimethylphenyl)-2-(2-methylaminopyridin-4-ylmethylthio)pyridine-3-carboxamide monohydrochloride (Compound No. 3-6)

¹H-NMR(500 MHz, DMSO-d₆)

δ 2.26(s,6H), 2.91(d,J=4.9 Hz,3H), 4.41(s,2H), 5.98(br s,1H), 6.77(s,1H), 6.87(dd,J=7.7,1.5 Hz,1H), 7.10(s,1H), 7.31(dd,J=7.6,4.9 Hz,1H), 7.35(s,2H), 7.81(d,J=7.7 Hz,1H), 8.00(dd,J=7.6,1.5 Hz,1H), 8.57(dd,J=4.9,1.5 Hz,1H), 10.39(s,1H), 13.48(br s,1H)

N-(Indan-5-yl)-2-(2-methylaminopyridin-4-ylmethylthio)pyridine-3-carboxamide monohydrochloride (Compound No. 3-7)

¹H-NMR(400 MHz, DMSO-d₆)

δ 1.98-2.06(m,2H), 2.81-2.87(m,4H), 2.91(d,J=4.9 Hz,3H), 4.40(s,2H), 6.87(dd, J=6.8,1.5 Hz,1H), 7.10(s,1H), 7.18(d,J=8.3 Hz,1H), 7.31(dd,J=7.6,4.9 Hz,1H), 7.42(d,J=8.8 Hz,1H), 7.63(s,1H), 7.80(d,J=6.6 Hz,1H), 8.01(dd,J=7.6,1.7 Hz,1H), 8.57(dd,J=4.9,1.7 Hz,1H), 8.97(br s,1H), 10.44(s,1H), 13.43(br s,1H)

2-(2-Methylaminopyridin-4-ylmethylthio)-N-(4-trifluoromethoxyphenyl)pyridine-3-carboxamide monohydrochloride (Compound No. 3-8)

¹H-NMR(500 MHz, DMSO-d₆)

δ 2.91(d,J=4.9 Hz,3H), 4.42(s,2H), 6.87(dd,J=6.7,1.5 Hz,1H), 7.09(s,1H), 7.33(dd,J=7.6,4.9 Hz,1H), 7.38(d,J=8.2 Hz,2H), 7.80-7.85(m,3H), 8.07(dd,J=7.6,1.8 Hz,1H), 8.59(dd,J=4.9,1.8 Hz,1H), 8.90(br s,1H), 10.77(s,1H), 13.32(br s,1H)

2-(2-Aminopyridin-4-ylmethylthio)-N-(4-chlorophenyl)pyridine-3-carboxamide monohydrochloride (Compound No. 3-9)

¹H-NMR(500 MHz, DMSO-d₆)

δ 4.41(s,2H), 6.89(d,J=6.4 Hz,1H), 7.03(s,1H), 7.33(dd,J=7.6,4.9 Hz,1H), 7.43(d,J=8.6 Hz,2H), 7.75(d,J=8.6 Hz,2H), 7.84(d,J=6.4 Hz,1H), 7.96(s,2H), 8.06(dd,J=7.6,1.5 Hz,1H), 8.57(dd,J=4.9,1.5 Hz,1H), 10.66(s,1H), 13.40(br s,1H)

2-(2-Aminopyridin-4-ylmethylthio)-N-(4-trifluoromethoxyphenyl)pyridine-3-carboxamide (Compound No. 3-10)

¹H-NMR(500 MHz, DMSO-d₆)

δ 4.25(s,2H), 5.83(s,2H), 6.45(s,1H), 6.48(dd,J=5.2,1.3 Hz,1H), 7.30(dd,J=7.8,4.8 Hz,1H), 7.37(d,J=8.2 Hz,2H), 7.77(dd,J=5.2 Hz,1H), 7.81(d,J=8.2 Hz,2H), 7.97(d,J=7.8, 1.8 Hz,1H), 8.60(dd,J=4.8,1.8 Hz,1H), 10.67(s,1H)

2-(2-Aminopyridin-4-ylmethylthio)-N-(3-chlorophenyl)pyridine-3-carboxamide monohydrochloride (Compound No. 3-11)

¹H-NMR(400 MHz, DMSO-d₆)

δ 4.41(s,2H), 6.88(d,J=6.6 Hz,1H), 7.05(s,1H), 7.19(d, J=8.1 Hz,1H), 7.33(dd,J=7.6,4.9 Hz,1H), 7.40(t,J=8.1 Hz,1H), 7.64(d,J=8.1 Hz,1H), 7.85(d,J=6.6 Hz,1H), 7.93(s,1H), 8.04 (br s, 2H), 8.08(dd,J=7.6,1.7 Hz,1H), 8.58(dd,J=4.9,1.7 Hz,1H), 10.78(s,1H), 13.64(br s,1H)

N-(3,5-Dimethylphenyl)-2-(2-ethylaminopyridin-4-ylmethylthio)pyridine-3-carboxamide (Compound No. 3-12)

¹H-NMR(400 MHz, DMSO-d₆)

δ 1.08(t,J=7.2 Hz,3H), 2.25(s,6H), 3.15-3.22(m,2H), 4.24 (s,2H), 6.39(t,J=5.5 Hz,1H), 6.42-6.46(m,2H), 6.76(s,1H), 7.27(dd,J=7.4,4.8 Hz,1H), 7.32(s,2H), 7.83(d,J=5.4 Hz,1H), 7.90(dd,J=7.4,1.5 Hz,1H), 8.57(dd,J=4.8,1.5 Hz,1H), 10.30 (s,1H)

2-(2-Aminopyridin-4-ylmethylthio)-N-(isoquinolin-3-yl)pyridine-3-carboxamide (Compound No. 3-13)

¹H-NMR(500 MHz, DMSO-d₆)

δ 4.25(s,2H), 5.83(s,2H), 6.46(s,1H), 6.49(dd,J=5.2,1.5 Hz,1H), 7.28(dd,J=7.6, 4.9 Hz,1H), 7.58(ddd,J=7.9,7.9,1.2 Hz,1H), 7.75(ddd,J=7.9,7.9,1.2 Hz,1H), 7.78(d,J=5.2 Hz,1H), 7.98(d,J=7.9 Hz,1H), 8.04(dd,J=7.6,1.8 Hz,1H), 8.09(d,J=7.9 Hz,1H), 8.59(dd,J=5.2,1.5 Hz,1H), 8.59(br s,1H), 9.19(br s,1H), 11.15(s,1H)

N-(4-Chlorophenyl)-2-(2-methylaminopyridin-4-ylmethylthio)pyridine-3-carboxamide (Compound No. 3-14)

¹H-NMR(400 MHz, DMSO-d₆)

δ 2.71(d,J=4.9 Hz,3H), 4.26(s,2H), 6.46-6.49(m,3H), 7.29 (dd,J=7.6,4.9 Hz,1H), 7.41(dd,J=6.7,2.1 Hz,2H), 7.73(d, J=8.8 Hz,2H), 7.85(d,J=5.1 Hz,1H), 7.96(dd,J=7.6,1.7 Hz,1H), 8.59(dd,J=4.9,1.7 Hz,1H), 10.60(s,1H)

N-(3-Chlorophenyl)-2-(2-methylaminopyridin-4-ylmethylthio)pyridine-3-carboxamide (Compound No. 3-15)

¹H-NMR(400 MHz, DMSO-d₆)

δ 2.71(d,J=4.9 Hz,3H), 4.26(s,2H), 6.42-6.49(m,3H), 7.18 (ddd,J=8.1,2.0,0.9 Hz,1H), 7.30(dd,J=7.6,4.9 Hz,1H), 7.39(t, J=8.1 Hz,1H), 7.58(d,J=8.1 Hz,1H), 7.85(d,J=5.1 Hz,1H), 7.89(t,J=2.0 Hz,1H), 7.97(dd,J=7.6,1.7 Hz,1H), 8.60(dd, J=4.9,1.7 Hz,1H), 10.65(s,1H)

N-(4-tert-Butylphenyl)-2-(2-methylaminopyridin-4-ylmethylthio)pyridine-3-carboxamide (Compound No. 3-16)

¹H-NMR(400 MHz, DMSO-d₆)

δ 1.27(s,9H), 2.71(d,J=4.9 Hz,3H), 4.25(s,2H), 6.40-6.49 (m,3H), 7.28(dd,J=7.6,4.9 Hz,1H), 7.36(d,J=8.8 Hz, 2H), 7.60(d,J=8.8 Hz,2H), 7.85(d,J=4.9 Hz,1H), 7.92(dd,J=7.6, 1.7 Hz,1H), 8.58(dd,J=4.9,1.7 Hz,1H), 10.39(s,1H)

N-(Isoquinolin-3-yl)-2-(2-methylaminopyridin-4-ylmethylthio)pyridine-3-carboxamide (Compound No. 3-17)

$^1$H-NMR(400 MHz, DMSO-d$_6$)

δ 2.71(d,J=4.9 Hz,3H), 4.27(s,2H), 6.39-6.50(m,3H), 7.27(dd,J=7.6,4.8 Hz,1H), 7.58(m,1H), 7.75(m,1H), 7.85(d,J=5.4 Hz,1H), 7.98(d,J=8.1 Hz,1H), 8.04(dd,J=7.6,1.7 Hz,1H), 8.09(d,J=8.3 Hz,1H), 8.58-8.60(m,2H), 9.19(s,1H), 11.16(s,1H)

N-(Adamantan-1-yl)-2-(2-aminopyridin-4-ylmethylthio)pyridine-3-carboxamide monohydrochloride (Compound No. 3-18)

$^1$H-NMR(400 MHz, DMSO-d$_6$)

δ 1.65(br s,6H), 2.04(br s,9H), 4.36(s,2H), 6.87(d,J=6.7 Hz,1H), 6.99(s,1H), 7.21(dd,J=7.6,4.9 Hz,1H), 7.74(dd,J=7.6,1.2 Hz,1H), 7.84(d,J=6.7 Hz,1H), 7.87(br s,2H), 7.92(s,1H), 8.47(dd,J=4.9,1.2 Hz,1H), 13.34(s,1H)

N-(3,5-Dimethylphenyl)-2-[2-(piperazin-1-yl)pyridin-4-ylmethylthio]pyridine-3-carboxamide dihydrochloride (Compound No. 3-19)

$^1$H-NMR(400 MHz, DMSO-d$_6$)

δ 2.25(s,6H), 3.50-4.30(m,8H), 4.39(s,2H), 6.76(s,1H), 6.92(s,1H), 7.23(s,1H), 7.30(dd,J=7.7,4.8 Hz,1H), 7.33(s,2H), 7.41(s,1H), 7.98(d,J=5.8 Hz,1H), 8.02(d,J=5.8 Hz,1H), 8.60(dd,J=4.8,1.8 Hz,1H), 9.20(s,2H), 10.35(s,1H)

2-(2-Aminopyridin-4-ylmethylthio)-N-(3,5-dimethylphenyl)benzamide monohydrochloride (Compound No. 3-20)

$^1$H-NMR(400 MHz, DMSO-d$_6$)

δ 2.26(s,6H), 4.25(s,2H), 6.75(s,1H), 6.82(m,1H), 6.85(s,1H), 7.28-7.35(m,3H), 7.40-7.45(m,2H), 7.52(d,J=7.3 Hz,1H), 7.84(d,J=6.6 Hz,1H), 7.95(br s,2H), 10.21(s,1H), 13.43(br s,1H)

2-(2-Aminopyridin-4-ylmethylthio)-N-(4-chlorophenyl)benzamide monohydrochloride (Compound No. 3-21)

$^1$H-NMR(500 MHz, DMSO-d$_6$)

δ 4.25(s,2H), 6.81(dd,J=6.7,1.5 Hz,1H), 6.85(s,1H), 7.35(t,J=8.6 Hz,1H), 7.41(d,J=8.6 Hz,2H), 7.45(t,J=8.6 Hz,1H), 7.46(d,J=1.5 Hz,1H), 7.56(d,J=8.6 Hz,1H), 7.75(d,J=8.6 Hz,2H), 7.83(d,J=6.7 Hz,1H), 7.92(br s,2H), 10.51(s,1H), 13.33(br s,1H)

2-(2-Aminopyridin-4-ylmethylthio)-N-(4-tert-butylphenyl)benzamide monohydrochloride (Compound No. 3-22)

$^1$H-NMR(400 MHz, DMSO-d$_6$)

δ 1.28(s,9H), 4.25(s,2H), 6.82(d,J=6.6 Hz,1H), 6.84(s,1H), 7.33(t,J=6.6 Hz,1H), 7.35(d,J=8.8 Hz,2H), 7.40-7.47(m,2H), 7.53(d,J=6.6 Hz,1H), 7.63(d,J=8.8 Hz,2H), 7.83(d,J=6.6 Hz,1H), 7.90(br s,2H), 10.29(s,1H), 13.36(br s,1H)

2-(2-Aminopyridin-4-ylmethylthio)-N-(4-trifluoromethoxyphenyl)benzamide monohydrochloride (Compound No. 3-23)

$^1$H-NMR(400 MHz, DMSO-d$_6$)

δ 4.25(s,2H), 6.81(d,J=6.7 Hz,1H), 6.84(s,1H), 7.35(m,1H), 7.37(d,J=8.9 Hz,2H), 7.43-7.49(m,2H), 7.57(d,J=6.7 Hz,1H), 7.83(s,1H), 7.83(d,J=8.9 Hz,2H), 7.88 (br s, 2H), 10.57(s,1H), 13.41(br s,1H)

2-(2-Aminopyridin-4-ylmethylthio)-N-(isoquinolin-3-yl)benzamide monohydrochloride (Compound No. 3-24)

$^1$H-NMR(400 MHz, DMSO-d$_6$)

δ 4.27(s,2H), 6.83(d,J=6.7 Hz,1H), 6.87(s,1H), 7.35(m,1H), 7.44-7.46(m,2H), 7.58(d,J=8.2 Hz,1H), 7.64(d,J=7.0 Hz,1H), 7.76(t,J=7.0 Hz,1H), 7.84(d,J=6.7 Hz,1H), 7.97(d,J=8.2 Hz,1H), 8.00(br s,2H), 8.09(d,J=8.2 Hz,1H), 8.59(s,1H), 9.20(s,1H), 10.99(s,1H), 13.51(br s,1H)

2-(2-Aminopyridin-4-ylmethylthio)-N-(3-isopropylphenyl)benzamide (Compound No. 3-25)

$^1$H-NMR(500 MHz, DMSO-d$_6$)

δ 1.20(d,J=7.0 Hz,6H), 2.86(m,1H), 4.06(s,2H), 5.86(s,2H), 6.43(s,1H), 6.49(d,J=5.2 Hz,1H), 6.98(d,J=7.6 Hz,1H), 7.24(t,J=7.6 Hz,1H), 7.28(d,J=8.2 Hz,1H), 7.42(t,J=8.2 Hz,1H), 7.43(d,J=7.6 Hz,1H), 7.51(d,J=7.6 Hz,1H), 7.54(d,J=8.2 Hz,1H), 7.64(br s,1H), 7.79(d,J=5.2 Hz,1H), 10.28(s,1H)

2-(2-Aminopyridin-4-ylmethylthio)-N-(4-chloro-3-methylphenyl)benzamide (Compound No. 3-26)

$^1$H-NMR(500 MHz, DMSO-d$_6$)

δ 2.32(s,3H), 4.06(s,2H), 5.87(s,2H), 6.42(s,1H), 6.48(d,J=5.2 Hz,1H), 7.28(t,J=7.6 Hz,1H), 7.37(d,J=8.6 Hz,1H), 7.43(t,J=7.6 Hz,1H), 7.44(d,J=7.6 Hz,1H), 7.51(d,J=7.6 Hz,1H), 7.55(d,J=8.6 Hz,1H), 7.75(br s,1H), 7.79(d,J=5.2 Hz, 1H), 10.42(s,1H)

2-(2-Aminopyridin-4-ylmethylthio)-N-(1H-indazol-6-yl)benzamide (Compound No. 3-27)

$^1$H-NMR(500 MHz, DMSO-d$_6$)

δ 4.08(s,2H), 5.86(s,2H), 6.43(s,1H), 6.49(d,J=5.2 Hz,1H), 7.26(d,J=8.6 Hz,1H), 7.30(t,J=7.3 Hz,1H), 7.43(t,J=7.6 Hz,1H), 7.46(d,J=7.6 Hz,1H), 7.54(d,J=7.6 Hz,1H), 7.68(d,J=8.6 Hz,1H), 7.85(d,J=5.2 Hz,1H), 7.99(br s,1H), 8.26(br s,1H), 10.50(s,1H), 12.93(s,1H)

3-(2-Aminopyridin-4-ylmethylthio)-N-(3,5-dimethylphenyl)thiophene-2-carboxamide (Compound No. 3-28)

$^1$H-NMR(400 MHz, DMSO-d$_6$)

δ 2.25(s,6H), 4.10(s,2H), 5.88(s,2H), 6.40(s,1H), 6.46(d,J=5.1 Hz,1H), 6.74(s,1H), 7.20(d,J=5.1 Hz,1H), 7.26(s,2H), 7.79(d,J=5.1 Hz,1H), 7.82(d,J=5.1 Hz,1H), 9.83(s,1H)

2-(3-Aminopyridin-4-ylmethylthio)-N-(3,5-dimethylphenyl)pyridine-3-carboxamide (Compound No. 3-29)

$^1$H-NMR(500 MHz, CDCl$_3$)
δ 2.30(s,6H), 4.15-4.60(br s,2H), 4.38(s,2H), 6.81(s,1H), 7.09(d,J=4.9 Hz,1H), 7.13(dd,J=7.6,4.9 Hz,1H), 7.24(s,2H), 7.86-7.88(m,2H), 7.97(s,1H), 8.13(s,1H), 8.53(dd,J=4.9,1.8 Hz,1H)

2-(2-Aminopyridin-4-ylmethylthio)-N-(3,5-dimethyl-4-hydroxyphenyl)pyridine-3-carboxamide (Compound No. 3-30)

$^1$H-NMR(500 MHz, DMSO-d$_6$)
δ 2.15(s,6H), 4.23(s,2H), 5.85(s,2H), 6.45(s,1H), 6.48(dd,J=5.2,1.2 Hz,1H), 7.23-7.27(m,3H), 7.77(d,J=5.2 Hz,1H), 7.88(dd,J=7.6,1.5 Hz,1H), 8.09(s,1H), 8.55(dd,J=4.9,1.5 Hz,1H), 10.09(s,1H)

2-(2-Aminopyridin-4-ylmethylthio)-N-(4-difluoromethoxyphenyl)pyridine-3-carboxamide (Compound No. 3-31)

$^1$H-NMR(500 MHz, DMSO-d$_6$)
δ 4.24(s,2H), 5.83(s,2H), 6.45(d,J=0.6 Hz,1H), 6.48(dd,J=5.2,1.5 Hz,1H), 7.18(d,J=8.8 Hz,2H), 7.18(t,J=74.1 Hz,1H), 7.29(dd,J=7.6,4.8 Hz,1H), 7.73(d,J=8.8 Hz,2H), 7.77(dd,J=5.2,0.6 Hz,1H), 7.96(dd,J=7.6,1.7 Hz,1H), 8.59(dd,J=4.8,1.7 Hz,1H), 10.55(s,1H)

2-(2-Aminopyridin-4-ylmethylthio)-N-(4-tert-butylphenyl)pyridine-3-carboxamide (Compound No. 3-32)

$^1$H-NMR(400 MHz, DMSO-d$_6$)
δ 1.27(s,9H), 4.24(s,2H), 5.83(s,2H), 6.45(s,1H), 6.48(dd,J=5.2,1.5 Hz,1H), 7.28(dd,J=7.6,4.9 Hz,1H), 7.36(d,J=8.5 Hz,2H), 7.61(d,J=8.5 Hz,2H), 7.77(d,J=5.2 Hz,1H), 7.92(dd,J=7.6,1.7 Hz,1H), 8.58(dd,J=4.9,1.7 Hz,1H), 10.40(s,1H)

2-(2-Aminopyridin-4-ylmethylthio)-N-(3-methylphenyl)pyridine-3-carboxamide (Compound No. 3-33)

$^1$H-NMR(400 MHz, DMSO-d$_6$)
δ 2.30(s,3H), 4.24(s,2H), 5.84(s,2H), 6.45(s,1H), 6.48(dd,J=5.2,1.6 Hz,1H), 6.93(d,J=7.8 Hz,1H), 7.22(t,J=7.8 Hz,1H), 7.28(dd,J=7.6,4.9 Hz,1H), 7.46(d,J=7.8 Hz,1H), 7.56(s,1H), 7.77(d,J=5.2 Hz,1H), 7.93(dd,J=7.6,1.7 Hz,1H), 8.58(dd,J=4.9,1.7 Hz,1H), 10.39(s,1H)

2-(2-Aminopyridin-4-ylmethylthio)-N-(4-trifluoromethylphenyl)pyridine-3-carboxamide (Compound No. 3-34)

$^1$H-NMR(400 MHz, DMSO-d$_6$)
δ 4.25(s,2H), 5.84(s,2H), 6.45(s,1H), 6.48(dd,J=5.4,1.5 Hz,1H), 7.31(dd,J=7.6,4.9 Hz,1H), 7.73(d,J=8.3 Hz,2H), 7.77(d,J=5.4 Hz,1H), 7.92(d,J=8.3 Hz,2H), 8.00(dd,J=7.6,1.7 Hz,1H), 8.61(dd,J=4.9,1.7 Hz,1H), 10.83(s,1H)

2-(2-Aminopyridin-4-ylmethylthio)-N-(3-chloro-4-trifluoromethoxyphenyl)pyridine-3-carboxamide (Compound No. 3-35)

$^1$H-NMR(500 MHz, DMSO-d$_6$)
δ 4.25(s,2H), 5.83(s,2H), 6.45(s,1H), 6.48(dd,J=5.1 Hz,1H), 7.31(dd,J=7.6,4.9 Hz,1H), 7.59(d,J=8.9 Hz,1H), 7.72(dd,J=8.9,2.4 Hz,1H), 7.77(d,J=5.1 Hz,1H), 8.00(dd,J=7.6,1.8 Hz,1H), 8.09(d,J=2.4 Hz,1H), 8.61(dd,J=4.9,1.8 Hz,1H), 10.82(s,1H)

2-(2-Aminopyridin-4-ylmethylthio)-N-(3-trifluoromethylphenyl)pyridine-3-carboxamide (Compound No. 3-36)

$^1$H-NMR(400 MHz, DMSO-d$_6$)
δ 4.25(s,2H), 5.84(s,2H), 6.45(s,1H), 6.48(d,J=5.1 Hz,1H), 7.31(dd,J=7.6,4.9 Hz,1H), 7.48(d,J=7.1 Hz,1H), 7.61(dd,J=8.1,7.1 Hz,1H), 7.77(d,J=5.1 Hz,1H), 7.91(d,J=8.1 Hz,1H), 8.02(dd,J=7.6,1.7 Hz,1H), 8.19(s,1H), 8.61(dd,J=4.9,1.7 Hz,1H), 10.80(s,1H)

2-(2-Aminopyridin-4-ylmethylthio)-N-(3-isopropylphenyl)pyridine-3-carboxamide (Compound No. 3-37)

$^1$H-NMR(500 MHz, DMSO-d$_6$)
δ 1.20(d,J=7.0 Hz,6H), 2.87(m,1H), 4.24(s,2H), 5.83(s,2H), 6.45(br s,1H), 6.48(d,J=5.2 Hz,1H), 7.00(d,J=7.6 Hz,1H), 7.26(t,J=7.6 Hz,1H), 7.28(dd,J=7.6,4.9 Hz,1H), 7.52(d,J=7.6 Hz,1H), 7.60(s,1H), 7.77(d,J=5.2 Hz,1H), 7.94(dd,J=7.6,1.5 Hz,1H), 8.58(dd,J=4.9,1.5 Hz,1H), 10.40(s,1H)

Example 4

2-(2-Acetylaminopyridin-4-ylmethylthio)-N-(3,5-dimethylphenyl)pyridine-3-carboxamide (Compound No. 4-1)

Acetic anhydride (1.0 mL, 10 mmol) was added to a solution of 2-(2-aminopyridin-4-ylmethylthio)-N-(3,5-dimethylphenyl)pyridine-3-carboxamide monohydrochloride (Compound No. 3-1, 1.0 g, 2.5 mmol) in pyridine (10 mL) at room temperature, and the mixture was stirred for 4 hours. Ethyl acetate (30 mL) was added to the reaction mixture, then the whole was washed with water (20 mL) and brine (20 mL), and then the organic layer was dried over anhydrous magnesium sulfate. The organic layer was evaporated under reduced pressure, and the resulting solid was filtered off with hexane/ethyl acetate(1:1) to give 770 mg of the target compound as a colorless crystal(Yield 76%).

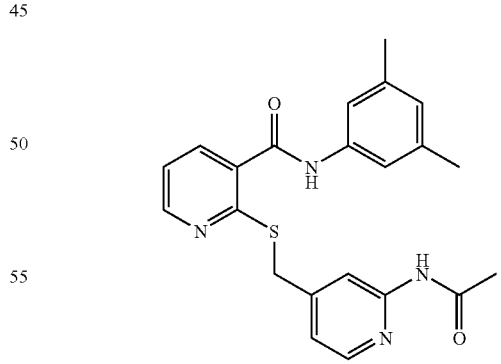

Or the compound is also synthesized in the following method. N-(3,5-Dimethylphenyl)-2-thioxo-1,2-dihydropyridine-3-carboxamide (Reference compound No. 10-1, 200 mg, 0.77 mmol) and 2-acetylamino-4-methanesulfonyloxymethylpyridine (Reference compound No. 13-1, 190 mg, 0.77 mmol) were suspended in N,N-dimethylformamide (2.0 mL) under ice-cooling and under nitrogen atmosphere, then triethylamine (0.22 mL, 1.5 mmol) was added thereto, and then the mixture was stirred for 2 hours at room temperature. Ethyl acetate (40 mL) was added to the reaction mixture, and then the whole was washed with water (30 mL) and brine (20 mL). The organic layer was dried over anhydrous magnesium sulfate, and the solvent was evaporated under reduced pressure. The resulting solid was filtered off with the solvent mixture consisting of diisopropyl ether and ethyl acetate and dried under reduced pressure at 40° C. to give 250 mg of the target compound as a pale yellow solid. (Yield 81%)

$^1$H-NMR(500 MHz, DMSO-$d_6$)

δ 2.05(s,3H), 2.25(s,6H), 4.39(s,2H), 6.76(s,1H), 7.09(dd, J=5.2,1.5 Hz,1H), 7.28(m,1H), 7.32(s,2H), 7.92(dd,J=7.6,1.8 Hz,1H), 8.15-8.18(m,2H), 8.57(dd,J=5.2, 1.5 Hz,1H), 10.29 (s,1H), 10.40(s,1H)

As described below, Compounds (No. 4-2~68) were obtained using the corresponding compounds selected from Compounds (No. 3~37), commercially available compounds or known compounds according to the synthetic method of Compound (No. 4-1).

N-(3,5-Dimethylphenyl)-2-(2-propionylaminopyridin-4-ylmethylthio)pyridine-3-carboxamide (Compound No. 4-2)

$^1$H-NMR(500 MHz, DMSO-$d_6$)

δ 1.05(t,J=7.3 Hz,3H), 2.25(s,6H), 2.36(q,J=7.3 Hz,2H), 4.39(s,2H), 6.76(s,1H), 7.09(d,J=5.1 Hz,1H), 7.28(dd,J=7.6, 4.9 Hz,1H), 7.32(s,2H), 7.93(dd,J=7.6, 1.5 Hz,1H), 8.16(s, 1H), 8.17(s,1H), 8.58(dd,J=4.9,1.5 Hz,1H), 10.30(s,1H), 10.35(s,1H)

N-(3,5-Dimethylphenyl)-2-(2-trifluoroacetylaminopyridin-4-ylmethylthio)pyridine-3-carboxamide (Compound No. 4-3)

$^1$H-NMR(400 MHz, DMSO-$d_6$)

δ 2.25(s,6H), 4.45(s,2H), 6.76(s,1H), 7.27-7.32(m,4H), 7.93(dd,J=7.6,1.7 Hz,1H), 8.03(s,1H), 8.31(d,J=4.9 Hz,1H), 8.58(dd,J=4.9,1.7 Hz,1H), 10.30(s,1H), 11.97(br s,1H)

N-(3,5-Dimethylphenyl)-2-(2-isobutyrylaminopyridin-4-ylmethylthio)pyridine-3-carboxamide (Compound No. 4-4)

$^1$H-NMR(500 MHz, DMSO-$d_6$)

δ 1.06(d,J=6.7 Hz,6H), 2.25(s,6H), 2.72(m,1H), 4.40(s, 2H), 6.76(s,1H), 7.10(dd,J=4.9,1.8 Hz,1H), 7.28(dd,J=7.6, 4.9 Hz,1H), 7.32(s,2H), 7.93(dd,J=7.6,1.8 Hz,1H), 8.17-8.19 (m,2H), 8.58(dd,J=4.9,1.8 Hz,1H), 10.30(s,1H), 10.34(s,1H)

N-(3,5-Dimethylphenyl)-2-(2-pivaloylaminopyridin-4-ylmethylthio)pyridine-3-carboxamide (Compound No. 4-5)

$^1$H-NMR(400 MHz, CDCl$_3$)

δ 1.30(s,9H), 2.32(s,6H), 4.49(s,2H), 6.80(d,J=0.7 Hz,1H), 7.07-7.13(m,2H), 7.29(s,2H), 7.86(dd,J=7.6,1.7 Hz,1H), 8.00(br s,1H), 8.11-8.15(m,1H), 8.31(d,J=0.7 Hz,1H), 8.51(dd,J=4.9,1.7 Hz,1H)

N-(3,5-Dimethylphenyl)-2-(2-trifluoromethanesulfonylaminopyridin-4-ylmethylthio)pyridine-3-carboxamide (Compound No. 4-6)

$^1$H-NMR(400 MHz, DMSO-$d_6$)

δ 2.26(s,6H), 4.43(s,2H), 6.77(s,1H), 7.14(d,J=6.3 Hz,1H), 7.28-7.32(m,3H), 7.72(s,1H), 7.95-7.99(m,2H), 8.53(dd,J=4.9,1.7 Hz,1H), 10.29(s,1H), 13.99(br s,1H)

N-(3,5-Dimethylphenyl)-2-(2-methanesulfonylaminopyridin-4-ylmethylthio)pyridine-3-carboxamide (Compound No. 4-7)

$^1$H-NMR(500 MHz, CDCl$_3$)

δ 2.32(s,6H), 2.94(s,3H), 4.42(s,2H), 6.81(s,1H), 6.85(dd, J=6.1,1.5 Hz,1H), 7.13(dd,J=7.6,4.9 Hz,1H), 7.28(s,2H), 7.46(s,1H), 7.83(dd,J=7.6,1.5 Hz,1H), 7.91(s,1H), 8.03(d, J=6.1 Hz,1H), 8.51(dd,J=4.9,1.5 Hz,1H), 11.80(br s,1H)

2-(2-Acetylaminopyridin-4-ylmethylthio)-N-(3-isopropylphenyl)pyridine-3-carboxamide (Compound No. 4-8)

$^1$H-NMR(400 MHz, DMSO-$d_6$)

δ 1.20(d,J=6.8 Hz,6H), 2.06(s,3H), 2.87(m,1H), 4.39(s, 2H), 7.00(d,J=7.6 Hz,1H), 7.10(dd,J=5.1,1.7 Hz,1H), 7.23-7.30(m,2H), 7.51(d,J=7.8 Hz,1H), 7.59(s,1H), 7.96(d,J=5.9 Hz,1H), 8.15-8.18(m,2H), 8.58(dd,J=4.9,1.7 Hz,1H), 10.39 (s,1H), 10.40(s,1H)

2-(2-Acetylaminopyridin-4-ylmethylthio)-N-(indan-5-yl)pyridine-3-carboxamide (Compound No. 4-9)

$^1$H-NMR(400 MHz, DMSO-$d_6$)

δ 1.97-2.06(m,2H), 2.06(s,3H), 2.79-2.87(m,4H), 4.39(s, 2H), 7.09(d,J=5.1,1.5 Hz,1H), 7.17(d,J=7.8 Hz,1H), 7.28(dd, J=7.6,4.9 Hz,1H), 7.37(d,J=8.3 Hz,1H), 7.61(s,1H), 7.93(d, J=5.9 Hz,1H), 8.15-8.18(m,2H), 8.57(dd,J=4.9,1.7 Hz,1H), 10.33(s,1H), 10.40(s,1H)

2-(2-Acetylaminopyridin-4-ylmethylthio)-N-(4-chlorophenyl)pyridine-3-carboxamide (Compound No. 4-10)

$^1$H-NMR(500 MHz, DMSO-$d_6$)

δ 2.06(s,3H), 4.40(s,2H), 7.09(d,J=5.2 Hz,1H), 7.29(dd, J=7.6,4.9 Hz,1H), 7.41(d,J=8.6 Hz,2H), 7.72(d,J=8.6 Hz,2H), 7.98(dd,J=7.6,1.8 Hz,1H), 8.16(s,1H), 8.17(d,J=5.2 Hz,1H), 8.59(dd,J=4.9,1.8 Hz,1H), 10.40(s,1H), 10.59(s,1H)

2-(2-Acetylaminopyridin-4-ylmethylthio)-N-(4-trifluoromethoxyphenyl)pyridine-3-carboxamide (Compound No. 4-11)

$^1$H-NMR(400 MHz, DMSO-$d_6$)

δ 2.06(s,3H), 4.40(s,2H), 7.10(dd,J=5.2,1.6 Hz,1H), 7.30 (dd,J=7.6,4.8 Hz,1H), 7.37(d,J=8.6 Hz,2H), 7.80(d,J=8.6 Hz,2H), 7.98(dd,J=7.6,1.7 Hz,1H), 8.14-8.18(m,2H), 8.60 (dd,J=4.8,1.7 Hz,1H), 10.41(s,1H), 10.66(s,1H)

2-[2-(N-Acetyl-N-methylamino)pyridin-4-ylmethylthio]-N-(3,5-dimethylphenyl)pyridine-3-carboxamide (Compound No. 4-12)

$^1$H-NMR(500 MHz, DMSO-d$_6$)
δ 1.96(s,3H), 2.25(s,6H), 3.22(s,3H), 4.43(s,2H), 6.76(s, 1H), 7.27-7.30(m,2H), 7.32(s,2H), 7.52(s,1H), 7.93(dd, J=7.6,1.5 Hz,1H), 8.34(d,J=4.9 Hz,1H), 8.58(dd,J=4.9,1.8 Hz,1H), 10.31(s,1H)

2-(2-Acetylaminopyridin-4-ylmethylthio)-N-(quinolin-6-yl)pyridine-3-carboxamide (Compound No. 4-13)

$^1$H-NMR(400 MHz, DMSO-d$_6$)
δ 2.06(s,3H), 4.42(s,2H), 7.11(d,J=5.2 Hz,1H), 7.33(dd, J=7.6,4.9 Hz,1H), 7.51(dd,J=8.2,4.3 Hz,1H), 7.89(dd,J=9.2, 2.4 Hz,1H), 8.00(d,J=9.2 Hz,1H), 8.05(dd,J=7.6,1.5 Hz,1H), 8.15-8.20(m,2H), 8.34(d,J=7.6 Hz,1H), 8.51(d,J=2.4 Hz,1H), 8.62(dd,J=4.9,1.5 Hz,1H), 8.81(dd,J=4.3,1.5 Hz,1H), 10.40(s,1H), 10.80(s,1H)

2-(2-Acetylaminopyridin-4-ylmethylthio)-N-(3-chloro-4-trifluoromethoxyphenyl)pyridine-3-carboxamide (Compound No. 4-14)

$^1$H-NMR(400 MHz, DMSO-d$_6$)
δ 2.06(s,3H), 4.41(s,2H), 7.10(d,J=4.9 Hz,1H), 7.32(dd, J=7.6,4.9 Hz,1H), 7.58(d,J=9.0 Hz,1H), 7.71(d,J=9.0 Hz,1H), 8.01(dd,J=7.6,1.7 Hz,1H), 8.08(s,1H), 8.16(s,1H), 8.17(d,J=4.9 Hz,1H), 8.61(dd,J=4.9,1.7 Hz,1H), 10.41(s, 1H), 10.80(s,1H)

2-(2-Acetylaminopyridin-4-ylmethylthio)-N-(isoquinolin-3-yl)pyridine-3-carboxamide (Compound No. 4-15)

$^1$H-NMR(400 MHz, DMSO-d$_6$)
δ 2.05(s,3H), 4.40(s,2H), 7.11(dd,J=5.1,1.5 Hz,1H), 7.28 (dd,J=7.6,4.9 Hz,1H), 7.58(m,1H), 7.75(m,1H), 7.97(d,J=8.0 Hz,1H), 8.06(dd,J=7.6, 1.7 Hz,1H), 8.09(d,J=8.0 Hz,1H), 8.15-8.20(m,2H), 8.58-8.60(m,2H) 9.19(s,1H), 10.42(s,1H), 11.16(s,1H)

2-(2-Acetylaminopyridin-4-ylmethylthio)-N-(3-chlorophenyl)pyridine-3-carboxamide (Compound No. 4-16)

$^1$H-NMR(500 MHz, DMSO-d$_6$)
δ 2.06(s,3H), 4.40(s,2H), 7.10(dd,J=5.1,1.5 Hz,1H), 7.18 (dd,J=8.1,1.1 Hz,1H), 7.31(dd,J=7.6,4.9 Hz,1H), 7.38(t, J=8.1 Hz,1H), 7.58(dd,J=8.1,1.1 Hz,1H), 7.88(s,1H), 7.99 (dd,J=7.6,1.8 Hz,1H), 8.16(s,1H), 8.17(d,J=5.2 Hz,1H), 8.60 (dd,J=4.9,1.8 Hz,1H), 10.40(s,1H), 10.64(s,1H)

2-(2-Acetylaminopyridin-4-ylmethylthio)-N-(4-tert-butylphenyl)pyridine-3-carboxamide (Compound No. 4-17)

$^1$H-NMR(400 MHz, DMSO-d$_6$)
δ 1.27(s,9H), 2.06(s,3H), 4.39(s,2H), 7.10(d,J=5.1 Hz,1H), 7.28(dd,J=7.7, 4.9 Hz,1H), 7.36(d,J=8.7 Hz,2H), 7.60(d,J=8.7 Hz,2H), 7.94(dd,J=7.7, 1.8 Hz,1H), 8.15-8.17 (m,2H), 8.57(dd,J=4.9,1.8 Hz,1H), 10.39(s,1H), 10.41(s,1H)

2-(2-Acetylaminopyridin-4-ylmethylthio)-N-(4-fluoro-3-methylphenyl)pyridine-3-carboxamide (Compound No. 4-18)

$^1$H-NMR(400 MHz, DMSO-d$_6$)
δ 2.06(s,3H), 2.23(d,J=1.5 Hz,3H), 4.39(s,2H), 7.09-7.14 (m,2H), 7.29(dd,J=7.6, 4.9 Hz,1H), 7.48(m,1H), 7.63(d, J=5.6 Hz,1H), 7.95(dd,J=7.6,1.7 Hz,1H), 8.16-8.17(m,2H), 8.58(dd,J=4.9,1.7 Hz,1H), 10.41(s,1H), 10.44(s,1H)

2-(2-Acetylaminopyridin-4-ylmethylthio)-N-(3-fluoro-4-methylphenyl)pyridine-3-carboxamide (Compound No. 4-19)

$^1$H-NMR(400 MHz, DMSO-d$_6$)
δ 2.06(s,3H), 2.20(d,J=1.2 Hz,3H), 4.40(s,2H), 7.09(dd, J=5.1,1.5 Hz, 1H), 7.24(t,J=8.4 Hz,1H), 7.29(dd,J=7.6,4.7 Hz,1H), 7.34(d,J=8.4 Hz, 1H), 7.59(d,J=13.7 Hz,1H), 7.96 (dd,J=7.6,1.7 Hz,1H), 8.15-8.17(m,2H), 8.59(dd,J=4.7,1.7 Hz,1H), 10.41(s,1H), 10.56(s,1H)

2-(2-Acetylaminopyridin-4-ylmethylthio)-N-(3-methylphenyl)pyridine-3-carboxamide (Compound No. 4-20)

$^1$H-NMR(400 MHz, DMSO-d$_6$)
δ 2.06(s,3H), 2.30(s,3H), 4.40(s,2H), 6.93(d,J=8.1 Hz,1H), 7.10(dd,J=5.1,1.5 Hz,1H), 7.22(t,J=8.1 Hz,1H), 7.29(dd,J=7.6,4.9 Hz,1H), 7.45(d,J=8.1 Hz,1H), 7.56(s,1H), 7.96(dd,J=7.6,1.7 Hz,1H), 8.16-8.17(m,2H), 8.58(dd,J=4.9, 1.7 Hz,1H), 10.39(s,1H), 10.41(s,1H)

2-(2-Acetylaminopyridin-4-ylmethylthio)-N-(1H-indazol-5-yl)pyridine-3-carboxamide (Compound No. 4-21)

$^1$H-NMR(400 MHz, DMSO-d$_6$)
δ 2.06(s,3H), 4.40(s,2H), 7.10(dd,J=5.1,1.5 Hz,1H), 7.30 (dd,J=7.6,4.9 Hz,1H), 7.50-7.55(m,2H), 7.98(dd,J=7.6,1.7 Hz,1H), 8.05(s,1H), 8.15-8.18(m,2H), 8.22(s,1H), 8.59(dd, J=4.9,1.7 Hz,1H), 10.41(s,1H), 10.47(s,1H), 13.03(s,1H)

2-(2-Acetylaminopyridin-4-ylmethylthio)-N-(1H-indazol-6-yl)pyridine-3-carboxamide (Compound No. 4-22)

$^1$H-NMR(400 MHz, DMSO-d$_6$)
δ 2.06(s,3H), 4.41(s,2H), 7.10(dd,J=5.2,1.6 Hz,1H), 7.24 (dd,J=8.8,1.7 Hz,1H), 7.31(dd,J=7.6,4.9 Hz,1H), 7.70(d, J=8.8 Hz,1H), 7.97-8.00(m,2H), 8.16-8.18(m,2H), 8.21(s, 1H), 8.60(dd,J=4.9,1.7 Hz,1H), 10.41(s,1H), 10.60(s,1H), 12.97(s,1H)

2-(2-Acetylaminopyridin-4-ylmethylthio)-N-(3,4-dimethylphenyl)pyridine-3-carboxamide (Compound No. 4-23)

$^1$H-NMR(400 MHz, DMSO-d$_6$)
δ 2.06(s,3H), 2.18(s,3H), 2.20(s,3H), 4.40(s,2H), 7.08-7.10(m,2H), 7.27(dd,J=7.6,4.9 Hz,1H), 7.39(d,J=8.1 Hz,1H), 7.48(s,1H), 7.93(dd,J=7.6,1.6 Hz,1H), 8.16-8.17(m, 2H), 8.57(dd,J=4.9,1.6 Hz,1H), 10.29(s,1H), 10.40(s,1H)

2-(2-Acetylaminopyridin-4-ylmethylthio)-N-(3,5-dichlorophenyl)pyridine-3-carboxamide (Compound No. 4-24)

$^1$H-NMR(400 MHz, DMSO-d$_6$)
δ 2.06(s,3H), 4.41(s,2H), 7.10(dd,J=5.1,1.7 Hz,1H), 7.32(dd,J=7.6,4.9 Hz,1H), 7.36(t,J=2.0 Hz,1H), 7.77(s,2H), 8.01(dd,J=7.6,1.7 Hz,1H), 8.17(s,1H), 8.17(d,J=5.1 Hz,1H), 8.61(dd,J=4.9,1.7 Hz,1H), 10.41(s,1H), 10.77(s,1H)

2-(2-Acetylaminopyridin-4-ylmethylthio)-N-(4-trifluoromethylphenyl)pyridine-3-carboxamide (Compound No. 4-25)

$^1$H-NMR(400 MHz, DMSO-d$_6$)
δ 2.06(s,3H), 4.41(s,2H), 7.10(dd,J=5.1,1.6 Hz,1H), 7.31(dd,J=7.6,4.9 Hz,1H), 7.73(d,J=8.5 Hz,2H), 7.92(d,J=8.5 Hz,2H), 8.01(dd,J=7.6,1.7 Hz,1H), 8.16(s,1H), 8.17(d,J=5.1 Hz,1H), 8.61(dd,J=4.9,1.7 Hz,1H), 10.41(s,1H), 10.81(s,1H)

2-(2-Acetylaminopyridin-4-ylmethylthio)-N-(4-n-propylphenyl)pyridine-3-carboxamide (Compound No. 4-26)

$^1$H-NMR(400 MHz, DMSO-d$_6$)
δ 0.88(t,J=7.3 Hz,3H), 1.52-1.60(m,2H), 2.06(s,3H), 2.50-2.53(m,2H), 4.39(s,2H), 7.09(dd,J=5.1,1.5 Hz,1H), 7.16(d,J=8.4 Hz,2H), 7.28(dd,J=7.6,4.9 Hz,1H), 7.59(d,J=8.4 Hz,2H), 7.94(dd,J=7.6,1.7 Hz,1H), 8.16(s,1H), 8.16(d,J=5.1 Hz,1H), 8.57(dd,J=4.9,1.7 Hz,1H), 10.38(s,1H), 10.40(s,1H)

2-[2-(N-Acetyl-N-methylamino)pyridin-4-ylmethylthio]-N-(4-chlorophenyl)pyridine-3-carboxamide (Compound No. 4-27)

$^1$H-NMR(500 MHz, DMSO-d$_6$)
δ 1.95(s,3H), 3.22(s,3H), 4.43(s,2H), 7.29-7.31(m,2H), 7.42(dd,J=6.7,2.1 Hz,2H), 7.52(s,1H), 7.72(d,J=8.9 Hz,2H), 7.99(dd,J=7.6,1.5 Hz,1H), 8.34(d,J=5.2 Hz,1H), 8.60(dd,J=4.9,1.8 Hz,1H), 10.60(s,1H)

2-[2-(N-Acetyl-N-methylamino)pyridin-4-ylmethylthio]-N-(4-trifluoromethoxyphenyl)pyridine-3-carboxamide (Compound No. 4-28)

$^1$H-NMR(400 MHz, DMSO-d$_6$)
δ 1.95(s,3H), 3.22(s,3H), 4.44(s,2H), 7.30-7.32(m,2H), 7.38(d,J=8.3 Hz,2H), 7.52(s,1H), 7.80(d,J=8.3 Hz,2H), 7.99(dd,J=7.6,1.7 Hz,1H), 8.34(d,J=5.1 Hz,1H), 8.60(dd,J=4.9,1.7 Hz,1H), 10.66(s,1H)

2-[2-(N-Acetyl-N-methylamino)pyridin-4-ylmethylthio]-N-(4-tert-butylphenyl)pyridine-3-carboxamide (Compound No. 4-29)

$^1$H-NMR(400 MHz, DMSO-d$_6$)
δ 1.27(s,9H), 1.95(s,3H), 3.22(s,3H), 4.43(s,2H), 7.28-7.30(m,2H), 7.36(d,J=8.5 Hz,2H), 7.51(s,1H), 7.60(d,J=8.5 Hz,2H), 7.95(d,J=6.1 Hz,1H), 8.34(d,J=5.1 Hz,1H), 8.58(dd,J=4.9,1.7 Hz,1H), 10.39(s,1H)

2-[2-(N-Acetyl-N-methylamino)pyridin-4-ylmethylthio]-N-(isoquinolin-3-yl)pyridine-3-carboxamide (Compound No. 4-30)

$^1$H-NMR(400 MHz, DMSO-d$_6$)
δ 1.95(s,3H), 3.22(s,3H), 4.45(s,2H), 7.28-7.31(m,2H), 7.52(s,1H), 7.58(m,1H), 7.75(m,1H), 7.98(d,J=8.1 Hz,1H), 8.06-8.09(m,2H), 8.35(d,J=5.1 Hz,1H), 8.58-8.60(m,2H), 9.20(s,1H), 11.17(s,1H)

2-[2-(N-Methyl-N-propionylamino)pyridin-4-ylmethylthio]-N-(4-trifluoromethoxyphenyl)pyridine-3-carboxamide (Compound No. 4-31)

$^1$H-NMR(500 MHz, DMSO-d$_6$)
δ 0.93(t,J=7.3 Hz,3H), 2.22(q,J=7.3 Hz,2H), 3.21(s,3H), 4.44(s,2H), 7.30-7.32(m,2H), 7.37(d,J=8.6 Hz,2H), 7.50(s,1H), 7.81(d,J=8.9 Hz,2H), 8.00(dd,J=7.6, 1.8 Hz,1H), 8.35(d,J=4.9 Hz,1H), 8.60(dd,J=4.7,1.8 Hz,1H), 10.66(s,1H)

N-(3-Chlorophenyl)-2-[2-(N-methyl-N-propionylamino)pyridin-4-ylmethylthio]pyridine-3-carboxamide (Compound No. 4-32)

$^1$H-NMR(500 MHz, DMSO-d$_6$)
δ 0.93(t,J=7.4 Hz,3H), 2.22(q,J=7.4 Hz,2H), 3.21(s,3H), 4.44(s,2H), 7.19(ddd, J=7.9,2.1,0.9 Hz,1H), 7.31-7.32(m,2H), 7.39(t,J=8.2 Hz,1H), 7.51(s,1H), 7.58(dd,J=8.2,1.2 Hz,1H), 7.89(t,J=1.8 Hz,1H), 8.00(dd,J=7.6,1.8 Hz,1H), 8.35(d, J=5.5 Hz,1H), 8.60(dd,J=4.9,1.8 Hz,1H), 10.64(s,1H)

2-(2-Acetylaminopyridin-4-ylmethylthio)-N-(2,2-dimethylpropyl)pyridine-3-carboxamide (Compound No. 4-33)

$^1$H-NMR(500 MHz, DMSO-d$_6$)
δ 0.90(s,9H), 2.06(s,3H), 3.04(d,J=6.4 Hz,2H), 4.36(s,2H), 7.08(dd,J=5.2,1.5 Hz,1H), 7.21(dd,J=7.6,4.9 Hz,1H), 7.77(dd,J=7.6,1.8 Hz,1H), 8.14(br s,1H), 8.16(d,J=5.2 Hz,1H), 8.43(t,J=6.4 Hz,1H), 8.51(dd,J=4.9,1.8 Hz,1H), 10.40(s,1H)

2-(2-Acetylaminopyridin-4-ylmethylthio)-N-[2-(4-methoxyphenyl)ethyl]pyridine-3-carboxamide (Compound No. 4-34)

$^1$H-NMR(500 MHz, DMSO-d$_6$)
δ 2.06(s,3H), 2.75(t,J=7.3 Hz,2H), 3.35-3.41(m,2H), 3.71(s,3H), 4.34(s,2H), 6.83(d,J=8.6 Hz,2H), 7.08(dd,J=5.2,1.5 Hz,1H), 7.15(d,J=8.6 Hz,2H), 7.21(dd,J=7.6,4.9 Hz,1H), 7.73(dd,J=7.6,1.8 Hz,1H), 8.15(br s,1H), 8.17(d,J=5.2 Hz,1H), 8.52(dd,J=4.9,1.8 Hz,1H), 8.57(t,J=5.5 Hz,1H), 10.41(s,1H)

2-(2-Acetylaminopyridin-4-ylmethylthio)-N-(2-chlorophenyl)pyridine-3-carboxamide (Compound No. 4-35)

$^1$H-NMR(400 MHz, DMSO-d$_6$)
δ 2.06(s,3H), 4.40(s,2H), 7.11(dd,J=4.9,1.5 Hz,1H), 7.24-7.33(m,2H), 7.39(m,1H), 7.55(dd,J=8.0,1.5 Hz,1H), 7.60(d,J=7.3 Hz,1H), 8.04(d,J=6.3 Hz,1H), 8.16-8.19(m,2H), 8.60(dd,J=4.6,1.7 Hz,1H), 10.23(s,1H), 10.42(s,1H)

2-(2-Acetylaminopyridin-4-ylmethylthio)-N-(5-chloro-2,4-dimethoxyphenyl)pyridine-3-carboxamide (Compound No. 4-36)

$^1$H-NMR(400 MHz, DMSO-d$_6$)
δ 2.06(s,3H), 3.85(s,3H), 3.90(s,3H), 4.38(s,2H), 6.87(s,1H), 7.10(dd,J=5.1,1.5 Hz,1H), 7.26(m,1H), 7.76(s,1H), 7.96(d,J=6.6 Hz,1H), 8.15-8.18(m,2H), 8.57(d,J=3.7 Hz,1H), 9.71(s,1H), 10.41(s,1H)

2-(2-Acetylaminopyridin-4-ylmethylthio)-N-(3,5-dimethyl-4-hydroxyphenyl)pyridine-3-carboxamide (Compound No. 4-37)

¹H-NMR(400 MHz, DMSO-d₆)
δ 2.06(s,3H), 2.15(s,6H), 4.38(s,2H), 7.10(dd,J=5.1,1.5 Hz,1H), 7.23-7.28(m,3H), 7.90(dd,J=7.6,1.7 Hz,1H), 8.09(s, 1H), 8.15-8.18(m,2H), 8.56(dd,J=4.8, 1.7 Hz,1H), 10.08(s, 1H), 10.41(s,1H)

N-(3,5-Dimethylphenyl)-2-[2-(2,5-dioxopyrrolidin-1-yl)pyridine-4-ylmethylthio]pyridine-3-carboxamide (Compound No. 4-38)

¹H-NMR(500 MHz, DMSO-d₆)
δ 2.26(s,6H), 2.80(s,4H), 4.48(s,2H), 6.76(s,1H), 7.28(dd, J=7.6,4.9 Hz,1H), 7.32(s,2H), 7.40(s,1H), 7.52(d,J=4.9 Hz,1H), 7.94(dd,J=7.6,1.5 Hz,1H), 8.47(d,J=4.9 Hz,1H), 8.57(dd,J=4.9,1.5 Hz,1H), 10.31(s,1H)

N-(3,5-Dimethylphenyl)-2-(2-methoxycarbonylaminopyridin-4-ylmethylthio)pyridine-3-carboxamide (Compound No. 4-39)

¹H-NMR(400 MHz, DMSO-d₆)
δ 2.25(s,6H), 3.65(s,3H), 4.39(s,2H), 6.76(s,1H), 7.06(m, 1H), 7.27-7.33(m,3H), 7.91-7.94(m,2H), 8.13(d,J=5.4 Hz,1H), 8.57(dd,J=4.9,1.7 Hz,1H), 10.10(s,1H), 10.30(s,1H)

2-[2-(4-Chlorophenyl)sulfonylaminopyridin-4-ylmethylthio]-N-(3,5-dimethylphenyl)pyridine-3-carboxamide (Compound No. 4-40)

¹H-NMR(400 MHz, DMSO-d₆)
δ 2.26(s,6H), 4.34(s,2H), 6.77(s,1H), 6.85(m,1H), 7.27-7.31(m,2H), 7.34(s,2H), 7.51(d,J=7.6 Hz,2H), 7.77-7.80(m, 3H), 7.97(d,J=6.3 Hz,1H), 8.50(m,1H), 10.31(s,1H)

N-(3,5-Dimethylphenyl)-2-[2-(1-oxo-3-buten-1-ylamino)pyridin-4-ylmethylthio]pyridine-3-carboxamide (Compound No. 4-41)

¹H-NMR(400 MHz, DMSO-d₆)
δ 2.25(s,6H), 3.16-3.20(m,2H), 4.40(s,2H), 5.10-5.19(m, 2H), 5.98(m,1H), 6.76(s,1H), 7.11(dd,J=5.1,1.5 Hz,1H), 7.28(dd,J=7.6,4.9 Hz,1H), 7.32(s,2H), 7.92(dd,J=7.6,1.7 Hz,1H), 8.15(s,1H), 8.18(d,J=5.1 Hz,1H), 8.57(m,1H), 10.29 (s, 1H), 10.44(s,1H)

2-(2-Acetylaminopyridin-4-ylmethylthio)-N-(4-chlorophenyl)benzamide (Compound No. 4-42)

¹H-NMR(500 MHz, DMSO-d₆)
δ 2.06(s,3H), 4.24(s,2H), 7.05(d,J=5.2 Hz,1H), 7.30(t, J=7.3 Hz,1H), 7.39(d,J=8.9 Hz,2H), 7.44(t,J=7.3 Hz,1H), 7.48(d,J=7.3 Hz,1H), 7.52(d,J=7.3 Hz,1H), 7.75(d,J=8.9 Hz,2H), 8.11(s,1H), 8.17(d,J=5.2 Hz,1H), 10.43(s,1H), 10.48(s,1H)

2-(2-Acetylaminopyridin-4-ylmethylthio)-N-(3,5-dimethylphenyl)benzamide (Compound No. 4-43)

¹H-NMR(500 MHz, DMSO-d₆)
δ 2.07(s,3H), 2.25(s,6H), 4.23(s,2H), 6.74(s,1H), 7.06(dd, J=4.9,1.5 Hz,1H), 7.28(m,1H), 7.35(s,2H), 7.40(m,1H), 7.45 (d,J=9.2 Hz,1H), 7.48(m,1H), 8.11(s,1H), 8.18(dd,J=5.2,0.6 Hz,1H), 10.18(s,1H), 10.44(s,1H)

2-(2-Acetylaminopyridin-4-ylmethylthio)-N-(4-tert-butylphenyl)benzamide (Compound No. 4-44)

¹H-NMR(500 MHz, DMSO-d₆)
δ 1.27(s,9H), 2.07(s,3H), 4.23(s,2H), 7.06(d,J=4.9 Hz,1H), 7.28(t,J=7.3 Hz,1H), 7.35(d,J=8.6 Hz,2H), 7.41(t, J=7.3 Hz,1H), 7.47(d,J=7.3 Hz,1H), 7.50(d,J=7.3 Hz,1H), 7.63(d,J=8.6 Hz,2H), 8.11(s,1H), 8.18(d,J=4.9 Hz,1H), 10.26(s,1H), 10.43(s,1H)

2-(2-Acetylaminopyridin-4-ylmethylthio)-N-(4-trifluoromethoxyphenyl)benzamide (Compound No. 4-45)

¹H-NMR(500 MHz, DMSO-d₆)
δ 2.06(s,3H), 4.24(s,2H), 7.06(d,J=5.2 Hz,1H), 7.30(t, J=7.6 Hz,1H), 7.35(d,J=8.6 Hz,2H), 7.43(t,J=7.6 Hz,1H), 7.49(d,J=7.6 Hz,1H), 7.53(d,J=7.6 Hz,1H), 7.83(d,J=8.6 Hz,2H), 8.11(s,1H), 8.17(d,J=5.2 Hz,1H), 10.43(s,1H), 10.54(s,1H)

2-(2-Acetylaminopyridin-4-ylmethylthio)-N-(isoquinolin-3-yl)benzamide (Compound No. 4-46)

¹H-NMR(500 MHz, DMSO-d₆)
δ 2.06(s,3H), 4.24(s,2H), 7.07(d,J=4.9 Hz,1H), 7.29(t, J=7.6 Hz,1H), 7.43(t,J=7.6 Hz,1H), 7.48(d,J=7.6 Hz,1H), 7.57(t,J=7.6 Hz,1H), 7.61(d,J=7.6 Hz,1H), 7.74(t,J=7.6 Hz,1H), 7.97(d,J=7.6 Hz,1H), 8.08(d,J=7.6 Hz,1H), 8.11(s, 1H), 8.17(d,J=4.9 Hz,1H), 8.60(s,1H), 9.18(s,1H), 10.43(s, 1H), 10.95(s,1H)

2-(2-Acetylaminopyridin-4-ylmethylthio)-N-(3-isopropylphenyl)benzamide (Compound No. 4-47)

¹H-NMR(500 MHz, DMSO-d₆)
δ 1.20(d,J=7.0 Hz,6H), 2.07(s,3H), 2.86(m,1H), 4.24(s, 2H), 6.98(d,J=7.6 Hz,1H), 7.07(d,J=5.2 Hz,1H), 7.24(t,J=7.6 Hz,1H), 7.28(t,J=7.6 Hz,1H), 7.41(t,J=7.6 Hz,1H), 7.46(d, J=7.6 Hz,1H), 7.52(d,J=7.6 Hz,1H), 7.53(d,J=7.6 Hz,1H), 7.62(s,1H), 8.11(s,1H), 8.18(d,J=5.2 Hz,1H), 10.27(s,1H), 10.44(s,1H)

2-(2-Acetylaminopyridin-4-ylmethylthio)-N-(4-chloro-3-methylphenyl)benzamide (Compound No. 4-48)

¹H-NMR(500 MHz, DMSO-d₆)
δ 2.06(s,3H), 2.32(s,3H), 4.23(s,2H), 7.06(d,J=5.2 Hz,1H), 7.29(t,J=7.6 Hz,1H), 7.36(d,J=8.6 Hz,1H), 7.42(t, J=7.6 Hz,1H), 7.48(d,J=7.6 Hz,1H), 7.51(d,J=7.6 Hz,1H), 7.53(m,1H), 7.74(s,1H), 8.11(s,1H), 8.18(d,J=5.2 Hz,1H), 10.40(s,1H), 10.43(s,1H)

2-(2-Acetylaminopyridin-4-ylmethylthio)-N-(1H-indazol-6-yl)benzamide (Compound No. 4-49)

¹H-NMR(500 MHz, DMSO-d₆)
δ 2.06(s,3H), 4.25(s,2H), 7.07(d,J=5.2 Hz,1H), 7.26(d, J=8.6 Hz,1H), 7.31(t,J=7.3 Hz,1H), 7.42(t,J=7.3 Hz,1H), 7.49(d,J=7.3 Hz,1H), 7.55(d,J=7.3 Hz,1H), 7.68(d,J=8.6 Hz,1H), 7.99(s,1H), 8.11(s,1H), 8.17(d,J=5.2 Hz,1H), 8.25 (s,1H), 10.43(s,1H), 10.49(s,1H), 12.93(s,1H)

2-(2-Acetylaminopyridin-4-ylmethylthio)-N-(2,2-dimethylpropyl)benzamide (Compound No. 4-50)

¹H-NMR(500 MHz, DMSO-d₆)
δ 0.91(s,9H), 2.07(s,3H), 3.04(d,J=6.4 Hz,2H), 4.20(s,2H), 7.05(dd,J=4.9,1.8 Hz,1H), 7.22(t,J=7.6 Hz,1H), 7.31-7.37(m,2H), 7.40(d,J=7.6 Hz,1H), 8.09(br s,1H), 8.18(d,J=5.2 Hz,1H), 8.25(t,J=6.4 Hz,1H), 10.43(s,1H)

3-(2-Acetylaminopyridin-4-ylmethylthio)-N-(4-tert-butylphenyl)thiophene-2-carboxamide (Compound No. 4-51)

¹H-NMR(500 MHz, DMSO-d₆)
δ 1.27(s,9H), 2.06(s,3H), 4.27(s,2H), 6.99(d,J=4.9 Hz,1H), 7.24(d,J=5.2 Hz,1H), 7.34(d,J=8.9 Hz,2H), 7.52(d,J=8.9 Hz,2H), 7.83(d,J=5.2 Hz,1H), 8.11(s,1H), 8.16(d,J=4.9 Hz,1H), 9.90(s,1H), 10.43(s,1H)

3-(2-Acetylaminopyridin-4-ylmethylthio)-N-(1H-indazol-6-yl)thiophene-2-carboxamide (Compound No. 4-52)

¹H-NMR(500 MHz, DMSO-d₆)
δ 2.04(s,3H), 4.28(s,2H), 7.01(d,J=4.9 Hz,1H), 7.20(d,J=8.6 Hz,1H), 7.27(d,J=5.2 Hz,1H), 7.68(d,J=8.6 Hz,1H), 7.85(d,J=5.2 Hz,1H), 7.99(br s,1H), 8.09(s,1H), 8.10(s,1H), 8.16(d,J=4.9 Hz,1H), 10.12(s,1H), 10.41(s,1H), 12.94(s,1H)

3-(2-Acetylaminopyridin-4-ylmethylthio)-N-(isoquinolin-3-yl)thiophene-2-carboxamide (Compound No. 4-53)

¹H-NMR(500 MHz, DMSO-d₆)
δ 1.96(s,3H), 4.31(s,2H), 6.92(d,J=5.2 Hz,1H), 7.32(d,J=5.2 Hz,1H), 7.57(t,J=7.6 Hz,1H), 7.75(t,J=7.6 Hz,1H), 7.91(d,J=5.2 Hz,1H), 7.93(d,J=7.6 Hz,1H), 8.03(s,1H), 8.08(d,J=5.2 Hz,1H), 8.10(d,J=7.6 Hz,1H), 8.45(s,1H), 9.17(s,1H), 10.32(s,1H), 10.55(s,1H)

3-(2-Acetylaminopyridin-4-ylmethylthio)-N-(2,2-dimethylpropyl)thiophene-2-carboxamide (Compound No. 4-54)

¹H-NMR(500 MHz, DMSO-d₆)
δ 0.85(s,9H), 2.07(s,3H), 3.01(d,J=6.1 Hz,2H), 4.24(s,2H), 6.88(d,J=5.1,1.7 Hz, 1H), 7.23(d,J=5.1 Hz,1H), 7.75(d,J=5.1 Hz,1H), 7.94(d,J=6.1 Hz,1H), 8.04(br s,1H), 8.16(d,J=5.1 Hz,1H), 10.45(s,1H)

3-(2-Acetylaminopyridin-4-ylmethylthio)-N-[2-(4-methoxyphenyl)ethyl]thiophene-2-carboxamide (Compound No. 4-55)

¹H-NMR(500 MHz, DMSO-d₆)
δ 2.06(s,3H), 2.71(t,J=7.3 Hz,2H), 3.33-3.38(m,2H), 3.71(s,3H), 4.19(s,2H), 6.85(d,J=8.6 Hz,2H), 6.95(dd,J=4.9,1.5 Hz,1H), 7.14(d,J=8.6 Hz,2H), 7.15(d,J=5.2 Hz,1H), 7.71(d,J=5.2 Hz,1H), 8.06(t,J=5.5 Hz,1H), 8.08(br s,1H), 8.18(d,J=4.9 Hz,1H), 10.46(s,1H)

3-(2-Acetylaminopyridin-4-ylmethylthio)-N-(3,5-dimethylphenyl)thiophene-2-carboxamide (Compound No. 4-56)

¹H-NMR(400 MHz, DMSO-d₆)
δ 2.05(s,3H), 2.25(s,6H), 4.27(s,2H), 6.74(s,1H), 6.97(dd,J=5.1,1.5 Hz,1H), 7.22-7.27(m,3H), 7.83(d,J=5.1 Hz,1H), 8.11(s,1H), 8.16(d,J=5.1 Hz,1H), 9.82(s,1H) 10.43(s,1H)

3-(2-Acetylaminopyridin-4-ylmethylthio)-N-(4-chlorophenyl)thiophene-2-carboxamide (Compound No. 4-57)

¹H-NMR(500 MHz, CDCl₃)
δ 2.11(s,3H), 3.96(s,2H), 6.44(dd,J=6.7,1.9 Hz,1H), 7.16(d,J=5.2 Hz,1H), 7.26(d,J=8.9 Hz,2H), 7.46(d,J=8.9 Hz,2H), 7.57(d,J=5.2 Hz,1H), 8.00(d,J=6.7 Hz,1H), 8.03(s,1H), 8.07(s,1H), 9.79(s,1H)

3-(2-Acetylaminopyridin-4-ylmethylthio)-N-(4-trifluoromethoxyphenyl)thiophene-2-carboxamide (Compound No. 4-58)

¹H-NMR(400 MHz, CDCl₃)
δ 2.10(s,3H), 3.98(s,2H), 6.48(dd,J=5.1,1.7 Hz,1H), 7.15(d,J=0.7 Hz,1H), 7.17(d,J=5.1 Hz,2H), 7.54(dd,J=7.8,2.2 Hz,1H), 7.58(d,J=5.1 Hz,2H), 8.00-8.02(m,2H), 8.09(s,1H), 9.84(s,1H) N-(3,5-Dimethylphenyl)-2-(2-methoxyacetylaminopyridin-4-ylmethylthio)pyridine-3-carboxamide (Compound No. 4-59)

¹H-NMR(500 MHz, DMSO-d₆)
δ 2.25(s,6H), 3.35(s,3H), 4.04(s,2H), 4.42(s,2H), 6.76(s,1H), 7.15(dd,J=5.2,1.5 Hz,1H), 7.28(dd,J=7.6,4.9 Hz,1H), 7.32(s,2H), 7.93(dd,J=7.6,1.8 Hz,1H), 8.17(s,1H), 8.19(d,J=4.9 Hz,1H), 8.58(dd,J=4.9,1.5 Hz,1H), 9.89(s,1H), 10.30(s,1H)

2-(2-Methoxyacetylaminopyridin-4-ylmethylthio)-N-(4-trifluoromethoxyphenyl)pyridine-3-carboxamide (Compound No. 4-60)

¹H-NMR(500 MHz, DMSO-d₆)
δ 3.35(s,3H), 4.03(s,2H), 4.43(s,2H), 7.15(dd,J=5.2,1.5 Hz,1H), 7.31(dd,J=7.6, 4.9 Hz,1H), 7.37(d,J=8.6 Hz,2H), 7.80(d,J=8.6 Hz,2H), 7.99(dd,J=7.6,1.5 Hz,1H), 8.17(s,1H), 8.19(dd,J=5.2,0.6 Hz,1H), 8.60(dd,J=4.9,1.8 Hz,1H), 9.89(s,1H), 10.66(s,1H)

N-(3,5-Dimethylphenyl)-2-(2-phenoxyacetylaminopyridin-4-ylmethylthio)pyridine-3-carboxamide (Compound No. 4-61)

¹H-NMR(500 MHz, DMSO-d₆)
δ 2.25(s,6H), 4.41(s,2H), 4.76(s,2H), 6.76(s,1H), 7.03-7.09(m,3H), 7.16(d,J=4.9 Hz,1H), 7.27(dd,J=7.6,4.9 Hz,1H), 7.28-7.30(m,3H), 7.31(s,1H), 7.92(dd,J=7.6, 1.8 Hz,1H), 8.15(s,1H), 8.22(d,J=4.9 Hz,1H), 8.56(dd,J=4.9,1.8 Hz,1H), 10.30(s,1H), 10.43(s,1H)

2-(2-Acetoxyacetylaminopyridin-4-ylmethylthio)-N-(4-chlorophenyl)pyridine-3-carboxamide (Compound No. 4-62)

¹H-NMR(500 MHz, DMSO-d₆)
δ 2.10(s,3H), 4.41(s,2H), 4.68(s,2H), 7.14(d,J=5.2 Hz,1H), 7.29(dd,J=7.6,4.9 Hz,1H), 7.41(d,J=8.6 Hz,2H), 7.72(d,J=8.6 Hz,2H), 7.98(dd,J=7.6,1.5 Hz, 1H), 8.10(br s,1H), 8.20(d,J=5.2 Hz,1H), 8.58(dd,J=4.9,1.5 Hz,1H), 10.59(s,1H), 10.60(s,1H)

N-(3,5-Dimethylphenyl)-2-(3-methanesulfonylaminopyridin-4-ylmethylthio)pyridine-3-carboxamide (Compound No. 4-63)

¹H-NMR(500 MHz, CDCl₃)
δ 2.32(s,6H), 3.07(s,3H), 4.36(s,2H), 6.83(s,1H), 7.21-7.25(m,4H), 7.90(d,J=6.4 Hz,1H), 7.94(s,1H), 8.33(d,J=4.9 Hz,1H), 8.72(dd,J=4.5,1.5 Hz,1H), 8.78(s,1H), 10.64(s,1H)

2-(3-Acetylaminopyridin-4-ylmethylthio)-N-(3,5-dimethylphenyl)pyridine-3-carboxamide (Compound No. 4-64)

¹H-NMR(400 MHz, CDCl₃)
δ 2.19(s,3H), 2.30(s,6H), 4.31(s,2H), 6.81(s,1H), 7.16-7.22(m,2H), 7.25(s,2H), 7.87(d,J=7.6 Hz,1H), 8.18(d,J=5.1 Hz,1H), 8.48-8.52(m,2H), 8.94(s,1H), 9.38(s,1H)

N-(4-Acetoxy-3,5-dimethylphenyl)-2-(2-acetylaminopyridin-4-ylmethylthio)pyridine-3-carboxamide (Compound No. 4-65)

¹H-NMR(500 MHz, DMSO-d₆)
δ 2.06(s,3H), 2.07(s,6H), 2.33(s,3H), 4.39(s,2H), 7.10(dd, J=5.2,1.5 Hz,1H), 7.29(dd,J=7.6,4.9 Hz,1H), 7.42(s,2H), 7.94(dd,J=7.6,1.8 Hz,1H), 8.16-8.18(m,2H), 8.58(dd,J=4.9, 1.8 Hz,1H), 10.38(s,1H), 10.41(s,1H)

2-(2-Acetylaminopyridin-4-ylmethylthio)-N-(3-trifluoromethylphenyl)pyridine-3-carboxamide (Compound No. 4-66)

¹H-NMR(400 MHz, DMSO-d₆)
δ 2.06(s,3H), 4.41(s,2H), 7.10(dd,J=5.1,1.6 Hz,1H), 7.32 (dd,J=7.6,4.9 Hz,1H), 7.48(d,J=7.6 Hz,1H), 7.61(dd,J=8.3, 7.6 Hz,1H), 7.91(d,J=8.3 Hz,1H), 8.03(dd,J=7.6,1.7 Hz,1H), 8.16-8.18(m,3H), 8.61(dd,J=4.9,1.7 Hz,1H), 10.41(s,1H), 10.79(s,1H)

2-[2-(4-Hydroxycarbonylbutyryl)aminopyridin-4-ylmethylthio]-N-(3,5-dimethylphenyl)pyridine-3-carboxamide (Compound No. 4-67)

¹H-NMR(400 MHz, DMSO-d₆)
δ 1.73-1.82(m,2H), 2.24(t,J=7.6 Hz,2H), 2.25(s,6H), 2.39 (t,J=7.3 Hz,2H), 4.39 (s,2H), 6.76(s,1H), 7.10(d,J=6.6 Hz,1H), 7.28(dd,J=7.6,4.9 Hz,1H), 7.32(s,2H), 7.92(dd, J=7.6,1.7 Hz,1H), 8.17(d,J=6.6 Hz,1H), 8.17(s,1H), 8.58(dd, J=4.9,1.7 Hz,1H), 10.31(s,1H) 10.40(s,1H), 12.04(br s,1H)

2-[2-(3,5-Dioxomorpholin-4-yl)pyridin-4-ylmethylthio]-N-(3,5-dimethylphenyl)pyridine-3-carboxamide (Compound No. 4-68)

¹H-NMR(400 MHz, DMSO-d₆)
δ 2.25(s, 6H), 4.48(s,2H), 4.54(s,4H), 6.76(s,1H), 7.29(dd, J=7.6,4.9 Hz,1H), 7.33(s,2H), 7.45(s,1H), 7.53(d,J=4.9 Hz,1H), 7.94(dd,J=7.6,1.7 Hz,1H), 8.46(d,J=4.9 Hz,1H), 8.57(dd,J=7.6,1.7 Hz,1H), 10.33(s,1H)

Example 5

N-(3,5-Dimethylphenyl)-2-[2-(N'-n-propylureido)pyridin-4-ylmethylthio]pyridine-3-carboxamide (Compound No. 5-1)

n-Propyl isocyanate (20 mg, 0.23 mmol) was added to a solution of 2-(2-aminopyridin-4-ylmethylthio)-N-(3,5-dimethylphenyl)pyridine-3-carboxamide (The free base of Compound No. 3-1, 28 mg, 0.077 mmol) in N,N-dimethylformamide (0.60 mL) at room temperature, and the mixture was stirred for 4 hours at 80° C. Ethyl acetate (10 mL) was added to the reaction mixture, the whole was washed with water (15 mL) and brine (15 mL), and then the organic layer was dried over anhydrous magnesium sulfate. The organic layer was evaporated under reduced pressure, and the resulting residue was purified by silica gel column chromatography to give 12 mg of the target compound as a colorless solid(Yield 33%).

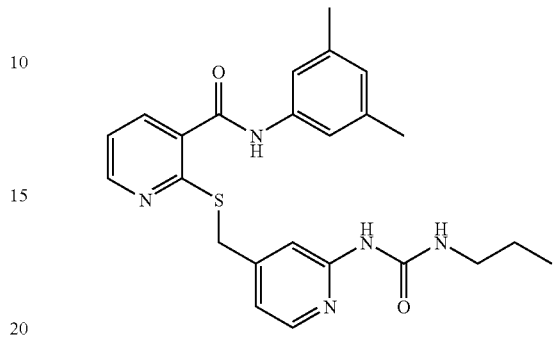

¹H-NMR(500 MHz, DMSO-d₆)
δ 0.87(t,J=7.6 Hz,3H), 1.46(m,2H), 2.25(s,6H), 3.11(m, 2H), 4.33(s,2H), 6.76(s,1H), 6.93(d,J=5.2 Hz,1H), 7.28(dd, J=7.6,4.9 Hz,1H), 7.32(s,2H), 7.37(s,1H), 7.93(dd,J=7.6,1.5 Hz,1H), 8.05(d,J=5.2 Hz,1H), 8.23(br s,1H), 8.57(dd,J=4.9, 1.5 Hz,1H), 9.13(s,1H), 10.29(s,1H)

As described below, Compounds (No. 5-2~6) were obtained using the corresponding compounds selected from Reference compounds (No. 3-1~37), commercially available compounds or known compounds according to the synthetic method of Compound (No. 5-1).

2-[2-(N'-tert-Butylureido)pyridin-4-ylmethylthio]-N-(3,5-dimethylphenyl)pyridine-3-carboxamide (Compound No. 5-2)

¹H-NMR(500 MHz, DMSO-d₆)
δ 1.30(s,9H), 2.25(s,6H), 4.33(s,2H), 6.76(s,1H), 6.91(d, J=5.2 Hz,1H), 7.28(dd,J=7.6,4.9 Hz,1H), 7.32(s,2H), 7.42(s, 1H), 7.93(dd,J=7.6,1.5 Hz,1H), 8.03(d,J=5.2 Hz,1H), 8.06(br s,1H), 8.57(dd,J=4.9,1.5 Hz,1H), 8.91(s,1H), 10.30(s,1H)

2-[2-(N'-4-Chlorophenylureido)pyridin-4-ylmethylthio]-N-(3,5-dimethylphenyl)pyridine-3-carboxamide (Compound No. 5-3)

¹H-NMR(400 MHz, DMSO-d₆)
δ 2.25(s,6H), 4.38(s,2H), 6.76(s,1H), 7.05(d,J=5.2 Hz,1H), 7.27-7.50(m,4H), 7.53-7.56(m,4H), 7.94(dd,J=7.6, 1.7 Hz,1H), 8.16(d,J=5.2 Hz,1H), 8.58(dd,J=4.9,1.7 Hz,1H), 9.48(s,1H), 10.30(s,1H), 10.69(s,1H)

N-(3,5-Dimethylphenyl)-2-[2-(N'-methylthioureido)pyridin-4-ylmethylthio]pyridine-3-carboxamide (Compound No. 5-4)

¹H-NMR(500 MHz, DMSO-d₆)
δ 2.26(s,6H), 3.05(d,J=4.6 Hz,3H), 4.35(s,2H), 6.76(s, 1H), 7.05(dd,J=5.5,1.5 Hz,1H), 7.21(s,1H), 7.29(dd,J=7.6, 4.9 Hz,1H), 7.32(s,2H), 7.94(dd,J=7.6,1.5 Hz,1H), 8.10(d, J=5.5 Hz,1H), 8.58(dd,J=4.9,1.5 Hz,1H), 10.29(s,1H), 10.54 (s,1H), 11.49(d,J=4.6 Hz,1H)

N-(4-Chlorophenyl)-2-[2-(N'-n-propylureido)pyridin-4-ylmethylthio]pyridine-3-carboxamide (Compound No. 5-5)

¹H-NMR(400 MHz, DMSO-d₆)
δ 0.87(t,J=6.3 Hz,3H), 1.40-1.50(m,2H), 3.10(q,J=6.8 Hz,2H), 4.34(s,2H), 6.93(d,J=5.4 Hz,1H), 7.30(dd,J=7.6,4.9 Hz,1H), 7.37(s,1H), 7.42(d,J=9.0 Hz,2H), 7.73(d,J=9.0 Hz,2H), 7.98(dd,J=7.6,1.7 Hz, 1H), 8.05(d,J=5.4 Hz,1H), 8.24(br s,1H), 8.59(dd,J=4.9,1.7 Hz,1H), 9.14(s,1H), 10.59 (s,1H)

2-[2-(N'-n-Propylureido)pyridin-4-ylmethylthio]-N-(4-trifluoromethoxyphenyl)pyridine-3-carboxamide (Compound No. 5-6)

¹H-NMR(500 MHz, DMSO-d₆)
δ 0.87(t,J=6.3 Hz,3H), 1.43-1.48(m,2H), 3.11(q,J=7.0 Hz,2H), 4.35(s,2H), 6.93(d,J=4.9 Hz,1H), 7.31(dd,J=7.6,4.9 Hz,1H), 7.36-7.38(m,3H), 7.81(d,J=8.6 Hz,2H), 7.99(dd, J=7.6,1.5 Hz,1H), 8.05(d,J=4.9 Hz,1H), 8.23(br s,1H), 8.60 (dd,J=4.9,1.5 Hz,1H), 9.13(s,1H), 10.65(s,1H)

Example 6

N-(3,5-Dimethylphenyl)-2-(2-formylaminopyridin-4-ylmethylthio)pyridine-3-carboxamide (Compound No. 6-1)

2-(2-Aminopyridin-4-ylmethylthio)-N-(3,5-dimethylphenyl)pyridine-3-carboxamide (the free base of Compound No. 3-1, 50 mg, 0.14 mmol) was dissolved in anhydrous tetrahydrofuran (0.20 mL), a solution of N-formylbenzotriazole (19 mg, 0.13 mmol) in anhydrous tetrahydrofuran (0.2 mL) was added thereto, and then the mixture was refluxed for 16 hours. The mixture was diluted with dichloromethane (15 mL), and then the whole was washed with 2 N aqueous sodium hydroxide solution (4.0 mL) twice and dried over anhydrous magnesium sulfate. The solvent was evaporated under reduced pressure to give 60 mg of the target compound quantitatively as a colorless solid.

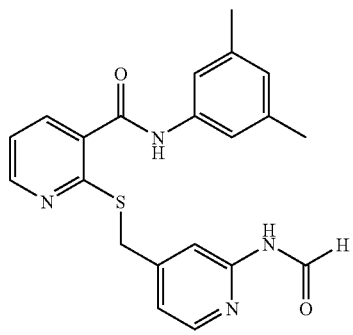

¹H-NMR(400 MHz, DMSO-d₆)
δ 2.25(s,6H), 3.30(s,1H), 4.37(s,2H), 6.76(s,1H), 6.97(s, 1H), 7.13(m,1H), 7.28(dd, J=7.6,4.9 Hz,1H), 7.32(s,2H), 7.93(d,J=7.6 Hz,1H), 8.16(m,1H), 8.57(dd,J=4.9,1.7 Hz,1H), 10.30(s,1H), 10.54(s,1H)

Example 7

2-(2-Aminopyridin-4-ylmethylthio)-N-(tert-butoxycarbonylmethyl)-N-(3,5-dimethylphenyl)pyridine-3-carboxamide (Compound No. 7-1)

A solution of 2-(2-aminopyridin-4-ylmethylthio)-N-(3,5-dimethylphenyl)pyridine-3-carboxamide (the free base of Compound No. 3-1, 50 mg, 0.14 mmol) in anhydrous N,N-dimethylformamide (2 mL) was added dropwise to a suspension of 60% sodium hydride (13 mg, 0.30 mmol) in anhydrous N,N-dimethylformamide (1.0 mL) under ice-cooling, and the mixture was stirred for 5 minutes. Bromoacetic acid tert-butyl ester (22 μL, 0.15 mmol) was added to the reaction mixture, and the mixture was stirred for 30 minutes at room temperature. The mixture was poured into ice water (15 mL), and the whole was extracted with ethyl acetate (15 mL). The organic layer was washed with saturated aqueous sodium hydrogen carbonate solution (30 mL) and brine (30 mL), and dried over anhydrous magnesium sulfate. The solvent was evaporated under reduced pressure, and the resulting residue was purified by silica gel column chromatography to give 45 mg of the target compound as a colorless amorphous. (Yield 69%)

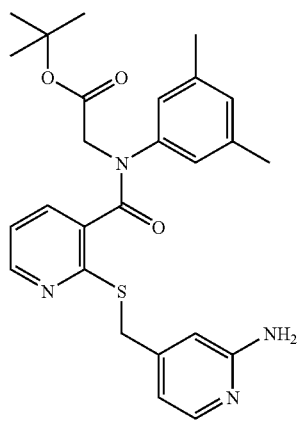

¹H-NMR(500 MHz, DMSO-d₆)
δ 61.42(s,9H), 2.05(s,6H), 4.27(s,2H), 4.38(s,2H), 5.85(s, 2H), 6.45-6.46(m,2H), 6.77-6.79(m,3H), 6.95(s,1H), 7.28(s, 1H), 7.78(dd,J=4.9,0.9 Hz,1H), 8.33(s,1H)

Example 8

N-(3,5-Dimethylphenyl)-2-(2-phenylaminopyridin-4-ylmethylthio)pyridine-3-carboxamide (Compound No. 8-1)

While nitrogen was bubbled, 2-(2-aminopyridin-4-ylmethylthio)-N-(3,5-dimethylphenyl)pyridine-3-carboxamide (the free base of Compound No. 3-1, 63 mg, 0.18 mmol), cesium carbonate (130 mg, 0.38 mmol), iodobenzene (37 μL, 0.33 mmol), 4,5-bis(diphenylphosphino)-9,9-dimethylxanthene (8.1 mg, 0.014 mmol) and tris(dibenzylideneacetone) dipalladium(0) (4.3 mg, 0.0047 mmol) were added to 1,4-dioxane (2.0 mL). The mixture was stirred for 20 hours at 90° C. in the sealed tube, the mixture was diluted with ethyl acetate (30 mL), and then the whole was washed with saturated aqueous sodium hydrogen carbonate solution (30 mL). The organic layer was dried over anhydrous magnesium sulfate and evaporated under reduced pressure. The resulting residue was purified by silica gel column chromatography. The resulting solid was filtered off with diethyl ether and dried under reduced pressure to give 31 mg of the target compound as a colorless solid. (Yield 31%)

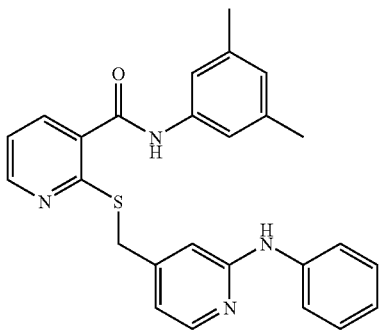

¹H-NMR(500 MHz, DMSO-d₆)

δ 2.25(s,6H), 4.34(s,2H), 6.75-6.76(m,2H), 6.85-6.87(m,2H), 7.22(t,J=7.8 Hz,2H), 7.29(dd,J=7.3,4.9 Hz,1H), 7.33(s,2H), 7.61(d,J=7.6 Hz,2H), 7.93(d,J=7.6 Hz,1H), 8.03(d,J=5.5 Hz,1H), 8.58(d,J=4.9 Hz,1H), 8.97(s,1H), 10.31(s,1H)

Example 9

N-(3,5-Dimethylphenyl)-2-[2-(N'-methylureido)pyridin-4-ylmethylthio]pyridine-3-carboxamide (Compound No. 9-1)

While nitrogen was bubbled, 2-(2-bromopyridin-4-ylmethylthio)-N-(3,5-dimethylphenyl)pyridine-3-carboxamide (Reference compound No. 3-4, 100 mg, 0.23 mmol), cesium carbonate (91 mg, 0.28 mmol), N-methylurea (52 mg, 0.70 mmol), 4,5-bis(diphenylphosphino)-9,9-dimethylxanthene (8.1 mg, 0.014 mmol) and tris(dibenzylideneacetone)dipalladium(0) (4.3 mg, 0.0047 mmol) were added to 1,4-dioxane (2.0 mL). The mixture was stirred for 5 hours at 100° C. in the sealed tube, the mixture was diluted with ethyl acetate (30 mL), and then the whole was washed with saturated aqueous sodium hydrogen carbonate solution (30 mL) twice. The organic layer was dried over anhydrous magnesium sulfate, and the solvent was evaporated under reduced pressure. The residue was purified by silica gel column chromatography. The resulting solid was filtered off with ethyl acetate and dried under reduced pressure to give 21 mg of the target compound as a colorless solid. (Yield 22%)

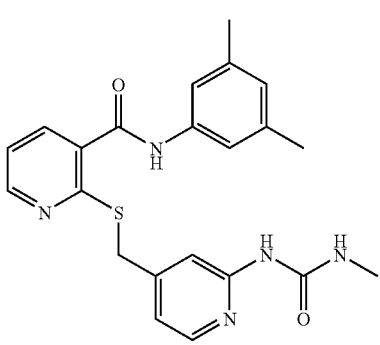

¹H-NMR(500 MHz, DMSO-d₆)

δ 2.25(s,6H), 2.71(d,J=4.6 Hz,3H), 4.33(s,2H), 6.76(s,1H), 6.93(d,J=5.3,1.4 Hz,1H), 7.28(dd,J=7.5,4.7 Hz,1H), 7.33(m,3H), 7.92(dd,J=7.5,1.5 Hz,1H), 8.05(d,J=5.3 Hz,1H), 8.15(s,1H), 8.57(dd,J=4.7,1.5 Hz,1H), 9.20(s,1H), 10.29(s,1H)

As described below, Compounds (No. 9-2~4) were obtained using the corresponding compounds selected from Compounds (No. 3-4~7), commercially available compounds or known compounds according to the synthetic method of Compound (No. 9-1).

2-[2-(N'-Methylureido)pyridin-4-ylmethylthio]-N-(4-trifluoromethoxyphenyl)pyridine-3-carboxamide (Compound No. 9-2)

¹H-NMR(500 MHz, DMSO-d₆)

δ 2.70(d,J=4.6 Hz,3H), 4.34(s,2H), 6.93(dd,J=5.5,1.5 Hz,1H), 7.30(dd,J=7.6, 4.8 Hz,1H), 7.33(s,1H), 7.37(d,J=8.9 Hz,2H), 7.80(d,J=8.9 Hz,2H), 7.99(dd,J=7.6,1.7 Hz,1H), 8.05(d,J=5.5 Hz,1H), 8.15(s,1H), 8.60(dd,J=4.8,1.7 Hz,1H), 9.21(s,1H), 10.66(s,1H)

N-(4-Chlorophenyl)-2-[2-(N'-methylureido)pyridin-4-ylmethylthio]pyridine-3-carboxamide (Compound No. 9-3)

¹H-NMR(400 MHz, DMSO-d₆)

δ 2.71(d,J=4.6 Hz,3H), 4.34(s,2H), 6.93(dd,J=5.1,1.4 Hz,1H), 7.28-7.33(m,2H), 7.41(d,J=8.9 Hz,2H), 7.72(d,J=8.9 Hz,2H), 7.98(dd,J=7.6,1.7 Hz,1H), 8.04(d,J=5.1 Hz,1H), 8.16(s,1H), 8.59(dd,J=4.9,1.7 Hz,1H), 9.21(s,1H), 10.60(s,1H)

N-(4-Difluoromethoxyphenyl)-2-[2-(N'-methylureido)pyridin-4-ylmethylthio]pyridine-3-carboxamide (Compound No. 9-4)

¹H-NMR(400 MHz, DMSO-d₆)

δ 2.70(d,J=4.6 Hz,3H), 4.34(s,2H), 6.93(dd,J=5.1,1.3 Hz,1H), 7.17(t,J=74.1 Hz,1H), 7.18(d,J=8.9 Hz,2H), 7.28-7.33(m,2H), 7.72(d,J=8.9 Hz,2H), 7.97(dd, J=7.8,1.7 Hz,1H), 8.04(d,J=5.1 Hz,1H), 8.17(s,1H), 8.59(dd,J=4.8,1.7 Hz,1H), 9.22(s,1H), 10.55(s,1H)

Example 10

2-(2-Acetoxyacetylaminopyridin-4-ylmethylthio)-N-(3,5-dimethylphenyl)pyridine-3-carboxamide (Compound No. 10-1)

While nitrogen was bubbled, 2-(2-bromopyridin-4-ylmethylthio)-N-(3,5-dimethylphenyl)pyridine-3-carboxamide (Reference compound No. 3-4, 1.9 g, 4.7 mmol), cesium carbonate (1.8 g, 5.6 mmol), acetoxyacetamide (1.6 g, 5.6 mmol), 4,5-bis(diphenylphosphino)-9,9-dimethylxanthene (810 mg, 1.4 mmol) and tris(dibenzylideneacetone)dipalladium(0) (430 mg, 0.47 mmol) were added to 1,4-dioxane (20 mL). The mixture was stirred for 3 hours at 100° C. in the sealed tube and diluted with ethyl acetate (300 mL), and then the whole was washed with saturated aqueous sodium hydrogen carbonate solution (300 mL). The organic layer was dried over anhydrous magnesium sulfate, and the solvent was evaporated under reduced pressure. The resulting residue was purified by silica gel column chromatography to give 1.0 g of the target compound as a pale yellow solid. (Yield 47%)

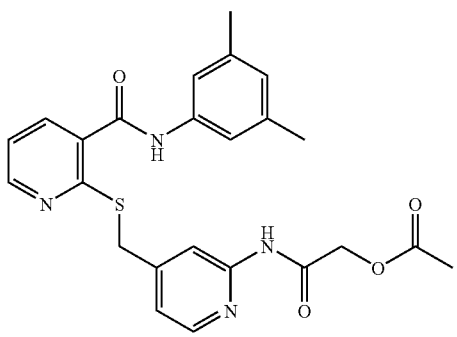

Or the compound is also synthesized as described below.

Acetoxyacetic acid (1.2 g, 10 mmol) was dissolved in pyridine (12 ml) at room temperature, acetoxyacetyl chloride (1.1 mL, 10 mmol) was added thereto, and the mixture was stirred for 4 hours at room temperature. In addition, 2-(2-aminopyridin-4-ylmethylthio)-N-(3,5-dimethylphenyl)pyridine-3-carboxamide (the free base of Compound No. 3-1, 1.0 g, 2.5 mmol) was added thereto, and the mixture was stirred for 15 hours. Ethyl acetate (100 mL) was added to the reaction mixture, and the whole was washed with 1 N hydrochloric acid (150 mL) three times, saturated aqueous sodium hydrogen carbonate solution (150 mL) twice and brine (150 mL). The organic layer was dried over anhydrous sodium sulfate. The solvent was evaporated under reduced pressure, and the resulting residue was purified by silica gel column chromatography. The resulting solid was filtered off with ethyl acetate, and then dried under reduced pressure to give 0.97 g of the target compound as a brown solid. (Yield 77%)

$^1$H-NMR(400 MHz, DMSO-$d_6$)

δ 2.10(s,3H), 2.25(s,6H), 4.40(s,2H), 4.68(s,2H), 6.76(s, 1H), 7.14(dd,J=5.1,1.5 Hz,1H), 7.28(dd,J=7.6,4.8 Hz,1H), 7.32(s,2H), 7.92(dd,J=7.6,1.8 Hz,1H), 8.10(s,1H), 8.20(d, J=5.1 Hz,1H), 8.57(dd,J=4.8,1.8 Hz,1H), 10.30 (s,1H), 10.60 (s,1H)

As described below, Compounds (No. 10-2~21) were obtained using the corresponding compounds selected from Reference compounds (No. 3-4,5), Compounds (No. 3-1~37), commercially available compounds or known compounds according to the synthetic method of Compound (No. 10-1).

2-(2-Acetoxyacetylaminopyridin-4-ylmethylthio)-N-(4-trifluoromethoxyphenyl)pyridine-3-carboxamide (Compound No. 10-2)

$^1$H-NMR(400 MHz, DMSO-$d_6$)

δ 2.09(s,3H), 4.41(s,2H), 4.68(s,2H), 7.14(dd,J=5.2,1.5 Hz,1H), 7.30(dd,J=7.6, 4.8 Hz,1H), 7.36(d,J=8.3 Hz,2H), 7.80(d,J=8.3 Hz,2H), 7.98(dd,J=7.6,1.8 Hz, 1H), 8.10(s,1H), 8.20(d,J=5.2 Hz, 1H), 8.59(dd,J=4.8,1.8 Hz,1H), 10.59(s, 1H), 10.65(s,1H)

2-(2-tert-Butoxycarbonylaminoacetylaminopyridin-4-ylmethylthio)-N-(3,5-dimethylphenyl)pyridine-3-carboxamide (Compound No. 10-3)

$^1$H-NMR(500 MHz, DMSO-$d_6$)

δ 1.39(s,9H), 2.25(s,6H), 3.75(d,J=6.3 Hz,2H), 4.40(s, 2H), 6.76(s,1H), 7.03(m,1H), 7.12(dd,J=5.1,1.7 Hz,1H), 7.28(m,1H), 7.32(s,2H), 7.92(dd,J=7.6,1.7 Hz, 1H), 8.14(d, J=0.7 Hz,1H), 8.18(dd,J=5.1,0.7 Hz,1H), 8.57(dd,J=4.9,1.7 Hz,1H), 10.30(s,1H), 10.31(s,1H)

2-[2-(2-Acetoxypropionylamino)pyridin-4-ylmethylthio]-N-(3,5-dimethylphenyl)pyridine-3-carboxamide (Compound No. 10-4)

$^1$H-NMR(400 MHz, CDCl$_3$)

δ 1.55(d,J=6.7 Hz,3H), 2.19(s,3H), 2.32(s,6H), 4.50(s, 2H), 5.31(q,J=6.7 Hz, 1H), 6.81(s,1H), 7.11-7.14(m,2H), 7.27(s,2H), 7.85(dd,J=7.6,1.8 Hz,1H), 8.03(s,1H), 8.17(d, J=5.2 Hz,1H), 8.29(s,1H), 8.43(s,1H), 8.52(dd,J=4.9,1.8 Hz,1H)

N-(3,5-Dimethylphenyl)-2-[2-(3-methoxypropionyl) aminopyridin-4-ylmethylthio]pyridine-3-carboxamide (Compound No. 10-5)

$^1$H-NMR(400 MHz, DMSO-$d_6$)

δ 2.25(s,6H), 2.60(t,J=6.2 Hz,2H), 3.21(s,3H), 3.59(t, J=6.2 Hz,2H), 4.40(s,2H), 6.76(s,1H), 7.11(dd,J=5.2,1.4 Hz,1H), 7.28(dd,J=7.6,4.9 Hz,1H), 7.32(s,2H), 7.92(dd, J=7.6,1.7 Hz,1H), 8.17(s,1H), 8.18(s,1H), 8.58(dd,J=4.9,1.7 Hz,1H), 10.31(s,1H), 10.42(s,1H)

2-(2-Acetoxyacetylaminopyridin-4-ylmethylthio)-N-(indan-5-yl)pyridine-3-carboxamide (Compound No. 10-6)

$^1$H-NMR(400 MHz, DMSO-$d_6$)

δ 2.02-2.06(m,2H), 2.10(s,3H), 2.79-2.87(m,4H), 4.40(s, 2H), 4.68(s,2H), 7.14(dd,J=5.1,1.5 Hz,1H), 7.17(d,J=8.1 Hz,1H), 7.28(dd,J=7.6,4.8 Hz,1H), 7.37(d,J=7.3 Hz,1H), 7.62(s,1H), 7.93(m,1H), 8.10(s,1H), 8.20(d,J=5.1 Hz,1H), 8.57(dd,J=4.8,1.7 Hz,1H), 10.34(s,1H), 10.60(s,1H)

2-(2-Acetoxyacetylaminopyridin-4-ylmethylthio)-N-(3-methylphenyl)pyridine-3-carboxamide (Compound No. 10-7)

$^1$H-NMR(400 MHz, DMSO-$d_6$)

δ 2.10(s,3H), 2.30(s,3H), 4.41(s,2H), 4.69(s,2H), 6.93(d, J=7.8 Hz,1H), 7.15(dd,J=5.1,1.5 Hz,1H), 7.22(t,J=7.8 Hz,1H), 7.29(dd,J=7.6,4.9 Hz,1H), 7.46(d,J=7.8 Hz,1H), 7.57(m,1H), 7.94(dd,J=7.6,1.7 Hz,1H), 8.11(s,1H), 8.20(d, J=5.1 Hz,1H), 8.57(dd,J=4.9,1.7 Hz,1H), 10.39(s,1H), 10.60 (s,1H)

2-(2-Acetoxyacetylaminopyridin-4-ylmethylthio)-N-(4-trifluoromethylphenyl)pyridine-3-carboxamide (Compound No. 10-8)

$^1$H-NMR(400 MHz, DMSO-$d_6$)

δ 2.10(s,3H), 4.42(s,2H), 4.72(s,2H), 7.15(dd,J=5.1,1.5 Hz,1H), 7.31(dd,J=7.6, 4.9 Hz,1H), 7.73(d,J=8.8 Hz,2H), 7.91(d,J=8.8 Hz,2H), 8.02(dd,J=7.6,1.7 Hz, 1H), 8.11(s,1H), 8.20(d,J=5.1 Hz,1H), 8.60(dd,J=4.9,1.7 Hz,1H), 10.60(s, 1H), 10.82(s,1H)

N-(4-Chlorophenyl)-2-(2-methoxyacetylaminopyridin-4-ylmethylthio)pyridine-3-carboxamide (Compound No. 10-9)

$^1$H-NMR(400 MHz, DMSO-$d_6$)

δ 3.35(s,3H), 4.04(s,2H), 4.42(s,2H), 7.15(dd,J=5.1,1.5 Hz,1H), 7.30(dd,J=7.6, 4.9 Hz,1H), 7.41(d,J=8.8 Hz,2H), 7.73(d,J=8.8 Hz,2H), 7.98(dd,J=7.6,1.7 Hz,1H), 8.17(s,1H), 8.19(d,J=5.1 Hz,1H), 8.60(dd,J=4.9,1.7 Hz,1H), 9.90(s,1H), 10.60(s,1H)

2-(2-Acetoxyacetylaminopyridin-4-ylmethylthio)-N-(4-tert-butylphenyl)pyridine-3-carboxamide (Compound No. 10-10)

$^1$H-NMR(400 MHz, DMSO-d$_6$)

δ 1.27(s,9H), 2.10(s,3H), 4.40(s,2H), 4.68(s,2H), 7.14(d,J=5.1 Hz,1H), 7.28(dd,J=7.6,4.9 Hz,1H), 7.36(d,J=8.5 Hz,2H), 7.60(d,J=8.5 Hz,2H), 7.94(d,J=7.6 Hz,1H), 8.10(br s,1H), 8.20(d,J=5.1 Hz,1H), 8.57(dd,J=4.9,1.7 Hz,1H), 10.39 (s,1H), 10.60(s,1H)

2-[2-(3-Methoxypropionyl)aminopyridin-4-ylmethylthio]-N-(4-trifluoromethoxyphenyl)pyridine-3-carboxamide (Compound No. 10-11)

$^1$H-NMR(400 MHz, DMSO-d$_6$)

δ 2.60(t,J=6.1 Hz,2H), 3.22(s,3H), 3.59(t,J=6.1 Hz,2H), 4.41(s,2H), 7.11(dd,J=5.1,1.5 Hz,1H), 7.31(dd,J=7.6,4.9 Hz,1H), 7.37(d,J=8.7 Hz,2H), 7.81(d,J=8.7 Hz,2H), 7.99(dd,J=7.6,1.7 Hz,1H), 8.18(d,J=5.1 Hz,1H), 8.18(s,1H), 8.60(d,J=4.9,1.7 Hz,1H), 10.42(s,1H), 10.66(s,1H)

2-(2-Acetoxyacetylaminopyridin-4-ylmethylthio)-N-(3-chloro-4-trifluoromethoxyphenyl)pyridine-3-carboxamide (Compound No. 10-12)

$^1$H-NMR(400 MHz, DMSO-d$_6$)

δ 2.10(s,3H), 4.42(s,2H), 4.68(s,2H), 7.15(d,J=5.1 Hz,1H), 7.32(d,J=7.6, 4.9 Hz,1H), 7.59(d,J=9.0 Hz,1H), 7.71(dd,J=9.0,2.4 Hz,1H), 8.01(dd,J=7.6,1.7 Hz,1H), 8.08(d,J=2.4 Hz,1H), 8.10(br s,1H), 8.20(d,J=5.1 Hz, 1H), 8.60(dd,J=4.9,1.7 Hz,1H), 10.61(s,1H), 10.81(s,1H)

2-(2-Acetoxyacetylaminopyridin-4-ylmethylthio)-N-(3-trifluoromethylphenyl)pyridine-3-carboxamide (Compound No. 10-13)

$^1$H-NMR(400 MHz, DMSO-d$_6$)

δ 2.10(s,3H), 4.42(s,2H), 4.68(s,2H), 7.15(d,J=5.1 Hz,1H), 7.32(d,J=7.6, 4.9 Hz,1H), 7.48(d,J=1.8 Hz,1H) 7.60 (t,J=8.1 Hz,1H), 7.91(d,J=8.1 Hz,1H), 8.03(dd,J=7.6,1.7 Hz,1H), 8.11 (br s, 1H), 8.18(s,1H), 8.20(d,J=5.1 Hz,1H), 8.60(dd,J=4.9,1.7 Hz,1H), 10.61(s,1H), 10.79(s,1H)

2-(2-Acetoxyacetylaminopyridin-4-ylmethylthio)-N-(3-isopropylphenyl)pyridine-3-carboxamide (Compound No. 10-14)

$^1$H-NMR(400 MHz, DMSO-d$_6$) P δ 1.20(d,J=6.8 Hz,6H), 2.13(s,3H), 2.85(m,1H), 4.40(s,2H), 4.68(s,2H), 7.15(d,J=5.1 Hz,1H), 7.23-7.30(m,2H), 7.50(m,1H), 7.58-7.60(m,2H), 7.96(dd,J=7.6,1.7 Hz,1H), 8.10(br s,1H), 8.20(d,J=5.1 Hz,1H), 8.57(dd,J=4.6,1.7 Hz,1H), 10.40(s,1H), 10.60(s,1H)

2-(2-Ethoxycarbonylacetylaminopyridin-4-ylmethylthio)-N-(4-trifluoromethoxyphenyl)pyridine-3-carboxamide (Compound No. 10-15)

$^1$H-NMR(400 MHz, DMSO-d$_6$)

δ 1.19(t,J=7.1 Hz,3H), 3.53(s,2H), 4.10(q,J=7.1 Hz,2H), 4.42(s,2H), 7.15(dd,J=5.1,1.1 Hz,1H), 7.31(d,J=7.6,4.9 Hz,1H), 7.37(d,J=8.8 Hz,2H), 7.81(d,J=8.8 Hz,2H), 7.99(dd,J=7.6,1.7 Hz,1H), 8.16(s,1H), 8.20(d,J=5.1 Hz,1H), 8.60(dd,J=4.9,1.7 Hz,1H), 10.63(s,1H), 10.66(s,1H)

2-[2-(3-tert-Butoxycarbonylaminopropionylamino)pyridin-4-ylmethylthio]-N-(4-trifluoromethoxyphenyl)pyridine-3-carboxamide (Compound No. 10-16)

$^1$H-NMR(500 MHz, CDCl$_3$)

δ 1.42(s,9H), 2.59(t,J=5.7 Hz,2H), 3.42-3.50(m,2H), 4.53 (s,2H), 5.05(s,1H), 7.09(dd,J=5.2,1.5 Hz,1H), 7.16(dd,J=7.6, 4.8 Hz,1H), 7.22(d,J=8.9 Hz,2H), 7.70(d,J=8.9 Hz,2H), 7.90 (dd,J=7.6,1.8 Hz,1H), 7.98(s,1H), 8.15(d,J=5.2 Hz,1H), 8.24 (s,1H), 8.28(s,1H), 8.54(dd,J=4.8,1.8 Hz,1H)

2-[2-((4S)-tert-Butoxycarbonylamino-5-hydroxypentanoyl)aminopyridin-4-ylmethylthio]-N-(4-trifluoromethoxyphenyl)pyridine-3-carboxamide (Compound No. 10-17)

$^1$H-NMR(400 MHz, DMSO-d$_6$)

δ 1.36(s,9H), 1.42(m,1H), 1.82(m,1H), 2.32-2.39(m,4H), 3.22(m,1H), 4.40(s,2H), 4.61(m,1H), 6.47(m,1H), 7.09(m,1H), 7.29(dd,J=7.6,4.8 Hz,1H), 7.37(d,J=8.8 Hz,2H), 7.80(d,J=8.8 Hz,2H), 7.98(dd,J=7.6,1.8 Hz,1H), 8.16(s,1H), 8.17(s,1H), 8.60(dd,J=4.8,1.8 Hz,1H), 10.34(s,1H), 10.66(s,1H)

2-[2-(2-Oxopyrrolidin-1-yl)pyridin-4-ylmethylthio]-N-(4-trifluoromethoxyphenyl)pyridine-3-carboxamide (Compound No. 10-18)

$^1$H-NMR(400 MHz, DMSO-d$_6$)

δ 1.97-2.05(m,2H), 2.51-2.57(m,2H), 3.94(t,J=7.1 Hz,2H), 4.42(s,2H), 7.15(dd,J=5.1,1.5 Hz,1H), 7.30(dd,J=7.6,4.8 Hz,1H), 7.37(d,J=8.7 Hz,2H), 7.80(d,J=8.7 Hz,2H), 7.99(dd,J=7.6,1.7 Hz,1H), 8.25(d,J=5.1 Hz,1H), 8.40(s,1H), 8.60(dd,J=4.8,1.7 Hz,1H), 10.65(s,1H)

2-(2-Cyanoacetylaminopyridin-4-ylmethylthio)-N-(4-trifluoromethoxyphenyl)pyridine-3-carboxamide (Compound No. 10-19)

$^1$H-NMR(500 MHz, CDCl$_3$)

δ 3.66(s,2H), 4.55(s,2H), 7.16(dd,J=7.6,4.9 Hz,1H), 7.23 (d,J=8.6 Hz,2H), 7.24-7.29(m,2H), 7.75(d,J=8.6 Hz,2H), 7.89(dd,J=7.6,1.8 Hz,1H), 8.16(d,J=5.5 Hz, 1H), 8.20(s,1H) 8.41(s,1H), 8.52(dd,J=4.9,1.8 Hz,1H)

2-(2-Acetoxyacetylaminopyridin-4-ylmethylthio)-N-(4-difluoromethoxyphenyl)pyridine-3-carboxamide (Compound No. 10-20)

$^1$H-NMR(400 MHz, DMSO-d$_6$)

δ 2.06(s,3H), 3.30(s,2H), 4.40(s,2H), 7.10(dd,J=5.1,1.5 Hz,1H), 7.16(t,J=74.2 Hz,1H), 7.18(d,J=8.8 Hz,2H), 7.30 (dd,J=7.6,4.9 Hz,1H), 7.72(d,J=8.8 Hz,2H), 7.97(dd,J=7.6, 1.7 Hz,1H), 8.16-8.17(m,2H), 8.59(dd,J=4.9,1.7 Hz,1H) 10.41(s,1H), 10.55(s,1H)

2-(2-tert-Butoxycarbonylaminoacetylaminopyridin-4-ylmethylthio)-N-(4-difluoromethoxyphenyl)pyridine-3-carboxamide (Compound No. 10-21)

$^1$H-NMR(400 MHz, DMSO-d$_6$)

δ 1.39(s,9H), 3.75(d,J=6.1 Hz,2H), 4.41(s,2H), 7.04(t,J=6.1 Hz,1H), 7.12(d,J=5.2 Hz,1H), 7.17(t,J=74.2 Hz,1H), 7.18(d,J=8.8 Hz,2H), 7.29(dd,J=7.6,4.9 Hz,1H), 7.72(d,

J=8.8 Hz,2H), 7.96(d,J=7.6,1.6 Hz,1H), 8.14(s,1H), 8.18(d, J=5.2 Hz,1H), 8.59(dd,J=4.9,1.6 Hz,1H), 10.31(s,1H), 10.54 (s,1H)

Example 11

2-(2-Aminopyridin-4-ylmethylthio)-N-carboxymethyl-N-(3,5-dimethylphenyl)pyridine-3-carboxamide monohydrochloride (Compound No. 11-1)

2-(2-Aminopyridin-4-ylmethylthio)-N-(tert-butoxycarbonylmethyl)-N-(3,5-dimethylphenyl)pyridine-3-carboxamide (Compound No. 7-1, 40 mg, 0.084 mmol) was dissolved in ethyl acetate (1.0 mL), and 4 N hydrochloric acid in ethyl acetate (1.0 mL) was added thereto, and then the mixture was stirred for 18 hours at room temperature. The precipitated solid was filtered off with diethyl ether and dried under reduced pressure to give 30 mg of the target compound as a colorless solid. (Yield 86%)

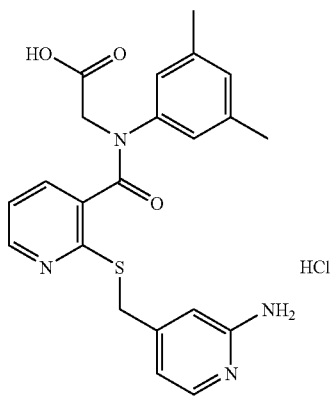

$^1$H-NMR(500 MHz, DMSO-$d_6$)

δ 2.04(s,6H), 4.44(br s,4H), 5.35(br s,1H), 6.77(s,3H), 6.87(d,J=6.9 Hz,1H), 6.98(s,1H), 7.03(s,1H), 7.31(s,1H), 7.87(d,J=6.9 Hz,1H), 8.02(s,2H), 8.32(s,1H), 13.52(s,1H)

As described below, Compounds (No. 11-2~3) were obtained using the corresponding compounds selected from Compounds (No. 10-3, 17), commercially available compounds or known compounds according to the synthetic method of Compound (No. 11-1).

2-(2-Aminoacetylaminopyridin-4-ylmethylthio)-N-(3,5-dimethylphenyl)pyridine-3-carboxamide monohydrochloride (Compound No. 11-2)

$^1$H-NMR(500 MHz, DMSO-$d_6$)

δ 2.25(s,6H), 3.81(s,2H), 4.46(s,2H), 6.76(s,1H), 7.10(br s,1H), 7.23(dd,J=5.2, 1.3 Hz,1H), 7.29(dd,J=7.6,4.9 Hz,1H), 7.34(s,2H), 7.97(dd,J=7.6,1.8 Hz,1H), 8.13(s,1H), 8.24(d, J=5.2 Hz,1H), 8.28(s,2H), 8.57(dd,J=4.9,1.5 Hz,1H), 10.36 (s,1H), 11.09(s,1H)

2-[2-((4S)-Amino-5-hydroxypentanoyl)aminopyridin-4-ylmethylthio]-N-(4-trifluoromethoxyphenyl) pyridine-3-carboxamide monohydrochloride (Compound No. 11-3)

$^1$H-NMR(500 MHz, DMSO-$d_6$)

δ 1.78-1.86(m,2H), 2.26-2.29(m,2H), 3.12(s,1H), 3.36-3.39(m,2H), 3.44(m,1H), 3.60(m,1H), 3.96(s,1H), 4.42(s, 2H), 7.17(d,J=5.2 Hz,1H), 7.31(dd,J=7.6,4.8 Hz,1H), 7.37(d, J=8.5 Hz,2H), 7.81(d,J=8.5 Hz,2H), 7.83(s,1H), 8.01(dd, J=7.6, 1.8 Hz,1H), 8.13(s,1H), 8.20(d,J=5.2 Hz,1H), 8.60(dd, J=4.8,1.8 Hz,1H), 10.64(s,1H), 10.68(s,1H)

Example 12

2-(2-Hydroxyacetylaminopyridin-4-ylmethylthio)-N-(4-trifluoromethoxyphenyl)pyridine-3-carboxamide (Compound No. 12-1)

2-(2-Acetoxyacetylaminopyridin-4-ylmethylthio)-N-(4-trifluoromethoxyphenyl)pyridine-3-carboxamide (Compound No. 10-2, 25 mg, 0.048 mmol) was dissolved in the mixture of methanol (2.0 mL) and tetrahydrofuran (1.0 mL), and 4 N aqueous sodium hydroxide solution (60 μL) was added thereto under ice-cooling. The mixture was stirred for 15 minutes at room temperature and diluted with ethyl acetate (30 mL), and then the whole was washed with saturated aqueous sodium hydrogen carbonate solution (30 mL) and brine (30 mL). The organic layer was dried over anhydrous magnesium sulfate, and the solvent was evaporated under reduced pressure to give 23 mg of the target compound quantitatively as a pale yellow solid.

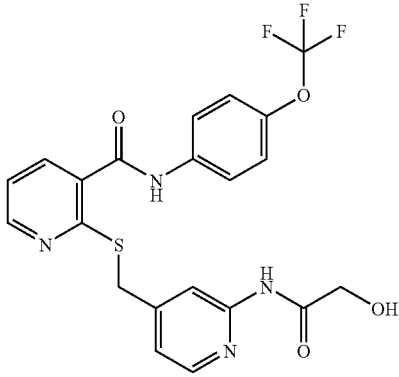

$^1$H-NMR(500 MHz, DMSO-$d_6$)

δ 4.01(d,J=5.8 Hz,2H), 4.43(s,2H), 5.72(t,J=5.8 Hz,1H), 7.15(d,J=6.7 Hz,1H), 7.31(dd,J=7.6,4.9 Hz,1H), 7.37(d, J=8.3 Hz,2H), 7.80(d,J=8.3 Hz,2H), 7.98(dd,J=7.6,1.8 Hz, H), 8.19(s,1H), 8.20(s,1H), 8.60(dd,J=4.9,1.8 Hz,1H), 9.58 (s,1H), 10.65(s,1H)

As described below, Compounds (No. 12-2~16) were obtained using the corresponding compounds selected from Compounds (No. 10-1~21), commercially available compounds or known compounds according to the synthetic method of Compound (No. 12-1).

N-(3,5-Dimethylphenyl)-2-(2-hydroxyacetylaminopyridin-4-ylmethylthio)pyridine-3-carboxamide (Compound No. 12-2)

$^1$H-NMR(500 MHz, DMSO-$d_6$)

δ 2.25(s,6H), 4.01(d,J=6.1 Hz,2H), 4.42(s,2H), 5.73(t, J=6.0 Hz,1H), 6.76(s,1H), 7.15(d,J=6.7 Hz,1H), 7.28(dd, J=7.3,4.9 Hz,1H), 7.32(s,2H), 7.93(d,J=5.8 Hz, 1H), 8.19-8.20(m,2H), 8.57(dd,J=4.9,1.8 Hz,1H), 9.58(s,1H), 10.30(s, 1H)

N-(4-Chlorophenyl)-2-(2-hydroxyacetylaminopyridin-4-ylmethylthio)pyridine-3-carboxamide (Compound No. 12-3)

$^1$H-NMR(400 MHz, DMSO-d$_6$)

δ 4.01(d,J=6.1 Hz,2H), 4.43(s,2H), 5.74(t,J=6.1 Hz,1H), 7.15(d,J=5.4 Hz,1H), 7.30(dd,J=7.6,4.9 Hz,1H), 7.41(d,J=8.8 Hz,2H), 7.72(d,J=8.8 Hz,2H), 7.98(dd,J=7.6,1.7 Hz,1H), 8.18-8.20(m,2H), 8.59(dd,J=4.9,1.7 Hz,1H), 9.59(s,1H), 10.60(s,1H)

N-(3,5-Dimethylphenyl)-2-[2-(2-hydroxypropionylamino)pyridin-4-ylmethylthio]pyridine-3-carboxamide (Compound No. 12-4)

$^1$H-NMR(400 MHz, CDCl$_3$)

δ 1.52(d,J=6.9 Hz,3H), 1.64(s,1H), 2.31(s,6H), 4.37(q,J=6.9 Hz,1H), 4.49(s,2H), 6.80(d,J=0.7 Hz,1H), 7.09-7.13 (m,2H), 7.27(s,2H), 7.84(dd,J=7.6,1.7 Hz,1H), 8.06(s,1H), 8.13(dd,J=5.1,0.5 Hz,1H), 8.34(s,1H), 8.51(dd,J=4.8,1.7 Hz,1H), 9.27(s,1H)

N-(3,5-Dimethyl-4-hydroxyphenyl)-2-(2-hydroxyacetylaminopyridin-4-ylmethylthio)pyridine-3-carboxamide (Compound No. 12-5)

$^1$H-NMR(500 MHz, DMSO-d$_6$)

δ 2.15(s,6H), 4.01-4.05(m,2H), 4.41(s,2H), 5.75(br s,1H), 7.15(dd,J=5.3,1.4 Hz,1H), 7.24(s,2H), 7.26(dd,J=7.6,4.9 Hz,1H), 7.90(dd,J=7.6,1.5 Hz,1H), 8.10(s, 1H), 8.18-8.20(m, 2H), 8.56(dd,J=4.9,1.5 Hz,1H), 9.59(s,1H), 10.09(s,1H)

2-(2-Hydroxyacetylaminopyridin-4-ylmethylthio)-N-(3-methylphenyl)pyridine-3-carboxamide (Compound No. 12-6)

$^1$H-NMR(500 MHz, DMSO-d$_6$)

δ 2.30(s,3H), 4.01(d,J=6.1 Hz,2H), 4.42(s,2H), 5.74(t,J=6.1 Hz,1H), 6.93(d,J=7.8 Hz,1H), 7.16(dd,J=5.2,1.5 Hz,1H), 7.22(t,J=7.8 Hz,1H), 7.29(dd,J=7.6, 4.9 Hz,1H), 7.46(d,J=7.8 Hz,1H), 7.56(s,1H), 7.95(dd,J=7.6,1.7 Hz,1H), 8.18-8.20(m,2H), 8.58(dd,J=4.9,1.7 Hz,1H), 9.59(s,1H), 10.38(s,1H)

2-(2-Hydroxyacetylaminopyridin-4-ylmethylthio)-N-(4-trifluoromethylphenyl)pyridine-3-carboxamide (Compound No. 12-7)

$^1$H-NMR(500 MHz, DMSO-d$_6$)

δ 4.01(d,J=6.1 Hz,2H), 4.44(s,2H), 5.74(t,J=6.1 Hz,1H), 7.16(dd,J=5.2,1.2 Hz,1H), 7.32(dd,J=7.6,4.9 Hz,1H), 7.73(d,J=8.6 Hz,2H), 7.92(d,J=8.6 Hz, 2H), 8.02(dd,J=7.6,1.8 Hz,1H), 8.18-8.20(m,2H), 8.61(dd,J=4.9,1.8 Hz,1H), 9.59(s,1H), 10.82(s,1H)

N-(4-tert-Butylphenyl)-2-(2-hydroxyacetylaminopyridin-4-ylmethylthio)pyridine-3-carboxamide (Compound No. 12-8)

$^1$H-NMR(400 MHz, DMSO-d$_6$)

δ 1.27(s,9H), 4.01(d,J=5.5 Hz,2H), 4.42(s,2H), 5.74(t,J=5.5 Hz,1H), 7.16(d,J=6.6 Hz,1H), 7.29(dd,J=7.6,4.9 Hz,1H), 7.36(d,J=8.5 Hz,2H), 7.60(d,J=8.5 Hz,2H), 7.94(d,J=7.6 Hz,1H), 8.18-8.20(m,2H), 8.58(dd,J=4.9,1.7 Hz,1H), 9.59(br s,1H), 10.40(s,1H)

2-(2-Hydroxyacetylaminopyridin-4-ylmethylthio)-N-(isoquinolin-3-yl)pyridine-3-carboxamide (Compound No. 12-9)

$^1$H-NMR(500 MHz, DMSO-d$_6$)

δ 4.03(d,J=5.9 Hz,2H), 4.44(s,2H), 5.74(t,J=5.9 Hz,1H), 7.17(dd,J=5.2,1.6 Hz,1H), 7.28(dd,J=7.6,4.9 Hz,1H), 7.58 (m,1H), 7.75(m,1H), 7.98(d,J=7.6 Hz, 1H), 8.05-8.10(m, 2H), 8.17-8.21(m,2H), 8.58(dd,J=4.9,1.6 Hz,1H), 8.60(s, 1H), 9.19(s,1H), 9.60(s,1H), 11.16(s,1H)

N-(3-Chlorophenyl)-2-(2-hydroxyacetylaminopyridin-4-ylmethylthio)pyridine-3-carboxamide (Compound No. 12-10)

$^1$H-NMR(400 MHz, DMSO-d$_6$)

δ 4.01(d,J=5.9 Hz,2H), 4.43(s,2H), 5.74(t,J=5.9 Hz,1H), 7.15-7.20(m,2H), 7.31(dd,J=7.6,4.9 Hz,1H), 7.39(t,J=7.6 Hz,1H), 7.58(m,1H), 7.88(d,J=1.7 Hz,1H), 7.99(dd,J=7.6, 1.7 Hz,1H), 8.16-8.19(m,2H), 8.60(dd,J=4.9,1.7 Hz,1H), 9.59(s,1H), 10.65(s,1H)

2-(2-Hydroxyacetylaminopyridin-4-ylmethylthio)-N-(indan-5-yl)pyridine-3-carboxamide (Compound No. 12-11)

$^1$H-NMR(400 MHz, DMSO-d$_6$)

δ 1.99-2.06(m,2H), 2.80-2.87(m,4H), 4.01(d,J=4.9 Hz,2H), 4.42(s,2H), 5.74(s,1H), 7.14-7.18(m,2H), 7.28(dd, J=7.6,4.9 Hz,1H), 7.38(d,J=6.9 Hz,1H), 7.61(s,1H), 7.93(dd, J=7.6,1.7 Hz,1H), 8.18-8.21(m,2H), 8.57(dd,J=4.9,1.7 Hz,1H), 9.58(s, 1H), 10.34(s,1H)

N-(3-Chloro-4-trifluoromethoxyphenyl)-2-(2-hydroxyacetylaminopyridin-4-ylmethylthio)pyridine-3-carboxamide (Compound No. 12-12)

$^1$H-NMR(400 MHz, DMSO-d$_6$)

δ 4.01(s,2H), 4.44(s,2H), 5.74(t,J=5.6 Hz,1H), 7.15(d,J=5.1 Hz,1H), 7.32(d,J=7.6,4.9 Hz,1H), 7.59(d,J=8.8 Hz,1H), 7.71(dd,J=8.8,2.4 Hz,1H), 8.01(dd,J=7.6,1.7 Hz,1H), 8.08(d,J=2.4 Hz,1H), 8.19(s,1H), 8.20(d,J=5.1 Hz,1H), 8.61(dd,J=4.9,1.7 Hz,1H), 9.59(s,1H), 10.81(s,1H)

2-(2-Hydroxyacetylaminopyridin-4-ylmethylthio)-N-(3-isopropylphenyl)pyridine-3-carboxamide (Compound No. 12-13)

$^1$H-NMR(400 MHz, DMSO-d$_6$)

δ 1.20(d,J=6.8 Hz,6H), 2.88(m,1H), 4.01(d,J=5.9 Hz,2H), 4.42(s,2H), 5.74(t,J=5.9 Hz,1H), 7.00(d,J=7.6 Hz,1H), 7.16 (d,J=6.6 Hz,1H), 7.26(t,J=8.2 Hz,1H), 7.29(dd,J=7.6,4.9 Hz,1H), 7.51(d,J=8.2 Hz,1H), 7.59(br s,1H), 7.96(d,J=6.6 Hz,1H), 8.19(d,J=8.2 Hz,1H), 8.20(s,1H), 8.58(dd,J=4.9,1.7 Hz,1H), 9.59(s,1H), 10.40(s,1H)

2-(2-Hydroxycarbonylacetylaminopyridin-4-ylmethylthio)-N-(4-trifluoromethoxyphenyl)pyridine-3-carboxamide (Compound No. 12-14)

$^1$H-NMR(400 MHz, DMSO-d$_6$)

δ 3.42(s,2H), 4.42(s,2H), 7.14(dd,J=5.1,1.3 Hz,1H), 7.31 (dd,J=7.6,4.9 Hz,1H), 7.37(d,J=8.8 Hz,2H), 7.81(d,J=8.8 Hz,2H), 7.98(dd,J=7.6,1.7 Hz,1H), 8.17(s,1H), 8.19(d,J=5.1 Hz,1H), 8.60(dd,J=4.9,1.7 Hz,1H), 10.58(s,1H), 10.67(s,1H)

N-(4-Difluoromethoxyphenyl)-2-(2-hydroxyacetylaminopyridin-4-ylmethylthio)pyridine-3-carboxamide (Compound No. 12-15)

$^1$H-NMR(400 MHz, DMSO-$d_6$)

δ 4.01(d,J=5.9 Hz,2H), 4.43(s,2H), 5.74(t,J=5.9 Hz,1H), 7.14-7.19(m,3H), 7.19(t,J=74.6 Hz,1H), 7.30(dd,J=7.6,4.9 Hz,1H), 7.73(d,J=8.8 Hz,2H), 7.97(dd,J=7.6,1.7 Hz,1H), 8.19-8.20(m,2H), 8.59(dd,J=4.9,1.7 Hz,1H), 9.59 (s,1H), 10.55(s,1H)

2-(2-Hydroxyacetylaminopyridin-4-ylmethylthio)-N-(3-trifluoromethylphenyl)pyridine-3-carboxamide (Compound No. 12-16)

$^1$H-NMR(400 MHz, DMSO-$d_6$)

δ 4.01(d,J=5.9 Hz,2H), 4.44(s,2H), 5.74(t,J=5.9 Hz,1H), 7.16(dd,J=5.4,1.2 Hz,1H), 7.32(dd,J=7.7,4.9 Hz,1H), 7.48(d,J=8.1 Hz,1H), 7.61(t,J=8.1 Hz,1H), 7.91(d,J=8.1 Hz,1H), 8.03(dd,J=7.7,1.7 Hz,1H), 8.17-8.20(m,3H), 8.61(dd,J=4.9,1.7 Hz,1H), 9.59(s,1H), 10.79(s,1H)

Example 13

2-[2-Bis(acetoxyacetyl)aminopyridin-4-ylmethylthio]-N-(4-trifluoromethoxyphenyl)pyridine-3-carboxamide (Compound No. 13-1)

2-(2-Aminopyridin-4-ylmethylthio)-N-(4-trifluoromethoxyphenyl)pyridine-3-carboxamide (Compound No. 3-11, 800 mg, 1.9 mmol) was dissolved in pyridine (10 mL), and acetoxyacetyl chloride (0.66 mL, 6.1 mmol) was added thereto under ice-cooling, and the mixture was stirred for 18 hours at room temperature. The mixture was diluted with ethyl acetate (100 mL), and the whole was washed with saturated aqueous sodium hydrogen carbonate solution (100 mL) and 1 N hydrochloric acid (50 mL) twice successively. The organic layer was washed with saturated aqueous sodium hydrogen carbonate solution (100 mL) again and dried over anhydrous magnesium sulfate, and then the solvent was evaporated under reduced pressure. The resulting solid was recrystallized from ethyl acetate-hexane to give 300 mg of the target compound as a colorless solid. (Yield 30%)

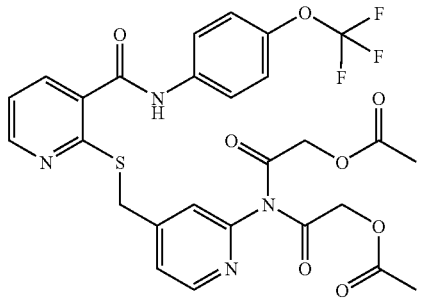

$^1$H-NMR(400 MHz, DMSO-$d_6$)

δ 2.06(s,6H), 4.48(s,2H), 4.72(s,4H), 7.31(dd,J=7.6,4.9 Hz,1H), 7.38(d,J=8.3 Hz,2H), 7.57-7.59(m,2H), 7.81(d,J=9.0 Hz,2H), 8.01(dd,J=7.6,1.7 Hz,1H), 8.49(d,J=5.8 Hz,1H), 8.56(dd,J=4.9,1.7 Hz,1H), 10.67(s,1H)

As described below, Compounds (No. 13-2~14) were obtained using the corresponding compounds selected from Compounds (No. 3-1~37), commercially available compounds or known compounds according to the synthetic method of Compound (No. 13-1).

2-[2-Bis(acetoxyacetyl)aminopyridin-4-ylmethylthio]-N-(3,5-dimethylphenyl)pyridine-3-carboxamide (Compound No. 13-2)

$^1$H-NMR(400 MHz, DMSO-$d_6$)

δ 2.07(s,6H), 2.26(s,6H), 4.47(s,2H), 4.72(s,4H), 6.76(s,1H), 7.28(dd,J=7.6,4.9 Hz,1H), 7.33(s,2H), 7.58(s,1H), 7.59(d,J=5.6 Hz,1H), 7.95(dd,J=7.6,1.7 Hz,1H), 8.49(d,J=5.6 Hz,1H), 8.54(dd,J=4.9,1.7 Hz,1H), 10.31(s,1H)

N-(3,5-Dimethylphenyl)-2-(2-ethoxycarbonyloxyacetylaminopyridin-4-ylmethylthio)pyridine-3-carboxamide (Compound No. 13-3)

$^1$H-NMR(500 MHz, DMSO-$d_6$)

δ 1.23(t,J=7.0 Hz,3H), 2.25(s,6H), 4.15(q,J=7.0 Hz,2H), 4.41(s,2H), 4.73(s,2H), 6.76(s,1H), 7.15(dd,J=5.2,1.6 Hz,1H), 7.28(dd,J=7.6,4.9 Hz,1H), 7.32(s,2H), 7.92(dd,J=7.6,1.6 Hz,1H), 8.11(s,1H), 8.20(d,J=5.2 Hz,1H), 8.57(dd,J=4.9,1.6 Hz,1H), 10.30(s,1H), 10.65(s,1H)

2-[2-(3-Hydroxycarbonylpropionyloxy)acetylaminopyridin-4-ylmethylthio]-N-(4-trifluoromethoxyphenyl)pyridine-3-carboxamide (Compound No. 13-4)

$^1$H-NMR(400 MHz, DMSO-$d_6$)

δ 2.49-2.52(m,2H), 2.60-2.64(m,2H), 4.41(s,2H), 4.71(s,2H), 7.15(dd,J=5.1,1.5 Hz,1H), 7.30(dd,J=7.6,4.9 Hz,1H), 7.37(d,J=8.3 Hz,2H), 7.80(d,J=8.3 Hz,2H), 7.98(dd,J=7.6,1.7 Hz,1H), 8.11(br s,1H), 8.20(d,J=5.1 Hz,1H), 8.59(dd,J=4.9,1.7 Hz,1H), 10.59(s,1H), 10.67(s,1H), 12.28(br s,1H)

N-(3,5-Dimethylphenyl)-2-(2-methanesulfonylaminoacetylaminopyridin-4-ylmethylthio)pyridine-3-carboxamide (Compound No. 13-5)

$^1$H-NMR(400 MHz, DMSO-$d_6$)

δ 2.25(s,6H), 2.96(s,3H), 3.89(s,2H), 4.41(s,2H), 6.76(s,1H), 7.14(m,1H), 7.28(dd,J=7.6,4.8 Hz,1H), 7.32(s,2H), 7.47(s,1H), 7.92(d,J=7.6 Hz,1H), 8.16(s,1H), 8.10(d,J=4.5 Hz,1H), 8.57(dd,J=4.8,1.5 Hz,1H), 10.30(s,1H), 10.38(s,1H)

2-(2-Diethylaminocarbonyloxyacetylaminopyridin-4-ylmethylthio)-N-(4-trifluoromethoxyphenyl)pyridine-3-carboxamide (Compound No. 13-6)

$^1$H-NMR(400 MHz, DMSO-$d_6$)

δ 1.02-1.14(m,6H), 3.20-3.34(m,4H), 4.41(s,2H), 4.66(s,2H), 7.13(dd,J=5.1,1.5 Hz,1H), 7.29(dd,J=7.6,4.9 Hz,1H), 7.37(d,J=8.8 Hz,2H), 7.80(d,J=8.8 Hz,2H), 7.98(dd,J=7.6,1.7 Hz,1H), 8.13(s,1H), 8.19(d,J=5.1 Hz,1H), 8.59(dd,J=4.9,1.7 Hz,1H), 10.52(s,1H), 10.66(s,1H)

2-(2-Dimethylaminocarbonyloxyacetylaminopyridin-4-ylmethylthio)-N-(4-trifluoromethoxyphenyl)pyridine-3-carboxamide (Compound No. 13-7)

$^1$H-NMR(400 MHz, DMSO-$d_6$)

δ 2.83(s,3H), 2.92(s,3H), 4.42(s,2H), 4.64(s,2H), 7.14(dd,J=5.1,1.3 Hz,1H), 7.30(dd,J=7.6,4.9 Hz,1H), 7.37(d,J=8.8

Hz,2H), 7.81(d,J=8.8 Hz,2H), 7.99(dd,J=7.6,1.7 Hz,1H), 8.12(s,1H), 8.19(d,J=5.1 Hz,1H), 8.60(dd,J=4.9,1.7 Hz,1H), 10.52(s,1H), 10.67(s,1H)

2-(2-Morpholinocarbonyoxyacetylaminopyridin-4-ylmethylthio)-N-(4-trifluoromethoxyphenyl)pyridine-3-carboxamide (Compound No. 13-8)

$^1$H-NMR(400 MHz, DMSO-$d_6$)
δ 3.30-3.35(m,4H), 3.58(t,J=4.9 Hz,4H), 4.42(s,2H), 4.68(s,2H), 7.14(dd,J=5.1, 1.5 Hz,1H), 7.30(dd,J=7.6,4.9 Hz,1H), 7.37(d,J=8.8 Hz,2H), 7.80(d,J=8.8 Hz,2H), 7.99(dd,J=7.6,1.7 Hz,1H), 8.12(s,1H), 8.19(d,J=5.1 Hz,1H), 8.59(dd,J=4.9,1.7 Hz,1H), 10.56(s,1H), 10.66(s,1H)

2-(2-Isobutyryloxyacetylaminopyridin-4-ylmethylthio)-N-(4-trifluoromethoxyphenyl)pyridine-3-carboxamide (Compound No. 13-9)

$^1$H-NMR(500 MHz, DMSO-$d_6$)
δ 1.13(d,J=7.0 Hz,6H), 2.64(m,1H), 4.41(s,2H), 4.70(s,2H), 7.14(dd,J=5.0,1.2 Hz,1H), 7.30(dd,J=7.5,4.7 Hz,1H), 7.37(d,J=8.9 Hz,2H), 7.80(d,J=8.9 Hz,2H), 7.98(dd,J=7.5,1.7 Hz,1H), 8.11(s,1H), 8.20(dd,J=5.0,0.6 Hz,1H), 8.59(dd,J=4.7,1.7 Hz,1H), 10.60(s,1H), 10.66(s,1H)

2-[2-(4-Hydroxycarbonylbutyryl)oxyacetylaminopyridin-4-ylmethylthio]-N-(4-trifluoromethoxyphenyl)pyridine-3-carboxamide (Compound No. 13-10)

$^1$H-NMR(400 MHz, DMSO-$d_6$)
δ 1.75-1.79(m,2H), 2.31(t,J=7.3 Hz,2H), 2.44(t,J=7.3 Hz,2H), 4.41(s,2H), 4.70(s,2H), 7.14(d,J=5.1 Hz,1H) 7.30(dd,J=7.6,4.9 Hz,1H), 7.37(d,J=8.3 Hz,2H), 7.80(d,J=8.3 Hz,2H), 7.98(dd,J=7.6,1.7 Hz,1H), 8.11(s,1H), 8.20(d,J=5.1 Hz,1H), 8.59(dd,J=4.9,1.7 Hz,1H), 10.61(s,1H), 10.67(s,1H), 12.17(br s,1H)

2-(2-Acetoxyacetoxyacetylaminopyridin-4-ylmethylthio)-N-(4-trifluoromethoxyphenyl)pyridine-3-carboxamide (Compound No. 13-11)

$^1$H-NMR(400 MHz, DMSO-$d_6$)
δ 2.11(s,3H), 4.42(s,2H), 4.77(s,2H), 4.79(s,2H), 7.15(dd,J=5.1,1.5 Hz,1H), 7.30(dd,J=7.6,4.9 Hz,1H), 7.37(d,J=8.8 Hz,2H), 7.80(d,J=8.8 Hz,2H), 7.98(dd,J=7.6,1.7 Hz,1H), 8.11(s,1H), 8.20(d,J=5.1 Hz,1H), 8.59(dd,J=4.9,1.7 Hz,1H), 10.64(s,1H), 10.66(s,1H)

2-(2-Methoxyethoxyethoxyacetylaminopyridin-4-ylmethylthio)-N-(4-trifluoromethoxyphenyl)pyridine-3-carboxamide (Compound No. 13-12)

$^1$H-NMR(400 MHz, DMSO-$d_6$)
δ 3.22(s,3H), 3.44-3.47(m,2H), 3.53-3.58(m,4H), 3.64-3.67(m,2H), 4.11(s,2H), 4.43(s,2H), 7.16(d,J=5.1 Hz,1H), 7.31(dd,J=7.6,4.9 Hz,1H), 7.37(d,J=8.9 Hz,2H), 7.81(d,J=8.9 Hz,2H), 7.99(dd,J=7.6,1.7 Hz,1H), 8.18-8.20(m,2H), 8.60(dd,J=4.9,1.7 Hz,1H), 9.78(s,1H), 10.66(s,1H)

2-(2-Dimethylaminoacetylaminoacetylaminopyridin-4-ylmethylthio)-N-(4-trifluoromethoxyphenyl)pyridine-3-carboxamide (Compound No. 13-13)

$^1$H-NMR(400 MHz, DMSO-$d_6$)
δ 2.25(s,6H), 2.92(s,2H), 3.95(d,J=5.9 Hz,2H), 4.41(s,2H), 7.12(dd,J=5.1,1.5 Hz,1H), 7.29(dd,J=7.7,4.8 Hz,1H), 7.37(d,J=8.8 Hz,2H), 7.80(d,J=8.8 Hz, 2H), 7.98(dd,J=7.7,1.6 Hz,1H), 8.01(s,1H), 8.13(s,1H), 8.19(dd,J=5.1,0.5 Hz,1H), 8.59(dd,J=4.8,1.6 Hz,1H), 10.45(s,1H), 10.66(s,1H)

N-(4-Difluoromethoxyphenyl)-2-(2-dimethylaminocarbonyloxyacetylaminopyridin-4-ylmethylthio)pyridine-3-carboxamide (Compound No. 13-14)

$^1$H-NMR(400 MHz, DMSO-$d_6$)
δ 2.83(s,3H), 2.92(s,3H), 4.41(s,2H), 4.64(s,2H), 7.13-7.20(m,3H), 7.17(t,J=74.0 Hz,1H), 7.29(dd,J=7.6,4.9 Hz,1H), 7.73(d,J=8.8 Hz,2H), 7.97(dd,J=7.6,1.7 Hz,1H), 8.11(s,1H), 8.19(d,J=4.9 Hz,1H), 8.59(dd,J=4.9,1.7 Hz,1H), 10.52(s,1H), 10.55(s,1H)

Example 14

N-(4-tert-Butylphenyl)-2-(2-dimethylaminopyridin-4-ylmethylthio)benzamide (Compound No. 14-1)

Triethylamine (6 μL, 0.44 mmol) was added to a solution of 4-chloromethyl-2-dimethylaminopyridine (36 mg, 0.21 mmol) and N-(4-tert-butylphenyl)-2-mercaptobenzamide (36 mg, 0.13 mmol) in N,N-dimethylformamide (1.0 mL) at room temperature, and the mixture was stirred for 68 hours. The mixture was diluted with ethyl acetate (30 mL), the whole was washed with saturated aqueous sodium hydrogen carbonate solution (30 mL) and brine (30 mL) successively, and dried over anhydrous magnesium sulfate. The solvent was evaporated under reduced pressure, and the resulting residue was purified by silica gel column chromatography to give 19 mg of the target compound as a pale yellow oil. (Yield 22%)

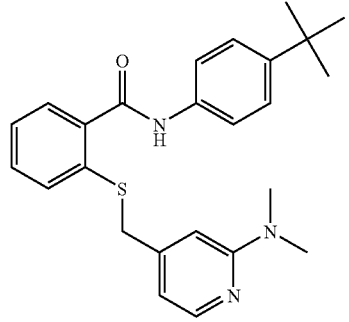

$^1$H-NMR(400 MHz, DMSO-$d_6$)
δ 1.27(s,9H), 2.95(s,6H), 4.12(s,2H), 6.55(dd,J=5.1,1.2 Hz,1H), 6.58(s,1H), 7.29(m,1H), 7.35(d,J=8.8 Hz,2H), 7.42(m,1H), 7.48-7.51(m,2H), 7.63(d,J=8.5 Hz, 2H), 7.95(dd,J=5.1,0.7 Hz,1H), 10.27(s,1H)

As described below, Compounds (No. 14-2) was obtained using the corresponding compounds selected from Reference compound (No. 10-1), commercially available compounds or known compounds according to the synthetic method of Compound (No. 14-1).

2-(2-Dimethylaminopyridin-4-ylmethylthio)-N-(3,5-dimethylphenyl)pyridine-3-carboxamide (Compound No. 14-2)

$^1$H-NMR(500 MHz, DMSO-$d_6$)
δ 2.28(s,6H), 2.96(s,6H), 4.35(s,2H), 6.55(dd,J=5.2,1.2 Hz,1H), 6.60(s,2H), 6.62(s,1H), 6.83(s,1H), 7.23(dd,J=7.6, 4.9 Hz,1H), 7.60(dd,J=7.6,1.8 Hz,1H), 7.96(d,J=5.2 Hz,1H), 8.53(dd,J=4.9,1.8 Hz,1H), 9.78(s,1H)

Example 15

2-(2-Acetylaminopyridin-4-ylmethylsulfinyl)-N-(3,5-dimethylphenyl)pyridine-3-carboxamide (Compound No. 15-1)

m-Chloroperbenzoic acid(75%, 60 mg, 0.26 mmol) was added to a solution of 2-(2-acetylaminopyridin-4-ylmethylthio)-N-(3,5-dimethylphenyl)pyridine-3-carboxamide (Compound No. 4-1, 60 mg, 0.15 mmol) in methylene chloride (3 mL) under ice-cooling, and the mixture was stirred for 1 hour. The reaction mixture was diluted with ethyl acetate (30 mL), the whole was washed with saturated aqueous sodium hydrogen carbonate solution (10 mL) twice and brine (10 mL), and dried over anhydrous magnesium sulfate. The solvent was evaporated under reduced pressure, and the precipitated solid was filtered off with ethyl acetate to give 30 mg of the target compound as a colorless solid. (Yield 48%)

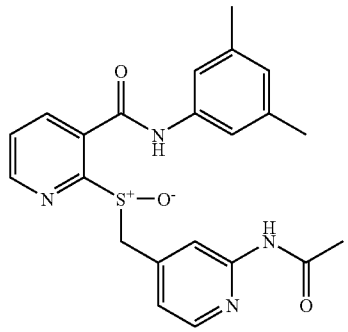

¹H-NMR(400 MHz, DMSO-$d_6$)

δ 2.08(s,3H), 2.29(s,6H), 4.20(d,J=12.2 Hz,1H), 4.48(d,J=12.2 Hz,1H), 6.80(s,1H), 6.94(dd,J=4.9,1.7 Hz,1H), 7.36 (s,2H), 7.74(dd,J=7.8,4.9 Hz,1H), 8.05(s,1H), 8.23(d,J=4.9 Hz,1H), 8.29(dd,J=7.8,1.5 Hz,1H), 8.86(dd,J=4.9,1.5 Hz,1H), 10.49(s,1H), 10.56(s,1H)

Example 16

N-(4-tert-Butylphenyl)-2-(2-chloroacetylaminopyridin-4-ylmethylthio)pyridine-3-carboxamide (Compound No. 16-1)

N-(4-tert-Butylphenyl)-2-(2-hydroxyacetylaminopyridin-4-ylmethylthio)pyridine-3-carboxamide (Compound No. 12-8, 250 mg, 0.55 mmol) was suspended in anhydrous dichloromethane (5.0 mL) under ice-cooling, and thionyl chloride (80 μL, 1.1 mmol) was added thereto. The mixture was stirred for 6 hours at room temperature, and the solvent was evaporated under reduced pressure. The resulting solid was filtered off with ethyl acetate and washed with diethyl ether to give 270 mg of the target compound quantitatively as a pale yellow solid.

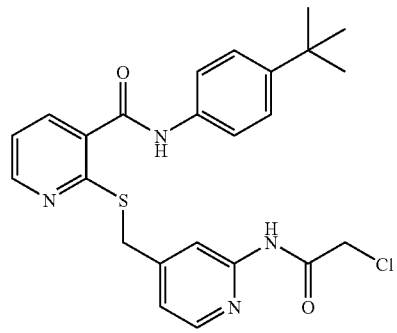

¹H-NMR(400 MHz, DMSO-$d_6$)

δ 1.27(s,9H), 4.37(s,2H), 4.45(s,2H), 7.27(d,J=5.4 Hz,1H), 7.30(dd,J=7.6,4.8 Hz,1H), 7.36(d,J=8.8 Hz,2H), 7.61(d,J=8.8 Hz,2H), 7.97(d,J=7.6 Hz,1H), 8.09(s,1H), 8.24 (d,J=5.4 Hz,1H), 8.58(dd,J=4.8,1.7 Hz,1H), 10.43(s,1H), 11.19(s,1H)

As described below, Compounds (No. 16-2~9) were obtained using the corresponding compounds selected from Compounds (No. 12-1~16), commercially available compounds or known compounds according to the synthetic method of Compound (No. 16-1).

2-(2-Chloroacetylaminopyridin-4-ylmethylthio)-N-(4-trifluoromethoxyphenyl)pyridine-3-carboxamide (Compound No. 16-2)

¹H-NMR(400 MHz, DMSO-$d_6$)

δ 4.32(s,2H), 4.43(s,2H), 7.17(dd,J=5.1,1.7 Hz,1H), 7.31 (dd,J=7.8,4.9 Hz,1H), 7.37(d,J=8.8 Hz,2H), 7.81(d,J=8.8 Hz,2H), 7.99(dd,J=7.8,1.7 Hz,1H), 8.15(s,1H), 8.21(d,J=5.1 Hz,1H), 8.60(dd,J=4.9,1.7 Hz,1H), 10.66(s,1H), 10.75(s,1H)

2-(2-Chloroacetylaminopyridin-4-ylmethylthio)-N-(4-chlorophenyl)pyridine-3-carboxamide (Compound No. 16-3)

¹H-NMR(400 MHz, DMSO-$d_6$)

δ 4.32(s,2H), 4.43(s,2H), 7.17(dd,J=5.1,1.5 Hz,1H), 7.30 (dd,J=7.6,4.9 Hz,1H), 7.41(d,J=8.8 Hz,2H), 7.73(d,J=8.8 Hz,2H), 7.98(dd,J=7.6,1.7 Hz,1H), 8.15(s,1H), 8.21(dd,J=5.1,1.5 Hz,1H), 8.60(dd,J=4.9,1.7 Hz,1H), 10.60(s,1H), 10.75(s,1H)

2-(2-Chloroacetylaminopyridin-4-ylmethylthio)-N-(3,5-dimethylphenyl)pyridine-3-carboxamide (Compound No. 16-4)

¹H-NMR(400 MHz, DMSO-$d_6$)

δ 2.25(s,6H), 4.32(s,2H), 4.42(s,2H), 6.76(s,1H), 7.17(dd,J=5.1,1.5 Hz,1H), 7.28(dd,J=7.6,4.9 Hz,1H), 7.32(s,2H), 7.93(dd,J=7.6,1.7 Hz,1H), 8.15(s,1H), 8.21(d,J=5.1,0.7 Hz,1H), 8.58(dd,J=4.9,1.7 Hz,1H), 10.30(s,1H), 10.75(s,1H)

2-(2-Chloroacetylaminopyridin-4-ylmethylthio)-N-(4-difluoromethoxyphenyl)pyridine-3-carboxamide (Compound No. 16-5)

¹H-NMR(400 MHz, DMSO-$d_6$)

δ 4.32(s,2H), 4.43(s,2H), 7.17(t,J=74.2 Hz,1H), 7.17-7.19 (m,3H), 7.30(dd,J=7.6,4.8 Hz,1H), 7.73(d,J=9.0 Hz,2H), 7.97(dd,J=7.6,1.7 Hz,1H), 8.15(s,1H), 8.19(d,J=5.1 Hz,1H), 8.59(dd,J=4.8,1.7 Hz,1H), 10.55(s,1H), 10.75(s,1H)

2-(2-Chloroacetylaminopyridin-4-ylmethylthio)-N-(3-methylphenyl)pyridine-3-carboxamide (Compound No. 16-6)

$^1$H-NMR(400 MHz, DMSO-d$_6$)

δ 2.30(s,3H), 4.32(s,2H), 4.42(s,2H), 6.93(d,J=7.8 Hz,1H), 7.17(dd,J=5.1,1.3 Hz,1H), 7.22(t,J=7.8 Hz,1H), 7.29(dd,J=7.7,4.9 Hz,1H), 7.46(d,J=7.8 Hz, 1H), 7.56(s,1H), 7.95(dd,J=7.7,1.6 Hz,1H), 8.15(s,1H), 8.22(d,J=5.1 Hz,1H), 8.58(dd,J=4.9,1.6 Hz,1H), 10.38(s,1H), 10.75(s,1H)

2-(2-Chloroacetylaminopyridin-4-ylmethylthio)-N-(4-trifluoromethylphenyl)pyridine-3-carboxamide (Compound No. 16-7)

$^1$H-NMR(400 MHz, DMSO-d$_6$)

δ 4.32(s,2H), 4.44(s,2H), 7.17(d,J=5.1,1.0 Hz,1H), 7.32 (dd,J=7.7,4.9 Hz,1H), 7.73(d,J=8.5 Hz,2H), 7.92(d,J=8.5 Hz,2H), 8.02(dd,J=7.7,1.7 Hz,1H), 8.15(s,1H), 8.22(d,J=5.1 Hz,1H), 8.61(dd,J=4.9,1.7 Hz,1H), 10.75(s,1H), 10.82(s,1H)

2-(2-Chloroacetylaminopyridin-4-ylmethylthio)-N-(3-trifluoromethylphenyl)pyridine-3-carboxamide (Compound No. 16-8)

$^1$H-NMR(400 MHz, DMSO-d$_6$)

δ 4.32(s,2H), 4.44(s,2H), 7.18(d,J=5.1,1.2 Hz,1H), 7.33 (dd,J=7.6,4.8 Hz,1H), 7.48(d,J=8.1 Hz,1H), 7.61(t,J=8.1 Hz,1H), 7.92(d,J=8.1 Hz,1H), 8.04(dd,J=7.6,1.7 Hz,1H), 8.16(s,1H), 8.19(s,1H), 8.22(d,J=5.1 Hz,1H), 8.62(dd,J=4.8, 1.7 Hz,1H), 10.76(s,1H), 10.80(s,1H)

2-(2-Chloroacetylaminopyridin-4-ylmethylthio)-N-(3-isopropylphenyl)pyridine-3-carboxamide (Compound No. 16-9)

$^1$H-NMR(500 MHz, DMSO-d$_6$)

δ 1.20(d,J=6.7 Hz,6H), 2.87(m,1H), 4.32(s,2H), 4.42(s, 2H), 7.00(d,J=7.6 Hz,1H), 7.17(dd,J=5.0,1.5 Hz,1H), 7.24-7.30(m,2H), 7.51(d,J=7.6 Hz,1H), 7.59(s,1H), 7.96(dd, J=7.6,1.5 Hz,1H), 8.15(s,1H), 8.21(dd,J=5.0,0.6 Hz,1H), 8.58(dd, J=4.9,1.5 Hz,1H), 10.39(s,1H), 10.75(s,1H)

Example 17

N-(4-tert-Butylphenyl)-2-(2-morpholinoacetylaminopyridin-4-ylmethylthio)pyridine-3-carboxamide (Compound No. 17-1)

N-(4-tert-Butylphenyl)-2-(2-chloroacetylaminopyridin-4-ylmethylthio)pyridine-3-carboxamide (Compound No. 16-1, 50 mg, 0.11 mmol) was suspended in morpholine (1.0 mL), and the mixture was stirred for 2 hours at 80° C. in the sealed tube. Ethyl acetate (50 mL) was added to the reaction mixture, the whole was washed with water (50 mL) and brine (50 mL), and dried over anhydrous sodium sulfate. The solvent was evaporated under reduced pressure, the resulting solid was filtered off with diethyl ether and dried under reduced pressure to give 17 mg of the target compound as a pale yellow solid. (Yield 32%)

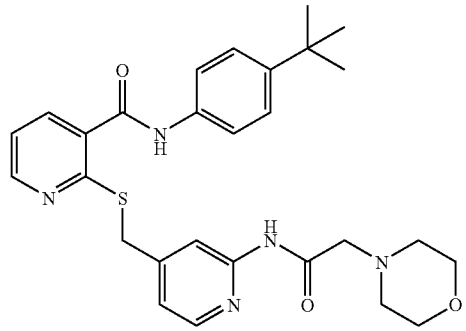

$^1$H-NMR(500 MHz, CDCl$_3$)

δ 1.32(s,9H), 2.60(t,J=4.6 Hz,4H), 3.14(s,2H), 3.78(t, J=4.6 Hz,4H), 4.51(s,2H), 7.10(dd,J=5.2,1.5 Hz,1H), 7.13 (dd,J=7.6,4.9 Hz,1H), 7.38(d,J=8.7 Hz,2H), 7.56(d,J=8.7 Hz,2H), 7.87(d,J=7.6 Hz,1H), 8.11(br s,1H), 8.18(d,J=5.2 Hz, 1H), 8.29(s,1H), 8.54(dd,J=4.9,1.7 Hz,1H), 9.48(s,1H)

As described below, Compounds (No. 17-2~88) were obtained using the corresponding compounds selected from Compounds (No. 16-1~9), commercially available compounds or known compounds according to the synthetic method of Compound (No. 17-1).

2-(2-Isopropylaminoacetylaminopyridin-4-ylmethylthio)-N-(4-trifluoromethoxyphenyl)pyridine-3-carboxamide (Compound No. 17-2)

$^1$H-NMR(400 MHz, DMSO-d$_6$)

δ 0.99(d,J=6.3 Hz,6H), 2.71(m,1H), 3.27(s,2H), 4.43(s, 2H), 7.14(dd,J=5.2,1.6 Hz,1H), 7.31(dd,J=7.6,4.9 Hz,1H), 7.37(d,J=8.8 Hz,2H), 7.81(d,J=8.8 Hz,2H), 7.99(dd,J=7.6, 1.7 Hz,1H), 8.17-8.20(m,2H), 8.60(dd,J=4.9,1.7 Hz,1H), 10.12(s,1H), 10.66(s,1H)

N-(3,5-Dimethylphenyl)-2-(2-morpholinoacetylaminopyridin-4-ylmethylthio)pyridine-3-carboxamide (Compound No. 17-3)

$^1$H-NMR(400 MHz, CDCl$_3$)

δ 2.32(s,6H), 2.60(t,J=4.6 Hz,4H), 3.14(s,2H), 3.78(t, J=4.6 Hz,4H), 4.51(s,2H), 6.81(s,1H), 7.10(dd,J=5.1,1.5 Hz,1H), 7.13(dd,J=7.6,4.9 Hz,1H), 7.27(s,2H), 7.67(m,1H), 7.87(dd,J=7.6,1.7 Hz,1H), 8.19(d,J=5.1 Hz,1H), 8.30(s,1H), 8.55(dd,J=4.9,1.7 Hz,1H), 9.48(s,1H)

2-(2-Dimethylaminoacetylaminopyridin-4-ylmethylthio)-N-(3,5-dimethylphenyl)pyridine-3-carboxamide (Compound No. 17-4)

$^1$H-NMR(400 MHz, CDCl$_3$)

δ 2.32(s,6H), 2.36(s,6H), 3.07(s,2H), 4.51(s,2H), 6.80(s, 1H), 7.08(dd,J=5.2,1.6 Hz,1H), 7.12(dd,J=7.5,4.8 Hz,1H), 7.27(s,2H), 7.86(dd,J=7.5,1.8 Hz,1H), 8.12(s,1H), 8.18(d, J=5.2 Hz,1H), 8.29(s,1H), 8.53(dd,J=4.8,1.8 Hz,1H), 9.64(s, 1H)

2-(2-Dimethylaminoacetylaminopyridin-4-ylmethylthio)-N-(4-trifluoromethoxyphenyl)pyridine-3-carboxamide (Compound No. 17-5)

¹H-NMR(500 MHz, CDCl₃)

δ 2.36(s,6H), 3.07(s,2H), 4.53(s,2H), 7.07(dd,J=5.2,1.5 Hz,1H), 7.15(dd,J=7.6, 4.9 Hz,1H), 7.21(d,J=8.2 Hz,2H), 7.70(d,J=8.2 Hz,2H), 7.88(dd,J=7.6,1.9 Hz,1H), 8.18(dd,J=5.2,0.6 Hz,1H), 8.28(d,J=0.6 Hz,1H), 8.44(s,1H), 8.54(dd,J=4.9,1.9 Hz,1H), 9.66(s,1H)

2-(2-Morpholinoacetylaminopyridin-4-ylmethylthio)-N-(4-trifluoromethoxyphenyl)pyridine-3-carboxamide (Compound No. 17-6)

¹H-NMR(500 MHz, CDCl₃)

δ 2.60(t,J=4.6 Hz,4H), 3.13(s,2H), 3.78(t,J=4.6 Hz,4H), 4.53(s,2H), 7.09(dd,J=5.2,1.8 Hz,1H), 7.15(dd,J=7.6,4.9 Hz,1H), 7.22(d,J=8.3 Hz,2H), 7.69(d,J=8.3 Hz,2H), 7.89(dd,J=7.6,1.5 Hz,1H), 8.19(d,J=5.2 Hz,1H), 8.28(s,1H), 8.36(s,1H), 8.54(dd,J=4.9,1.5 Hz,1H), 9.50(s,1H)

N-(4-tert-Butylphenyl)-2-(2-cyclopropylaminoacetylaminopyridin-4-ylmethylthio)pyridine-3-carboxamide (Compound No. 17-7)

¹H-NMR(500 MHz, CDCl₃)

δ 0.46-0.49(m,4H), 1.32(s,9H), 2.15(br s,1H), 2.27(m,1H), 3.49(s,2H), 4.51(s,2H), 7.07(dd,J=4.9,1.4 Hz,1H), 7.13(dd,J=7.3,4.9 Hz,1H), 7.38(d,J=8.4 Hz,2H), 7.56(d,J=8.4 Hz,2H), 7.88(d,J=7.3 Hz,1H), 8.15-8.17(m,2H), 8.28(s,1H), 8.54(dd,J=4.9,1.8 Hz,1H), 9.41(s,1H)

N-(4-tert-Butylphenyl)-2-[2-(N-methyl-N-(1-methylpiperidin-4-yl)amino)acetylaminopyridin-4-ylmethylthio]pyridine-3-carboxamide (Compound No. 17-8)

¹H-NMR(500 MHz, CDCl₃)

δ 1.26(s,9H), 1.77-1.80(m,2H), 1.86-2.01(m,4H), 2.26(s,3H), 2.37(s,3H), 2.80-2.91(m,3H), 3.17(s,2H), 4.51(s,2H), 7.07(dd,J=5.2,1.8 Hz,1H), 7.13(dd,J=7.5, 4.9 Hz,1H), 7.38(d,J=8.4 Hz,2H), 7.56(d,J=8.4 Hz,2H), 7.87(d,J=7.5 Hz,1H), 8.17(s,1H), 8.17(dd,J=5.2,0.8 Hz,1H), 8.29(d,J=0.8 Hz,1H), 8.54(dd,J=4.9, 1.8 Hz,1H), 9.75(s,1H)

N-(4-tert-Butylphenyl)-2-[2-(2-methylthioethyl)aminoacetylaminopyridin-4-ylmethylthio]pyridine-3-carboxamide (Compound No. 17-9)

¹H-NMR(400 MHz, CDCl₃)

δ 1.31(s,9H), 2.10(s,3H), 2.68(t,J=6.1 Hz,2H), 2.86(t,J=6.1 Hz,2H), 3.40(s,2H), 4.51(s,2H), 7.08(dd,J=5.1,1.5 Hz,1H), 7.13(dd,J=7.6,4.9 Hz,1H), 7.38(d,J=8.7 Hz,2H), 7.56(d,J=8.7 Hz,2H), 7.87(dd,J=7.6,1.7 Hz,1H), 8.17-8.18(m,2H), 8.29(s,1H), 8.53(dd,J=4.9,1.7 Hz,1H), 9.75(S,1H)

2-[2-(2-Dimethylaminoethyl)aminoacetylaminopyridin-4-ylmethylthio]-N-(4-trifluoromethoxyphenyl)pyridine-3-carboxamide (Compound No. 17-10)

¹H-NMR(400 MHz, CDCl₃)

δ 2.22(s,6H), 2.41-2.44(m,2H), 2.69-2.73(m,2H), 3.38(s,2H), 4.53(s,2H), 7.06(dd,J=5.1,1.7 Hz,1H), 7.14(dd,J=7.7,4.9 Hz,1H), 7.22(d,J=8.5 Hz,2H), 7.71(d,J=8.5 Hz,2H), 7.87(dd,J=7.7,1.8 Hz,1H), 8.18(dd,J=5.1,0.7 Hz,1H), 8.28(d,J=0.7 Hz,1H), 8.51(s,1H), 8.53(dd,J=4.9,1.8 Hz,1H), 9.93(s,1H)

2-[2-(2-Morpholinoethyl)aminoacetylaminopyridin-4-ylmethylthio]-N-(4-trifluoromethoxyphenyl)pyridine-3-carboxamide (Compound No. 17-11)

¹H-NMR(400 MHz, CDCl₃)

δ 2.41-2.43(m,4H), 2.48-2.51(m,2H), 2.73-2.76(m,2H), 3.38(s,2H), 3.63-3.66 (m,4H), 4.53(s,2H), 7.06(dd,J=5.1,1.7 Hz,1H), 7.15(dd,J=7.6,4.9 Hz,1H), 7.21(d,J=9.0 Hz,2H), 7.70(d,J=9.0 Hz,2H), 7.86(dd,J=7.6,1.7 Hz,1H), 8.17(dd,J=5.1,0.9 Hz,1H), 8.29(d,J=0.9 Hz,1H), 8.50(s,1H), 8.55(dd,J=4.9,1.7 Hz,1H), 9.84(s,1H)

2-[2-(N-Methyl-N-(1-methylpiperidin-4-yl)amino)acetylaminopyridin-4-ylmethylthio]-N-(4-trifluoromethoxyphenyl)pyridine-3-carboxamide (Compound No. 17-12)

¹H-NMR(400 MHz, CDCl₃)

δ 1.54-1.65(m,2H), 1.76-1.79(m,2H), 1.88-1.96(m,2H), 2.26(s,3H), 2.37(s,3H), 2.39(m,1H), 2.88-2.92(m,2H), 3.16(s,2H), 4.53(s,2H), 7.06(dd,J=5.1,1.5 Hz,1H), 7.14(dd,J=7.6, 4.9 Hz,1H), 7.22(d,J=8.9 Hz,2H), 7.70(d,J=8.9 Hz,2H), 7.88(dd,J=7.6,1.7 Hz,1H), 8.17(d,J=5.1 Hz,1H), 8.28(s,1H), 8.48(s,1H), 8.54(dd,J=4.9,1.7 Hz,1H), 9.76(s,1H)

2-[2-(3-Methoxypropyl)aminoacetylaminopyridin-4-ylmethylthio]-N-(4-trifluoromethoxyphenyl)pyridine-3-carboxamide (Compound No. 17-13)

¹H-NMR(400 MHz, DMSO-d₆)

δ 1.60-1.67(m,2H), 2.55(t,J=7.0 Hz,2H), 3.20(s,3H), 3.26(s,2H), 3.37(t,J=6.3 Hz,2H), 4.42(s,2H), 7.14(dd,J=5.1,1.5 Hz,1H), 7.31(dd,J=7.7,4.9 Hz,1H), 7.37(d,J=8.8 Hz,2H), 7.81(d,J=8.8 Hz,2H), 7.99(dd,J=7.7,1.7 Hz,1H), 8.18(d,J=5.1 Hz,1H), 8.21(s,1H), 8.60(dd,J=4.9,1.7 Hz,1H), 10.08(s,1H), 10.66(s,1H)

2-[2-(3-Hydroxypropyl)aminoacetylaminopyridin-4-ylmethylthio]-N-(4-trifluoromethoxyphenyl)pyridine-3-carboxamide (Compound No. 17-14)

¹H-NMR(500 MHz, DMSO-d₆)

δ 1.53-1.59(m,2H), 2.57(t,J=6.9 Hz,2H), 3.26(s,2H), 3.46(t,J=6.3 Hz,2H), 4.41(br s,1H), 4.42(s,2H), 7.14(dd,J=5.2,1.5 Hz,1H), 7.31(dd,J=7.6,4.9 Hz,1H), 7.37(d,J=8.6 Hz,2H), 7.80(d,J=8.6 Hz,2H), 7.99(dd,J=7.6,1.8 Hz,1H), 8.18(d,J=5.2 Hz,1H), 8.21(s,1H), 8.60(dd,J=4.9,1.8 Hz,1H), 10.08(s,1H), 10.66(s,1H)

2-[2-(Tetrahydropyran-4-yl)aminoacetylaminopyridin-4-ylmethylthio]-N-(4-trifluoromethoxyphenyl)pyridine-3-carboxamide (Compound No. 17-15)

¹H-NMR(400 MHz, DMSO-d₆)

δ 1.20-1.30(m,2H), 1.72-1.75(m,2H), 2.59(m,1H), 3.22-3.32(m,4H), 3.79-3.82(m,2H), 4.42(s,2H), 7.14(dd,J=5.1,1.5 Hz,1H), 7.31(dd,J=7.6,4.9 Hz,1H), 7.37(d,J=9.0 Hz,2H), 7.81(d,J=9.0 Hz,2H), 7.99(dd,J=7.6,1.7 Hz,1H), 8.19(d,J=5.1 Hz,1H), 8.20(s,1H), 8.60(dd,J=4.9,1.7 Hz,1H), 10.11(br s,1H), 10.66(s,1H)

2-[2-(4-Hydroxypiperidin-1-yl)acetylaminopyridin-4-ylmethylthio]-N-(4-trifluoromethoxyphenyl)pyridine-3-carboxamide (Compound No. 17-16)

$^1$H-NMR(400 MHz, DMSO-d$_6$)
δ 1.42-1.47(m,2H), 1.72-1.75(m,2H), 2.23-2.28(m,2H), 2.71-2.75(m,2H), 3.11(s,2H), 3.47(m,1H), 4.42(s,2H), 4.59 (d,J=4.2 Hz,1H), 7.15(d,J=6.6 Hz,1H), 7.31(dd,J=7.6,4.9 Hz,1H), 7.37(d,J=8.8 Hz,2H), 7.80(d,J=8.8 Hz,2H), 7.99(dd, J=7.6,1.7 Hz,1H), 8.18-8.19(m,2H), 8.60(dd,J=4.9,1.7 Hz,1H), 9.82(s,1H), 10.66(s,1H)

2-[2-(1,4-trans-4-Hydroxycyclohexan-1-yl)aminoacetylaminopyridin-4-ylmethylthio]-N-(4-trifluoromethoxyphenyl)pyridine-3-carboxamide (Compound No. 17-17)

$^1$H-NMR(500 MHz, DMSO-d$_6$)
δ 1.00-1.15(m,4H), 1.74-1.82(m,4H), 2.31(m,1H), 3.27(s, 2H), 3.34(m,1H), 4.42(s,2H), 4.47(d,J=4.6 Hz,1H), 7.14(d, J=5.2,1.5 Hz,1H), 7.31(dd,J=7.6,4.9 Hz,1H), 7.37(d,J=8.2 Hz,2H), 7.81(d,J=8.2 Hz,2H), 7.99(dd,J=7.6,1.8 Hz,1H), 8.17-8.20(m,2H), 8.60(dd,J=4.9,1.8 Hz,1H), 10.08(s,1H), 10.65(s,1H)

2-[2-(4-Ethoxycarbonylpiperidin-1-yl)acetylaminopyridin-4-ylmethylthio]-N-(4-trifluoromethoxyphenyl)pyridine-3-carboxamide (Compound No. 17-18)

$^1$H-NMR(500 MHz, DMSO-d$_6$)
δ 1.17(t,J=7.0 Hz,3H), 1.57-1.66(m,2H), 1.80-1.84(m,2H) 2.20-2.37(m,3H), 2.78-2.83(m,2H), 3.13(s,2H), 4.07(q, J=7.0 Hz,2H), 4.42(s,2H), 7.15(d,J=5.2,1.2 Hz,1H), 7.31(dd, J=7.6,4.9 Hz,1H), 7.37(d,J=8.6 Hz,2H), 7.81(d,J=8.6 Hz,2H), 7.99(dd,J=7.6,1.8 Hz,1H), 8.18(s,1H), 8.19(d,J=1.8 Hz,1H), 8.60(dd,J=4.9,1.8 Hz,1H), 9.84(s,1H), 10.66 (s,1H)

2-(2-Diethylaminoacetylaminopyridin-4-ylmethylthio)-N-(4-trifluoromethoxyphenyl)pyridine-3-carboxamide (Compound No. 17-19)

$^1$H-NMR(400 MHz, DMSO-d$_6$)
δ 1.00(t,J=7.1 Hz,6H), 2.59(q,J=7.1 Hz,4H), 3.16(s,2H), 4.43(s,2H), 7.16(dd,J=5.1,1.5 Hz,1H), 7.31(dd,J=7.8,4.9 Hz,1H), 7.37(d,J=8.9 Hz,2H), 7.81(d,J=8.9 Hz,2H), 7.99(dd, J=7.8,1.7 Hz,1H), 8.17-8.19(m,2H), 8.60(dd,J=4.9,1.7 Hz,1H), 9.82(s,1H), 10.66(s,1H)

2-[2-(Pyrrolidin-1-yl)acetylaminopyridin-4-ylmethylthio]-N-(4-trifluoromethoxyphenyl)pyridine-3-carboxamide (Compound No. 17-20)

$^1$H-NMR(500 MHz, DMSO-d$_6$)
δ 1.71-1.77(m,4H), 2.55-2.59(m,4H), 3.27(s,2H), 4.42(s, 2H), 7.14(dd,J=5.2,1.5 Hz,1H), 7.31(dd,J=7.6,4.9 Hz,1H), 7.37(d,J=8.6 Hz,2H), 7.80(d,J=8.6 Hz,2H), 7.99(dd,J=7.6, 1.8 Hz,1H), 8.18(d,J=5.2 Hz,1H), 8.18(s,1H), 8.60(dd,J=4.9, 1.8 Hz,1H), 9.81(s,1H), 10.66(s,1H)

N-(4-Chlorophenyl)-2-(2-dimethylaminoacetylaminopyridin-4-ylmethylthio)pyridine-3-carboxamide (Compound No. 17-21)

$^1$H-NMR(400 MHz, DMSO-d$_6$)
δ 2.28(s,6H), 3.09(s,2H), 4.42(s,2H), 7.14(d,J=6.6 Hz,1H), 7.30(dd,J=7.7,4.8 Hz,1H), 7.41(d,J=8.8 Hz,2H), 7.73(d,J=8.8 Hz,2H), 7.98(dd,J=7.7,1.6 Hz, 1H), 8.17(s,1H), 8.19(s,1H), 8.59(dd,J=4.8,1.6 Hz,1H), 9.81(s,1H), 10.60(s, 1H)

N-(4-Chlorophenyl)-2-(2-morpholinoacetylaminopyridin-4-ylmethylthio)pyridine-3-carboxamide (Compound No. 17-22)

$^1$H-NMR(500 MHz, DMSO-d$_6$)
δ 2.45-2.55(m,4H), 3.16(s,2H), 3.61(t,J=4.9 Hz,4H), 4.42 (s,2H), 7.15(d,J=4.9 Hz,1H), 7.30(dd,J=7.6,4.9 Hz,1H), 7.41 (d,J=8.9 Hz,2H), 7.72(d,J=8.9 Hz,2H), 7.98(dd,J=7.6,1.5 Hz,1H), 8.19(s,1H), 8.19(d,J=4.9 Hz,1H), 8.59(dd,J=4.9,1.5 Hz,1H), 9.89(s,1H), 10.59(s,1H)

N-(4-Chlorophenyl)-2-[2-[2-(2-dimethylaminoethyl)aminoacetylaminopyridin-4-ylmethylthio]pyridine-3-carboxamide (Compound No. 17-23)

$^1$H-NMR(400 MHz, DMSO-d$_6$)
δ 2.13(s,6H), 2.31(t,J=6.1 Hz,2H), 2.60(t,J=6.1 Hz,2H), 3.30(s,2H), 4.42(s,2H), 7.13(d,J=5.1 Hz,1H), 7.30(dd,J=7.6, 4.9 Hz,1H), 7.41(d,J=9.0 Hz,2H), 7.72(d,J=9.0 Hz, 2H), 7.98 (dd,J=7.6,1.7 Hz,1H), 8.18(d,J=5.1 Hz,1H), 8.20(s,1H), 8.59 (dd,J=4.9,1.7 Hz,1H), 10.25(br s,1H), 10.60(s,1H)

N-(4-Chlorophenyl)-2-[2-(pyridin-2-yl)methylaminoacetylaminopyridin-4-ylmethylthio]pyridine-3-carboxamide (Compound No. 17-24)

$^1$H-NMR(500 MHz, DMSO-d$_6$)
δ 3.36(s,2H), 3.84(s,2H), 4.42(s,2H), 7.13(d,J=4.9 Hz,1H), 7.24(m,1H), 7.30(dd,J=7.6,4.9 Hz,1H), 7.40-7.44 (m,3H), 7.71-7.78(m,3H), 7.98(dd,J=7.6,1.8 Hz,1H), 8.17-8.20(m,2H), 8.50(d,J=4.9 Hz,1H), 8.59(dd,J=4.9, 1.8 Hz,1H), 10.20(s,1H), 10.59(s,1H)

N-(4-Chlorophenyl)-2-[2-(pyridinium-1-yl)acetylaminopyridin-4-ylmethylthio]pyridine-3-carboxamide bromide (Compound No. 17-25)

$^1$H-NMR(400 MHz, DMSO-d$_6$)
δ 4.40(s,2H), 5.70(s,2H), 7.20(d,J=5.1 Hz,1H), 7.28(dd, J=7.6,4.9 Hz,1H), 7.41(d,J=8.8 Hz,2H), 7.73(d,J=8.8 Hz,2H), 8.01(dd,J=7.6,1.5 Hz,1H), 8.07(s,1H), 8.19-8.27(m, 3H), 8.55(dd,J=4.9,1.5 Hz,1H), 8.69(t,J=7.7 Hz,1H), 9.06(d, J=5.6 Hz,2H), 10.68(s,1H), 11.27(s,1H)

2-(2-Aminoacetylaminopyridin-4-ylmethylthio)-N-(4-trifluoromethoxyphenyl)pyridine-3-carboxamide (Compound No. 17-26)

$^1$H-NMR(400 MHz, DMSO-d$_6$)
δ 3.27(s,2H), 4.42(s,2H), 7.13(dd,J=5.2,1.5 Hz,1H), 7.31 (dd,J=7.6,4.9 Hz,1H), 7.37(d,J=8.5 Hz,2H), 7.81(d,J=8.5 Hz,2H), 7.99(dd,J=7.6,1.8 Hz,1H), 8.18(dd,J=5.2,0.8 Hz,1H), 8.21(s,1H), 8.60(dd,J=4.9,1.8 Hz,1H), 10.66(s,1H)

2-(2-Methylaminoacetylaminopyridin-4-ylmethylthio)-N-(4-trifluoromethoxyphenyl)pyridine-3-carboxamide (Compound No. 17-27)

$^1$H-NMR(400 MHz, DMSO-d$_6$)
δ 2.29(s,3H), 3.24(s,2H), 4.42(s,2H), 7.14(dd,J=5.1,1.5 Hz,1H), 7.31(dd,J=7.7, 4.8 Hz,1H), 7.37(d,J=9.0 Hz,2H), 7.80(d,J=9.0 Hz,2H), 7.99(dd,J=7.7,1.6 Hz, 1H), 8.18(d, J=5.1 Hz,1H), 8.21(s,1H), 8.60(dd,J=4.8,1.6 Hz,1H), 10.66(s,1H)

2-[2-(N-(2-Dimethylaminoethyl)-N-methylamino)acetylaminopyridin-4-ylmethylthio]-N-(4-trifluoromethoxyphenyl)pyridine-3-carboxamide (Compound No. 17-28)

$^1$H-NMR(500 MHz, DMSO-$d_6$)

δ 2.13(s,6H), 2.33(s,3H), 2.35(t,J=6.4 Hz,2H), 2.55(t, J=6.4 Hz,2H), 3.17(s,2H), 4.42(s,2H), 7.12(d,J=5.0 Hz,1H), 7.31(dd,J=7.6,4.9 Hz,1H), 7.37(d,J=8.7 Hz,2H), 7.80(d, J=8.7 Hz,2H), 7.99(dd,J=7.6,1.7 Hz,1H), 8.18(d,J=5.0 Hz,1H), 8.21(s,1H), 8.60(dd,J=4.9,1.7 Hz,1H), 10.37(s,1H), 10.65(s,1H)

2-[2-(N-(2-Diethylaminoethyl)-N-ethylamino)acetylaminopyridin-4-ylmethylthio]-N-(4-trifluoromethoxyphenyl)pyridine-3-carboxamide (Compound No. 17-29)

$^1$H-NMR(400 MHz, DMSO-$d_6$)

δ 0.91(t,J=7.2 Hz,6H), 0.98(t,J=7.1 Hz,3H), 2.43-2.51(m, 6H), 2.61(q,J=7.2 Hz,4H), 3.20(s,2H), 4.42(s,2H), 7.12(d, J=5.1 Hz,1H), 7.31(dd,J=7.6,4.9 Hz,1H), 7.37(d,J=8.8 Hz,2H), 7.81(d,J=8.8 Hz,2H), 7.99(dd,J=7.6,1.7 Hz,1H), 8.18(d,J=5.1 Hz,1H), 8.20(s,1H), 8.60(dd,J=4.9,1.7 Hz,1H), 10.40(s,1H), 10.66(s,1H)

2-[2-(3-Dimethylaminopropyl)aminoacetylamino]pyridin-4-ylmethylthio]-N-(4-trifluoromethoxyphenyl)pyridine-3-carboxamide (Compound No. 17-30)

$^1$H-NMR(500 MHz, DMSO-$d_6$)

δ 1.50-1.56(m,2H), 2.09(s,6H), 2.23(t,J=7.0 Hz,2H), 2.45-2.50(m,2H), 3.26(s,2H), 3.30(br s,1H), 4.42(s,2H), 7.13(d, J=5.2,1.5 Hz,1H), 7.31(dd,J=7.6,4.9 Hz,1H), 7.37(d,J=8.9 Hz,2H), 7.81(d,J=8.9 Hz,2H), 7.99(dd,J=7.6,1.8 Hz,1H), 8.18(d,J=5.2 Hz,1H), 8.20(s,1H), 8.60(dd,J=4.9,1.8 Hz,1H), 10.09(s,1H), 10.66(s,1H)

2-[2-(2-Hydroxyethyl)aminoacetylaminopyridin-4-ylmethylthio]-N-(4-trifluoromethoxyphenyl)pyridine-3-carboxamide (Compound No. 17-31)

$^1$H-NMR(500 MHz, DMSO-$d_6$)

δ 2.60(t,J=5.7 Hz,2H), 3.31(s,2H), 3.43-3.47(m,2H), 4.42 (s,2H), 4.57(t,J=5.3 Hz,1H), 7.14(d,J=5.0,1.5 Hz,1H), 7.31 (dd,J=7.6,4.9 Hz,1H), 7.37(d,J=8.7 Hz,2H), 7.81(d,J=8.7 Hz,2H), 7.99(dd,J=7.6,1.8 Hz,1H), 8.18(d,J=5.0 Hz,1H), 8.21(s,1H), 8.60(dd,J=4.9,1.8 Hz,1H), 10.12(br s,1H), 10.66(s,1H)

2-[2-(2-Ethoxyethyl)aminoacetylaminopyridin-4-ylmethylthio]-N-(4-trifluoromethoxyphenyl)pyridine-3-carboxamide (Compound No. 17-32)

$^1$H-NMR(400 MHz, DMSO-$d_6$)

δ 1.08(t,J=7.0 Hz,3H), 2.68(t,J=5.5 Hz,2H), 3.30(s,2H), 3.36-3.42(m,4H), 4.42(s,2H), 7.13(d,J=5.1 Hz,1H), 7.31(dd, J=7.7,4.9 Hz,1H), 7.37(d,J=8.8 Hz,2H), 7.81(d,J=8.8 Hz,2H), 7.99(dd,J=7.7,1.7 Hz,1H), 8.18(d,J=5.1 Hz,1H), 8.21(s, 1H), 8.60(dd,J=4.9,1.7 Hz,1H), 10.12(br s,1H), 10.66(s,1H)

2-[2-(2-(2-Hydroxyethoxy)ethyl)aminoacetylaminopyridin-4-ylmethylthio]-N-(4-trifluoromethoxyphenyl)pyridine-3-carboxamide (Compound No. 17-33)

$^1$H-NMR(400 MHz, DMSO-$d_6$)

δ 2.69(t,J=5.2 Hz,2H), 3.30(s,2H), 3.40(t,J=5.2 Hz,2H), 3.44-3.49(m,4H), 4.42(s,2H), 4.66(br s,1H), 7.14(dd,J=5.0, 1.5 Hz,1H), 7.31(dd,J=7.6,4.9 Hz,1H), 7.37(d,J=8.9 Hz, 2H), 7.81(d,J=8.9 Hz,2H), 7.99(dd,J=7.6,1.7 Hz,1H), 8.17 (d,J=5.0 Hz,1H), 8.22(s,1H), 8.60(dd,J=4.9,1.7 Hz,1H), 10.13(br s,1H), 10.66(s,1H)

2-[2-(Piperazin-1-yl)acetylaminopyridin-4-ylmethylthio]-N-(4-trifluoromethoxyphenyl)pyridine-3-carboxamide (Compound No. 17-34)

$^1$H-NMR(500 MHz, CDCl$_3$)

δ 2.57(br s,4H), 2.95-2.98(m,4H), 3.11(s,2H), 4.53(s,2H), 7.08(d,J=5.2,1.8 Hz,1H), 7.14(dd,J=7.6,4.9 Hz,1H), 7.22(d, J=8.6 Hz,2H), 7.70(d,J=8.6 Hz,2H), 7.88(dd,J=7.6,1.7 Hz,1H), 8.19(dd,J=5.2,0.6 Hz,1H), 8.28(d,J=0.6 Hz,1H), 8.41(br s,1H), 8.54(dd,J=4.9,1.7 Hz,1H), 9.56(s,1H)

N-(4-Difluoromethoxyphenyl)-2-(2-dimethylaminoacetylaminopyridin-4-ylmethylthio)pyridine-3-carboxamide monohydrochloride(Compound No. 17-35)

$^1$H-NMR(400 MHz, DMSO-$d_6$)

δ 2.86(s,6H), 4.18(s,2H), 4.44(s,2H), 7.18(t,J=74.2 Hz,1H), 7.18-7.24(m,3H), 7.30(dd,J=7.6,4.9 Hz,1H), 7.75(d, J=9.1 Hz, 2H), 8.03(dd,J=7.6,1.8 Hz,1H), 8.15(s,1H), 8.25 (d,J=5.1 Hz,1H), 8.59(dd,J=4.9,1.8 Hz,1H), 10.02(s,1H), 10.63(s,1H), 11.20(s,1H)

2-[2-(2-Acetylaminoethyl)aminoacetylaminopyridin-4-ylmethylthio]-N-(4-trifluoromethoxyphenyl)pyridine-3-carboxamide (Compound No. 17-36)

$^1$H-NMR(500 MHz, DMSO-$d_6$)

δ 1.79(s,3H), 2.57(t,J=6.1 Hz,2H), 3.11(m,2H), 3.29(s, 2H), 4.42(s,2H), 7.14(dd,J=5.0,1.5 Hz,1H), 7.31(dd,J=7.6, 4.9 Hz,1H), 7.37(d,J=8.9 Hz,2H), 7.79-7.84(m,3H), 7.99(dd, J=7.6,1.8 Hz,1H), 8.18(d,J=5.0 Hz,1H), 8.20(s,1H), 8.60(dd, J=4.9,1.8 Hz,1H), 10.08(s,1H), 10.66(s,1H)

N-(4-Chlorophenyl)-2-[2-(2-hydroxyethyl)aminoacetylaminopyridin-4-ylmethylthio]pyridine-3-carboxamide (Compound No. 17-37)

$^1$H-NMR(500 MHz, DMSO-$d_6$)

δ 2.60(t,J=5.5 Hz,2H), 3.30(s,2H), 3.44-3.47(m,2H), 4.42 (s,2H), 4.57(t,J=5.2 Hz,1H), 7.13(d,J=4.9 Hz,1H), 7.30(dd, J=7.5,4.9 Hz,1H), 7.41(d,J=8.7 Hz, 2H), 7.72(d,J=8.7 Hz,2H), 7.98(d,J=7.5 Hz,1H), 8.18(d,J=4.9 Hz,1H), 8.20(s, 1H), 8.59(d,J=4.9 Hz,1H), 10.13(s,1H), 10.59(s,1H)

N-(4-Chlorophenyl)-2-[2-(3-hydroxypropyl)aminoacetylaminopyridin-4-ylmethylthio]pyridine-3-carboxamide (Compound No. 17-38)

$^1$H-NMR(500 MHz, DMSO-$d_6$)

δ 1.54-1.59(m,2H), 2.57(t,J=6.9 Hz,2H), 3.27(s,2H), 3.46 (t,J=6.3 Hz,2H), 4.42(s,2H), 7.14(d,J=5.0 Hz,1H), 7.30(dd, J=7.5,5.0 Hz,1H), 7.41(d,J=8.7 Hz,2H), 7.72(d,J=8.7

Hz,2H), 7.98(d,J=7.5 Hz,1H), 8.18(d,J=5.0 Hz,1H), 8.20(s, 1H), 8.59(d,J=5.0 Hz,1H), 10.07(s,1H), 10.59(s,1H)

N-(4-Chlorophenyl)-2-[2-(N-(2-hydroxyethyl)-N-methylamino)acetylaminopyridin-4-ylmethylthio]pyridine-3-carboxamide (Compound No. 17-39)

$^1$H-NMR(500 MHz, DMSO-d$_6$)

δ 2.31(s,3H), 2.54(t,J=5.7 Hz,2H), 3.19(s,2H), 3.46-3.51 (m,2H), 4.42(s,2H), 4.63(t,J=5.2 Hz,1H), 7.14(dd,J=5.0,1.5 Hz,1H), 7.30(dd,J=7.6,4.9 Hz,1H), 7.41(d,J=8.9 Hz,2H), 7.72(d,J=8.9 Hz,2H), 7.98(m,1H), 8.18(d,J=5.0 Hz,1H), 8.20 (s,1H), 8.59(dd,J=4.9,1.5 Hz,1H), 9.95(s,1H), 10.59(s,1H)

N-(4-Chlorophenyl)-2-[2-(piperazin-1-yl)acetylaminopyridin-4-ylmethylthio]pyridine-3-carboxamide (Compound No. 17-40)

$^1$H-NMR(500 MHz, DMSO-d$_6$)

δ 2.43(br s,4H), 2.72(t,J=4.9 Hz,4H), 3.09(s,2H), 4.42(s, 2H), 7.15(m,1H), 7.30(dd,J=7.5,4.9 Hz,1H), 7.41(d,J=8.9 Hz,2H), 7.72(d,J=8.9 Hz,2H), 7.98(m,1H), 8.18-8.19(m,2H), 8.59(dd,J=4.9,1.5 Hz,1H), 9.81(s,1H), 10.59(s,1H)

2-[2-(2-Acetylaminoethyl)aminoacetylaminopyridin-4-ylmethylthio]-N-(4-chlorophenyl)pyridine-3-carboxamide (Compound No. 17-41)

$^1$H-NMR(500 MHz, DMSO-d$_6$)

δ 1.79(s,3H), 2.57(t,J=6.4 Hz,2H), 3.09-3.13(m,2H), 3.29 (d,J=2.4 Hz,2H), 4.42(s,2H), 7.14(d,J=5.2 Hz,1H), 7.30(dd, J=7.6,4.9 Hz,1H), 7.41(d,J=8.9 Hz,2H), 7.72(d,J=8.9 Hz,2H), 7.84(m,1H), 7.98(d,J=7.6 Hz,1H), 8.18(d,J=5.2 Hz,1H), 8.20(s,1H), 8.59(dd,J=4.9,1.7 Hz,1H), 10.08(s,1H), 10.59(s,1H)

N-(4-Chlorophenyl)-2-[2-(3-dimethylaminopropyl)aminoacetylaminopyridin-4-ylmethylthio]pyridine-3-carboxamide (Compound No. 17-42)

$^1$H-NMR(500 MHz, DMSO-d$_6$)

δ 1.51-1.57(m,2H), 2.10(s,6H), 2.25(t,J=7.0 Hz,2H), 2.52-2.54(m,2H), 3.26(s,2H), 4.42(s,2H), 7.13(dd,J=5.2,1.5 Hz,1H), 7.30(dd,J=7.5,4.7 Hz,1H), 7.41(d,J=8.9 Hz,2H), 7.73(d,J=8.9 Hz,2H), 7.98(dd,J=7.5,1.7 Hz,1H), 8.18(d, J=5.2 Hz,1H), 8.20(s,1H), 8.59(dd,J=4.7,1.7 Hz,1H), 10.09 (s,1H), 10.59(s,1H)

2-(2-Dimethylaminoacetylaminopyridin-4-ylmethylthio)-N-(3-methylphenyl)pyridine-3-carboxamide monohydrochloride (Compound No. 17-43)

$^1$H-NMR(400 MHz, DMSO-d$_6$)

δ 2.30(s,3H), 2.86(s,6H), 4.17(s,2H), 4.44(s,2H), 6.94(d, J=7.7 Hz,1H), 7.20-7.25(m,2H), 7.30(dd,J=7.6,4.9 Hz,1H), 7.47(d,J=7.7 Hz,1H), 7.57(s,1H), 7.99(dd,J=7.6,1.6 Hz,1H), 8.15(s,1H), 8.25(d,J=5.4 Hz,1H), 8.58(dd,J=4.9,1.6 Hz,1H), 9.97(s,1H), 10.43(s,1H), 11.15(s,1H)

2-[2-(2-Dimethylaminoethyl)aminoacetylaminopyridin-4-ylmethylthio]-N-(3-methylphenyl)pyridine-3-carboxamide (Compound No. 17-44)

$^1$H-NMR(400 MHz, DMSO-d$_6$)

δ 2.29(s,3H), 2.30(s,6H), 2.48-2.50(m,2H), 2.69(t,J=6.3 Hz,2H), 3.36-3.38(m,2H), 4.41(s,2H), 6.94(d,J=6.6 Hz,1H), 7.12-7.31(m,3H), 7.45(d,J=7.3 Hz,1H), 7.56(s,1H), 7.95(d, J=7.6 Hz,1H), 8.18-8.20(m,2H), 8.58(dd,J=4.9,1.7 Hz,1H), 10.31(s,1H), 10.39(s,1H)

N-(3-Methylphenyl)-2-[2-(piperazin-1-yl)acetylaminopyridin-4-ylmethylthio]pyridine-3-carboxamide (Compound No. 17-45)

$^1$H-NMR(400 MHz, DMSO-d$_6$)

δ 2.30(s,3H), 2.46-2.50(m,4H), 2.80(t,J=4.6 Hz,4H), 3.14 (s,2H), 4.41(s,2H), 6.93(d,J=7.9 Hz,1H), 7.15(d,J=6.1 Hz,1H), 7.22(t,J=7.9 Hz,1H), 7.29(dd,J=7.6,4.9 Hz,1H), 7.46(d,J=7.9 Hz,1H), 7.56(s,1H), 7.96(dd,J=7.6,1.7 Hz,1H), 8.18-8.20(m,2H), 8.58(dd,J=4.9,1.7 Hz,1H), 9.87(s,1H), 10.41(s,1H)

2-[2-(2-Hydroxyethyl)aminoacetylaminopyridin-4-ylmethylthio]-N-(3-methylphenyl)pyridine-3-carboxamide (Compound No. 17-46)

$^1$H-NMR(400 MHz, DMSO-d$_6$)

δ 2.30(s,3H), 2.60(t,J=5.6 Hz,2H), 3.30-3.32(m,2H), 3.43-3.47(m,2H), 4.41 (s,2H), 4.58(t,J=5.2 Hz,1H), 6.93(d,J=7.8 Hz,1H), 7.13(dd,J=5.1,1.5 Hz,1H), 7.22(t,J=7.8 Hz,1H), 7.29(dd,J=7.6,4.9 Hz,1H), 7.45(d,J=7.8 Hz,1H), 7.55 (s,1H), 7.94(dd,J=7.6,1.6 Hz,1H), 8.18(d,J=5.1 Hz,1H), 8.20(s,1H), 8.58(dd,J=4.9,1.6 Hz,1H), 10.14(s,1H), 10.38(s,1H)

N-(4-Difluoromethoxyphenyl)-2-[2-(2-dimethylaminoethyl)aminoacetylaminopyridin-4-ylmethylthio]pyridine-3-carboxamide (Compound No. 17-47)

$^1$H-NMR(400 MHz, DMSO-d$_6$)

δ 2.13(s,6H), 2.31(t,J=6.2 Hz,2H), 2.60(t,J=6.2 Hz,2H), 3.30(s,2H), 4.41(s,2H), 7.12(dd,J=5.1,1.5 Hz,1H), 7.18(d, J=8.0 Hz,2H), 7.18(t,J=74.3 Hz,1H), 7.30 (dd,J=7.6,4.8 Hz,1H), 7.72(d,J=8.0 Hz,2H), 7.97(dd,J=7.6,1.7 Hz,1H), 8.18-8.20(m,2H), 8.59(dd,J=4.8,1.7 Hz,1H), 10.25(s,1H), 10.54(s,1H)

N-(4-Difluoromethoxyphenyl)-2-[2-(2-hydroxyethyl)aminoacetylaminopyridin-4-ylmethylthio]pyridine-3-carboxamide (Compound No. 17-48)

$^1$H-NMR(400 MHz, DMSO-d$_6$)

δ 2.60(t,J=5.6 Hz,2H), 3.31(s,2H), 3.44-3.48(m,2H), 4.42 (s,2H), 4.58(t,J=5.2 Hz,1H), 7.14(dd,J=5.1,1.7 Hz,1H), 7.17 (t,J=74.2 Hz,1H), 7.18(d,J=8.8 Hz,2H), 7.30(dd,J=7.6,4.9 Hz,1H), 7.73(d,J=8.8 Hz,2H), 7.97(dd,J=7.6,1.7 Hz, 1H), 8.18-8.21(m,2H), 8.59(dd,J=4.9,1.7 Hz,1H), 10.13(s,1H), 10.55(s,1H)

2-[2-(2-Acetylaminoethyl)aminoacetylaminopyridin-4-ylmethylthio]-N-(4-difluoromethoxyphenyl)pyridine-3-carboxamide (Compound No. 17-49)

$^1$H-NMR(400 MHz, DMSO-d$_6$)

δ 1.79(s,3H), 2.57(t,J=6.4 Hz,2H), 3.09-3.13(m,2H), 3.29 (s,2H), 4.42(s,2H), 7.14(dd,J=5.1,1.5 Hz,1H), 7.18(t,J=74.2 Hz,1H), 7.18(d,J=9.0 Hz,2H), 7.30(dd,J=7.6,4.9 Hz,1H), 7.72(d,J=9.0 Hz,2H), 7.84(s,1H), 7.97(dd,J=7.6,1.6 Hz,1H), 8.18-8.20(m,2H), 8.59(dd,J=4.9,1.6 Hz,1H), 10.08(s,1H), 10.55(s,1H)

N-(4-Difluoromethoxyphenyl)-2-[2-(N-(2-dimethylaminoethyl)-N-methylamino)acetylaminopyridin-4-ylmethylthio]pyridine-3-carboxamide (Compound No. 17-50)

$^1$H-NMR(400 MHz, DMSO-d$_6$)

δ 2.14(s,6H), 2.33(s,3H), 2.36(t,J=6.4 Hz,2H), 2.56(t,J=6.4 Hz,2H), 3.17(s,2H), 4.41(s,2H), 7.13(dd,J=5.1,1.1 Hz,1H), 7.17(t,J=74.2 Hz,1H), 7.18(d,J=8.8 Hz,2H), 7.30(dd,J=7.6,4.9 Hz,1H), 7.73(d,J=8.8 Hz,2H), 7.79(dd,J=7.6,1.7 Hz,1H), 8.18-8.20(m,2H), 8.59(dd,J=4.9,1.7 Hz,1H), 10.38(s,1H), 10.55(s,1H)

2-(2-Dimethylaminoacetylaminopyridin-4-ylmethylthio)-N-(4-trifluoromethylphenyl)pyridine-3-carboxamide (Compound No. 17-51)

$^1$H-NMR(500 MHz, DMSO-d$_6$)

δ 2.28(s,6H), 3.09(s,2H), 4.43(s,2H), 7.15(dd,J=5.2,1.5 Hz,1H), 7.32(dd,J=7.6, 4.9 Hz,1H), 7.73(d,J=8.7 Hz,2H), 7.91(d,J=8.7 Hz,2H), 8.02(dd,J=7.6,1.7 Hz, 1H), 8.18(d,J=5.2 Hz,1H), 8.18(s,1H), 8.61(dd,J=4.9,1.7 Hz,1H), 9.81(s,1H), 10.81(s,1H)

2-[2-(2-Dimethylaminoethyl)aminoacetylaminopyridin-4-ylmethylthio]-N-(4-trifluoromethylphenyl)pyridine-3-carboxamide (Compound No. 17-52)

$^1$H-NMR(400 MHz, DMSO-d$_6$)

δ 2.12(s,6H), 2.30(t,J=6.1 Hz,2H), 2.59(t,J=6.1 Hz,2H), 3.30(s,2H), 4.43(s,2H), 7.13(d,J=5.2,1.5 Hz,1H), 7.31(dd,J=7.7,4.9 Hz,1H), 7.73(d,J=8.7 Hz,2H), 7.91(d,J=8.7 Hz,2H), 8.02(dd,J=7.7,1.7 Hz,1H), 8.18(d,J=5.2 Hz,1H), 8.21(s,1H), 8.61(dd,J=4.9,1.7 Hz,1H), 10.26(br s,1H), 10.82(s,1H)

2-[2-(2-Hydroxyethyl)aminoacetylaminopyridin-4-ylmethylthio]-N-(4-trifluoromethylphenyl)pyridine-3-carboxamide (Compound No. 17-53)

$^1$H-NMR(500 MHz, DMSO-d$_6$)

δ 2.60(t,J=5.5 Hz,2H), 3.30(s,2H), 3.43-3.47(m,2H), 4.43(s,2H), 4.57(t,J=5.2 Hz,1H), 7.14(dd,J=5.2,1.5 Hz,1H), 7.32(dd,J=7.6,4.9 Hz,1H), 7.73(d,J=8.7 Hz,2H), 7.92(d,J=8.7 Hz,2H), 8.02(dd,J=7.6,1.8 Hz,1H), 8.18(d,J=5.2 Hz,1H), 8.21(s,1H), 8.61(dd,J=4.9,1.8 Hz,1H), 10.22(br s,1H), 10.82(s,1H)

2-[2-(Piperazin-1-yl)acetylaminopyridin-4-ylmethylthio]-N-(4-trifluoromethylphenyl)pyridine-3-carboxamide (Compound No. 17-54)

$^1$H-NMR(400 MHz, DMSO-d$_6$)

δ 2.43(br s,4H), 2.70-2.73(m,4H), 3.10(s,2H), 4.43(s,2H), 7.15(d,J=5.5 Hz,1H), 7.32(dd,J=7.6,4.9 Hz,1H), 7.73(d,J=8.8 Hz,2H), 7.91(d,J=8.8 Hz,2H), 8.02(dd,J=7.6,1.7 Hz,1H), 8.19(d,J=5.5 Hz,1H), 8.20(s,1H), 8.61(dd,J=4.9,1.7 Hz, 1H), 9.82(br s,1H), 10.82(s,1H)

2-(2-Dimethylaminoacetylaminopyridin-4-ylmethylthio)-N-(3-trifluoromethylphenyl)pyridine-3-carboxamide (Compound No. 17-55)

$^1$H-NMR(400 MHz, DMSO-d$_6$)

δ 2.28(s,6H), 3.09(s,2H), 4.43(s,2H), 7.15(dd,J=5.1,1.7 Hz,1H), 7.32(dd,J=7.6,4.9 Hz,1H), 7.48(d,J=7.8 Hz,1H), 7.61(t,J=7.8 Hz,1H), 7.91(d,J=7.8 Hz,1H), 8.03(dd,J=7.6,1.7 Hz,1H), 8.18(s,1H), 8.18(d,J=5.1 Hz,1H), 8.19 (s,1H), 8.61(dd,J=4.9,1.7 Hz,1H), 9.81(s,1H), 10.79(s,1H)

2-[2-(2-Dimethylaminoethyl)aminoacetylaminopyridin-4-ylmethylthio]-N-(3-trifluoromethylphenyl)pyridine-3-carboxamide (Compound No. 17-56)

$^1$H-NMR(400 MHz, DMSO-d$_6$)

δ 2.13(s,6H), 2.31(t,J=6.2 Hz,2H), 2.59(t,J=6.2 Hz,2H), 3.30(s,2H), 4.43(s,2H), 7.13(dd,J=5.1,1.5 Hz,1H), 7.32(dd,J=7.7,4.9 Hz,1H), 7.48(d,J=7.9 Hz,1H), 7.61(t,J=7.9 Hz,1H), 7.91(d,J=7.9 Hz,1H), 8.03(dd,J=7.7,1.7 Hz,1H), 8.18(s,1H), 8.18(d,J=5.1 Hz,1H), 8.21(s,1H), 8.61(dd,J=4.9,1.7 Hz,1H), 10.26(br s,1H), 10.79(s,1H)

2-[2-(Piperazin-1-yl)acetylaminopyridin-4-ylmethylthio]-N-(3-trifluoromethylphenyl)pyridine-3-carboxamide monohydrochloride (Compound No. 17-57)

$^1$H-NMR(400 MHz, DMSO-d$_6$)

δ 3.40(br s,4H), 3.49(br s,4H), 4.14(br s,2H), 4.45(s,2H), 7.26(d,J=5.0 Hz,1H), 7.33(dd,J=7.6,4.9 Hz,1H), 7.49(d,J=7.9 Hz,1H), 7.61(t,J=7.9 Hz,1H), 7.95 (d,J=7.9 Hz,1H), 8.10(dd,J=7.6,1.5 Hz,1H), 8.18(br s,1H), 8.22(s,1H), 8.27(d,J=5.0 Hz,1H), 8.61(dd,J=4.9,1.5 Hz,1H), 9.70(br s,2H), 10.91(s,1H), 11.08(s,1H)

2-[2-(4-(2-Hydroxyethyl)piperazin-1-yl)acetylaminopyridin-4-ylmethylthio]-N-(4-trifluoromethoxyphenyl)pyridine-3-carboxamide (Compound No. 17-58)

$^1$H-NMR(400 MHz, DMSO-d$_6$)

δ 2.38(t,J=6.3 Hz,2H), 2.45(br s,8H), 3.13(s,2H), 3.32-3.50(m,2H), 4.38(t,J=5.4 Hz,1H), 4.42(s,2H), 7.15(d,J=5.1 Hz,1H), 7.31(dd,J=7.6,4.9 Hz,1H), 7.37(d,J=8.9 Hz,2H), 7.80(d,J=8.9 Hz,2H), 7.99(dd,J=7.6,1.5 Hz,1H), 8.18-8.19 (m,2H), 8.60(dd,J=4.9,1.5 Hz,1H), 9.81(s,1H), 10.66(s,1H)

2-[2-(4-Acetylpiperazin-1-yl)acetylaminopyridin-4-ylmethylthio]-N-(4-trifluoromethoxyphenyl)pyridine-3-carboxamide (Compound No. 17-59)

$^1$H-NMR(400 MHz, DMSO-d$_6$)

δ 1.99(s,3H), 2.46-2.53(m,4H), 3.20(s,2H), 3.45-3.47(m,4H), 4.43(s,2H), 7.15(dd, J=5.4,1.2 Hz,1H), 7.31(dd,J=7.6,4.9 Hz,1H), 7.37(d,J=8.8 Hz,2H), 7.81(d,J=8.8 Hz,2H), 7.99 (dd,J=7.6,1.6 Hz,1H), 8.18-8.20(m,2H), 8.60(dd,J=4.9, 1.6 Hz,1H), 9.94(s,1H), 10.66(s,1H)

2-[2-(2-Hydroxyethyl)aminoacetylaminopyridin-4-ylmethylthio]-N-(3-isopropylphenyl)pyridine-3-carboxamide (Compound No. 17-60)

$^1$H-NMR(500 MHz, DMSO-d$_6$)

δ 1.20(d,J=7.1 Hz,6H), 2.60(br s,2H), 2.86(m,1H), 3.30(s,2H), 3.45(t,J=5.5 Hz, 2H), 4.41(s,2H), 7.00(d,J=7.8 Hz,1H), 7.14(m,1H), 7.23-7.30(m,2H), 7.51(d,J=8.5 Hz,1H), 7.59(s,1H), 7.96(d,J=7.8 Hz,1H), 8.18(d,J=5.4 Hz,1H), 8.20(s,1H), 8.58(dd,J=4.9,1.7 Hz,1H), 10.15(s,1H), 10.39(s,1H)

2-[2-(2-Dimethylaminoethyl)aminoacetylaminopyridin-4-ylmethylthio]-N-(3-isopropylphenyl)pyridine-3-carboxamide (Compound No. 17-61)

¹H-NMR(400 MHz, CDCl₃)

δ 1.25(d,J=6.8 Hz,6H), 2.23(s,6H), 2.43(t,J=5.7 Hz,2H), 2.71(t,J=5.7 Hz,2H), 2.91(m,1H), 3.32(m,1H), 3.38(s,2H), 4.50(s,2H), 7.03(d,J=7.6 Hz,1H), 7.07(d,J=5.0 Hz,1H), 7.11 (dd,J=7.6,4.9 Hz,1H), 7.27(m,1H), 7.46(d,J=7.6 Hz,1H), 7.52(s,1H), 7.86(d,J=7.3 Hz,1H), 8.17(d,J=5.0 Hz,1H), 8.29 (m,2H), 8.52(m,1H), 9.89(s,1H)

2-[2-(4-Methylpiperazin-1-yl)acetylaminopyridin-4-ylmethylthio]-N-(4-trifluoromethoxyphenyl)pyridine-3-carboxamide (Compound No. 17-62)

¹H-NMR(400 MHz, CDCl₃)

δ 2.38(s,3H), 2.61-2.69(m,8H), 3.15(s,2H), 4.53(s,2H), 7.08(dd,J=5.1,1.1 Hz, 1H), 7.15(dd,J=7.6,4.8 Hz,1H), 7.22 (d,J=8.9 Hz,2H), 7.70(d,J=8.9 Hz,2H), 7.88(dd,J=7.6,1.7 Hz,1H), 8.19(d,J=5.1 Hz,1H), 8.28(s,1H), 8.39(s,1H), 8.54 (dd,J=4.8,1.7 Hz,1H), 9.50(s,1H)

N-(4-Chlorophenyl)-2-[2-(2-propyn-1-yl)aminoacetylaminopyridin-4-ylmethylthio]pyridine-3-carboxamide (Compound No. 17-63)

¹H-NMR(400 MHz, DMSO-d₆)

δ 2.80(br s,1H), 3.10(t,J=2.4 Hz,1H), 3.30-3.40(m,4H), 4.42(s,2H), 7.12(d,J=5.1 Hz,1H), 7.30(dd,J=7.6,4.9 Hz,1H), 7.41(d,J=8.8 Hz,2H), 7.73(d,J=8.8 Hz,2H), 7.98(dd,J=7.6, 1.7 Hz,1H), 8.17-8.20(m,2H), 8.59(dd,J=4.9,1.7 Hz,1H), 10.04(s,1H), 10.60(s,1H)

N-(4-Chlorophenyl)-2-[2-(4-(2-hydroxyethyl)piperazin-1-yl)acetylaminopyridin-4-ylmethylthio]pyridine-3-carboxamide (Compound No. 17-64)

¹H-NMR(400 MHz, DMSO-d₆)

δ 2.39(t,J=6.3 Hz,2H), 2.40-2.60(m,8H), 3.13(s,2H), 3.45-3.49(m,2H), 4.38(t,J=5.1 Hz,1H), 4.42(s,2H), 7.15(d,J=5.9 Hz,1H), 7.30(dd,J=7.6, 4.9 Hz,1H), 7.41(d,J=8.8 Hz,2H), 7.72(d,J=8.8 Hz,2H), 7.98(m,1H) 8.18(s,1H), 8.19(d,J=5.9 Hz,1H), 8.59(dd,J=4.9,1.5 Hz,1H), 9.81(s,1H), 10.60(s,1H)

N-(4-Difluoromethoxyphenyl)-2-[2-(N-(2-hydroxyethyl)-N-methylamino)acetylaminopyridin-4-ylmethylthio]pyridine-3-carboxamide (Compound No. 17-65)

¹H-NMR(400 MHz, DMSO-d₆)

δ 2.31(s,3H), 2.54(t,J=5.8 Hz,2H), 3.19(s,2H), 3.47-3.51 (m,2H), 4.42(s,2H), 4.63(t,J=5.3 Hz,1H), 7.14(dd,J=5.0,1.5 Hz,1H), 7.17(d,J=9.0 Hz,2H), 7.17 (t,J=74.2 Hz,1H), 7.30 (dd,J=7.6,4.9 Hz,1H), 7.72(d,J=9.0 Hz,2H), 7.97(dd,J=7.6, 1.7 Hz,1H), 8.16-8.20(m,2H), 8.59(dd,J=4.9,1.7 Hz,1H), 10.41(s,1H), 10.54(s,1H)

N-(4-Difluoromethoxyphenyl)-2-[2-(piperazin-1-yl)acetylaminopyridin-4-ylmethylthio]pyridine-3-carboxamide (Compound No. 17-66)

¹H-NMR(400 MHz, DMSO-d₆)

δ 2.42(br s,4H), 2.72(br s,4H), 3.10(s,2H), 4.42(s,2H), 7.15(m,1H), 7.17(t,J=74.2 Hz,1H), 7.18(d,J=8.9 Hz,2H), 7.30(dd,J=7.6,4.9 Hz,1H), 7.72(d,J=8.9 Hz,2H), 7.98(d, J=7.6 Hz,1H), 8.18-8.19(m,2H), 8.59(dd,J=4.9,1.7 Hz,1H), 9.82 (s,1H), 10.55(s,1H)

2-(2-Aminoacetylaminopyridin-4-ylmethylthio)-N-(4-chlorophenyl)pyridine-3-carboxamide (Compound No. 17-67)

¹H-NMR(400 MHz, DMSO-d₆)

δ 3.33-3.34(m,2H), 4.42(s,2H), 7.14(m,1H), 7.30(dd, J=7.6,4.9 Hz,1H), 7.41(d,J=8.8 Hz,2H), 7.73(d,J=8.8 Hz,2H), 7.95-8.01(m,1H), 8.19(m,1H), 8.59(dd,J=4.9,1.7 Hz,1H), 10.64(s,1H)

2-(2-Acetylaminoacetylaminopyridin-4-ylmethylthio)-N-(4-chlorophenyl)pyridine-3-carboxamide (Compound No. 17-68)

¹H-NMR(400 MHz, DMSO-d₆)

δ 1.87(s,3H), 3.89(d,J=5.9 Hz,2H), 4.41(s,2H), 7.12(dd, J=5.1,1.2 Hz,1H), 7.29(dd,J=7.6,4.9 Hz,1H), 7.41(d,J=8.8 Hz,2H), 7.73(d,J=8.8 Hz,2H), 7.97(dd,J=7.6,1.7 Hz,1H), 8.13-8.19(m,3H), 8.59(dd,J=4.9,1.7 Hz,1H), 10.39 (s,1H), 10.60(s,1H)

N-(4-Difluoromethoxyphenyl)-2-(2-phthaloylaminoacetylaminopyridin-4-ylmethylthio)pyridine-3-carboxamide (Compound No. 17-69)

¹H-NMR(400 MHz, DMSO-d₆)

δ 4.39(s,2H), 4.49(s,2H), 7.15-7.19(m,3H), 7.18(t,J=74.2 Hz,1H), 7.27(dd,J=7.6,4.9 Hz,1H), 7.70(d,J=9.0 Hz,2H), 7.83-7.95(m,5H), 8.06(s,1H), 8.22(d,J=5.1 Hz,1H), 8.55(dd, J=4.9,1.7 Hz,1H), 10.52(s,1H), 10.90(s,1H)

N-(4-Difluoromethoxyphenyl)-2-[2-(4-methylpiperazin-1-yl)acetylaminopyridin-4-ylmethylthio]pyridine-3-carboxamide (Compound No. 17-70)

¹H-NMR(400 MHz, DMSO-d₆)

δ 2.17(s,3H), 2.36(br s,4H), 2.51(br s,4H), 3.14(s,2H), 4.42(s,2H), 7.14-7.19(m,3H), 7.18(t,J=74.2 Hz,1H), 7.30(dd, J=7.6,4.9 Hz,1H), 7.73(d,J=9.0 Hz,2H), 7.97(dd,J=7.6,1.7 Hz,1H), 8.18-8.19 (m,2H), 8.59(dd,J=4.9,1.7 Hz,1H), 9.82(s, 1H), 10.54(s,1H)

N-(4-Difluoromethoxyphenyl)-2-(2-isopropylaminoacetylaminopyridin-4-ylmethylthio)pyridine-3-carboxamide (Compound No. 17-71)

¹H-NMR(400 MHz, DMSO-d₆)

δ 0.99(d,J=6.1 Hz,6H), 2.72(m,1H), 3.26(s,2H), 4.42(s, 2H), 7.14(dd,J=5.1,1.5 Hz,1H), 7.17(t,J=74.2 Hz,1H), 7.18 (d,J=9.0 Hz,2H), 7.30(dd,J=7.6,4.9 Hz. 1H), 7.72(d,J=9.0 Hz,2H), 7.97(dd,J=7.6,1.7 Hz,1H), 8.16-8.20(m,2H), 8.59 (dd,J=4.9,1.7 Hz,1H), 10.10(s,1H), 10.54(s,1H)

2-[2-(2-Dimethylaminoethyl)aminoacetylaminopyridin-4-ylmethylthio]-N-(3,5-dimethylphenyl)pyridine-3-carboxamide (Compound No. 17-72)

$^1$H-NMR(400 MHz, DMSO-d$_6$)

δ 2.15(s,6H), 2.25(s,6H), 2.33(t,J=6.1 Hz,2H), 2.61(t, J=6.1 Hz,2H), 3.31(s,2H), 4.41(s,2H), 6.76(s,1H), 7.13(dd, J=5.1,1.5 Hz,1H), 7.28(dd,J=7.6,4.9 Hz,1H), 7.32(s,2H), 7.92(dd,J=7.6,1.7 Hz,1H), 8.18-8.20(m,2H), 8.57(dd,J=4.9, 1.7 Hz, 1H), 10.26(s,1H), 10.29(s,1H)

N-(3,5-Dimethylphenyl)-2-(2-isopropylaminoacetylaminopyridin-4-ylmethylthio)pyridine-3-carboxamide (Compound No. 17-73)

$^1$H-NMR(400 MHz, DMSO-d$_6$)

δ 0.99(d,J=6.1 Hz,6H), 2.25(s,6H), 2.73(m,1H), 3.27(s, 2H), 4.41(s,2H), 6.76(s, 1H), 7.14(dd,J=5.1,1.2 Hz,1H), 7.28 (dd,J=7.6,4.9 Hz,1H), 7.32(s,2H), 7.92(dd,J=7.6,1.7 Hz,1H), 8.16-8.20(m,2H), 8.57(dd,J=4.9,1.7 Hz,1H), 10.12(s,1H), 10.30(s,1H)

2-[2-(2-Propen-1-yl)aminoacetylaminopyridin-4-ylmethylthio]-N-(4-trifluoromethoxyphenyl)pyridine-3-carboxamide (Compound No. 17-74)

$^1$H-NMR(400 MHz, DMSO-d$_6$)

δ 3.18(d,J=5.4 Hz,2H), 3.27(s,2H), 4.42(s,2H), 5.07(d, J=10.0 Hz,1H), 5.17(d,J=17.1 Hz,1H), 5.83(m,1H), 7.14(d, J=5.0 Hz,1H), 7.31(dd,J=7.7,4.9 Hz,1H), 7.37(d,J=8.7 Hz,2H), 7.81(d,J=8.7 Hz,2H), 7.99(d,J=7.7 Hz,1H), 8.18(d, J=5.0 Hz,1H), 8.20(s,1H), 8.60(d,J=4.9 Hz,1H), 10.09(br s,1H), 10.66(s,1H)

2-[2-(2-Methylaziridin-1-yl)acetylaminopyridin-4-ylmethylthio]-N-(4-trifluoromethoxyphenyl)pyridine-3-carboxamide (Compound No. 17-75)

$^1$H-NMR(400 MHz, DMSO-d$_6$)

δ 1.13(d,J=5.4 Hz,3H), 1.45(d,J=6.3 Hz,1H), 1.54(d,J=3.7 Hz,1H), 1.63(m,1H), 3.01(d,J=15.9 Hz,1H), 3.10(d,J=15.9 Hz,1H), 4.43(s,2H), 7.16(dd,J=5.1, 1.5 Hz,1H), 7.31(dd, J=7.6,4.9 Hz,1H), 7.37(d,J=8.8 Hz,2H), 7.81(d,J=8.8 Hz,2H), 7.99(dd,J=7.6,1.7 Hz,1H), 8.20(d,J=5.1 Hz,1H), 8.20(s,1H), 8.60(dd,J=4.9,1.7 Hz,1H), 9.83(s,1H), 10.66(s, 1H)

2-[2-(N-Ethyl-N-methylaminoacetylamino)pyridin-4-ylmethylthio]-N-(4-trifluoromethoxyphenyl)pyridine-3-carboxamide (Compound No. 17-76)

$^1$H-NMR(400 MHz, DMSO-d$_6$)

δ 1.02(t,J=7.1 Hz,3H), 2.28(s,3H), 2.49-2.51(m,2H), 3.13 (s,2H), 4.43(s,2H), 7.15(dd,J=5.1,1.5 Hz,1H), 7.31(dd,J=7.6, 4.9 Hz,1H), 7.37(d,J=8.8 Hz,2H), 7.81(d,J=8.8 Hz,2H), 7.99 (dd,J=7.6,1.7 Hz,1H), 8.18(d,J=5.1 Hz,1H), 8.19(s,1H), 8.60 (dd,J=4.9,1.7 Hz,1H), 9.80(s,1H), 10.66(s,1H)

2-[2-(Azetidin-1-yl)acetylaminopyridin-4-ylmethylthio]-N-(4-trifluoromethoxyphenyl)pyridine-3-carboxamide (Compound No. 17-77)

$^1$H-NMR(400 MHz, DMSO-d$_6$)

δ 1.99-2.06(m,2H), 3.21(s,2H), 3.28(t,J=7.0 Hz,4H), 4.42 (s,2H), 7.14(d,J=5.1 Hz,1H), 7.30(dd,J=7.6,4.9 Hz,1H), 7.37 (d,J=8.9 Hz,2H), 7.80(d,J=8.9 Hz,2H), 7.99(d,J=7.6 Hz,1H), 8.15(s,1H), 8.18(d,J=5.1 Hz,1H), 8.60(dd,J=4.9,1.7 Hz,1H), 9.81(s,1H), 10.66(s,1H)

2-[2-(2-(Pyrrolidin-1-yl)ethyl)aminoacetylaminopyridin-4-ylmethylthio]-N-(4-trifluoromethoxyphenyl)pyridine-3-carboxamide (Compound No. 17-78)

$^1$H-NMR(400 MHz, DMSO-d$_6$)

δ 1.65-1.67(m,4H), 2.41-2.48(m,6H), 2.63(t,J=6.2 Hz,2H), 3.32(s,2H), 4.42(s,2H), 7.13(dd,J=5.1,1.5 Hz,1H), 7.30(dd,J=7.6,4.9 Hz, 1H), 7.37(d,J=8.8 Hz,2H), 7.80(d, J=8.8 Hz,2H), 7.99(dd,J=7.6,1.6 Hz,1H), 8.18(d,J=5.1 Hz,1H), 8.20(s,1H), 8.60(dd,J=4.9,1.6 Hz,1H), 10.23(s,1H), 10.66(s,1H)

N-(4-Chlorophenyl)-2-[2-(2-(pyrrolidin-1-yl)ethyl)aminoacetylaminopyridin-4-ylmethylthio]pyridine-3-carboxamide (Compound No. 17-79)

$^1$H-NMR(500 MHz, DMSO-d$_6$)

δ 1.65-1.66(m,4H), 2.42-2.45(m,4H), 2.47-2.52(m,2H), 2.62-2.64(m,2H), 3.29(s,2H), 4.42(s,2H), 7.12(dd,J=5.2,1.7 Hz,1H), 7.30(dd,J=7.6,4.9 Hz,1H), 7.41(d,J=8.9 Hz,2H), 7.72(d,J=8.9 Hz,2H), 7.98(dd,J=7.6,1.7 Hz,1H), 8.18(d, J=5.2 Hz,1H), 8.20(s,1H), 8.59(dd,J=4.9,1.7 Hz,1H), 10.22 (s,1H), 10.59(s,1H)

2-[2-(1,4-Dihydro-4-oxopyridin-1-yl)acetylaminopyridin-4-ylmethylthio]-N-(4-trifluoromethoxyphenyl)pyridine-3-carboxamide (Compound No. 17-80)

$^1$H-NMR(400 MHz, DMSO-d$_6$)

δ 4.41(s,2H), 4.82(s,2H), 6.06(d,J=7.6 Hz,2H), 7.16(d, J=5.1 Hz,1H), 7.30(dd,J=7.6,4.9 Hz,1H), 7.37(d,J=8.9 Hz,2H), 7.58(d,J=7.6 Hz,2H), 7.80(d,J=8.9 Hz,2H), 7.98(dd, J=7.6,1.7 Hz,1H), 8.11(s,1H), 8.22(d,J=5.1 Hz,1H), 8.58(dd, J=4.9,1.7 Hz,1H), 10.65(s,1H), 10.83(s,1H)

N-(4-Chlorophenyl)-2-[2-(4-methylpiperazin-1-yl)acetylaminopyridin-4-ylmethylthio]pyridine-3-carboxamide (Compound No. 17-81)

$^1$H-NMR(400 MHz, DMSO-d$_6$)

δ 2.17(s,3H), 2.35(br s,6H), 3.14(s,2H), 3.32(s,2H), 4.42 (s,2H), 7.15(d,J=6.3 Hz,1H), 7.30(dd,J=7.6,4.9 Hz,1H), 7.41 (d,J=8.8 Hz,2H), 7.72(d,J=8.8 Hz,2H), 7.98(dd,J=7.6,1.6 Hz,1H), 8.18-8.19(m,2H), 8.59(dd,J=4.9,1.6 Hz,1H), 9.82(s, 1H), 10.60(s,1H)

2-[2-(Imidazol-1-yl)acetylaminopyridin-4-ylmeth-ylthio]-N-(4-trifluoromethoxyphenyl)pyridine-3-carboxamide (Compound No. 17-82)

$^1$H-NMR(400 MHz, DMSO-d$_6$)

δ 4.41(s,2H), 4.94(s,2H), 6.88(d,J=1.0 Hz,1H), 7.15-7.16 (m,2H), 7.29(dd,J=7.6,4.9 Hz,1H), 7.37(d,J=8.8 Hz,2H), 7.62(s,1H), 7.79(d,J=8.8 Hz,2H), 7.98(dd,J=7.6,1.7 Hz,1H), 8.11(s,1H), 8.22(d,J=5.1 Hz,1H), 8.57(dd,J=4.9,1.7 Hz,1H), 10.65(s,1H), 10.78(s,1H)

N-(4-Chlorophenyl)-2-[2-(azetidin-1-yl)acetylami-nopyridin-4-ylmethylthio]pyridine-3-carboxamide (Compound No. 17-83)

$^1$H-NMR(400 MHz, DMSO-d$_6$)

δ 1.90-2.08(m,2H), 3.21(s,2H), 3.25-3.34(m,4H), 4.41(s, 2H), 7.14(d,J=5.1 Hz,1H), 7.30(dd,J=7.6,4.9 Hz,1H), 7.41(d, J=8.8 Hz,2H), 7.72(d,J=8.8 Hz,2H), 7.98(m,1H), 8.15-8.19 (m,2H), 8.59(dd,J=4.9,1.7 Hz,1H), 9.80(s,1H), 10.59(s,1H)

N-(3,5-Dimethylphenyl)-2-[2-(3-hydroxypropyl) aminoacetylaminopyridin-4-ylmethylthio]pyridine-3-carboxamide (Compound No. 17-84)

$^1$H-NMR(400 MHz, DMSO-d$_6$)

δ 1.50-1.60(m,2H), 2.25(s,6H), 2.57(t,J=6.8 Hz,2H), 3.27 (s,2H), 3.46(t,J=6.8 Hz,2H), 4.40(br s,1H), 4.41(s,2H), 6.76 (s,1H), 7.14(d,J=5.1 Hz,1H), 7.28(dd,J=7.6,4.9 Hz,1H), 7.32 (s,2H), 7.93(dd,J=7.6,1.7 Hz,1H), 8.17-8.21(m,2H), 8.57(dd, J=4.9,1.7 Hz,1H), 10.07(br s,1H), 10.59(s,1H)

N-(3,5-Dimethylphenyl)-2-[2-(2-morpholinoethyl) aminoacetylaminopyridin-4-ylmethylthio]pyridine-3-carboxamide (Compound No. 17-85)

$^1$H-NMR(400 MHz, DMSO-d$_6$)

δ 2.25(s,6H), 2.30-2.40(m,6H), 2.63(t,J=6.1 Hz,2H), 3.30 (s,2H), 3.54(t,J=4.6 Hz,4H), 4.41(s,2H), 6.76(s,1H), 7.13(d, J=5.1 Hz,1H), 7.28(dd,J=7.6,4.9 Hz,1H), 7.32(s,2H), 7.93 (dd,J=7.6,1.7 Hz,1H), 8.17-8.21(m,2H), 8.57(dd,J=4.9, 1.7 Hz,1H), 10.17(br s,1H), 10.30(s,1H)

2-(2-Ethylaminoacetylaminopyridin-4-ylmeth-ylthio)-N-(4-trifluoromethoxyphenyl)pyridine-3-carboxamide (Compound No. 17-86)

$^1$H-NMR(400 MHz, CDCl$_3$)

δ 1.15(t,J=7.1 Hz,3H), 2.72(q,J=7.1 Hz,2H), 3.39(s,2H), 4.52(s,2H), 7.06(d,J=5.1 Hz,1H), 7.13(dd,J=7.6,4.9 Hz,1H), 7.21(d,J=8.3 Hz,2H), 7.70(d,J=8.3 Hz,2H), 7.87(dd,J=7.6, 1.7 Hz,1H), 8.18(d,J=5.1 Hz,1H), 8.26(s,1H), 8.51-8.54(m, 2H), 9.82(br s,1H)

2-(2-Cyclopropylmethoxyacetylaminopyridin-4-ylmethylthio)-N-(4-trifluoromethoxyphenyl)pyri-dine-3-carboxamide (Compound No. 17-87)

$^1$H-NMR(400 MHz, DMSO-d$_6$)

δ 0.19-0.23(m,2H), 0.46-0.51(m,2H), 1.11(m,1H), 3.35(d, J=6.8 Hz,2H), 4.09(s,2H), 4.43(s,2H), 7.16(dd,J=5.0,1.5 Hz,1H), 7.31(dd,J=7.7,4.9 Hz,1H), 7.37(d,J=8.8 Hz,2H), 7.81(d,J=8.8 Hz,2H), 7.99(dd,J=7.7,1.7 Hz,1H), 8.18(d, J=5.0 Hz,1H), 8.20(s,1H), 8.60(dd,J=4.9,1.7 Hz,1H), 9.74(s, 1H), 10.66(s,1H)

N-(3,5-Dimethylphenyl)-2-(2-phthaloylaminoacety-laminopyridin-4-ylmethylthio)pyridine-3-carboxam-ide (Compound No. 17-88)

$^1$H-NMR(400 MHz, DMSO-d$_6$)

δ 2.24(s,6H), 4.38(s,2H), 4.50(s,2H), 6.74(s,1H), 7.15(d, J=5.1 Hz,1H), 7.25(dd,J=7.8,4.9 Hz,1H), 7.30(s,2H), 7.83(s, 1H), 7.88-7.94(m,4H), 8.06(br s,1H), 8.22(d,J=5.1 Hz,1H), 8.53(dd,J=4.9,1.7 Hz,1H), 10.28(s,1H), 10.90(s,1H)

Example 18

2-(2-Aminoacetylaminopyridin-4-ylmethylthio)-N-(4-difluoromethoxyphenyl)pyridine-3-carboxamide (Compound No. 18-1)

N-(4-Difluoromethoxyphenyl)-2-(2-phthaloylami-noacetylaminopyridin-4-ylmethylthio)pyridine-3-carboxa-mide (Compound No. 17-69, 50 mg, 0.085 mmol) and hydra-zine monohydrate (42 μl, 0.42 mmol) were suspended in the mixture of methanol(2.0 mL) and 1,4-dioxane(2.0 mL) at room temperature, then the mixture was stirred for 1 hour at 80° C. The mixture was diluted with ethyl acetate (30 mL), and the whole was washed with brine (30 mL) twice and dried over anhydrous magnesium sulfate. The solvent was evapo-rated under reduced pressure, and the resulting residue was purified by silica gel column chromatography to give 11 mg of the target compound as a colorless solid. (Yield 29%)

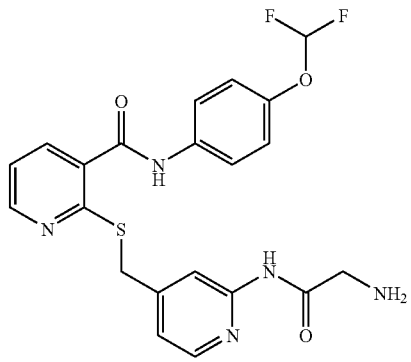

$^1$H-NMR(400 MHz, DMSO-d$_6$)

δ 3.30(s,2H), 3.41(s,2H), 4.43(s,2H), 7.14-7.20(m,3H), 7.18(t,J=74.2 Hz,1H), 7.30(dd,J=7.6,4.9 Hz,1H), 7.73(d, J=9.0 Hz,2H), 7.84(s,1H), 7.98(d,J=7.6 Hz,1H), 8.30(d,J=5.1 Hz,1H), 8.60(d,J=4.9Hz,1H), 10.54(s,1H)

The chemical structures of the compounds of the present invention described above are shown below.

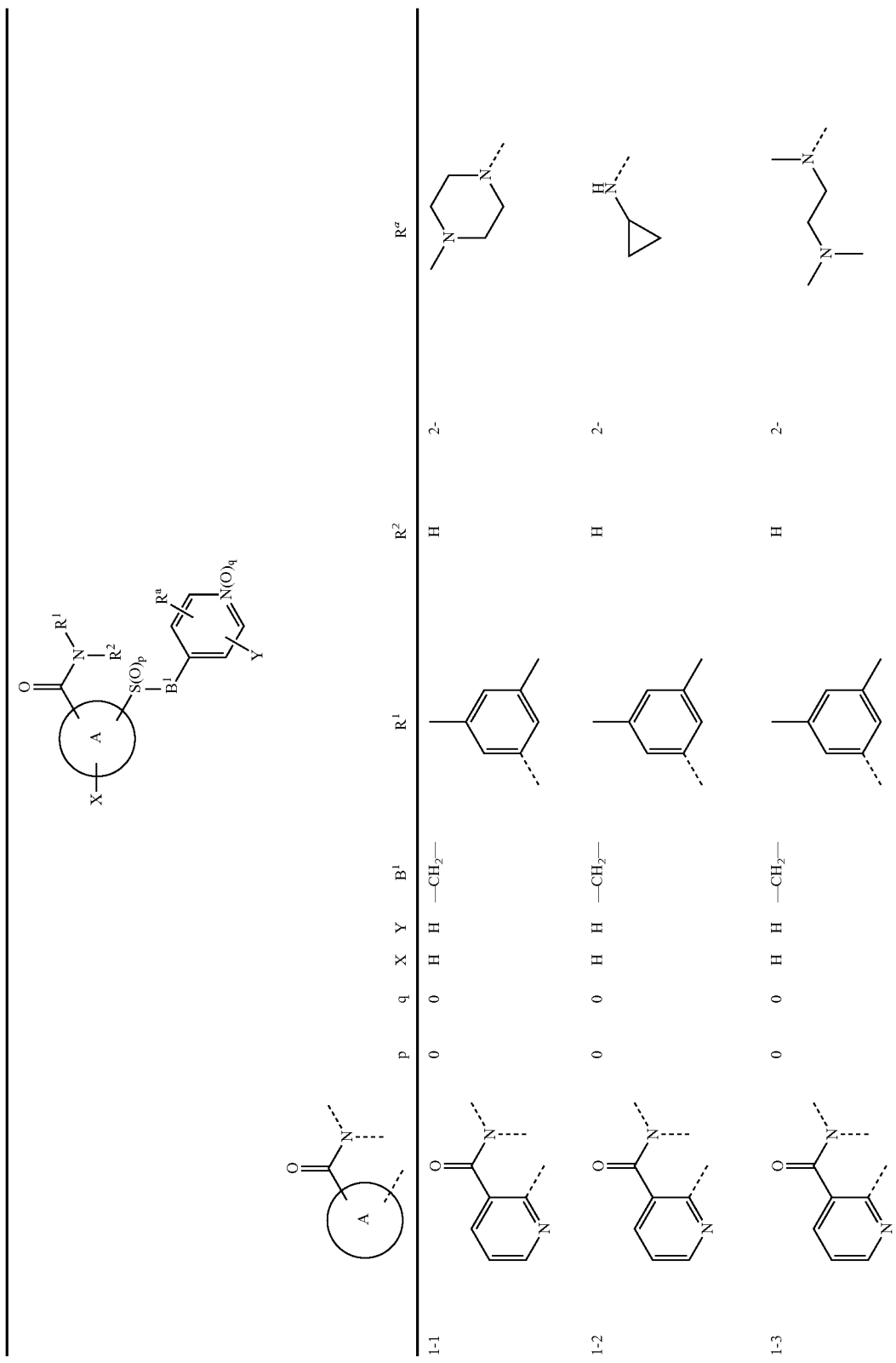

-continued

| | p | q | X | Y | B¹ | R¹ | R² | | Rᵃ |
|---|---|---|---|---|---|---|---|---|---|
| 1-4 | 0 | 0 | H | H | —CH₂— | | H | 2- | |
| 1-5 | 0 | 0 | H | H | —CH₂— | | H | 2- | |
| 1-6 | 0 | 0 | H | H | —CH₂— | | H | 2- | |

-continued

| | A | p | q | X | Y | B¹ | R¹ | R² | 2- | Rᵃ |
|---|---|---|---|---|---|---|---|---|---|---|
| 1-7 | 2-pyridyl-3-carbonyl (N-linked) | 0 | 0 | H | H | —CH₂— | 3,5-dimethylphenyl | H | 2- | N-Boc-piperazine-1-carbonyl |
| 1-8 | 2-pyridyl-3-carbonyl (N-linked) | 0 | 0 | H | H | —CH₂— | 3,5-dimethylphenyl | H | 2- | N-methyl-N-(2-hydroxyethyl)amino |
| 1-9 | 2-pyridyl-3-carbonyl (N-linked) | 0 | 0 | H | H | —CH₂— | 3,5-dimethylphenyl | H | 2- | 4-hydroxy-1-methylpiperidin-1-yl |

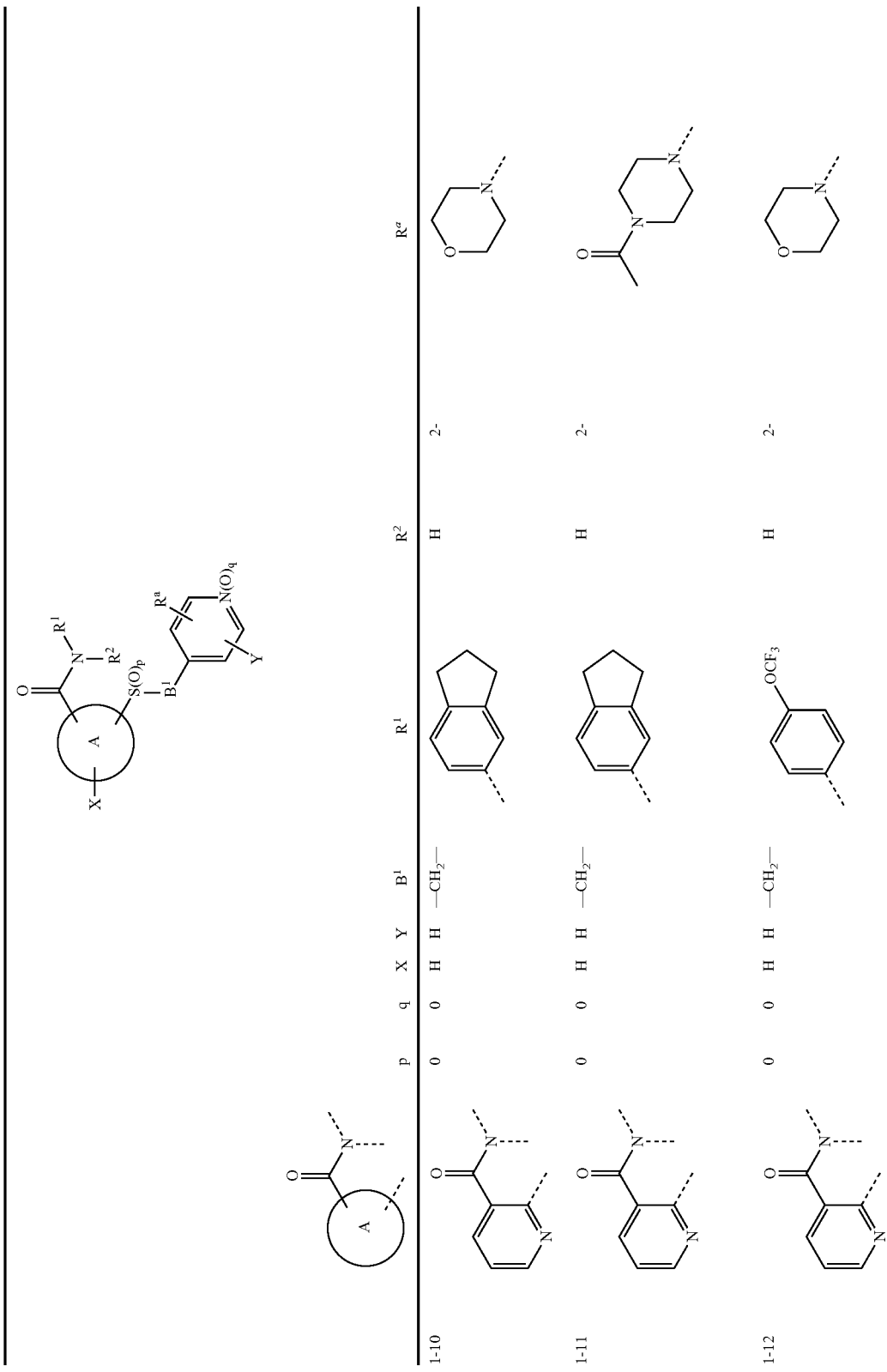

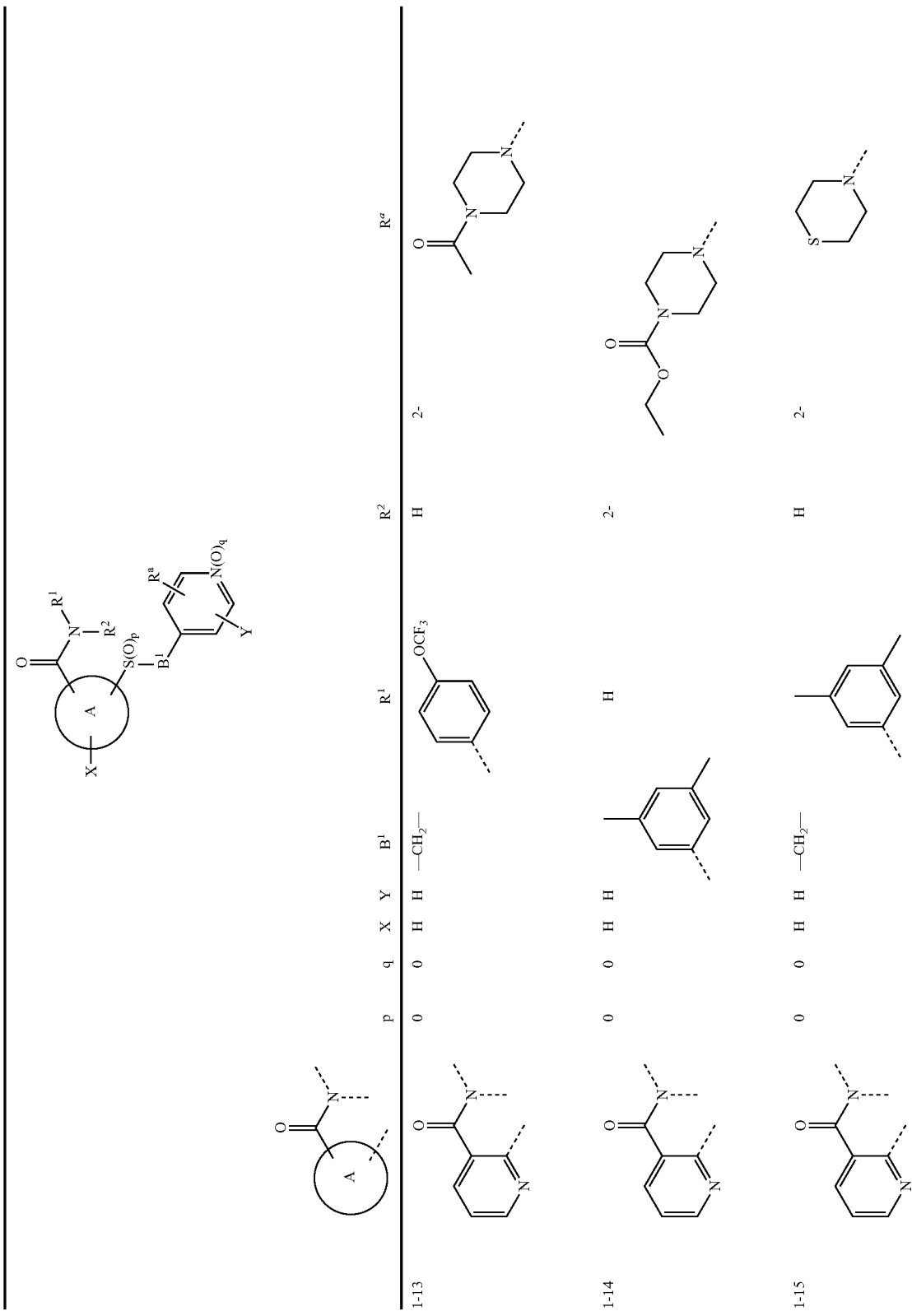

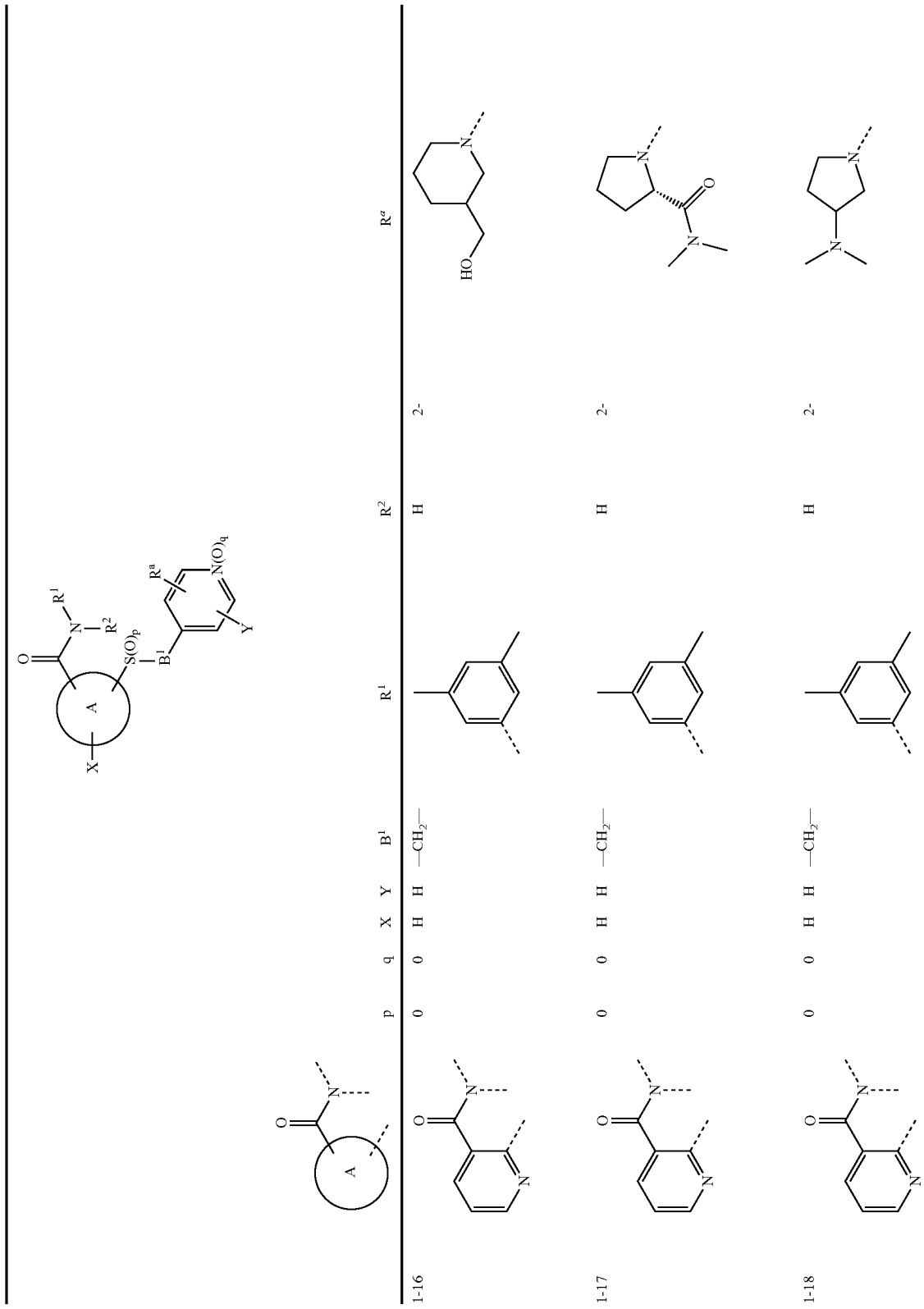

| | p | q | X | Y | B¹ | R¹ | R² | | Rᵃ |
|---|---|---|---|---|---|---|---|---|---|
| 1-19 | | 0 | 0 | H | H | —CH₂— | 3,5-dimethylphenyl | H | 2- | HOCH₂CH₂NH— |
| 1-20 | | 0 | 0 | H | H | —CH₂— | 3,5-dimethylphenyl | H | 2- | n-pentyl-NH— |
| 1-21 | | 0 | 0 | H | H | —CH₂— | 3,5-dimethylphenyl | H | 2- | ethyl 1-methylpiperidine-4-carboxylate |

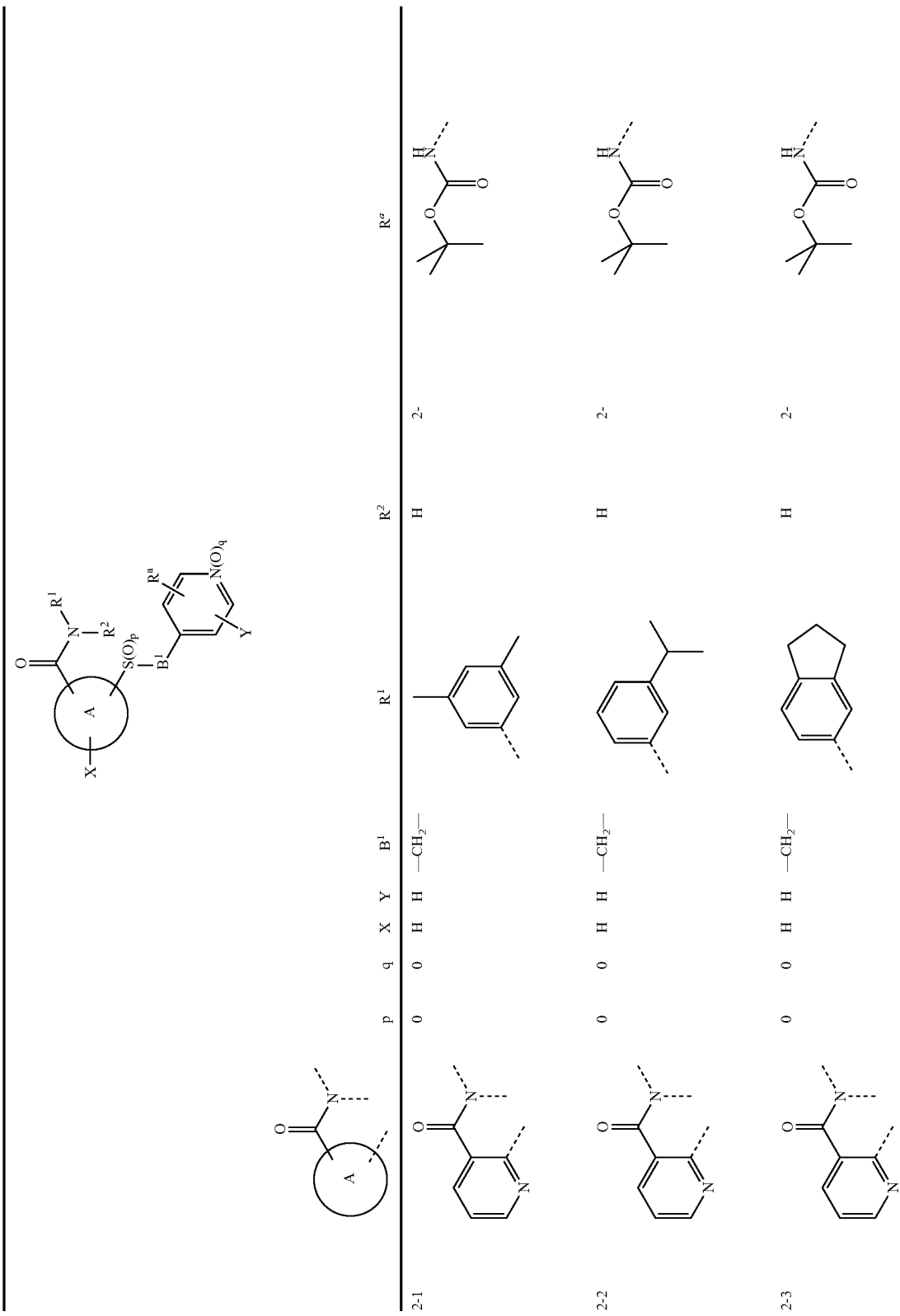

| | p | q | X | Y | B¹ | R¹ | R² | Rᵃ |
|---|---|---|---|---|---|---|---|---|
| 2-4 ![pyridine amide] | 0 | 0 | H | H | —CH₂— | 4-OCF₃-phenyl | H | 2- NHC(O)O-tBu |
| 2-5 ![pyridine amide] | 0 | 0 | H | H | —CH₂— | 4-tBu-phenyl | H | 2- NHC(O)O-tBu |
| 2-6 ![pyridine amide] | 0 | 0 | H | H | —CH₂— | 6-(1H-indazolyl) | H | 2- NHC(O)O-tBu |

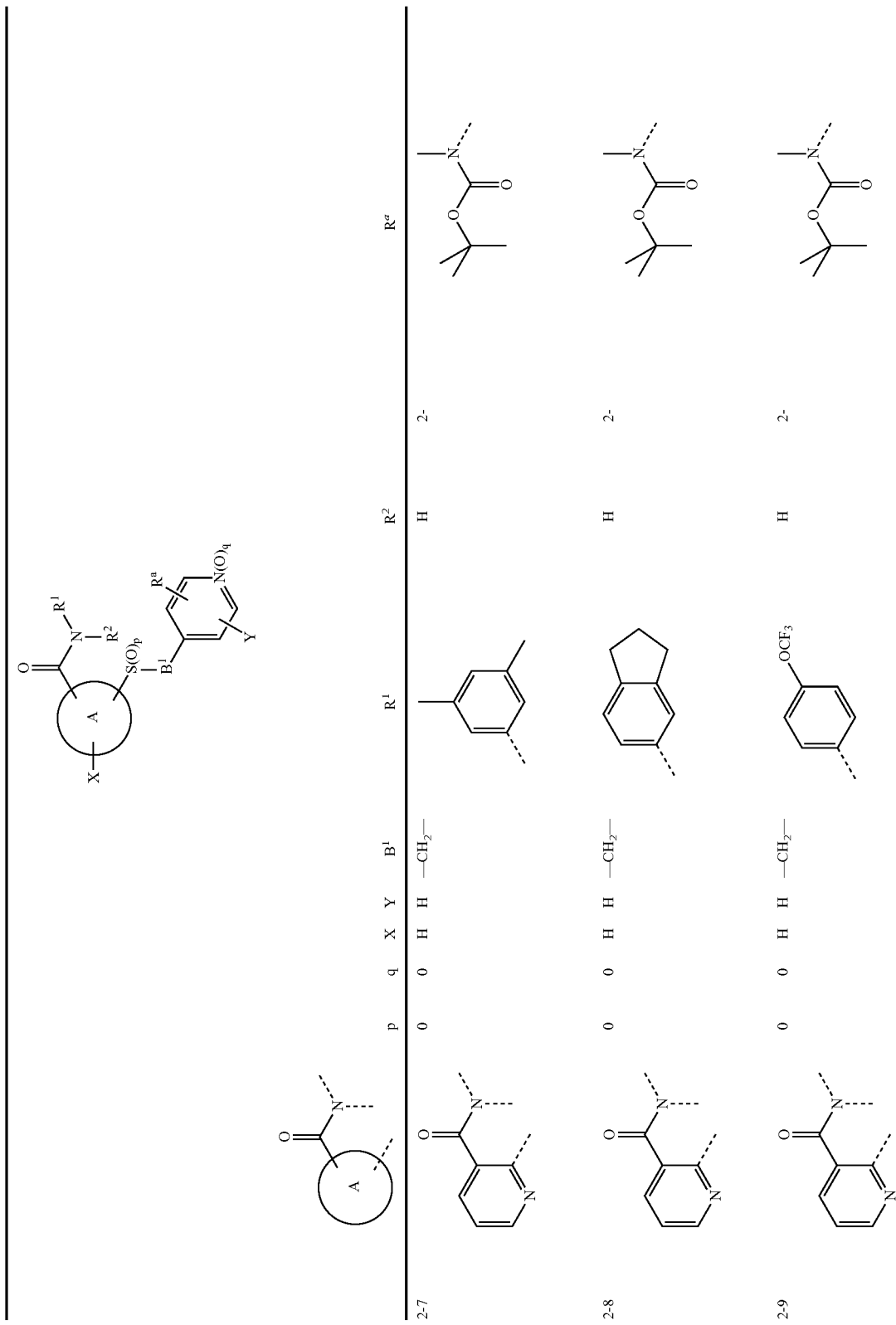

-continued

| | p | q | X | Y | B¹ | R¹ | R² | Rᵃ | [A group] |
|---|---|---|---|---|---|---|---|---|---|
| 2-10 | 0 | 0 | H | H | —CH₂— | 4-chlorophenyl | H | 2- | tert-butyl NH-carbamate |
| 2-11 | 0 | 0 | H | H | —CH₂— | 3,5-dimethylphenyl | H | 2- | tert-butyl N-ethyl-carbamate |
| 2-12 | 0 | 0 | H | H | —CH₂— | 3-chlorophenyl | H | 2- | tert-butyl NH-carbamate |

(A group for 2-10, 2-11, 2-12: 2-pyridyl-3-carboxamide)

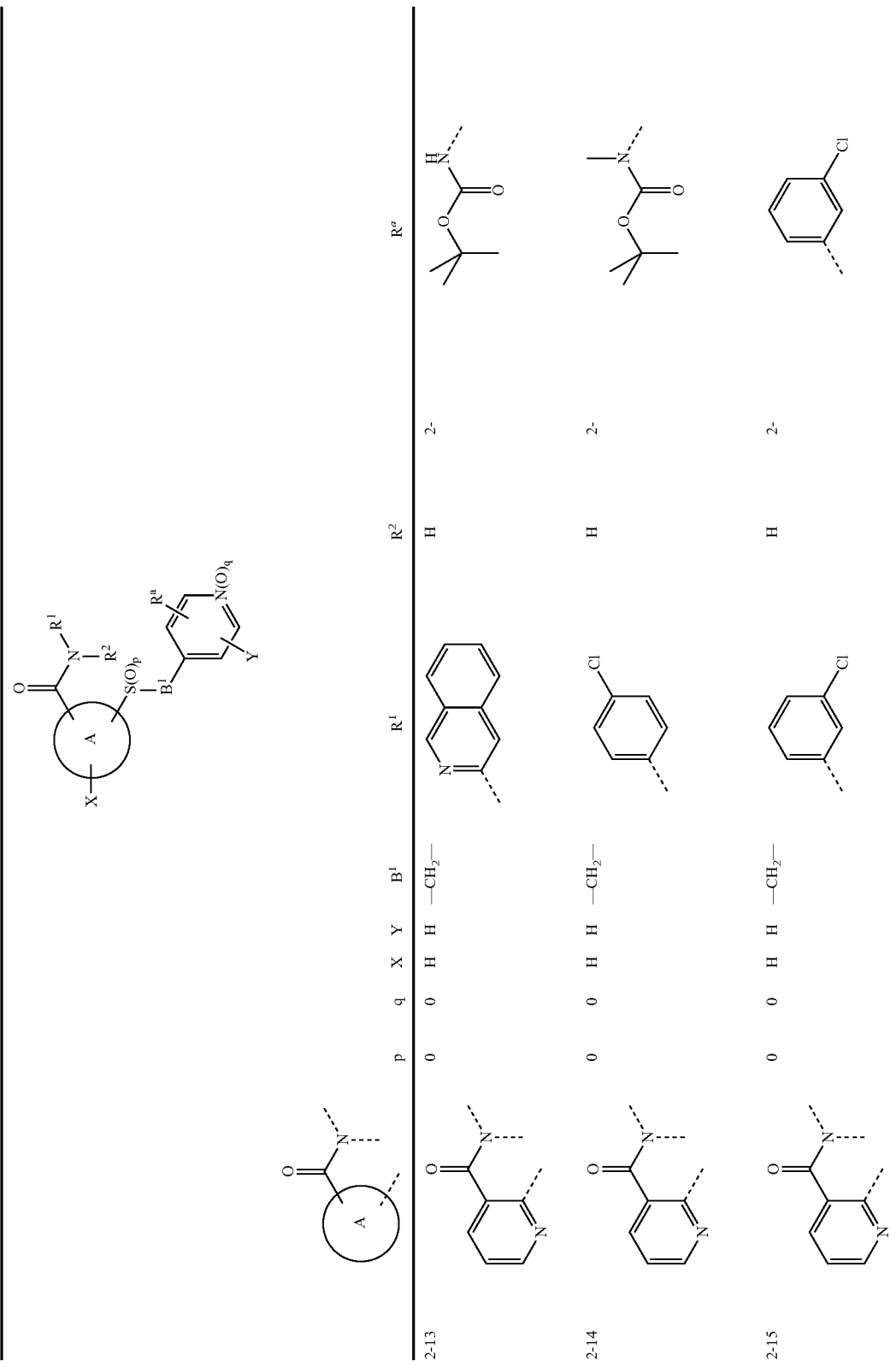

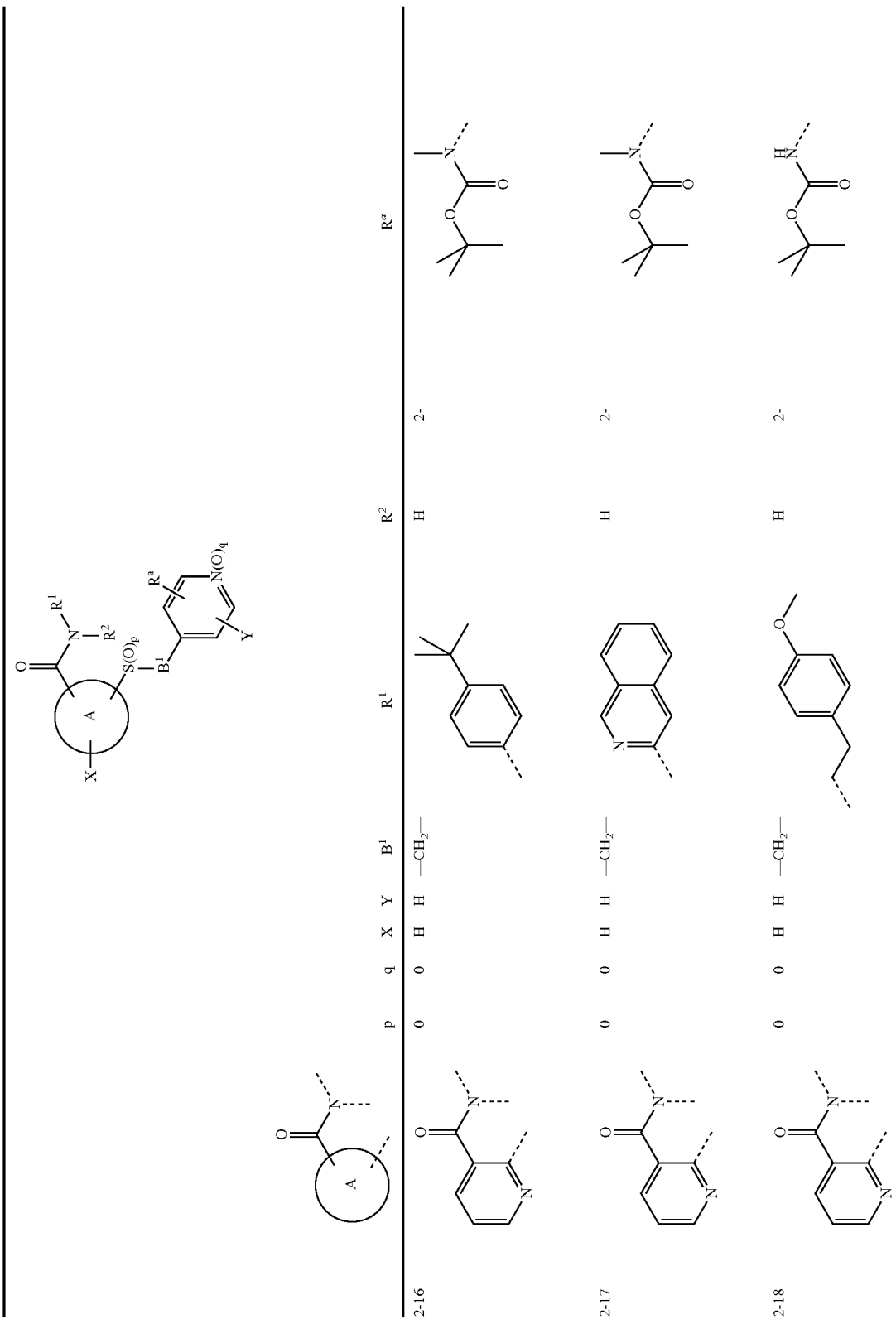

| | | p | q | X | Y | B¹ | R¹ | R² | | Rᵃ |
|---|---|---|---|---|---|---|---|---|---|---|
| 2-19 | [pyridine-carbonyl-N] | 0 | 0 | H | H | —CH₂— | [adamantyl] | H | 2- | [NHC(O)OtBu] |
| 2-20 | [pyridine-carbonyl-N] | 0 | 0 | H | H | —CH₂— | [3,5-dimethylphenyl] | Me | 2- | [NMeC(O)OtBu] |
| 2-21 | [pyridine-carbonyl-N] | 0 | 0 | H | H | —CH₂— | [3,5-dimethylphenyl] | H | 2- | [phthalimide] |

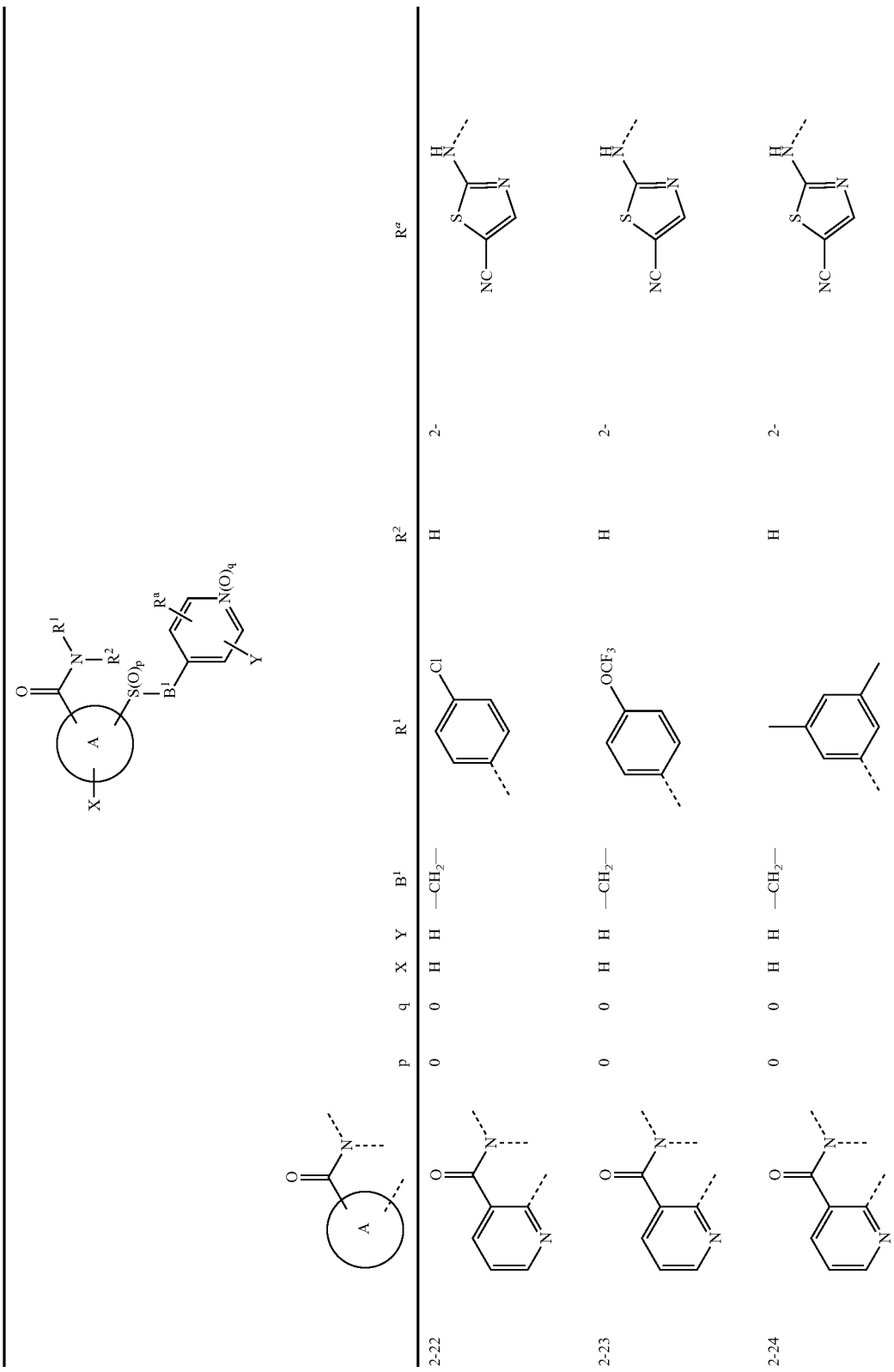

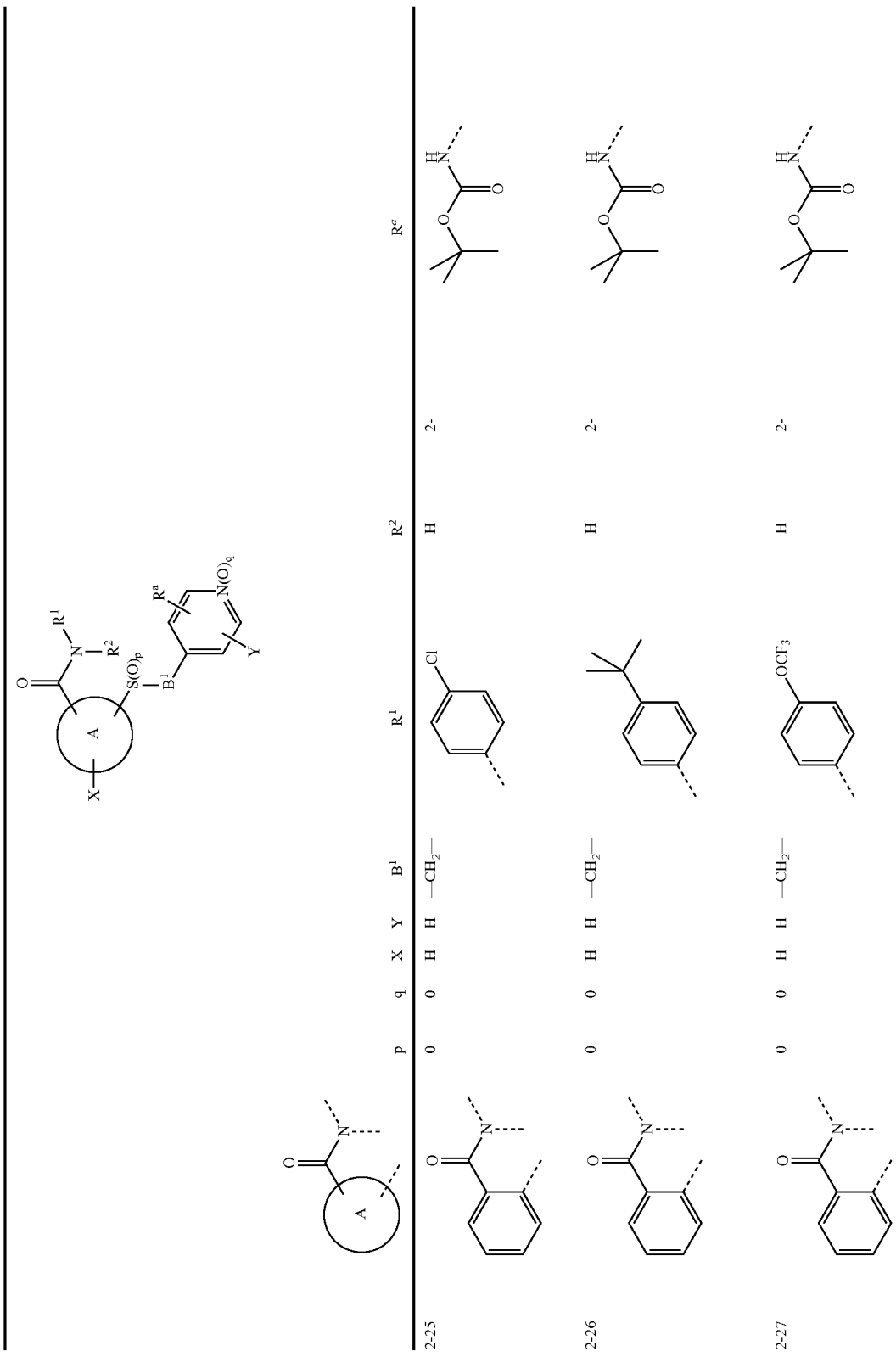

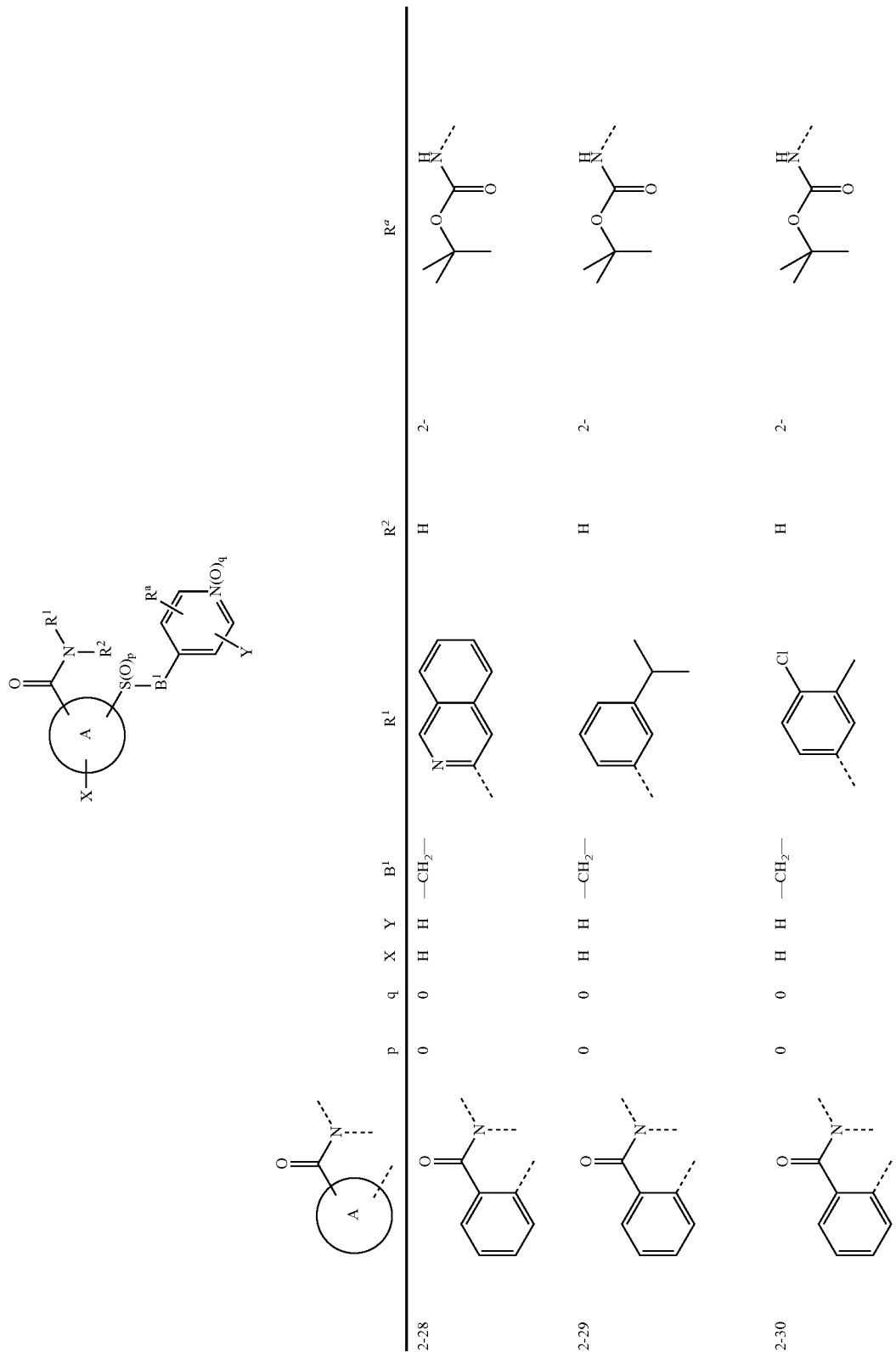

-continued

| | p | q | X | Y | B¹ | R¹ | R² | Rᵃ |
|---|---|---|---|---|---|---|---|---|
| 2-31 | 0 | 0 | H | H | —CH₂— | indazolyl | H | 2- | tBoc-NH |
| 2-32 | 0 | 0 | H | H | —CH₂— | 3,5-dimethylphenyl | H | 2- | tBoc-NH |
| 2-33 | 0 | 0 | H | H | —CH₂— | 3,5-dimethylphenyl | H | 2- | tBoc-NH |

-continued

| | p | q | X | Y | B¹ | R¹ | R² | | Rᵃ |
|---|---|---|---|---|---|---|---|---|---|
| 2-34 | 0 | 0 | H | H | —CH₂— | 2,6-dimethyl-4-OH phenyl | H | 2- | NHC(O)O-tBu |
| 2-35 | 0 | 0 | H | H | —CH₂— | 2-Cl-4-OCF₃ phenyl | H | 2- | NHC(O)O-tBu |
| 2-36 | 0 | 0 | H | H | —CH₂— | 3-CF₃ phenyl | H | 2- | NHC(O)O-tBu |

-continued

| | A | p | q | X | Y | B¹ | R¹ | R² | Rᵃ |
|---|---|---|---|---|---|---|---|---|---|
| 3-1 | 2-pyridyl carbonyl | 0 | 0 | H | H | —CH₂— | 3,5-dimethylphenyl | H | 2- H₂N, HCl |
| 3-2 | 2-pyridyl carbonyl | 0 | 0 | H | H | —CH₂— | 3-isopropylphenyl | H | 2- H₂N, HCl |
| 3-3 | 2-pyridyl carbonyl | 0 | 0 | H | H | —CH₂— | indanyl | H | 2- H₂N, HCl |

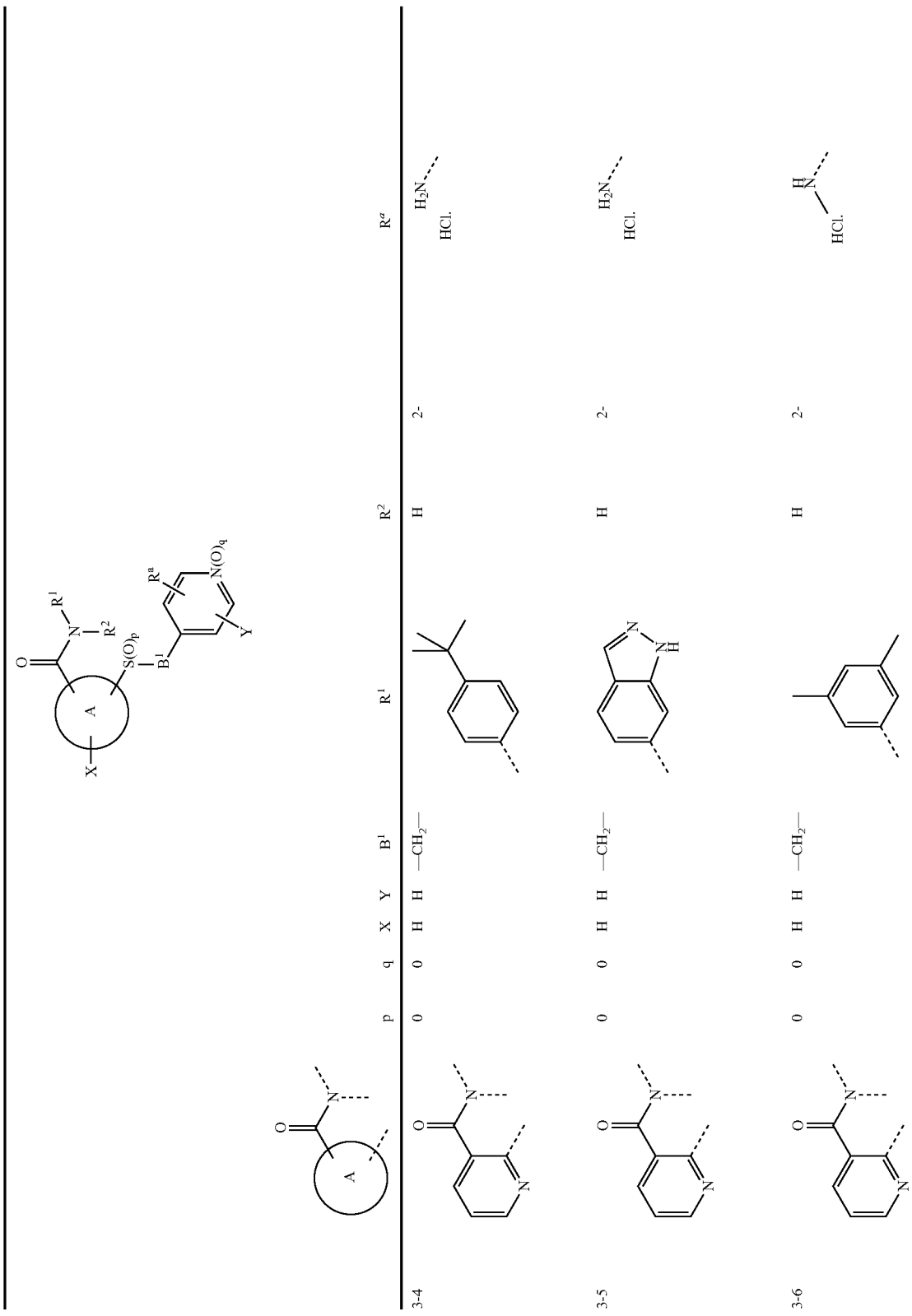

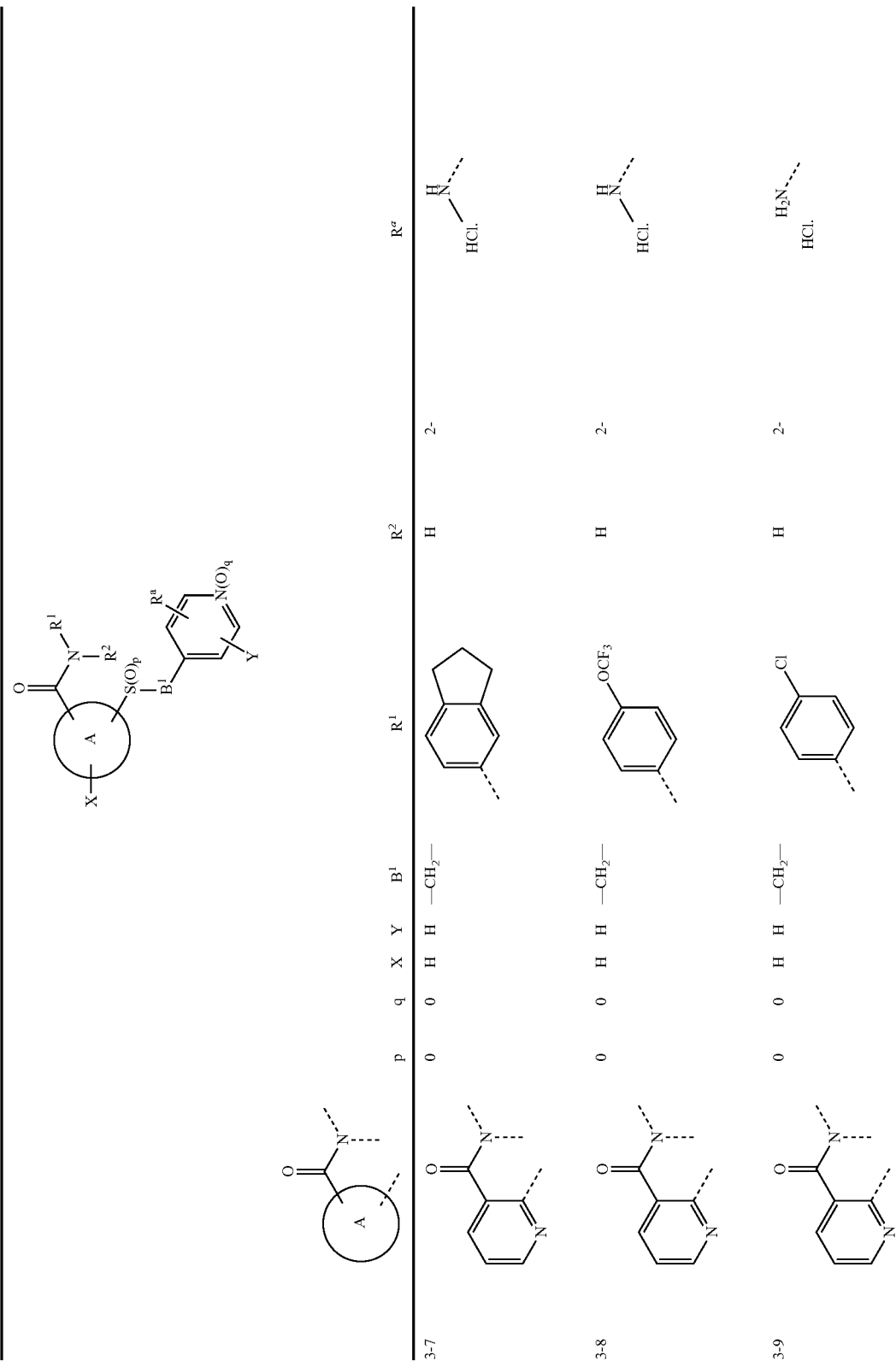

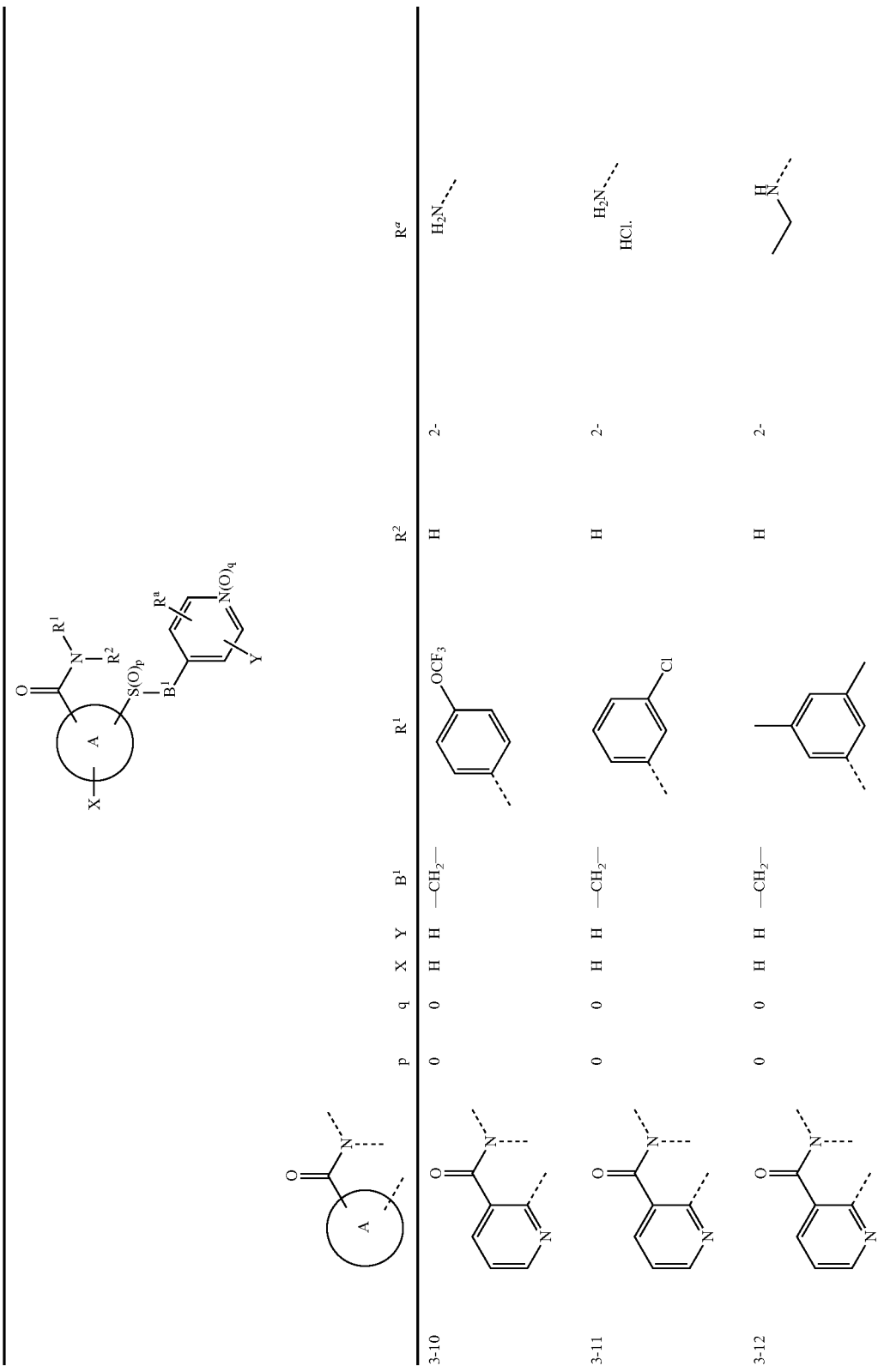

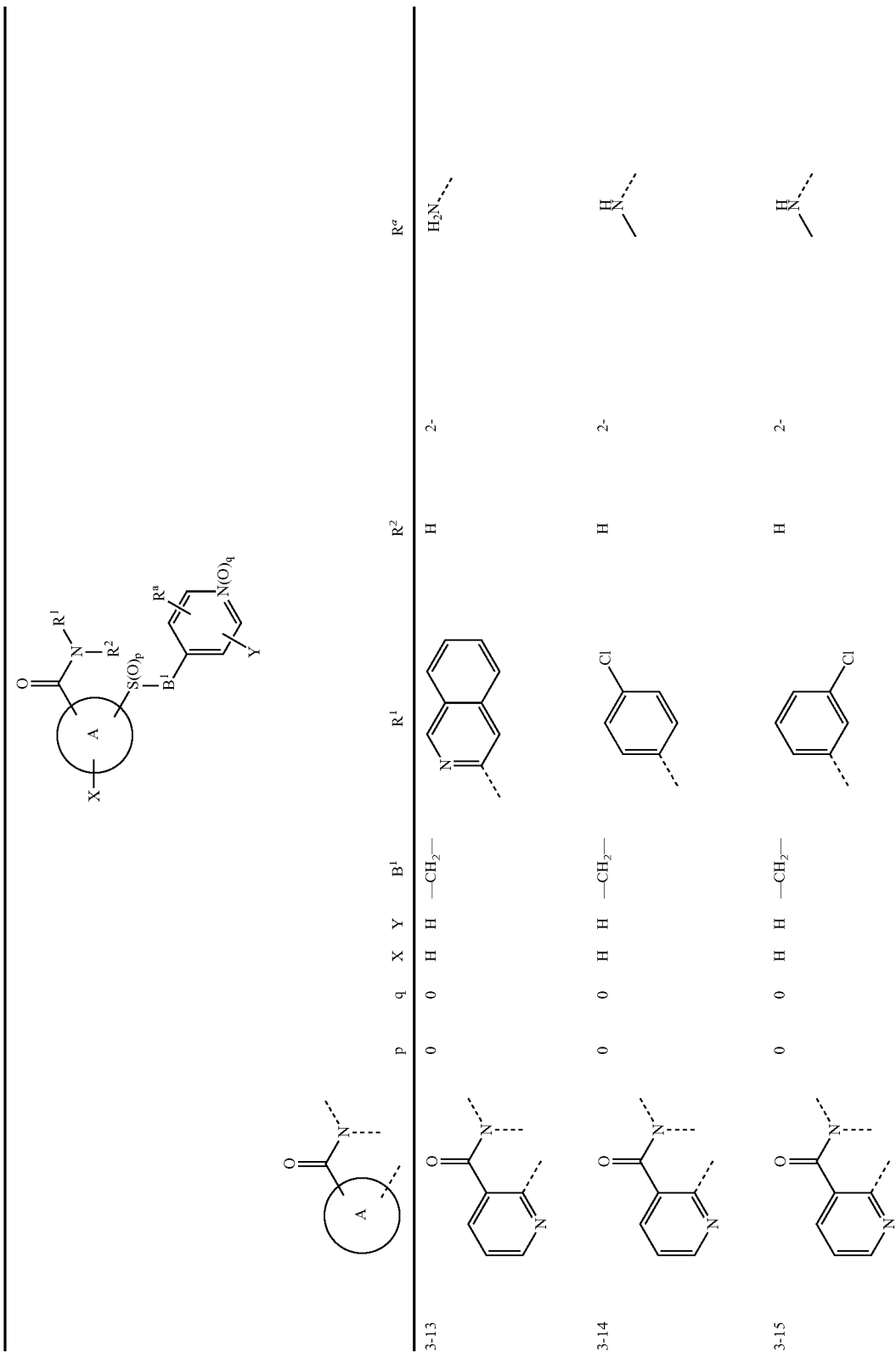

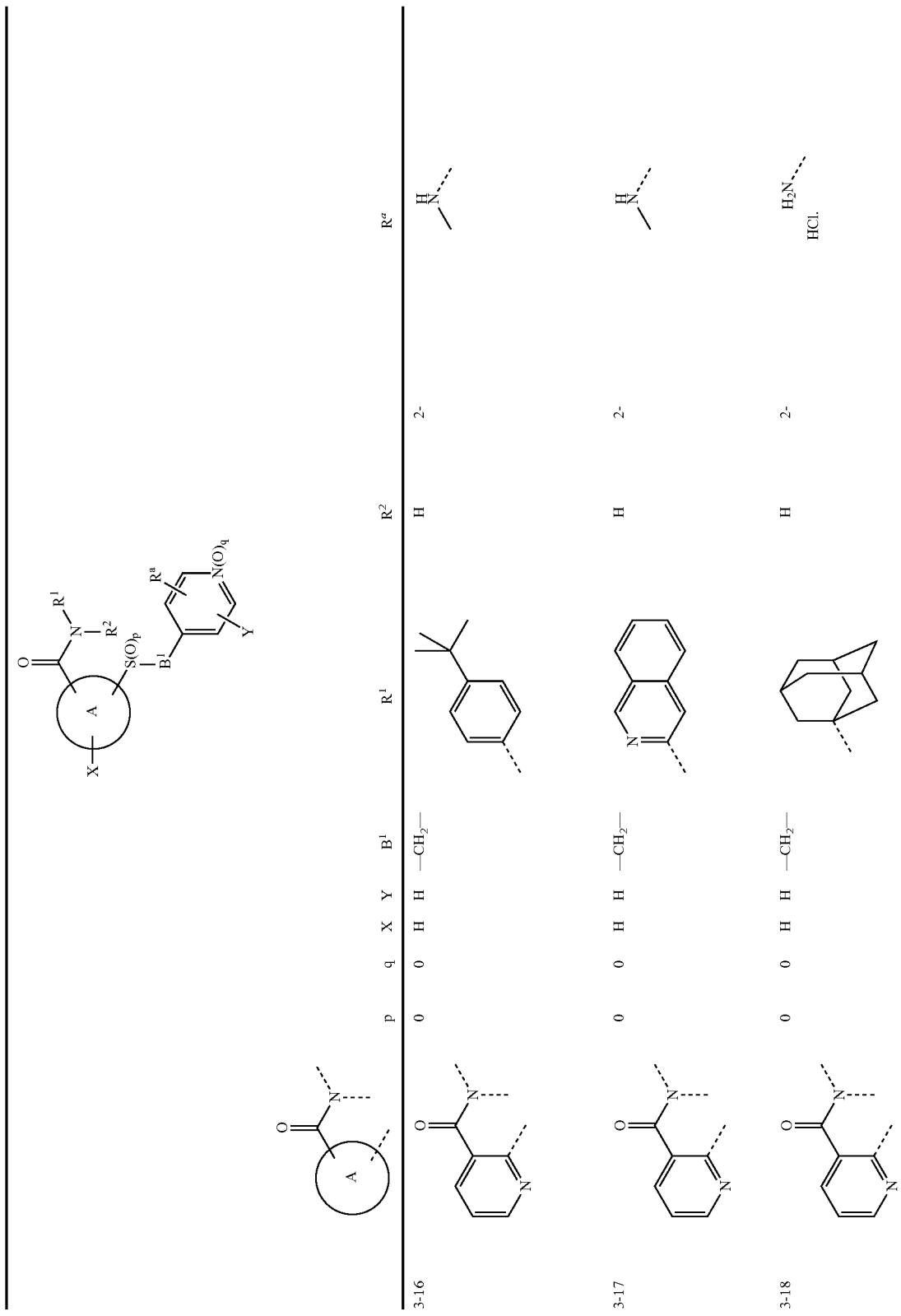

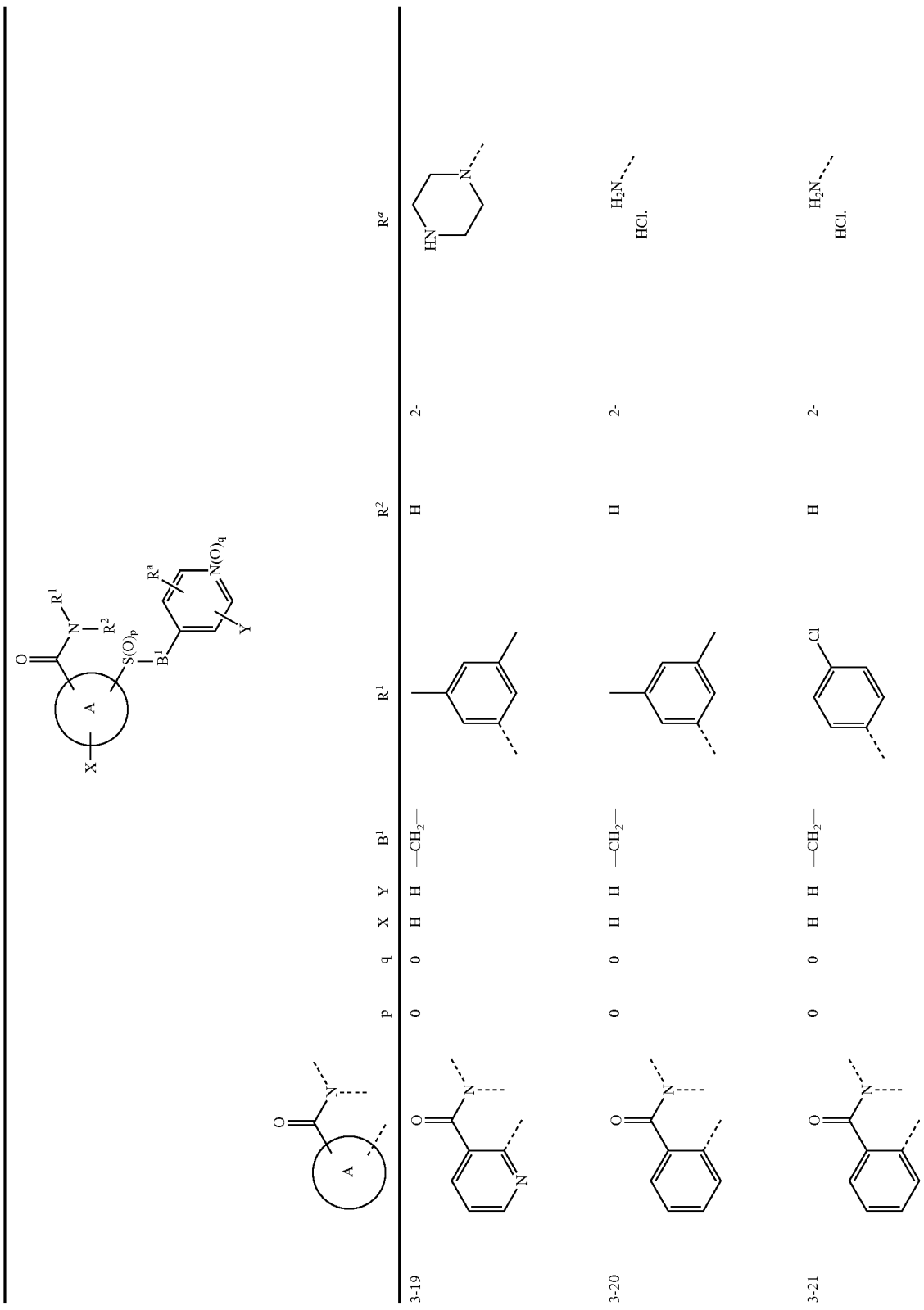

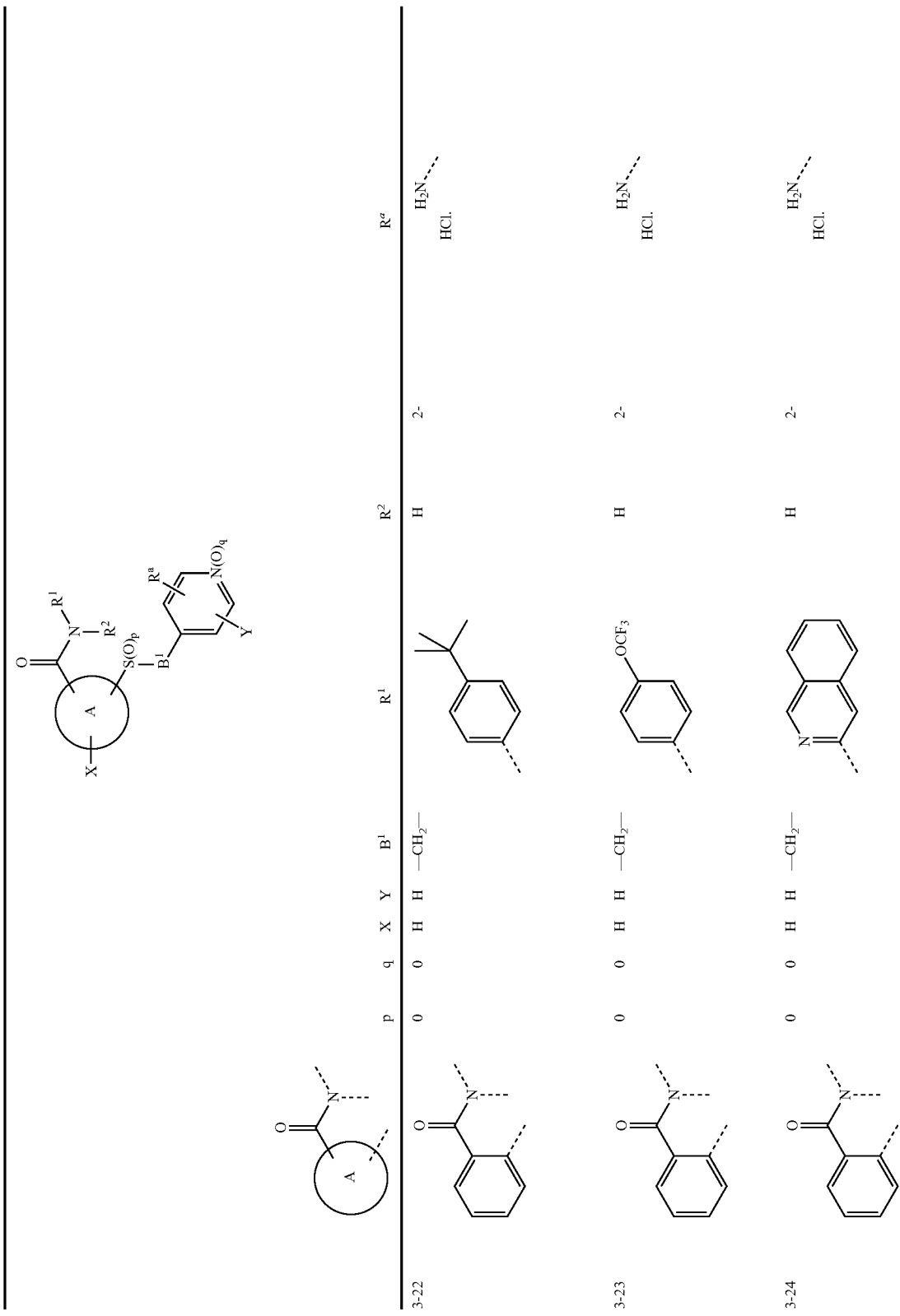

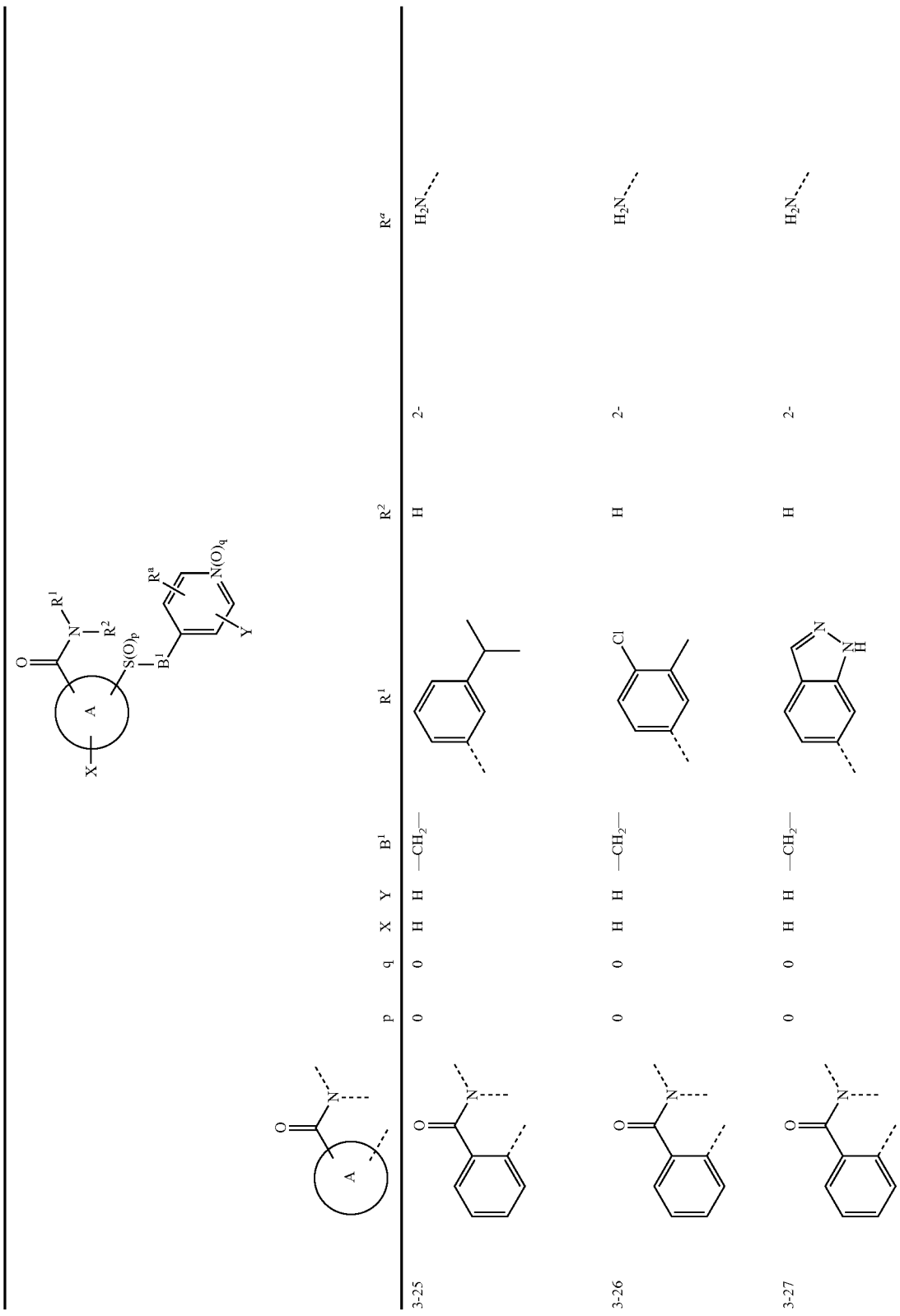

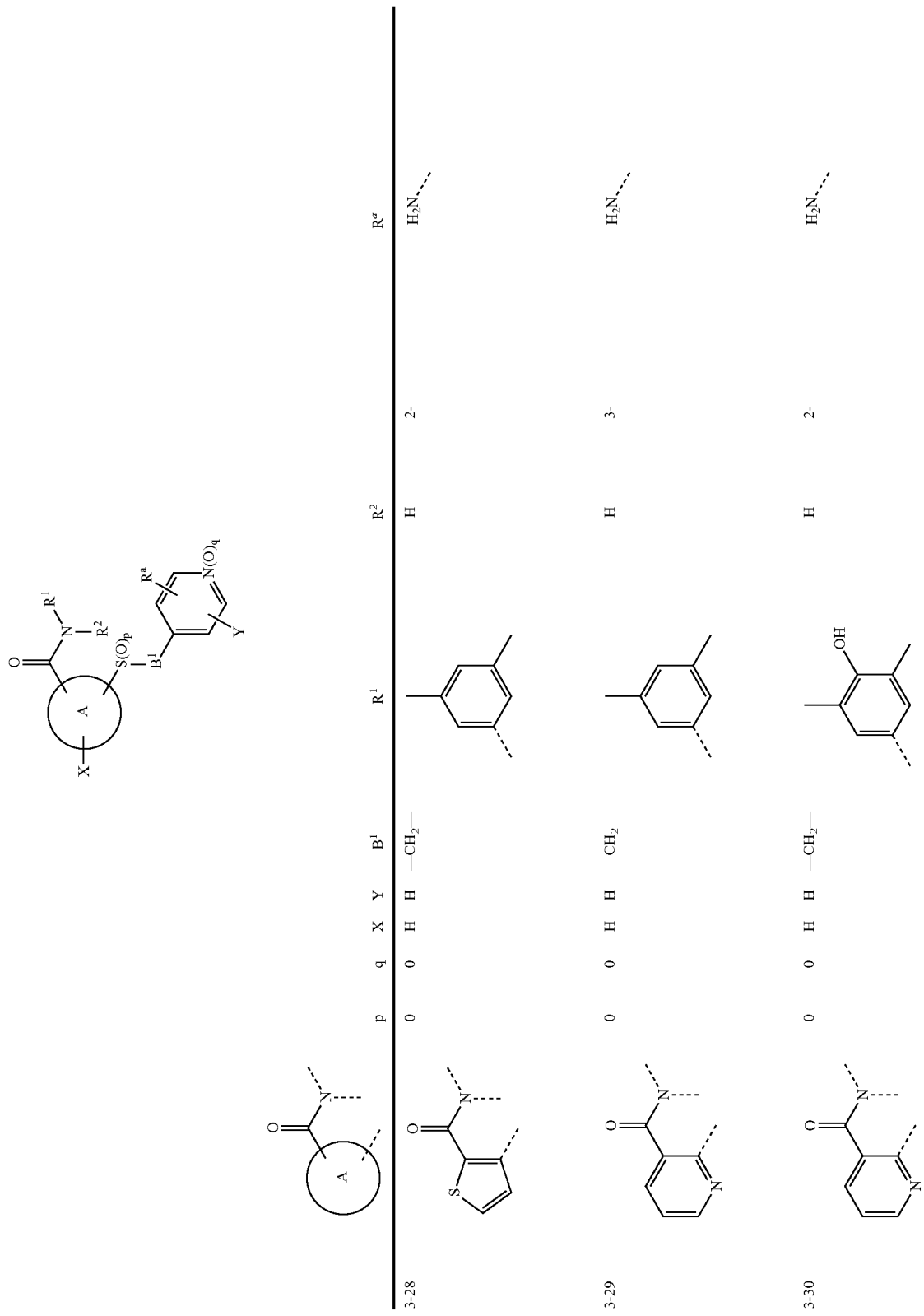

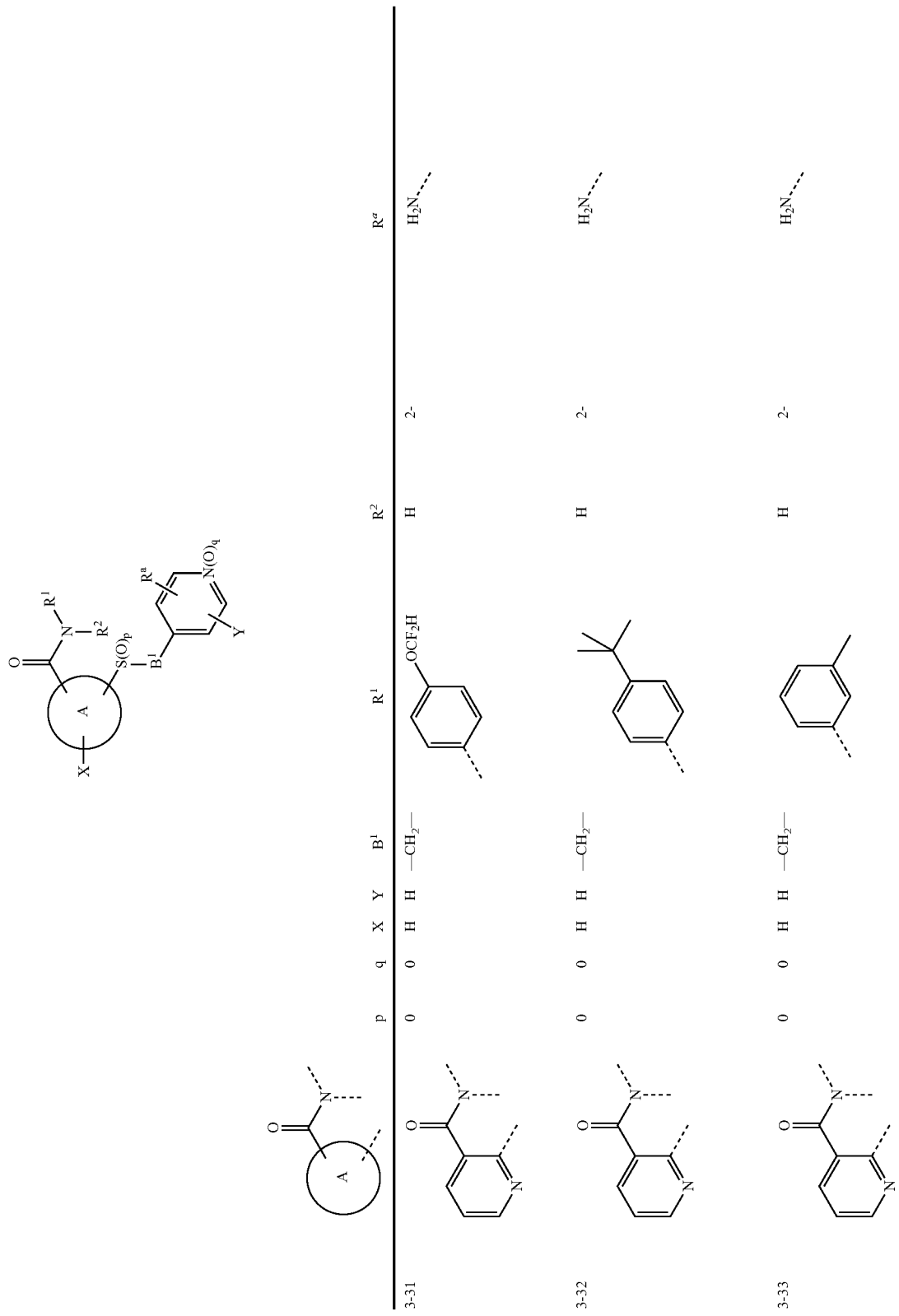

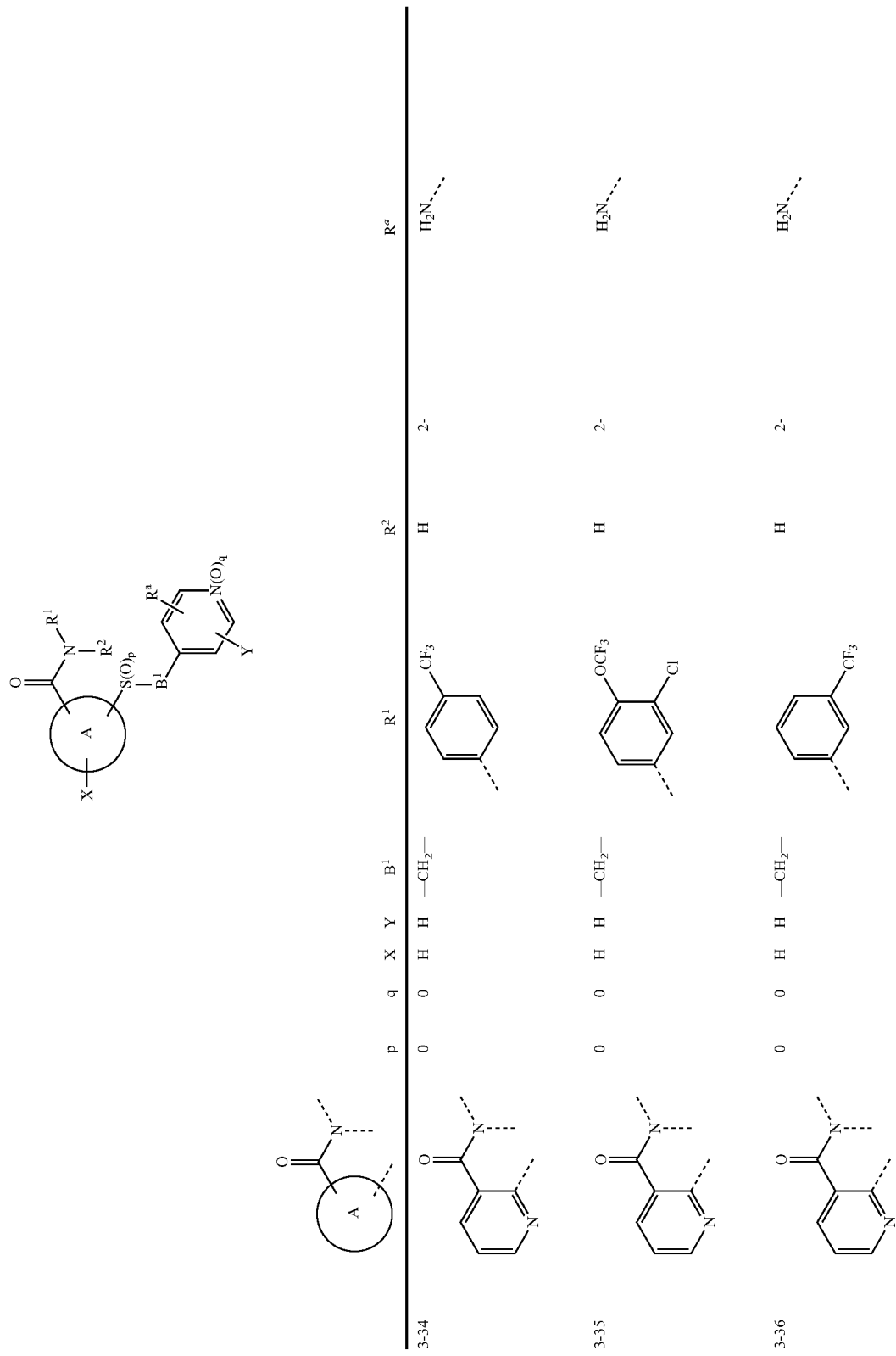

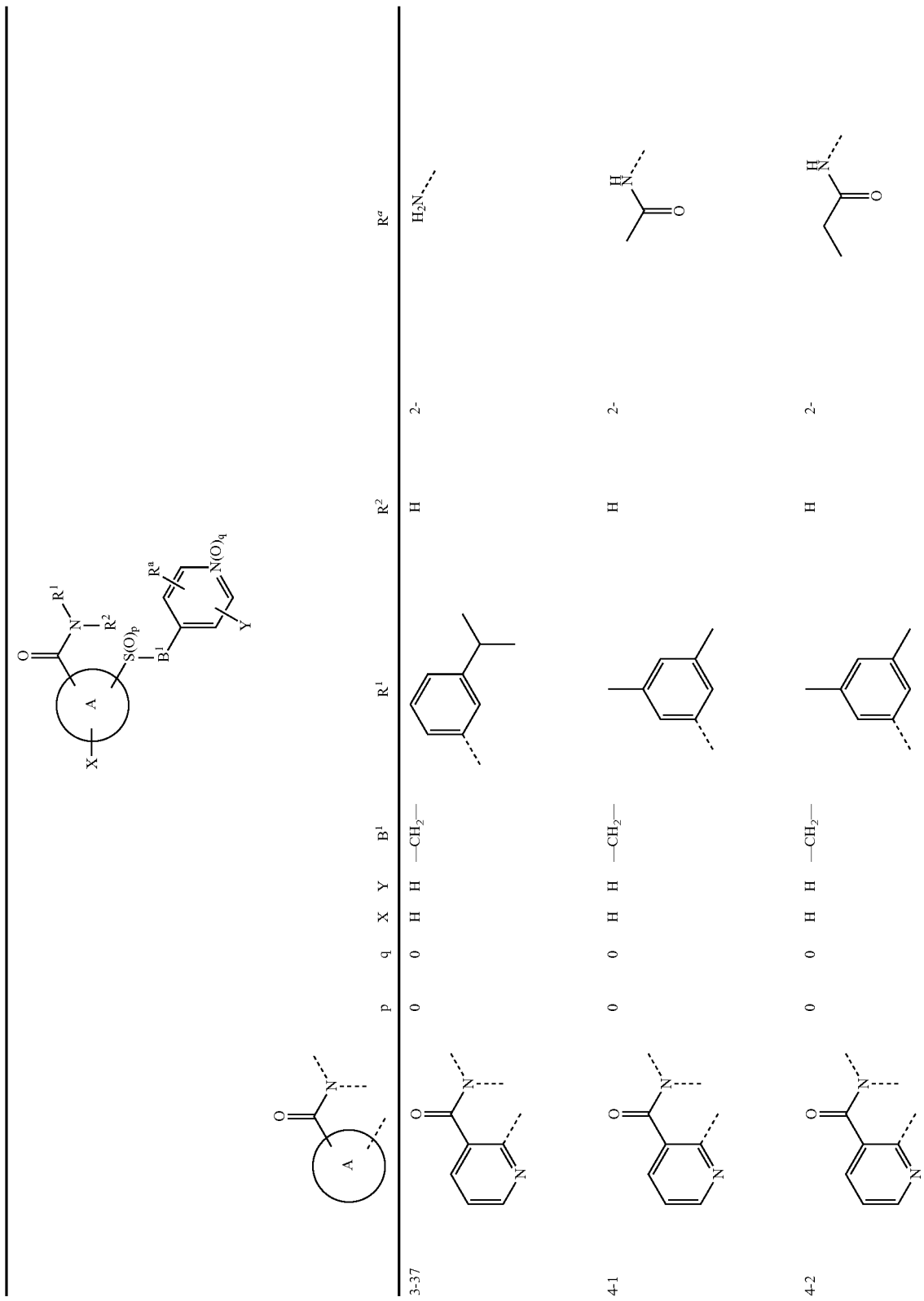

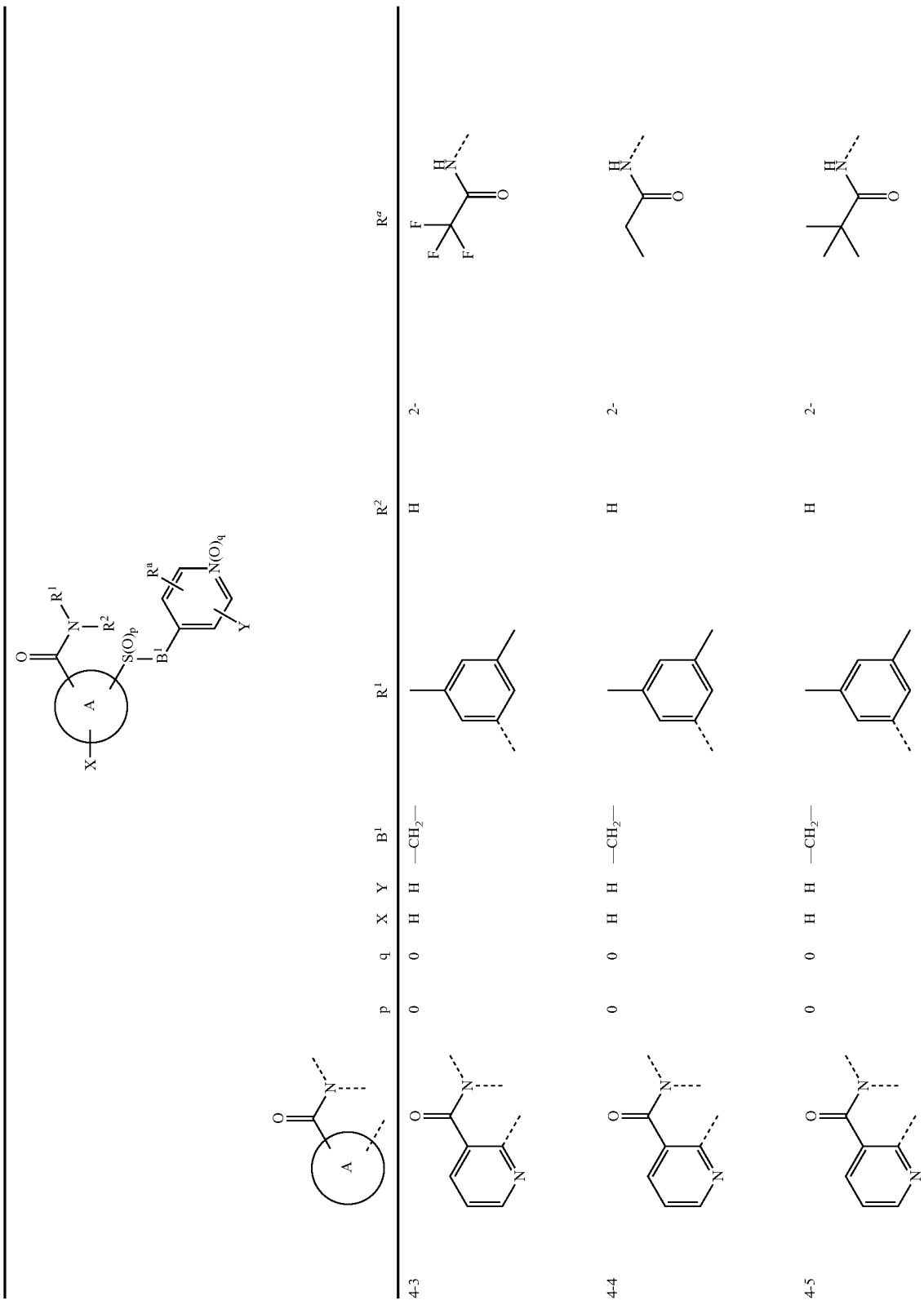

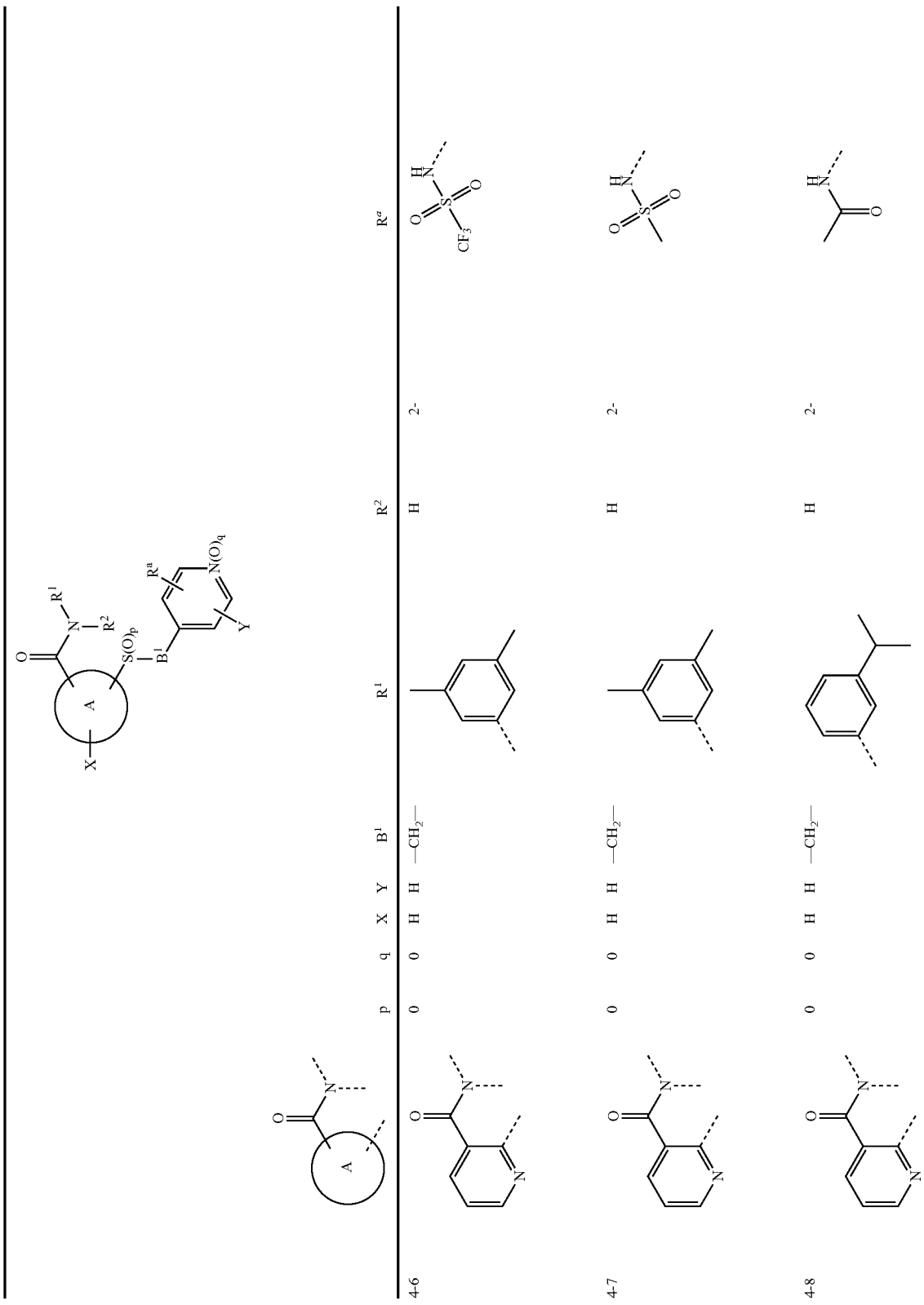

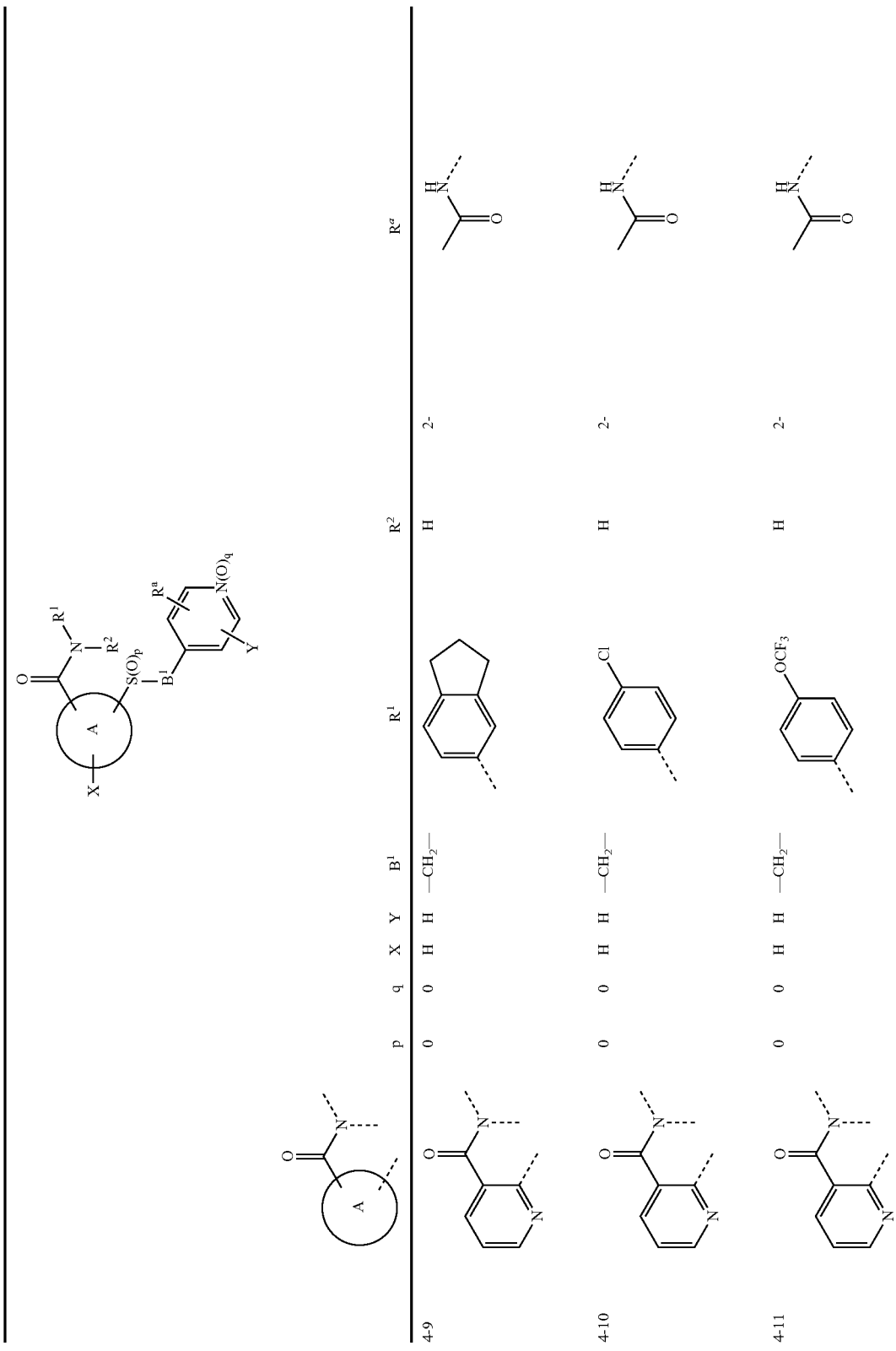

-continued

| | p | q | X | Y | B¹ | R¹ | R² | | Rᵃ |
|---|---|---|---|---|---|---|---|---|---|
| 4-12 | 0 | 0 | H | H | —CH₂— | 3,5-dimethylphenyl | H | 2- | N-acetyl |
| 4-13 | 0 | 0 | H | H | —CH₂— | quinolinyl | H | 2- | NH-acetyl |
| 4-14 | 0 | 0 | H | H | —CH₂— | 2-chloro-4-(OCF₃)phenyl | H | 2- | NH-acetyl |

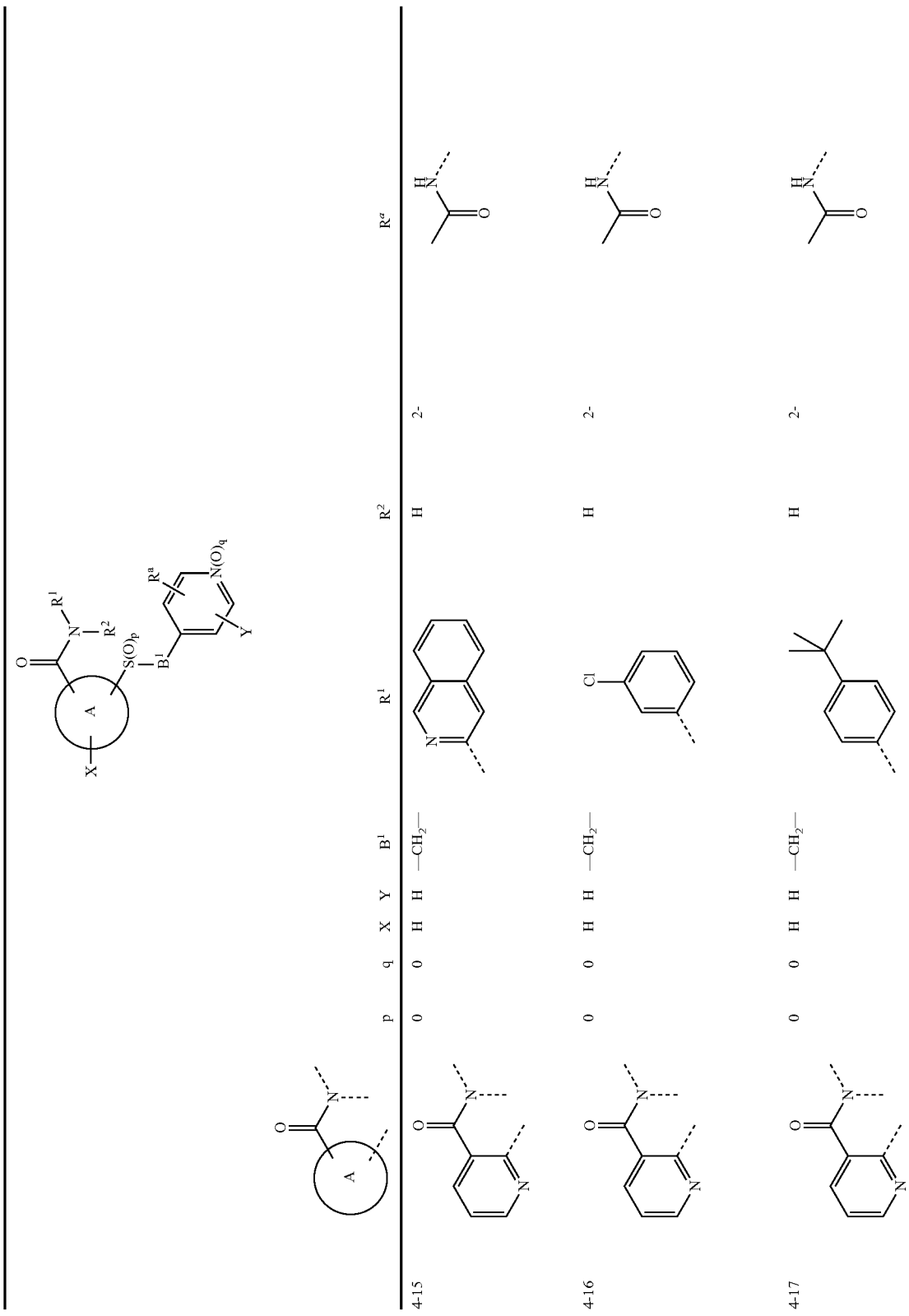

-continued

| | A | p | q | X | Y | B¹ | R¹ | R² | | Rᵃ |
|---|---|---|---|---|---|---|---|---|---|---|
| 4-18 | 2-methylpyridin-3-yl carboxamide | 0 | 0 | H | H | —CH₂— | 4-fluoro-2-methylphenyl | H | 2- | NHC(O)CH₃ |
| 4-19 | 2-methylpyridin-3-yl carboxamide | 0 | 0 | H | H | —CH₂— | 2-fluoro-4-methylphenyl | H | 2- | NHC(O)CH₃ |
| 4-20 | 2-methylpyridin-3-yl carboxamide | 0 | 0 | H | H | —CH₂— | 3,5-dimethylphenyl | H | 2- | NHC(O)CH₃ |

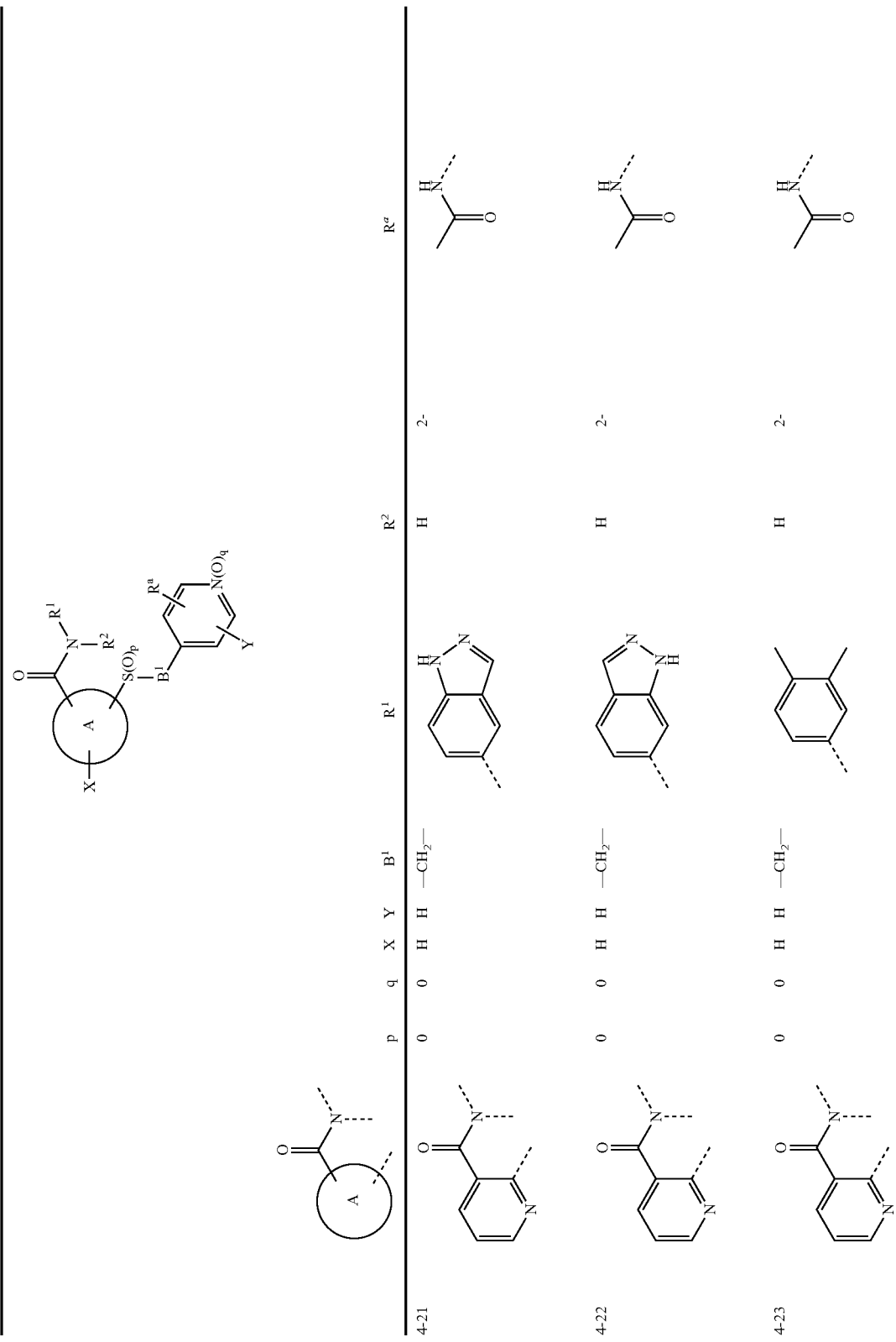

-continued
| | | p | q | X | Y | B¹ | R¹ | R² | 2- | Rª |
|---|---|---|---|---|---|---|---|---|---|---|
| 4-24 | 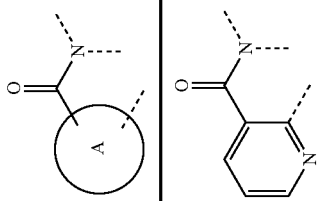 | 0 | 0 | H | H | —CH₂— | 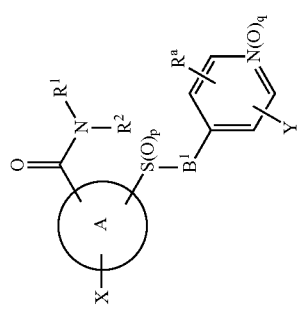 | H | 2- | 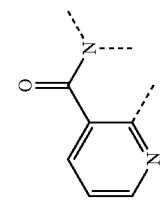 |
| 4-25 | 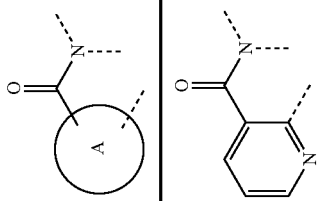 | 0 | 0 | H | H | —CH₂— | 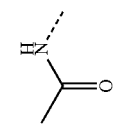 | H | 2- | 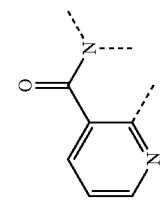 |
| 4-26 | 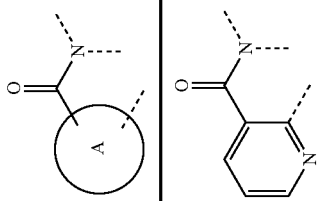 | 0 | 0 | H | H | —CH₂— | 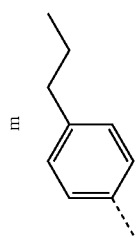 | H | 2- | 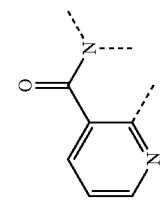 |

-continued

| | p | q | X | Y | B¹ | R¹ | R² | | Rᵃ |
|---|---|---|---|---|---|---|---|---|---|
| 4-27 | 0 | 0 | H | H | —CH₂— | 4-Cl-phenyl | H | 2- | N-acetyl |
| 4-28 | 0 | 0 | H | H | —CH₂— | 4-OCF₃-phenyl | H | 2- | N-acetyl |
| 4-29 | 0 | 0 | H | H | —CH₂— | 4-tBu-phenyl | H | 2- | N-acetyl |

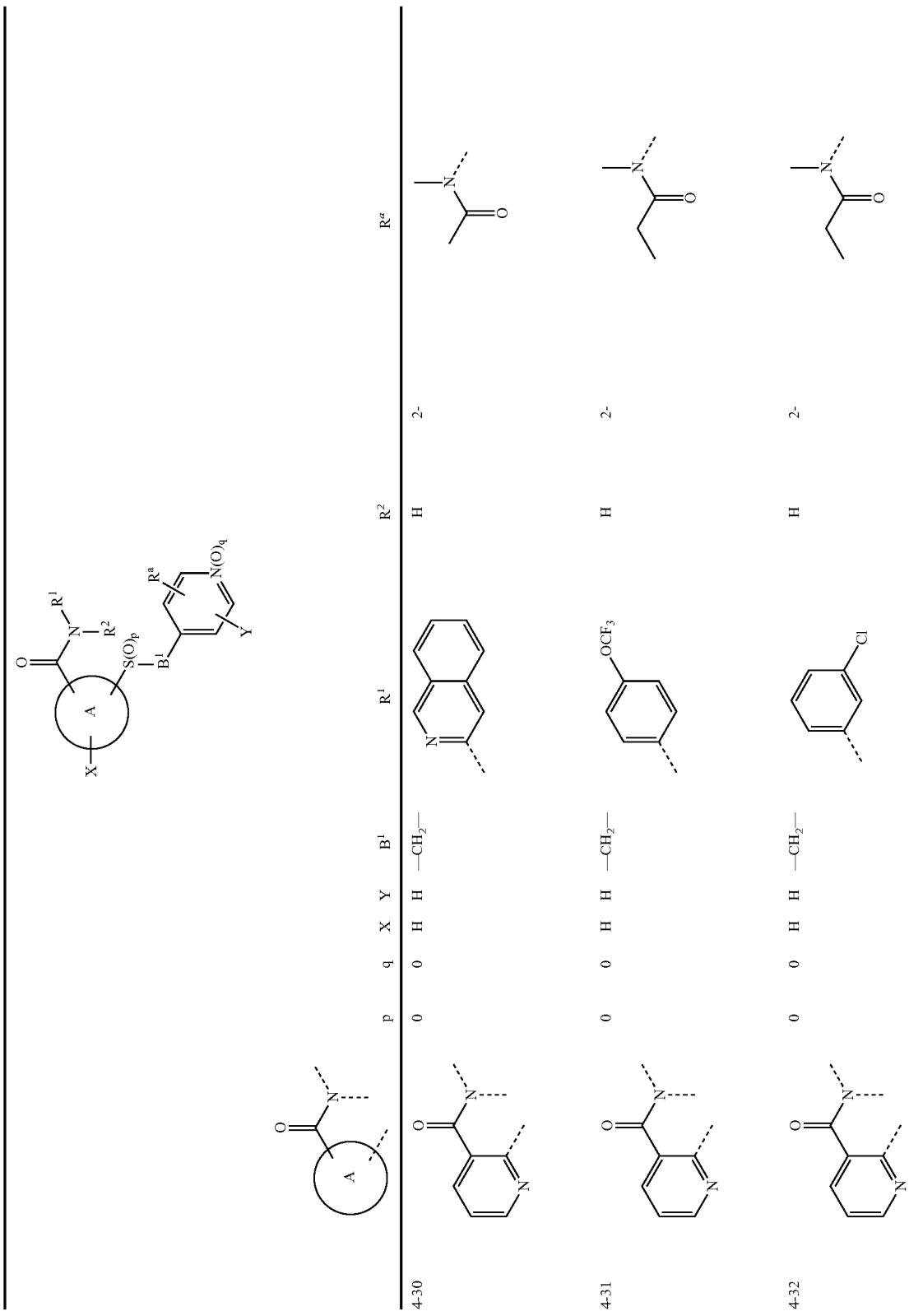

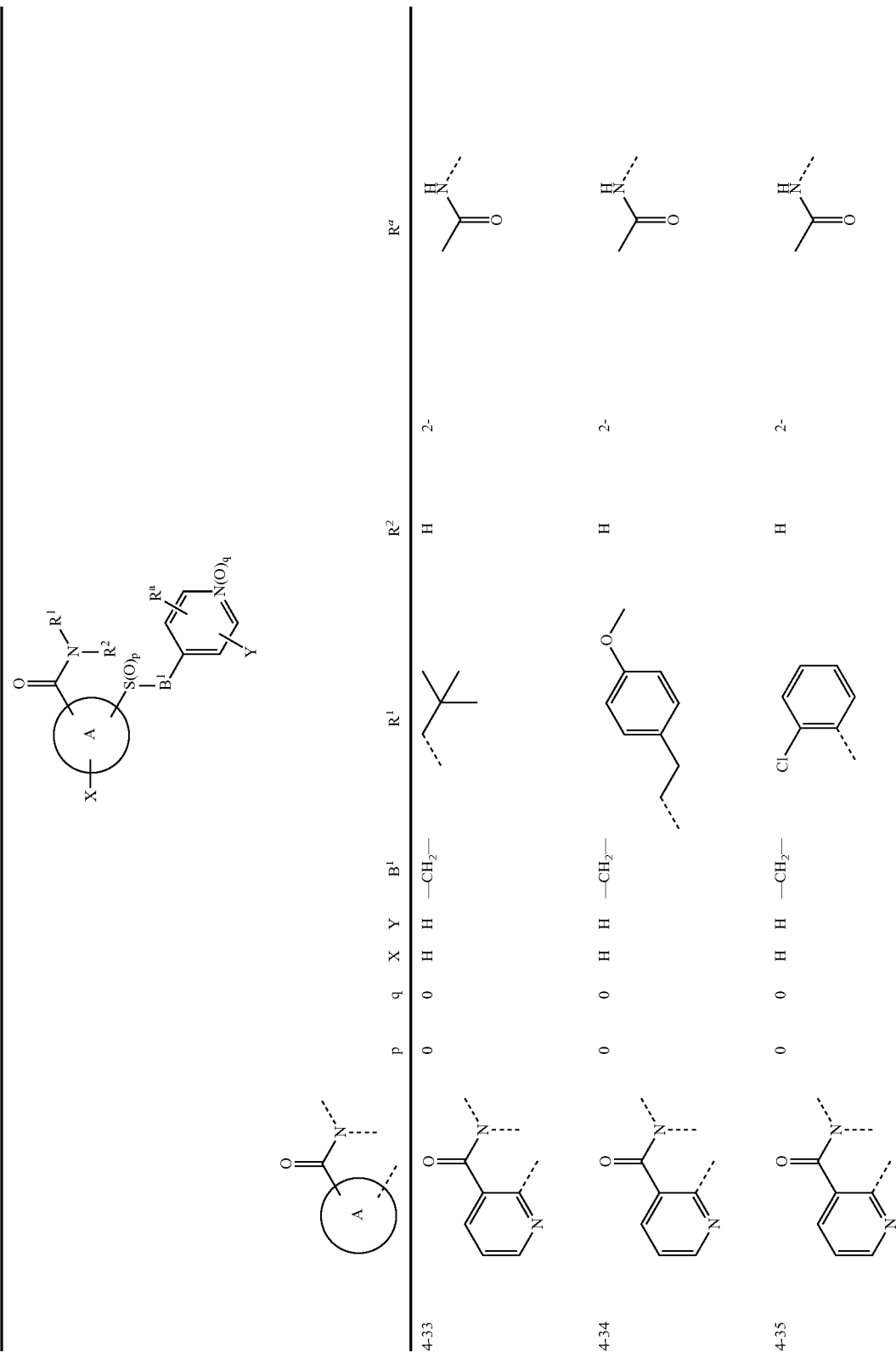

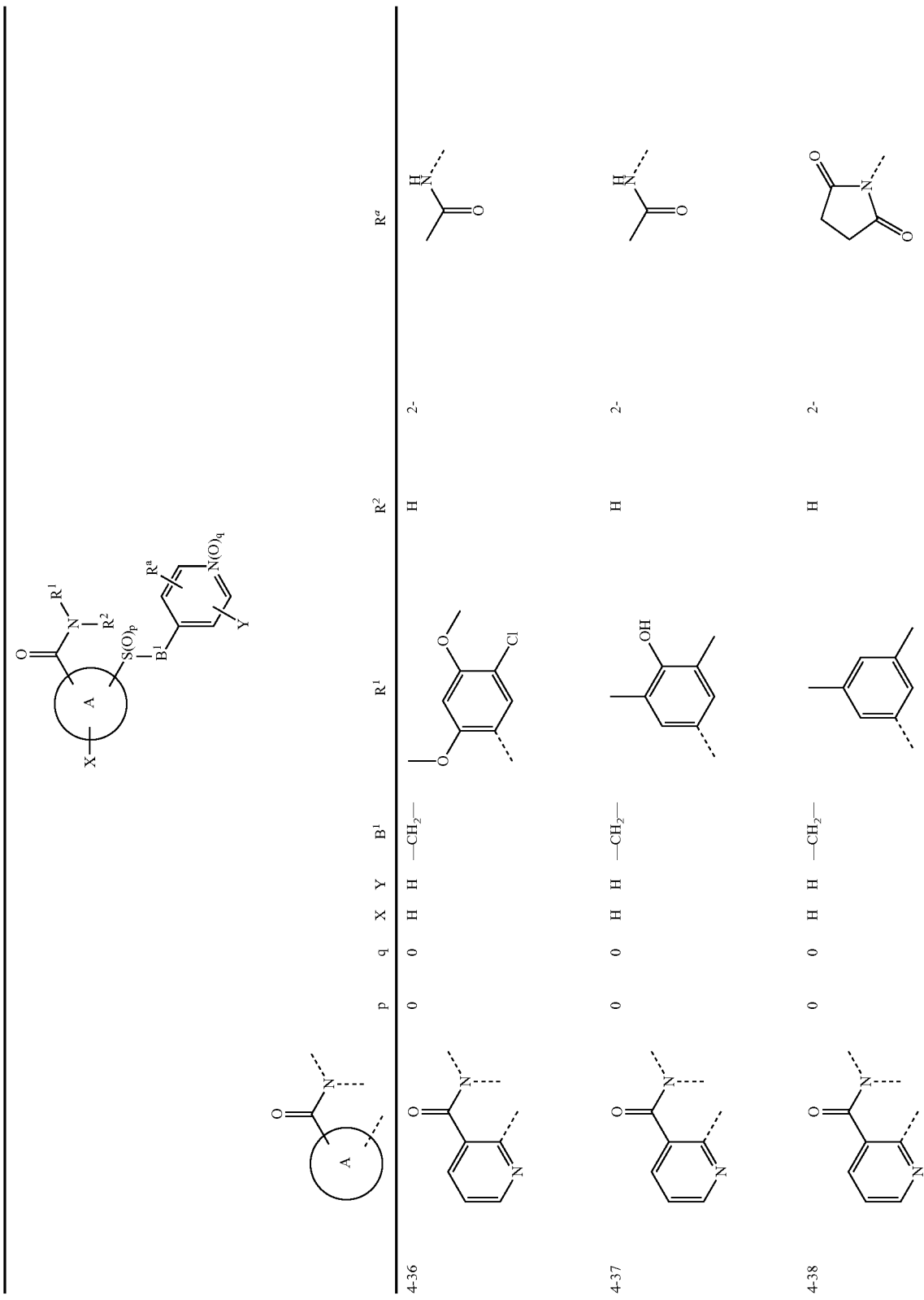

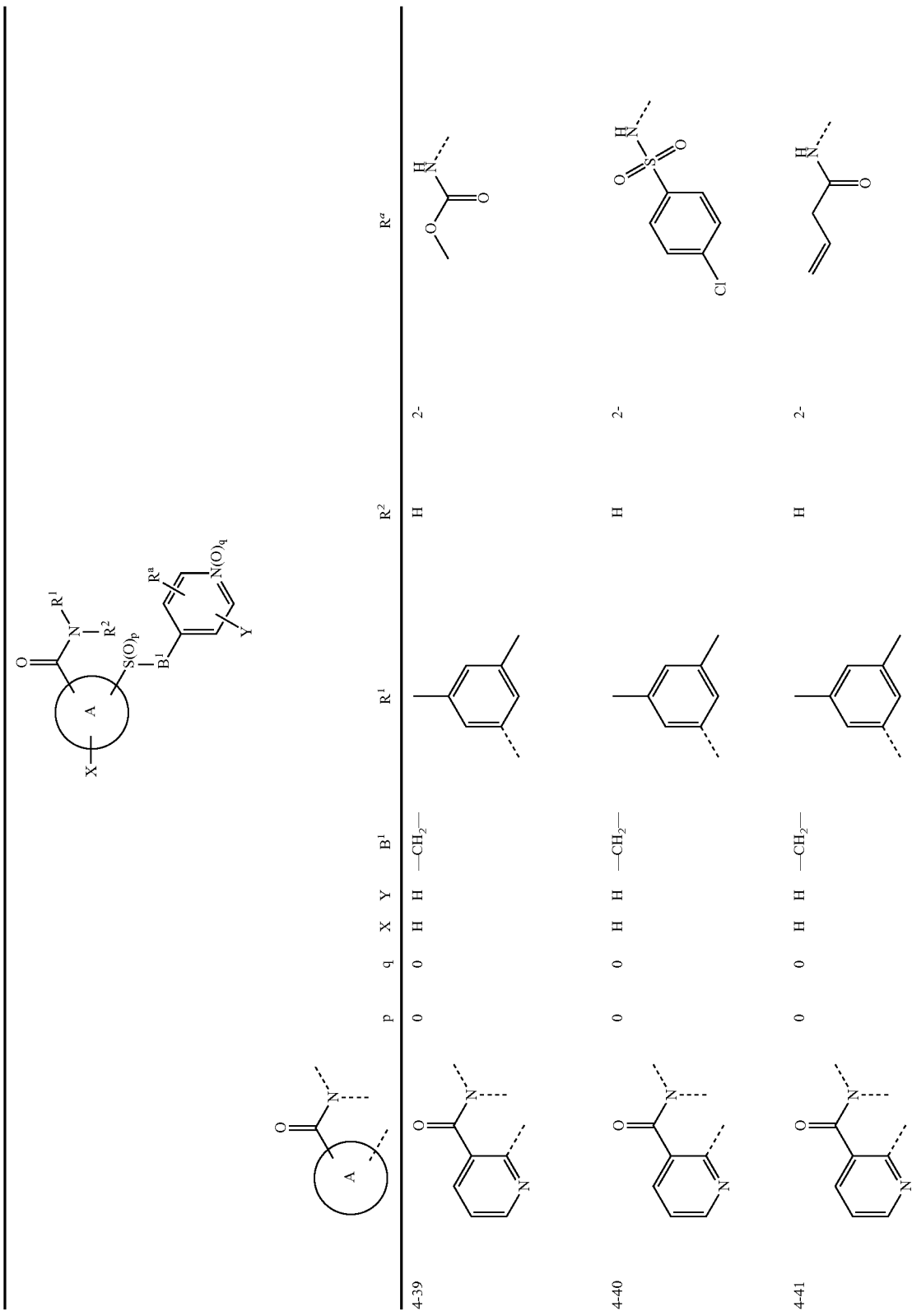

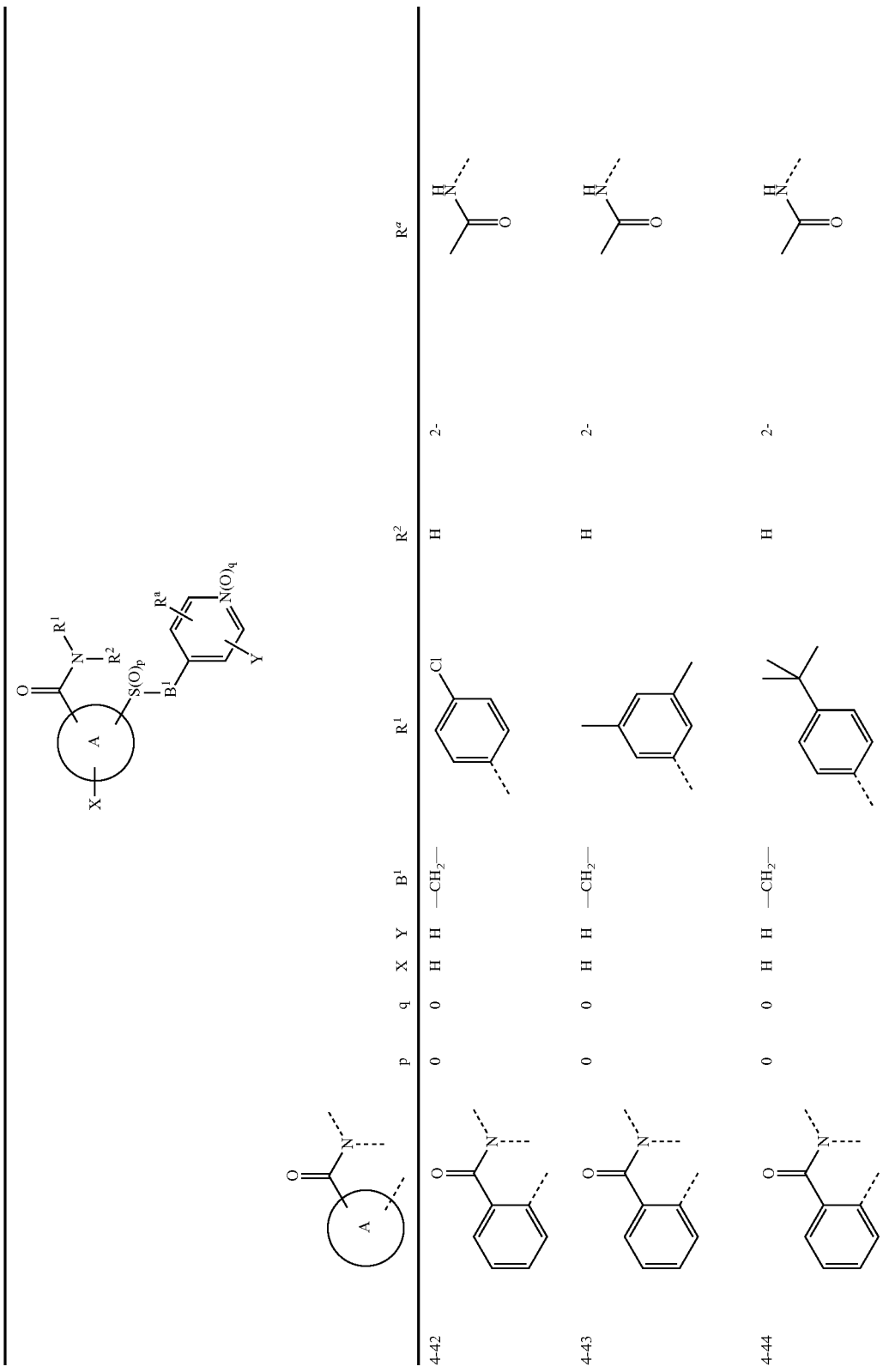

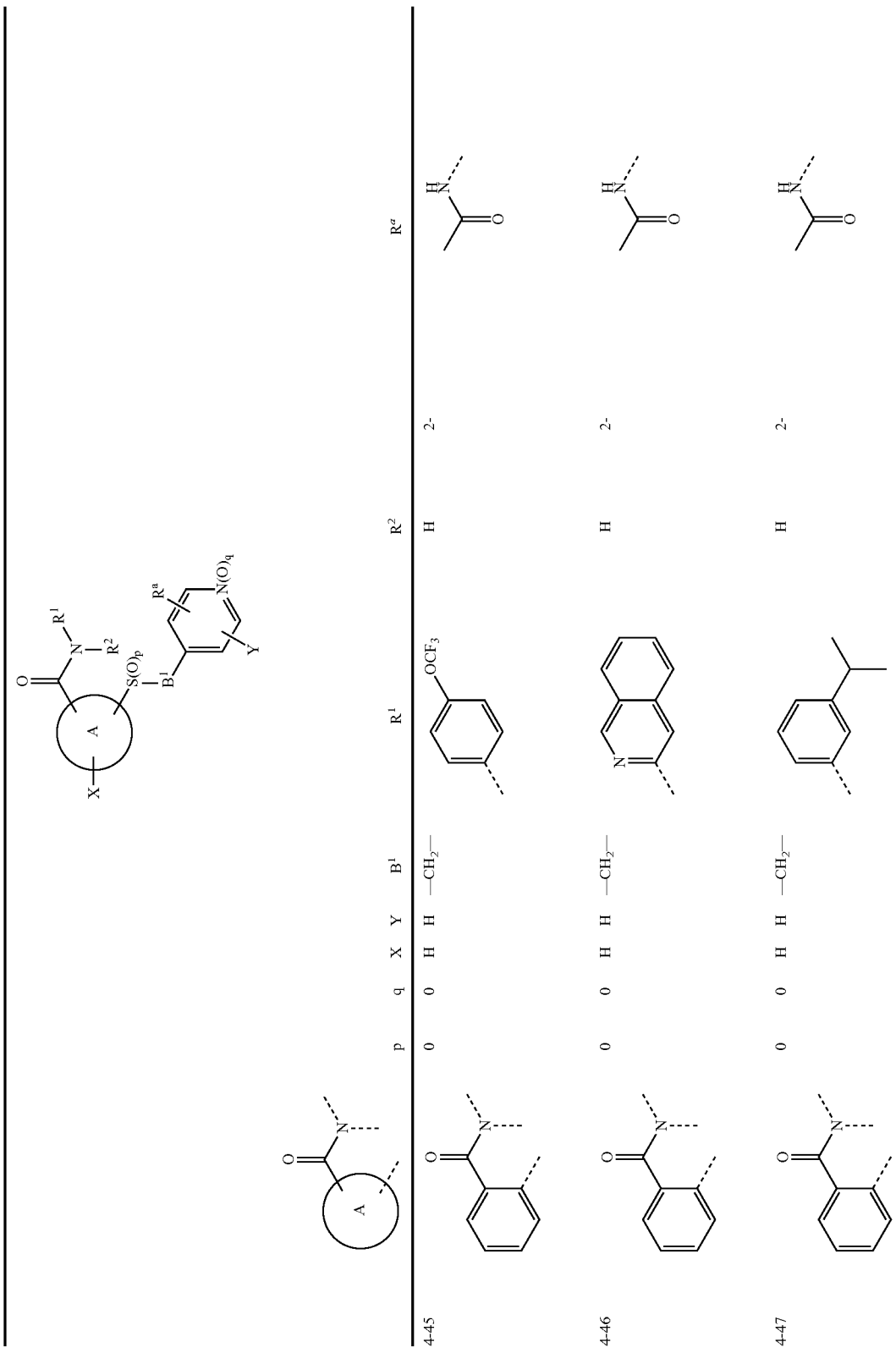

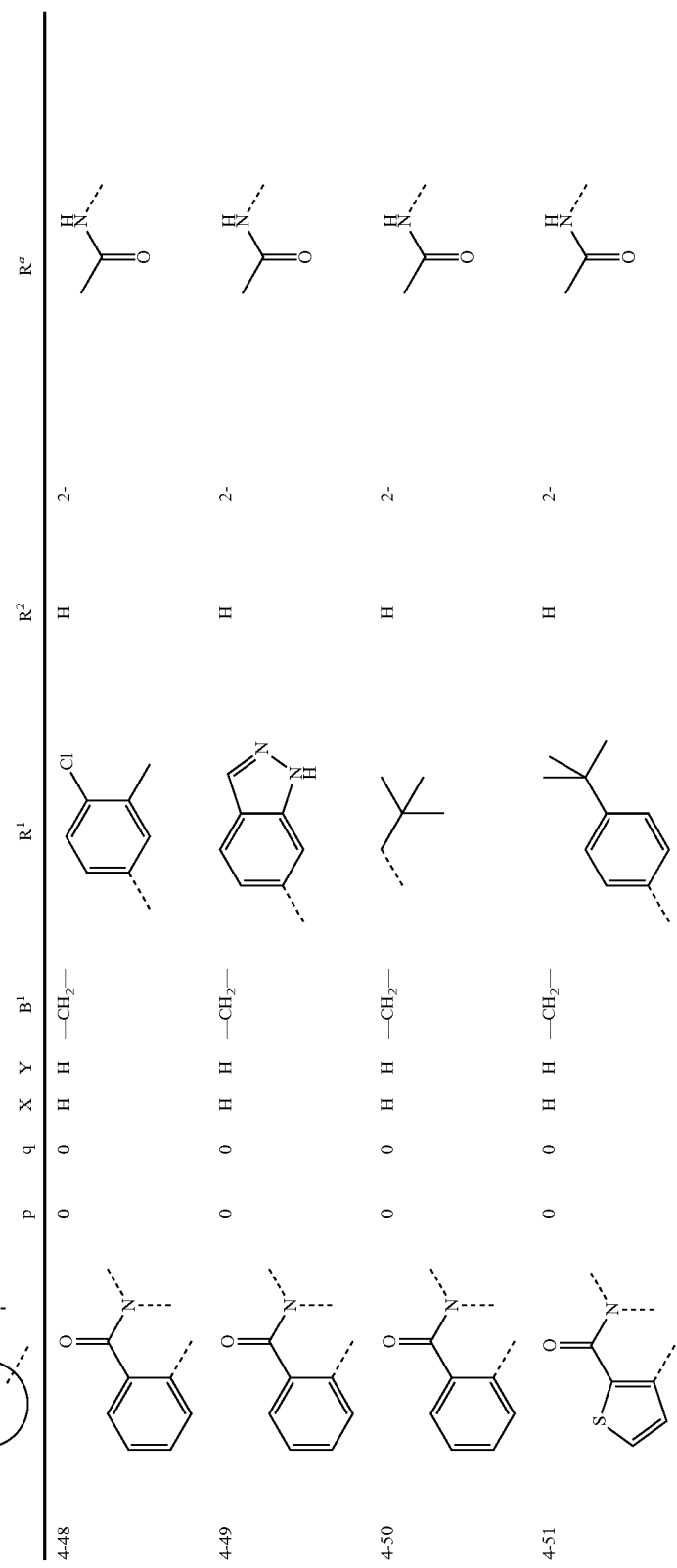

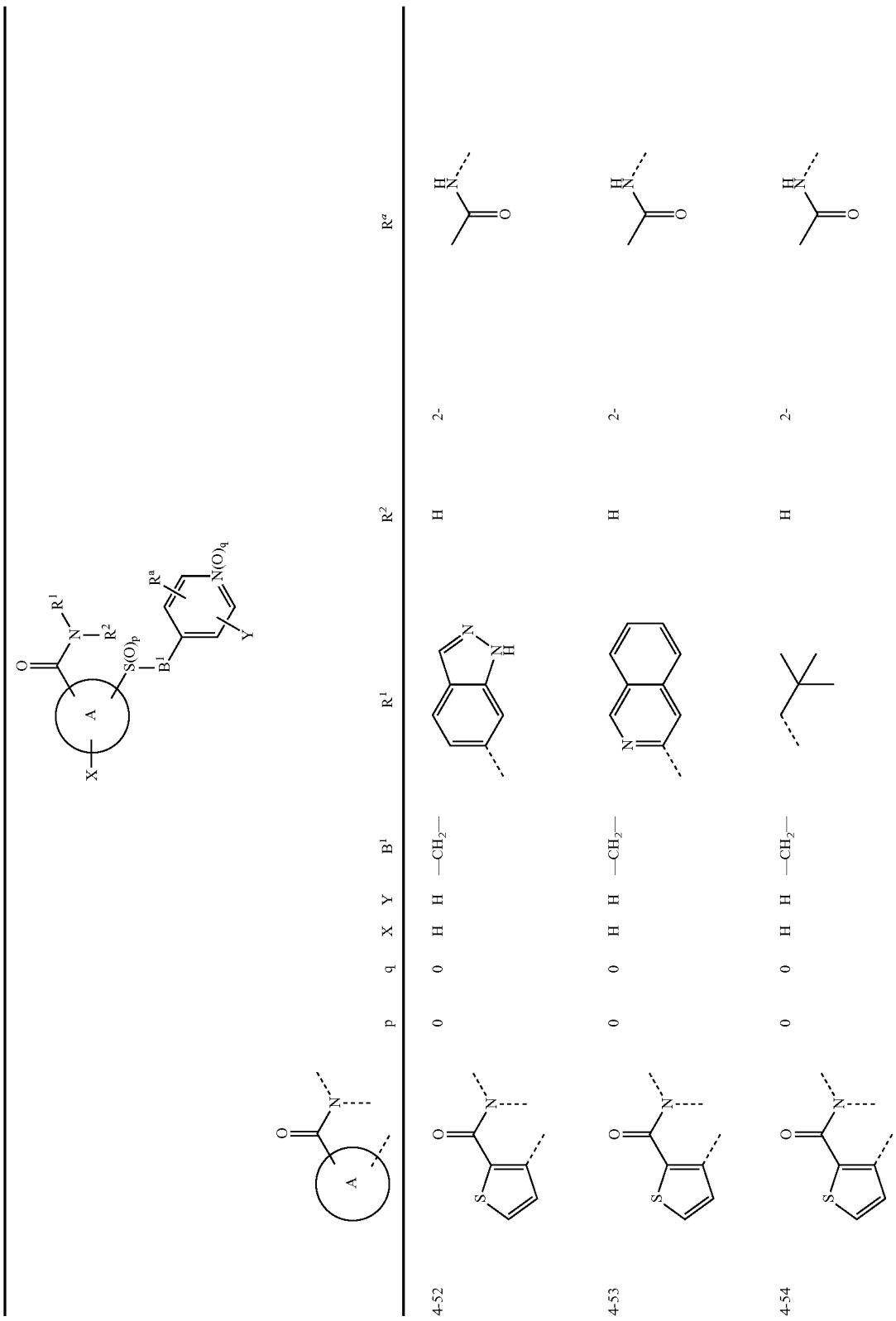

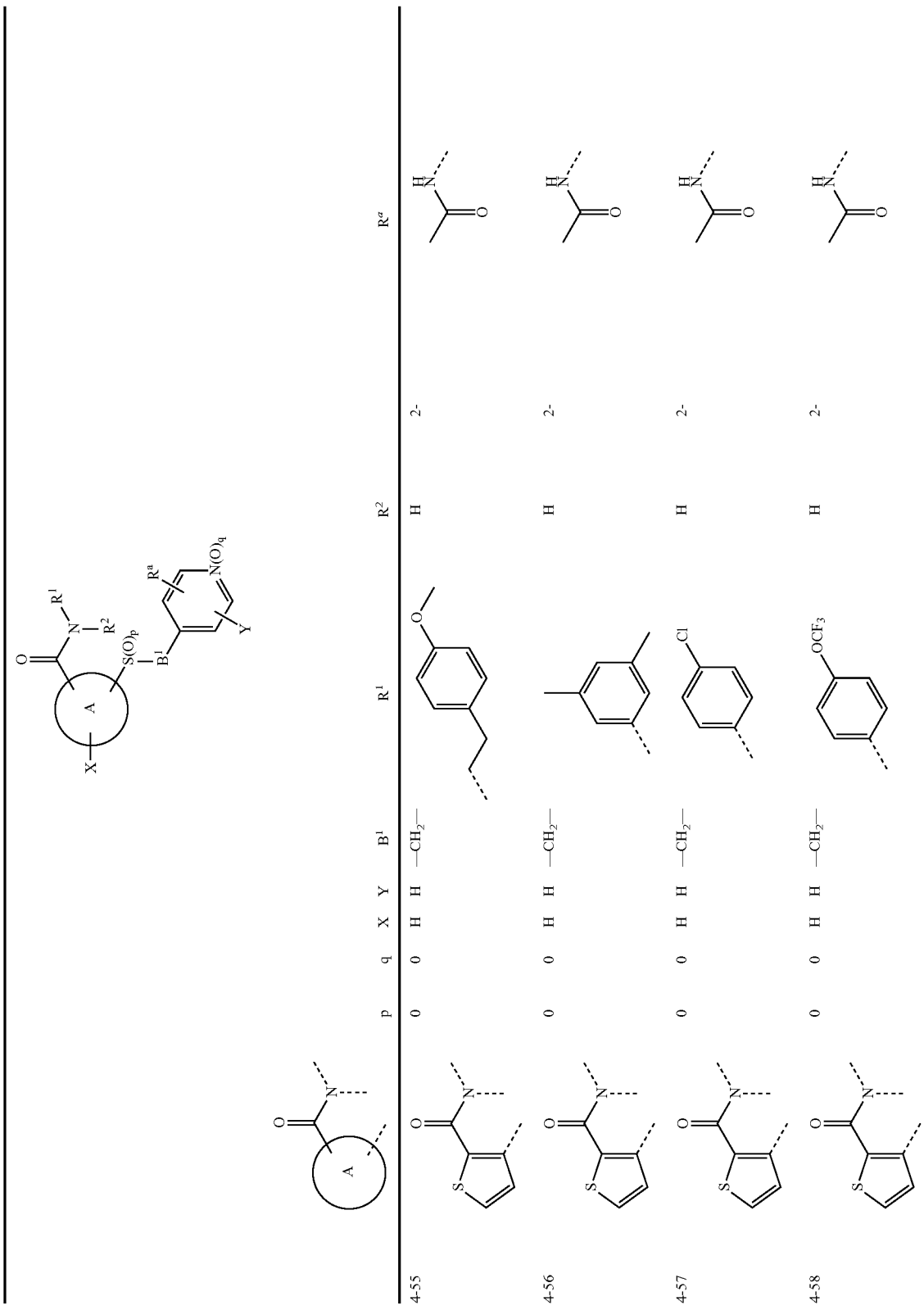

-continued

| | A | p | q | X | Y | B¹ | R¹ | R² | Rᵃ |
|---|---|---|---|---|---|---|---|---|---|
| 4-59 | 3-pyridyl-2-carbonyl | 0 | 0 | H | H | —CH₂— | 3,5-dimethylphenyl | H | 2- CH₂OCH₂C(O)NH— |
| 4-60 | 3-pyridyl-2-carbonyl | 0 | 0 | H | H | —CH₂— | 4-OCF₃-phenyl | H | 2- CH₂OCH₂C(O)NH— |
| 4-61 | 3-pyridyl-2-carbonyl | 0 | 0 | H | H | —CH₂— | 3,5-dimethylphenyl | H | 2- PhOCH₂C(O)NH— |

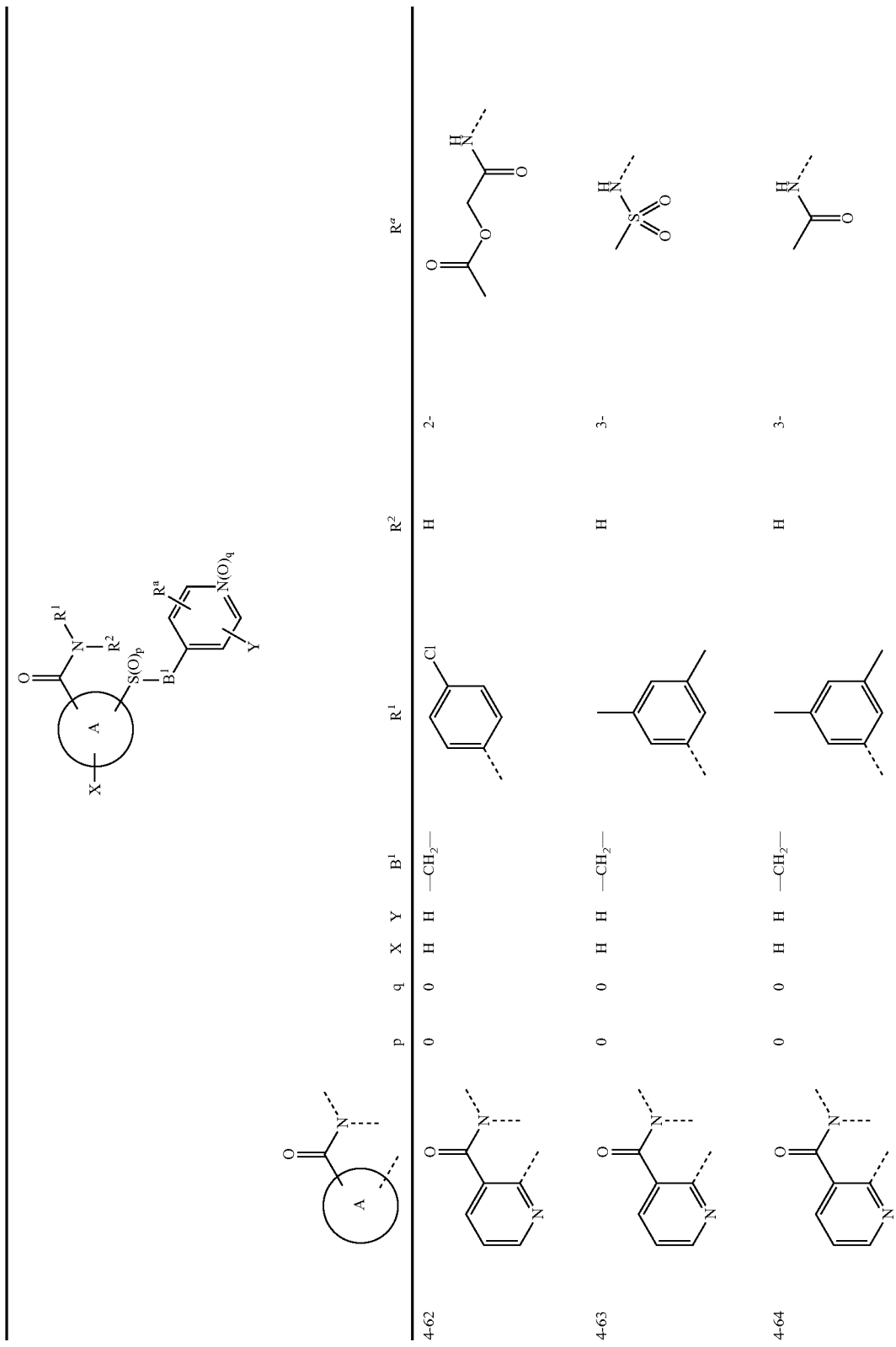

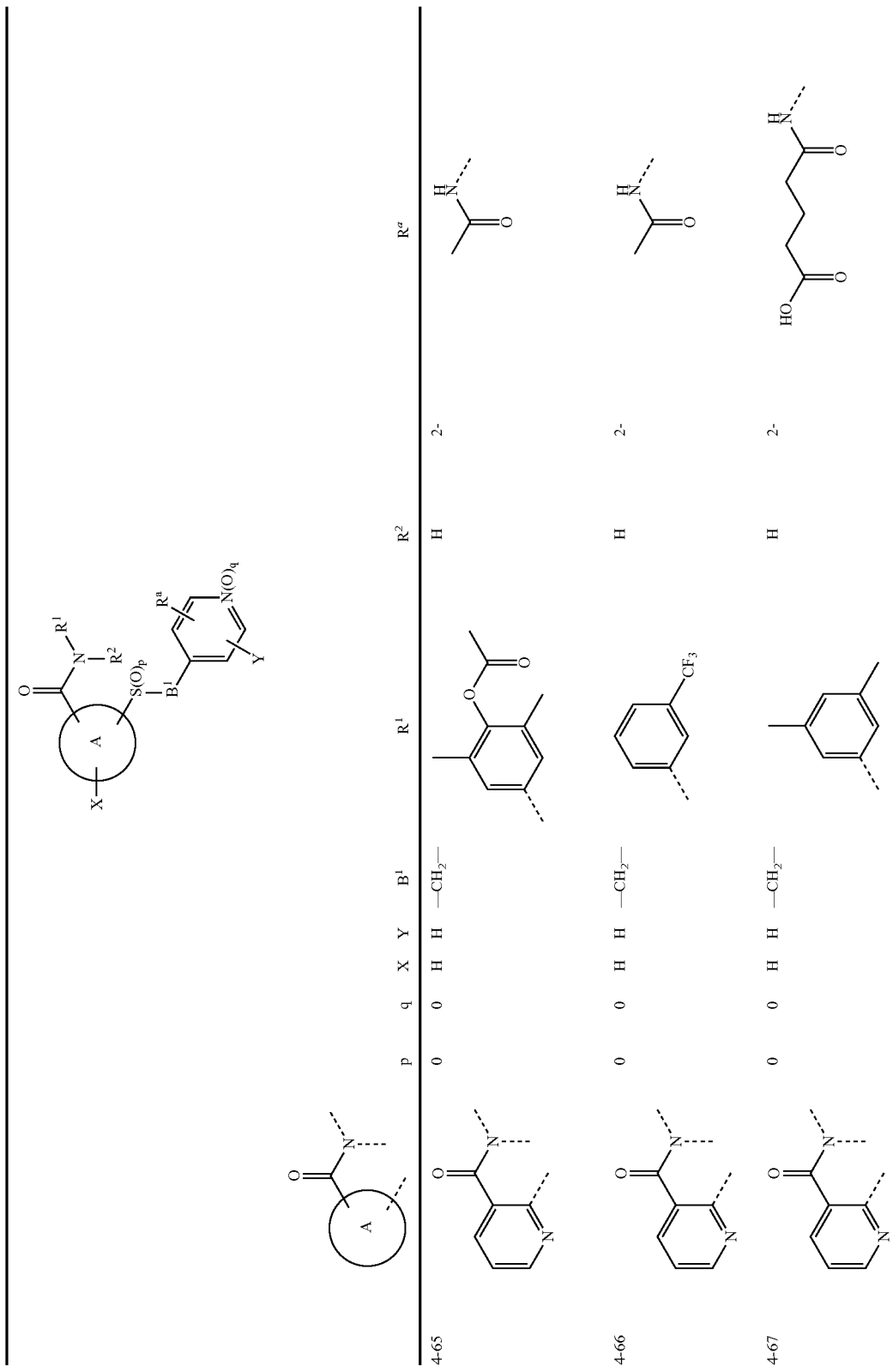

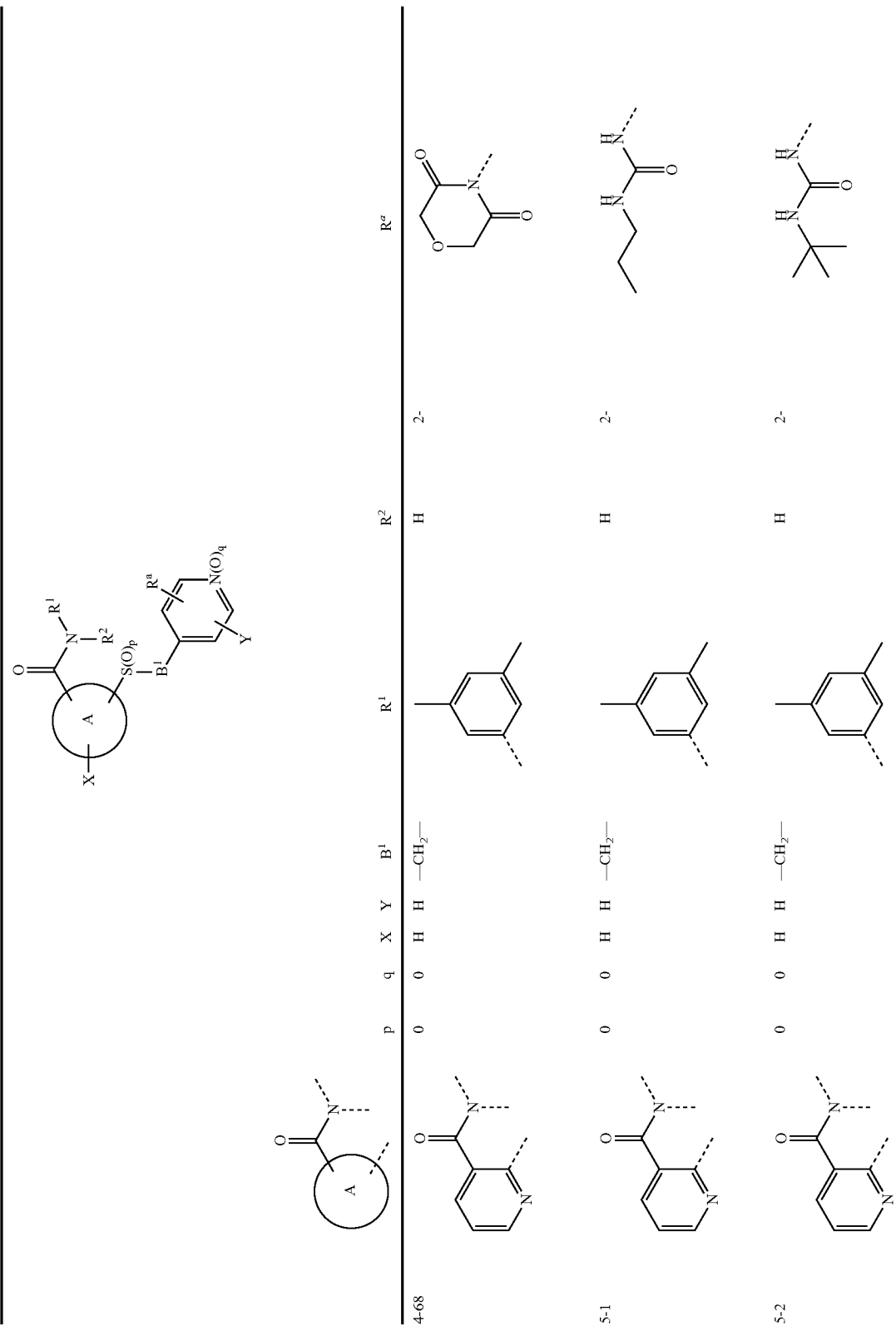

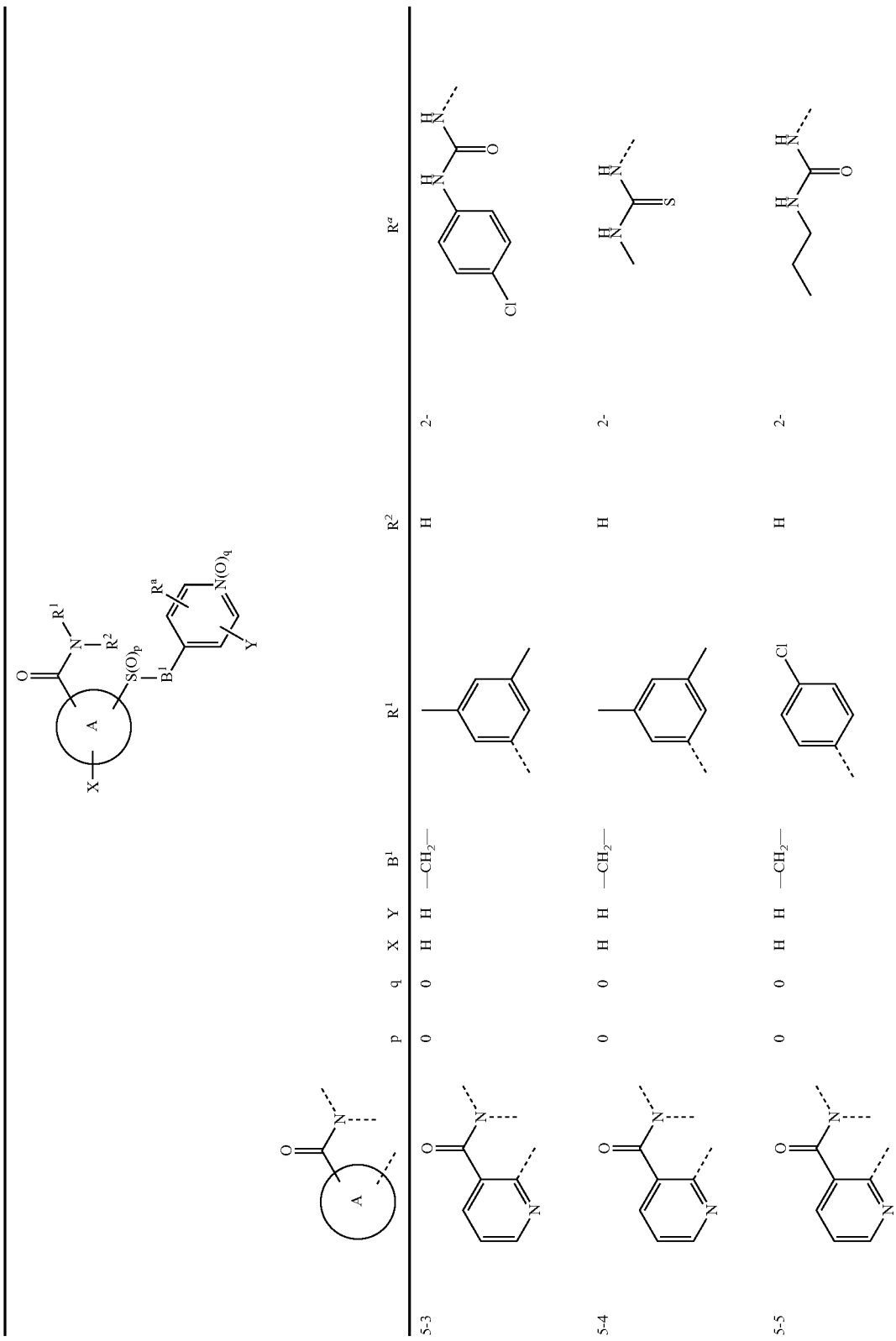

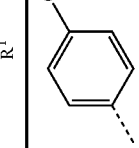

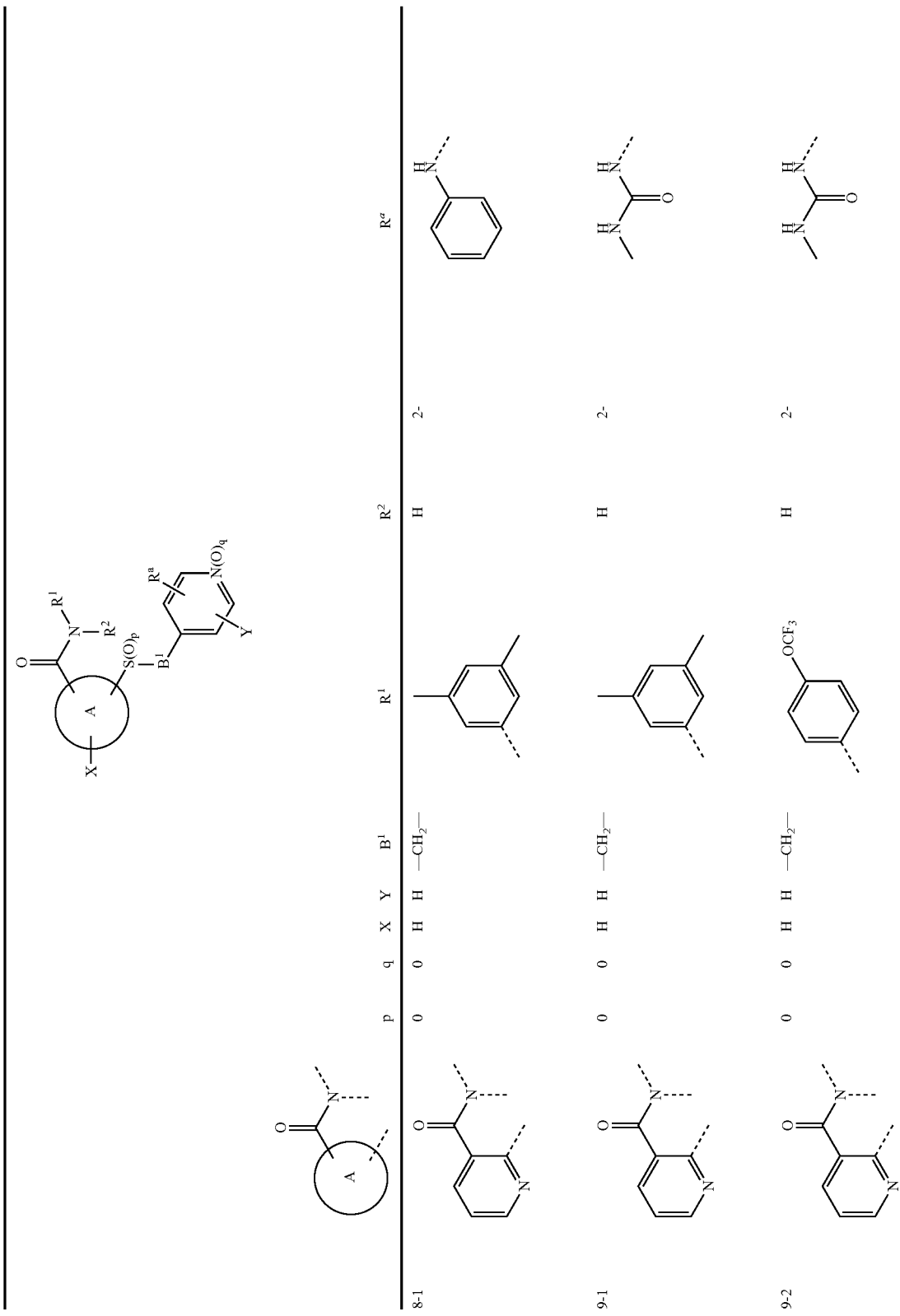

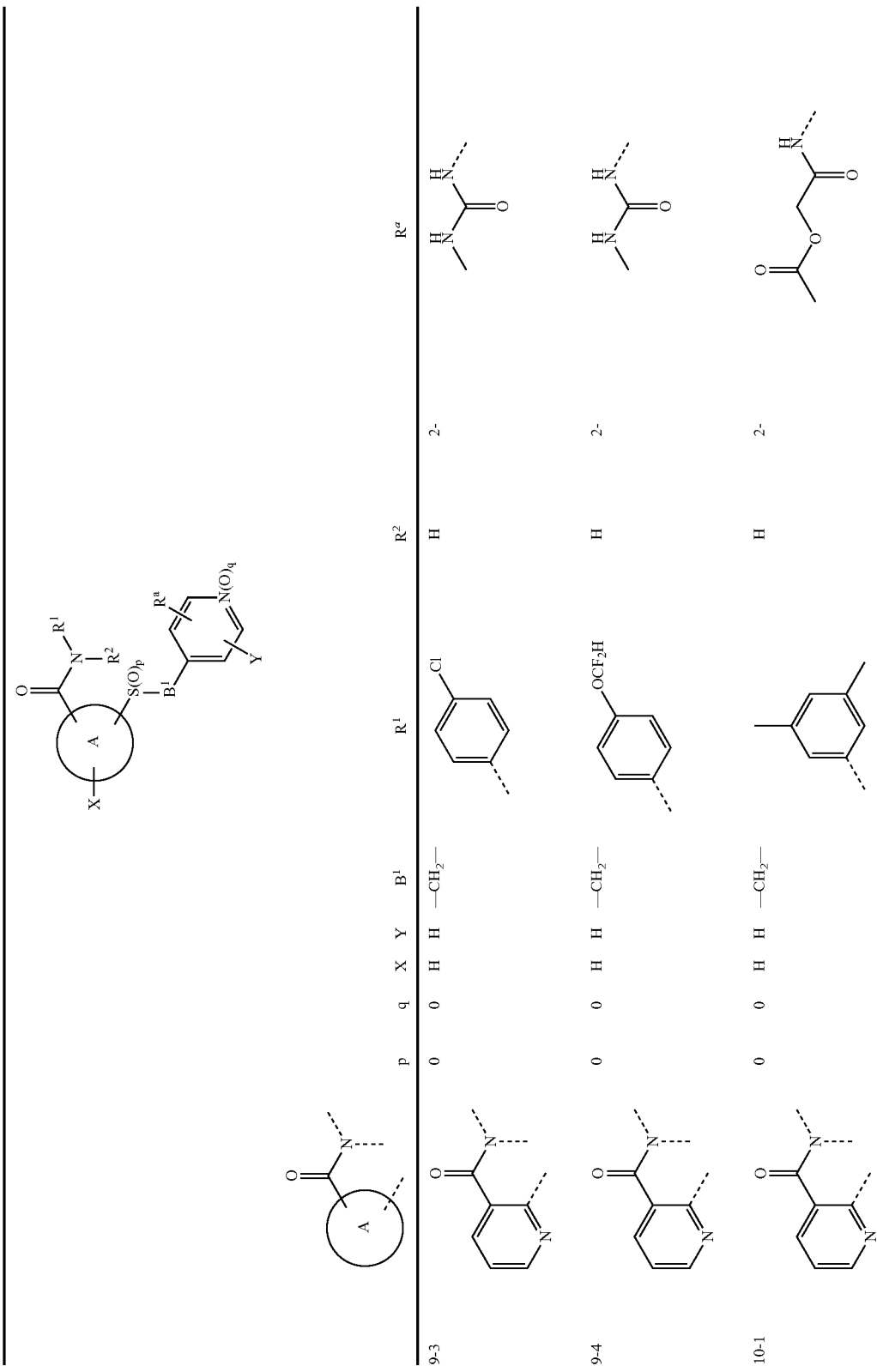

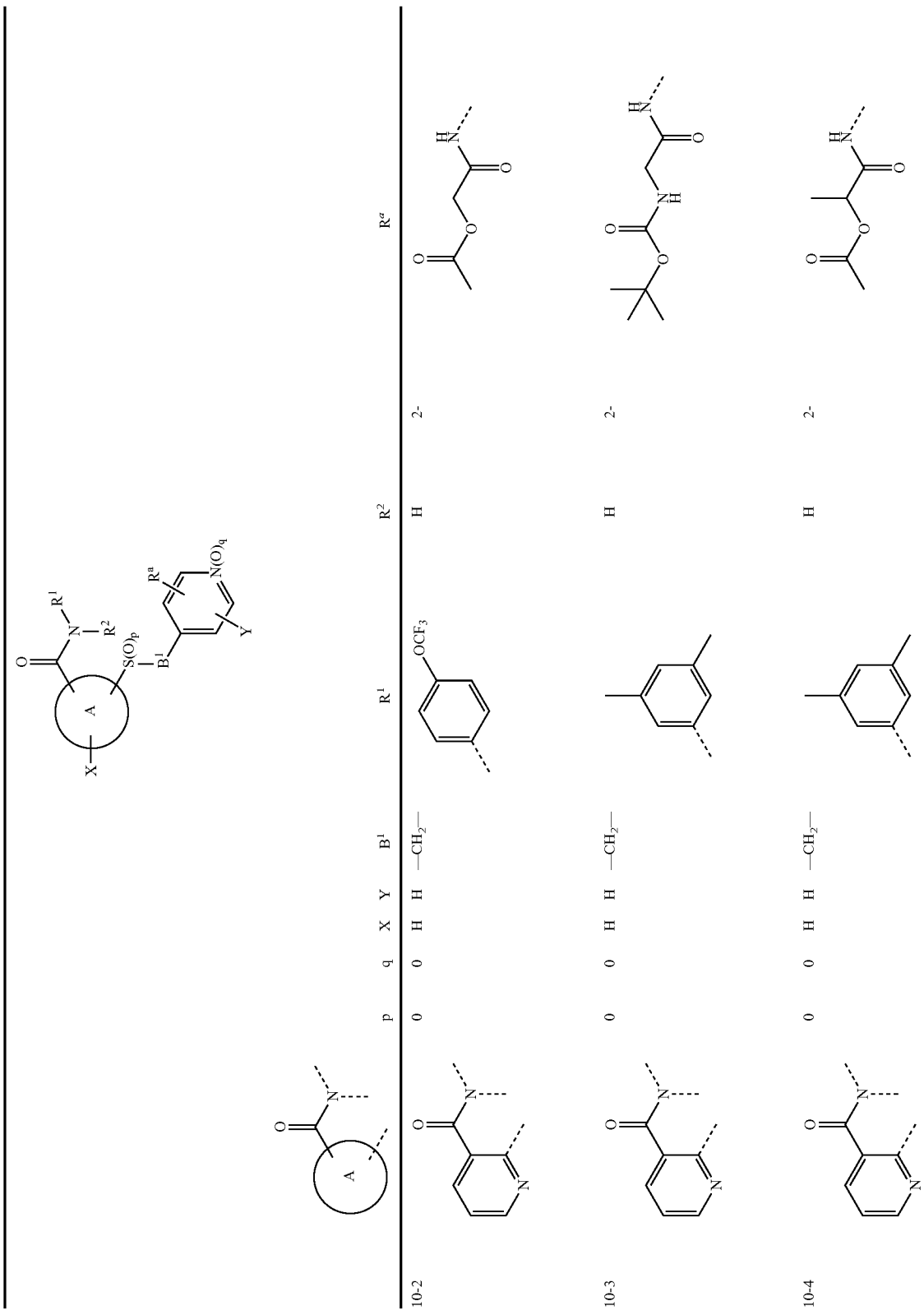

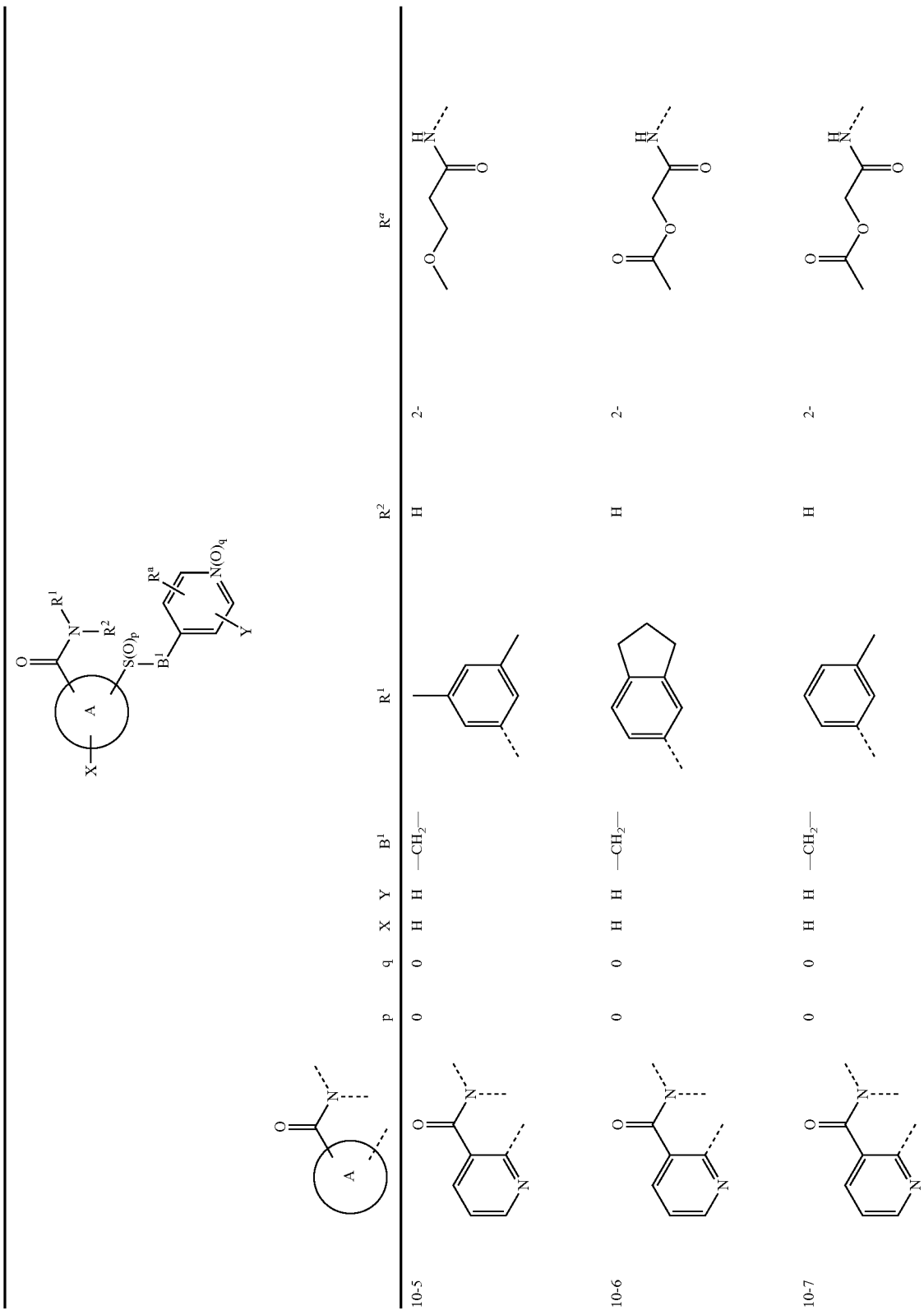

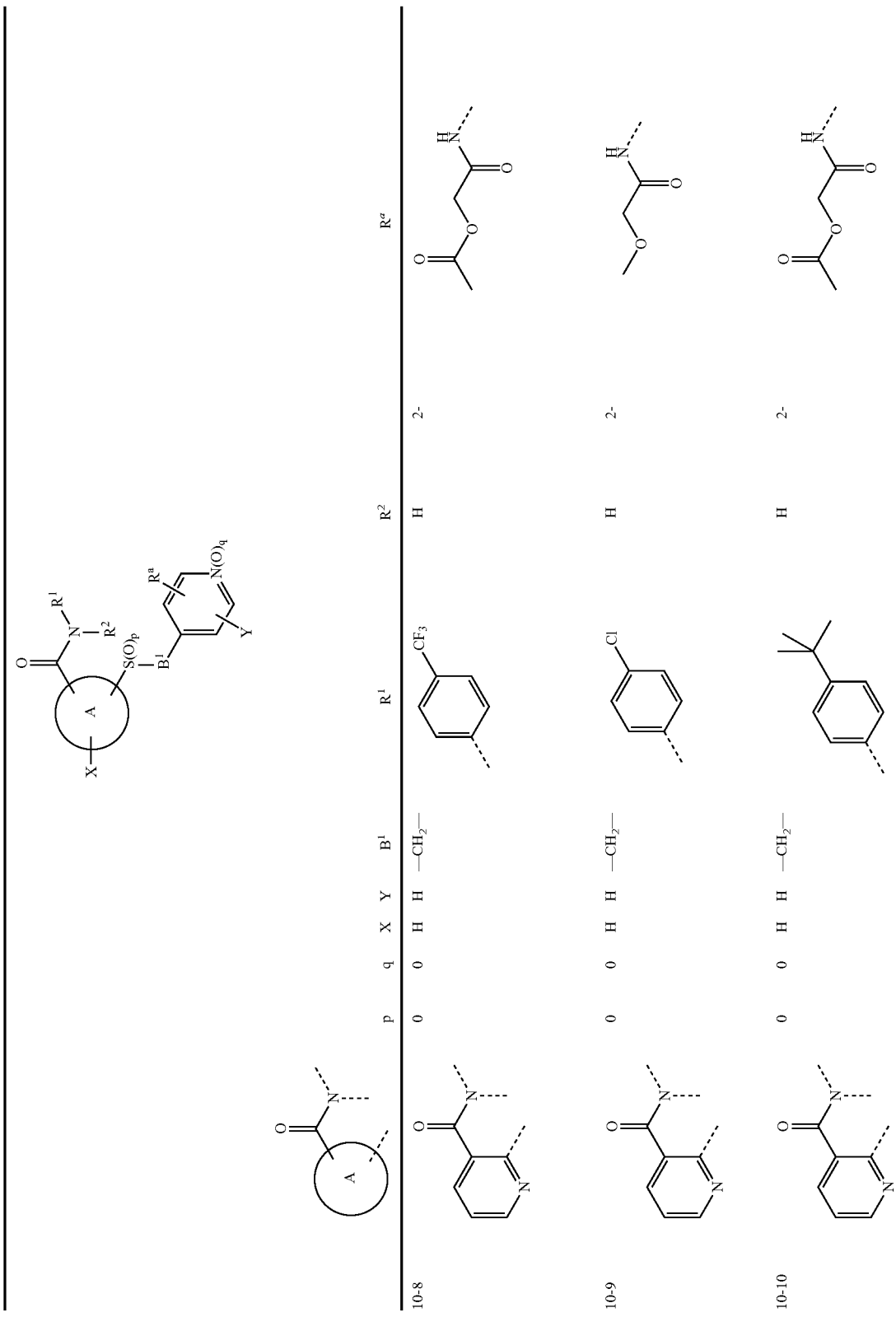

-continued

| | p | q | X | Y | B¹ | R¹ | R² | Rᵃ |
|---|---|---|---|---|---|---|---|---|
| 10-11 | pyridine-C(O)N | 0 | 0 | H | H | 4-OCF₃-phenyl | 2- | methoxypropanamide | |
| 10-12 | pyridine-C(O)N | 0 | 0 | H | —CH₂— | | 3-Cl-4-OCF₃-phenyl | H | acetoxy-acetamide |
| 10-13 | pyridine-C(O)N | 0 | 0 | H | —CH₂— | | 3-CF₃-phenyl | H | acetoxy-acetamide |

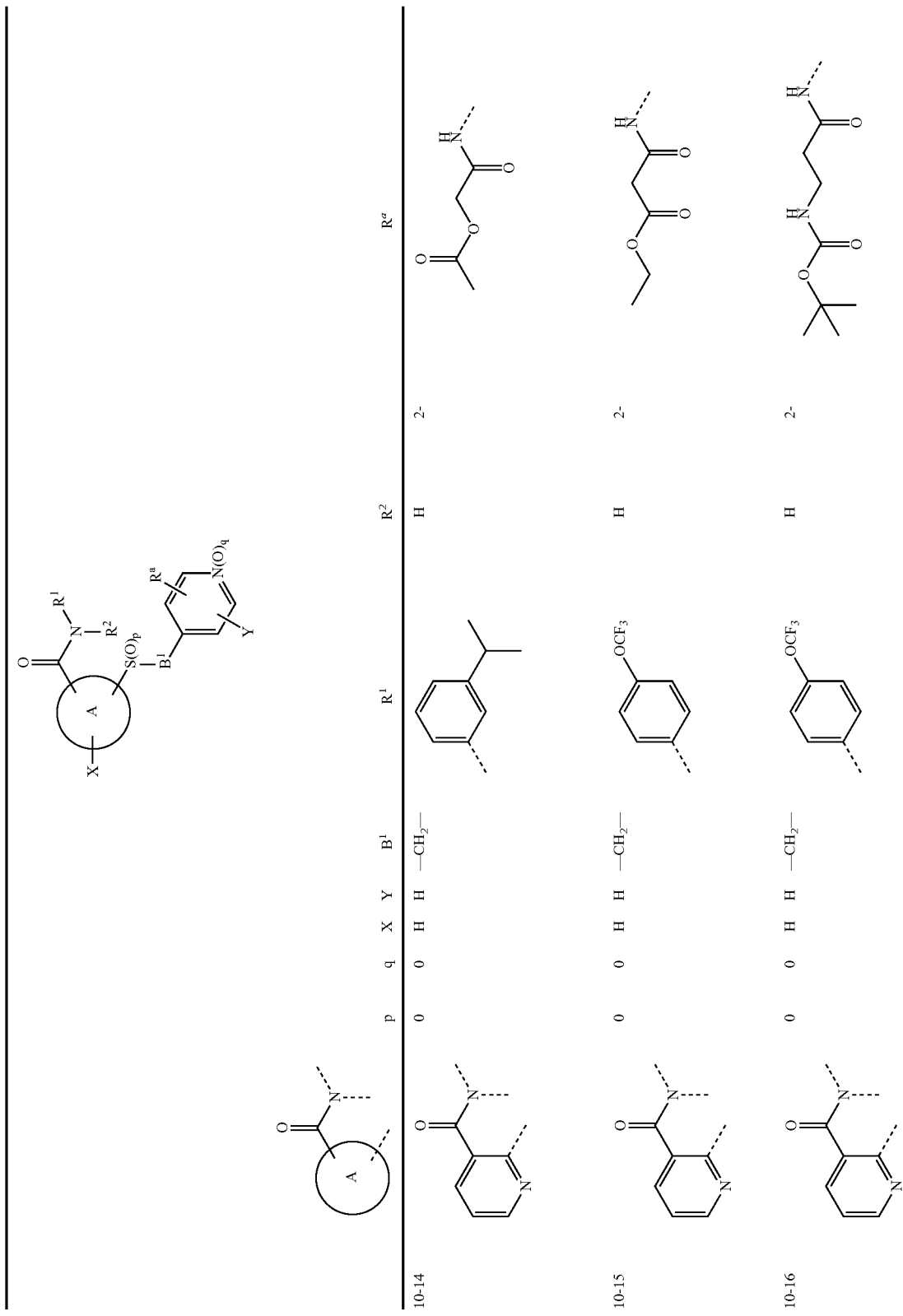

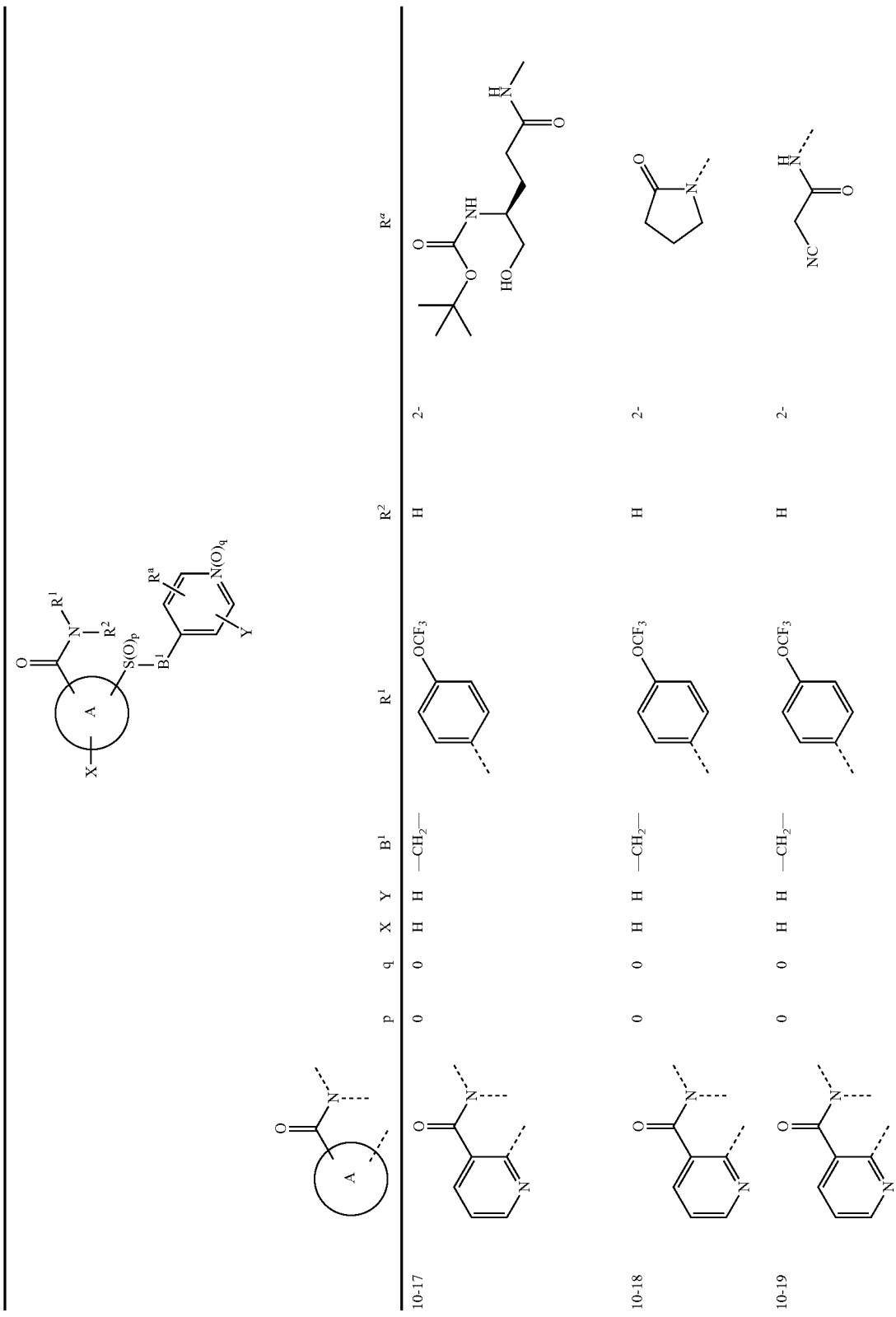

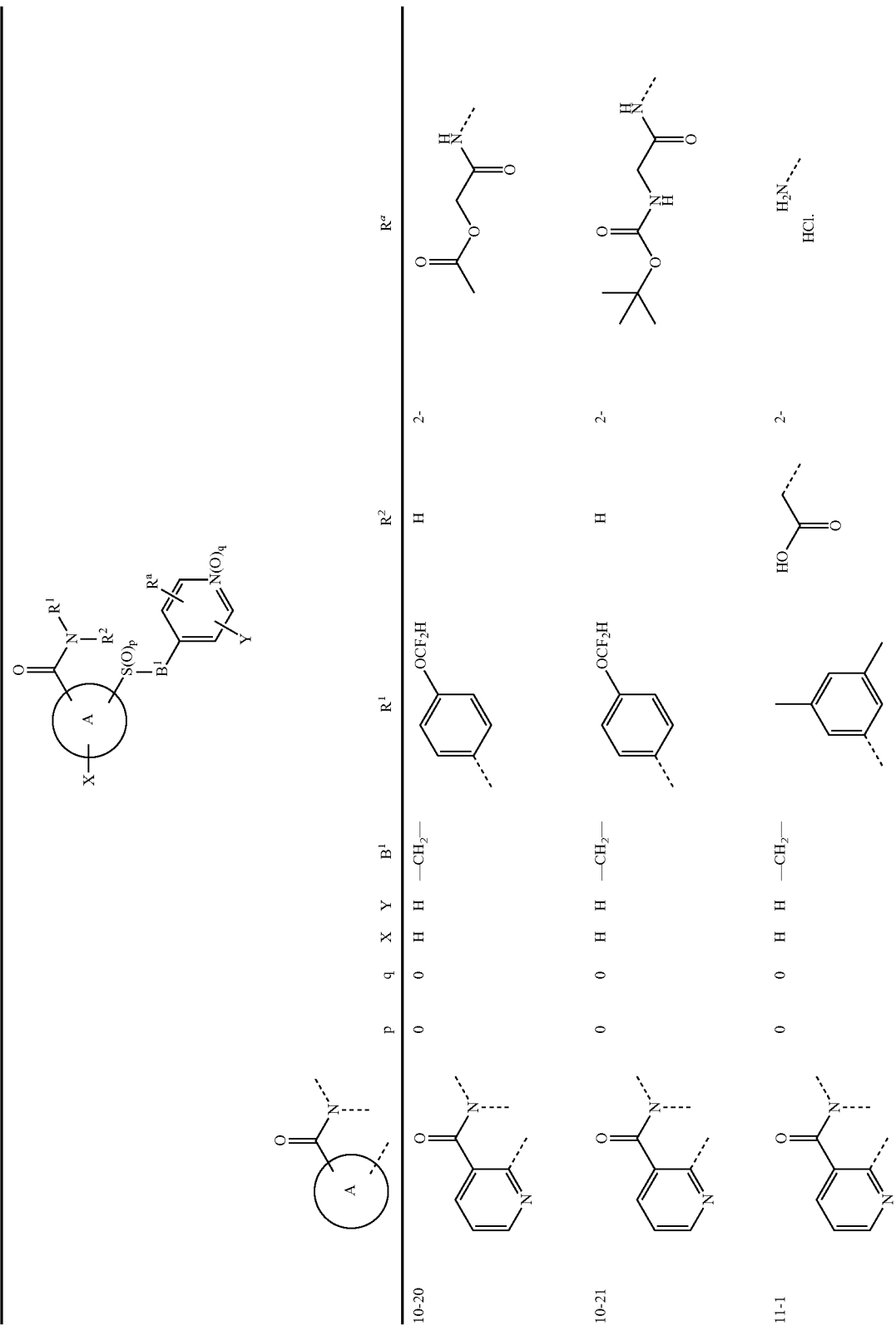

| | A | p | q | X | Y | B¹ | R¹ | R² | Rᵃ |
|---|---|---|---|---|---|---|---|---|---|
| 11-2 | 2-methylpyridin-3-yl carbonyl | 0 | 0 | H | H | —CH₂— | 3,5-dimethylphenyl | H | 2- glycinamide, HCl |
| 11-3 | 2-methylpyridin-3-yl carbonyl | 0 | 0 | H | H | —CH₂— | 4-(trifluoromethoxy)phenyl | H | 2- (S)-2-amino-4-hydroxybutanamide, HCl |
| 12-1 | 2-methylpyridin-3-yl carbonyl | 0 | 0 | H | H | —CH₂— | 4-(trifluoromethoxy)phenyl | H | 2- 2-hydroxyacetamide |

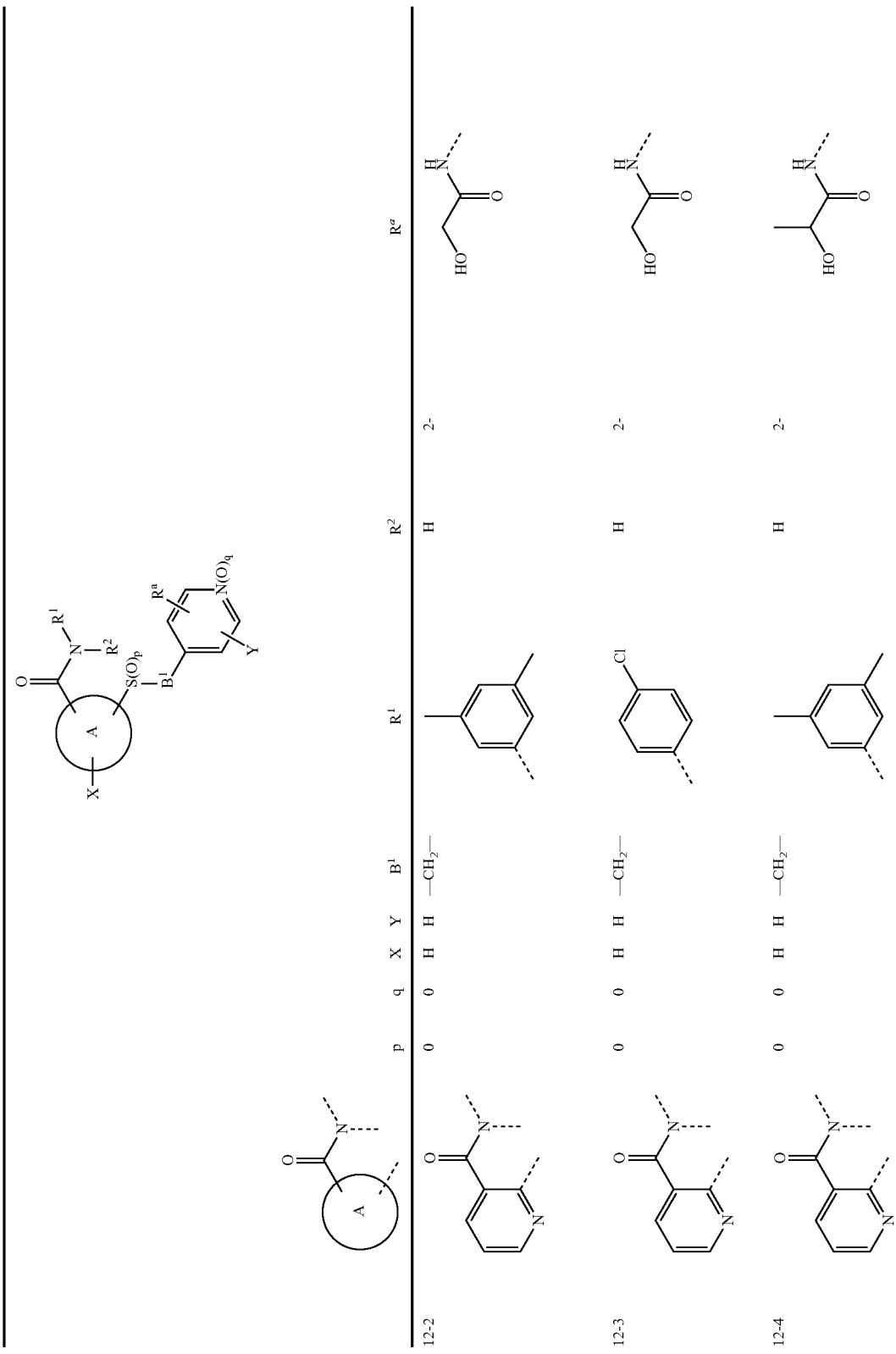

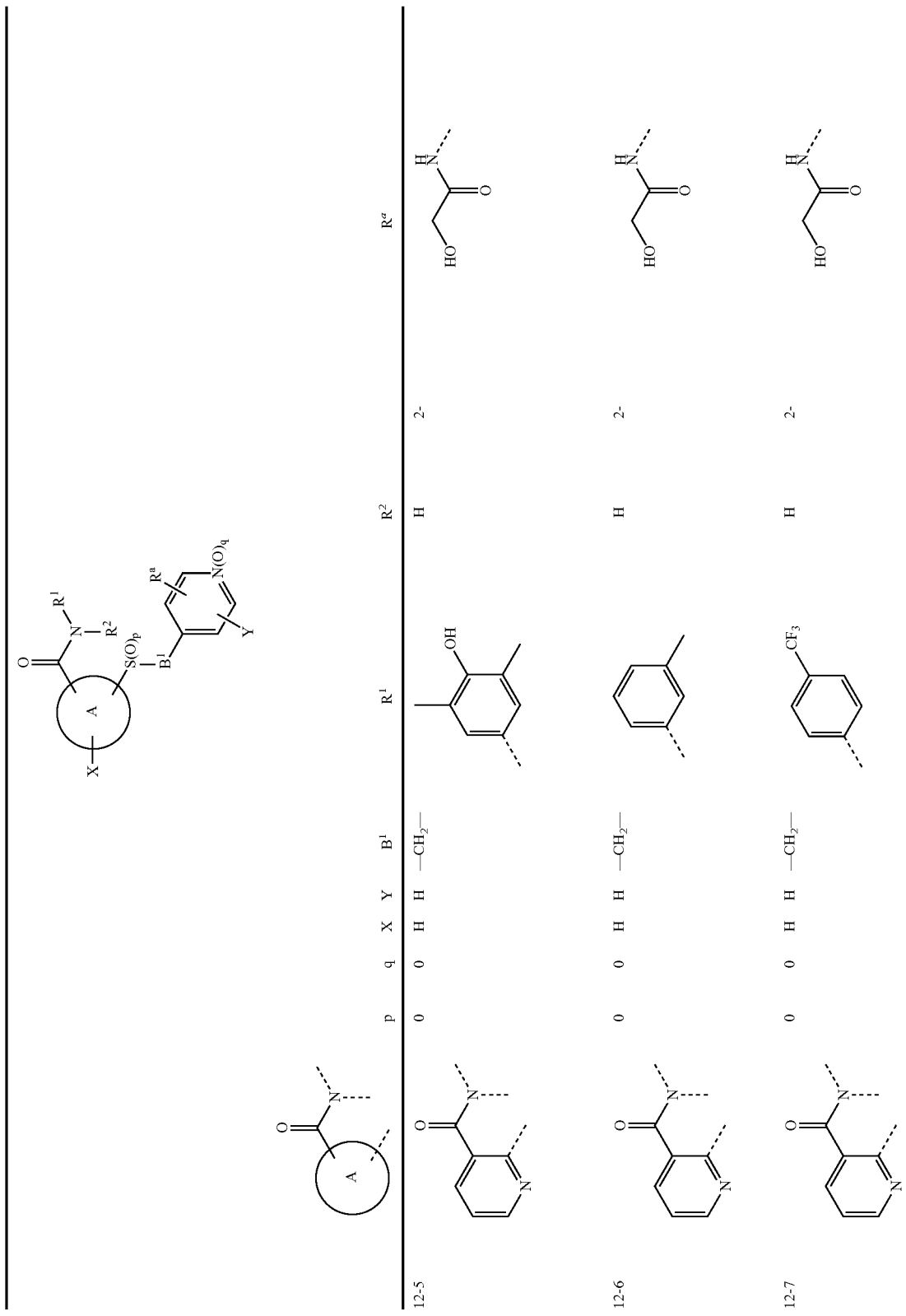

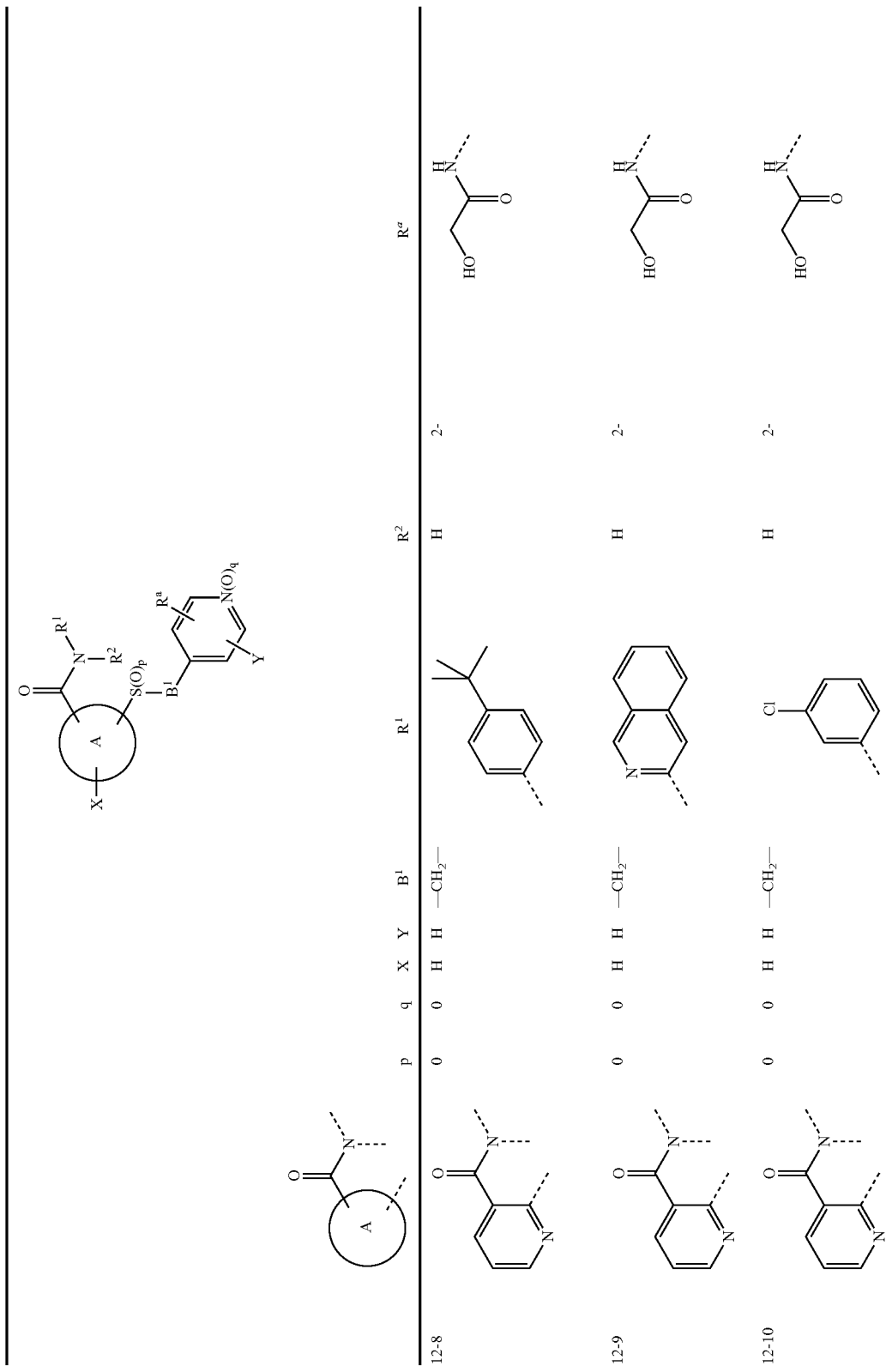

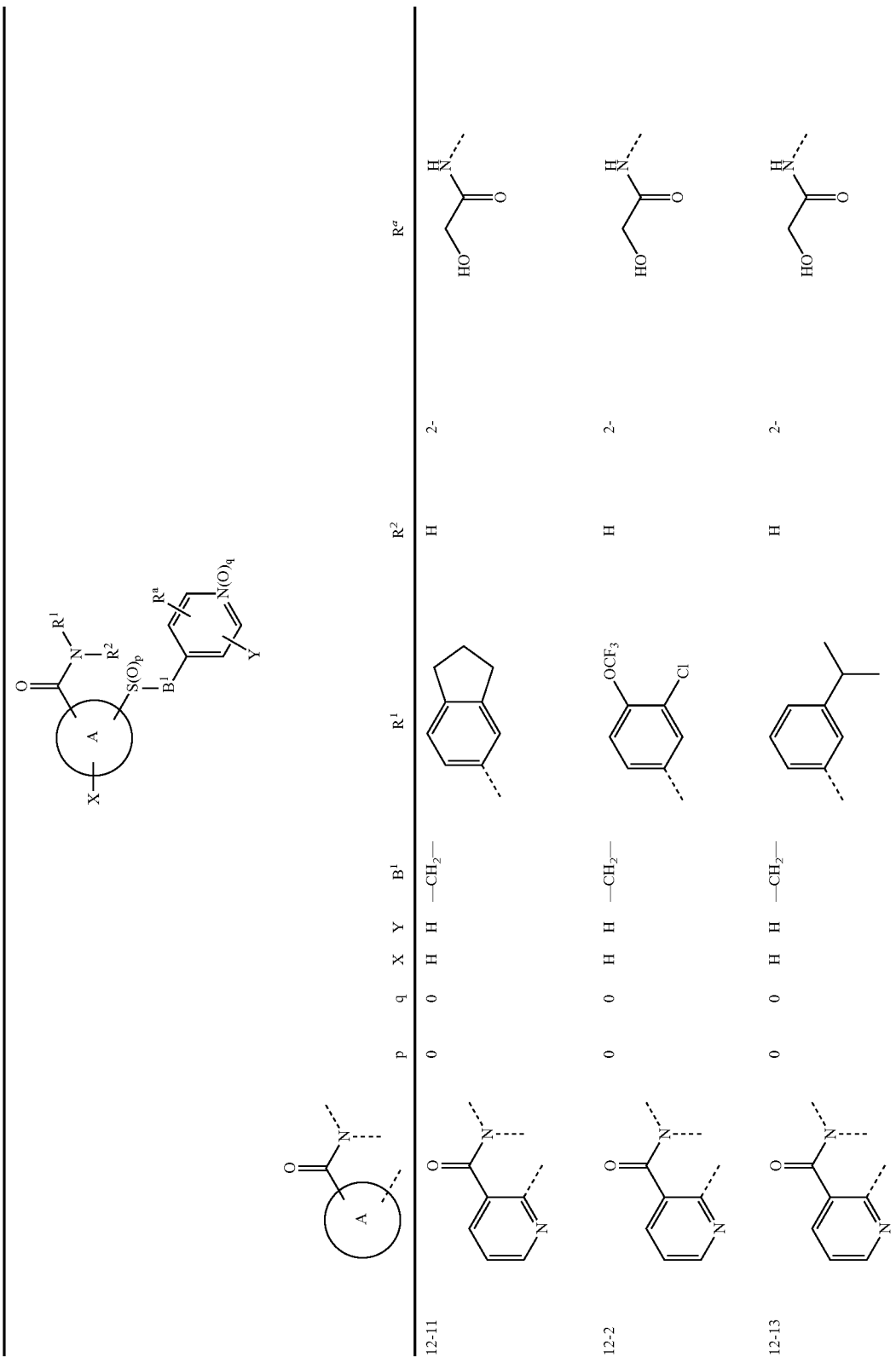

-continued

| | | p | q | X | Y | B¹ | R¹ | R² | | Rᵃ |
|---|---|---|---|---|---|---|---|---|---|---|
| 12-14 | pyridine-3-carbonyl (2-methyl) | 0 | 0 | H | H | —CH₂— | 4-OCF₃-phenyl | H | 2- | NHC(O)CH₂C(O)OH |
| 12-15 | pyridine-3-carbonyl (2-methyl) | 0 | 0 | H | H | —CH₂— | 4-OCF₂H-phenyl | H | 2- | NHC(O)CH₂OH |
| 12-16 | pyridine-3-carbonyl (2-methyl) | 0 | 0 | H | H | —CH₂— | 3-CF₃-phenyl | H | 2- | NHC(O)CH₂OH |

-continued
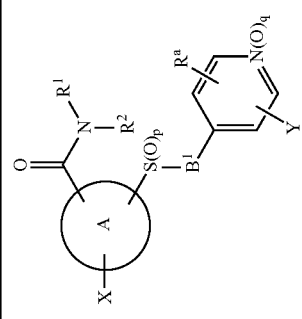
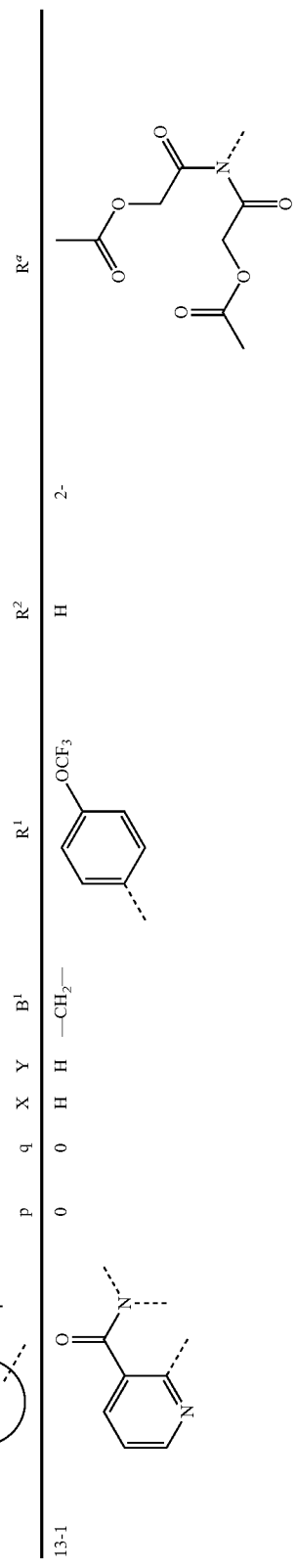
| | p | q | X | Y | B¹ | R¹ | R² | Rᵃ |
|---|---|---|---|---|---|---|---|---|
| 13-1 | 0 | 0 | H | H | —CH₂— | 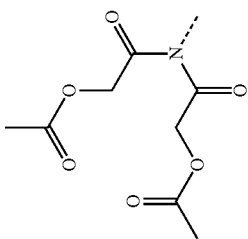 | H | 2- 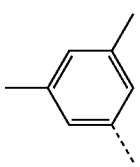 |
| 13-2 | 0 | 0 | H | H | —CH₂— | | H | 2- |
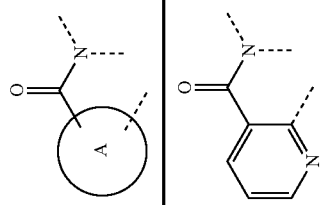

-continued

| | p | q | X | Y | B¹ | R¹ | R² | Rᵃ |
|---|---|---|---|---|---|---|---|---|
| 13-3 | 0 | 0 | H | H | —CH₂— | 3,5-dimethylphenyl | H | 2- ethyl carbonate-CH₂-C(O)NH- |
| 13-4 | 0 | 0 | H | H | —CH₂— | 4-OCF₃-phenyl | H | 2- HOOC-CH₂CH₂-C(O)-O-CH₂-C(O)NH- |
| 13-5 | 0 | 0 | H | H | —CH₂— | 3,5-dimethylphenyl | H | 2- CH₃SO₂-NH-CH₂-C(O)NH- |

-continued

| | p | q | X | Y | B¹ | R¹ | R² | 2- | Rᵃ |
|---|---|---|---|---|---|---|---|---|---|
| 13-6 | 0 | 0 | H | H | —CH₂— | 4-OCF₃-phenyl | H | 2- | glycolate diethylamide |
| 13-7 | 0 | 0 | H | H | —CH₂— | 4-OCF₃-phenyl | H | 2- | glycolate dimethylamide |
| 13-8 | 0 | 0 | H | H | —CH₂— | 4-OCF₃-phenyl | H | 2- | glycolate morpholinamide |

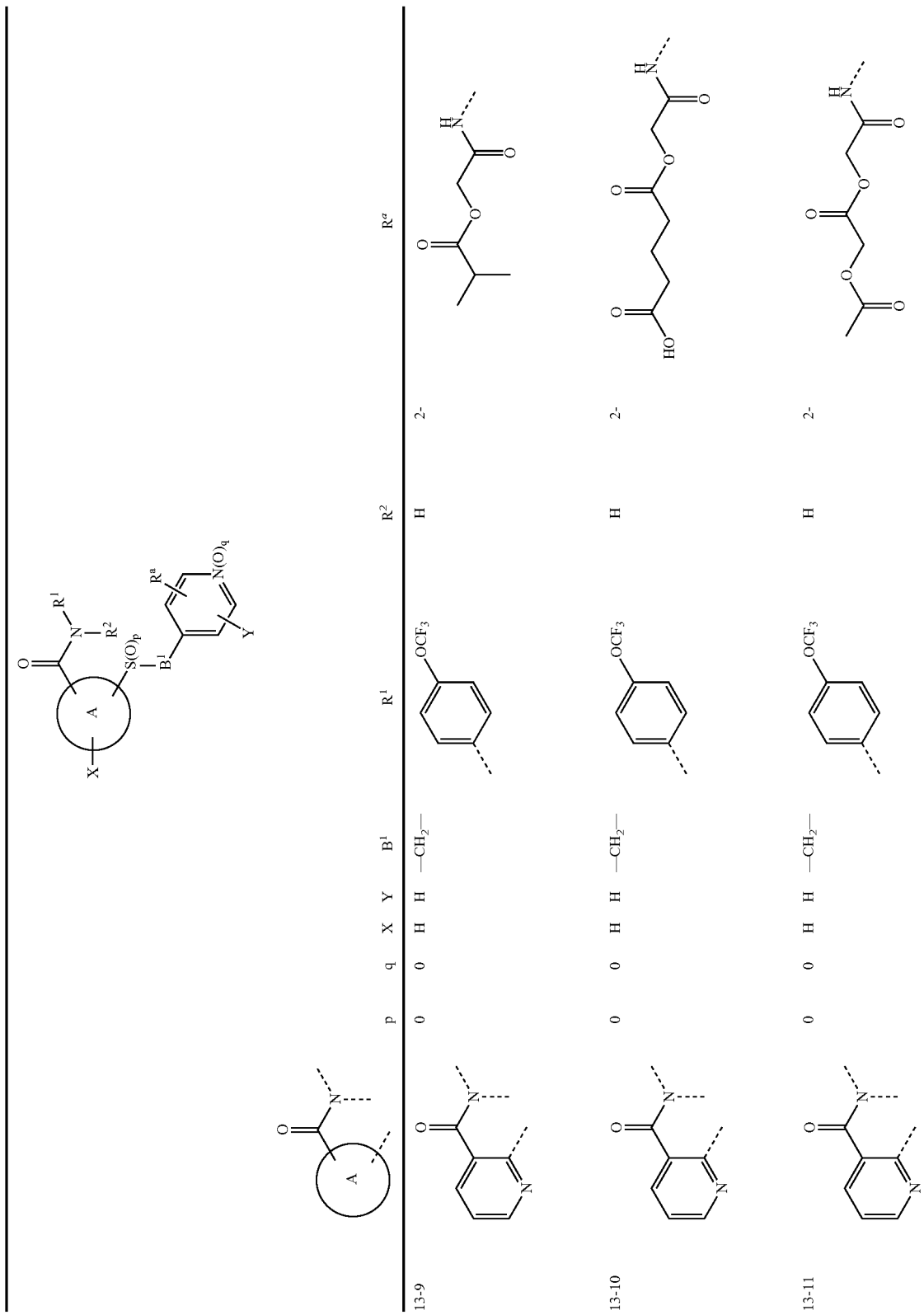

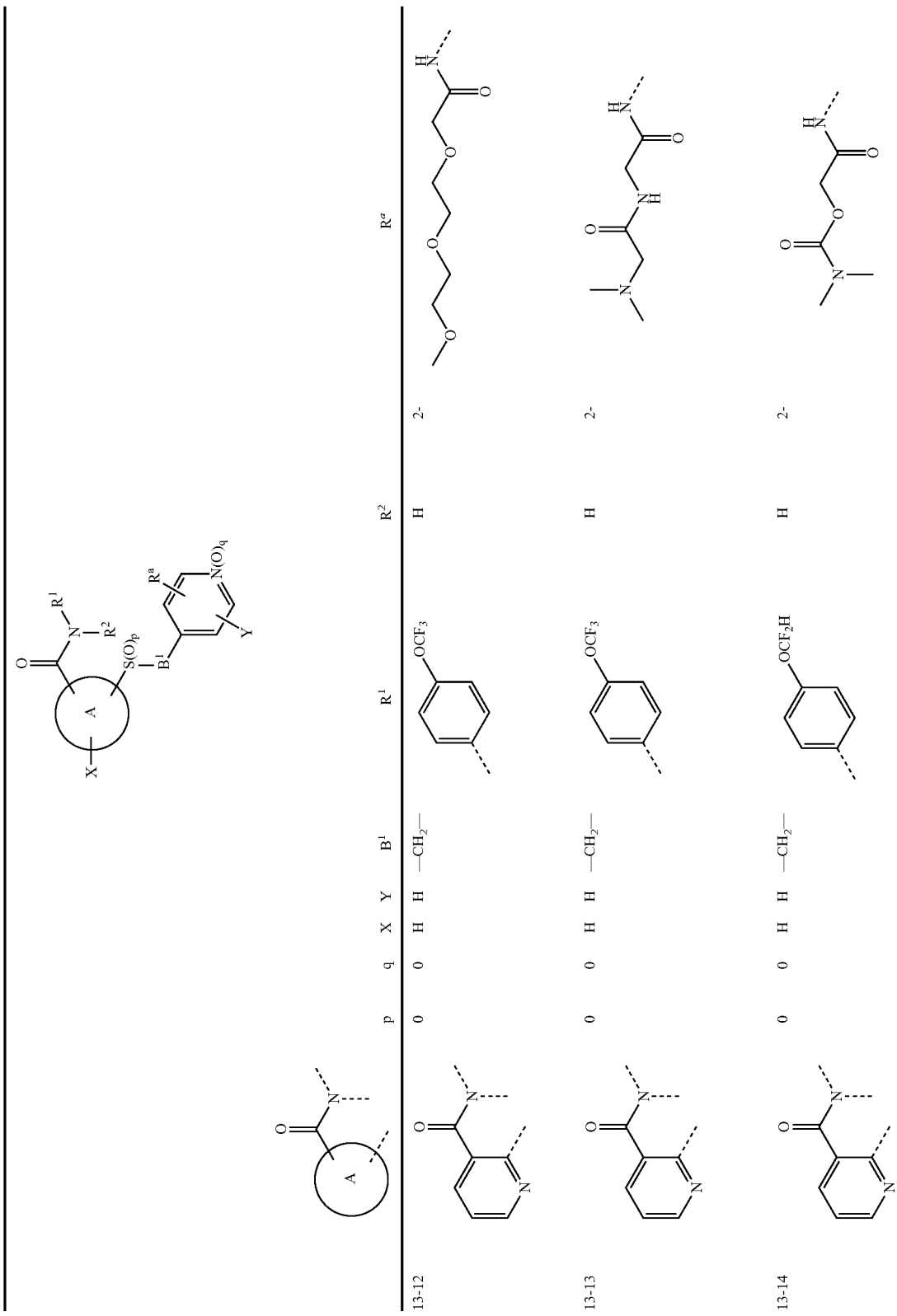

-continued
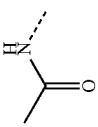
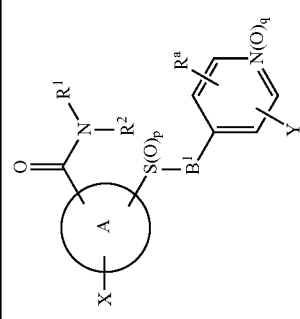
| | p | q | X | Y | B¹ | R¹ | R² | | Rᵃ |
|---|---|---|---|---|---|---|---|---|---|
| 14-1 | 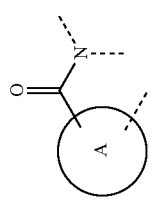 | 0 | 0 | H | H | —CH₂— | 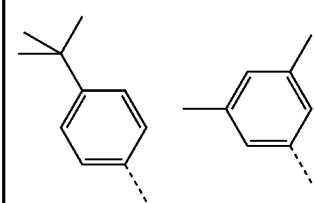 | H | 2- | 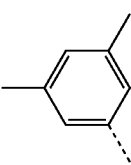 |
| 14-2 | | 0 | 0 | H | H | —CH₂— | | H | 2- | |
| 15-1 | 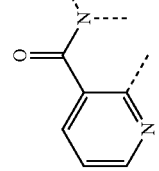 | 1 | 0 | H | H | —CH₂— | | H | 2- | |

-continued

| | p | q | X | Y | B¹ | R¹ | R² | Rᵃ |
|---|---|---|---|---|---|---|---|---|
| 16-1 | 0 | 0 | H | H | —CH₂— | 4-tBu-phenyl | H | 2- | ClCH₂C(O)NH— |
| 16-2 | 0 | 0 | H | H | —CH₂— | 4-OCF₃-phenyl | H | 2- | ClCH₂C(O)NH— |
| 16-3 | 0 | 0 | H | H | —CH₂— | 4-Cl-phenyl | H | 2- | ClCH₂C(O)NH— |

-continued

| | p | q | X | Y | B¹ | R¹ | R² | Rᵃ |
|---|---|---|---|---|---|---|---|---|
| 16-4 | 0 | 0 | H | H | —CH₂— | 3,5-dimethylphenyl | H | 2- | ClCH₂C(O)NH— |
| 16-5 | 0 | 0 | H | H | —CH₂— | 4-(OCF₂H)phenyl | H | 2- | ClCH₂C(O)NH— |
| 16-6 | 0 | 0 | H | H | —CH₂— | 3-methylphenyl | H | 2- | ClCH₂C(O)NH— |

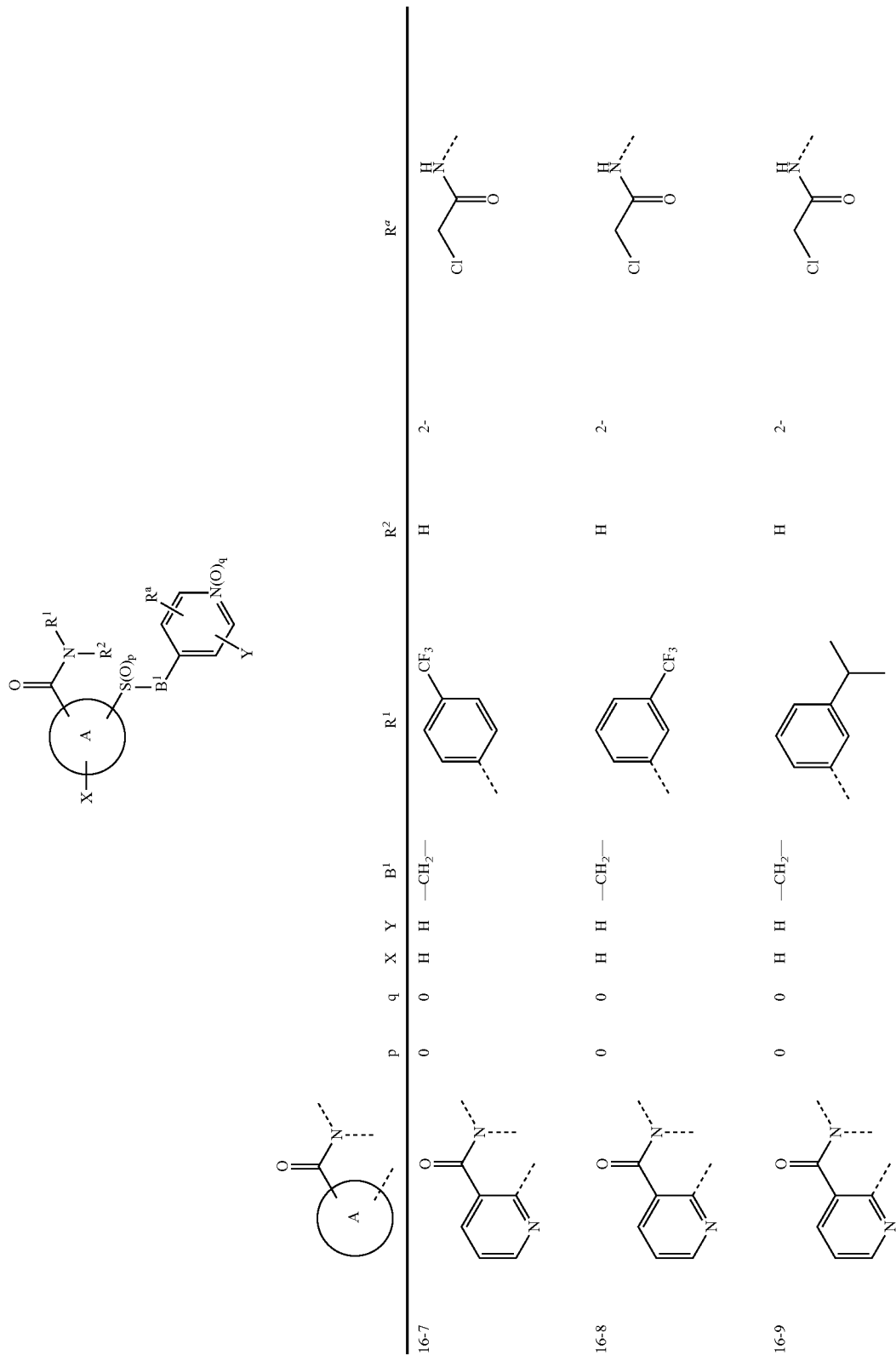

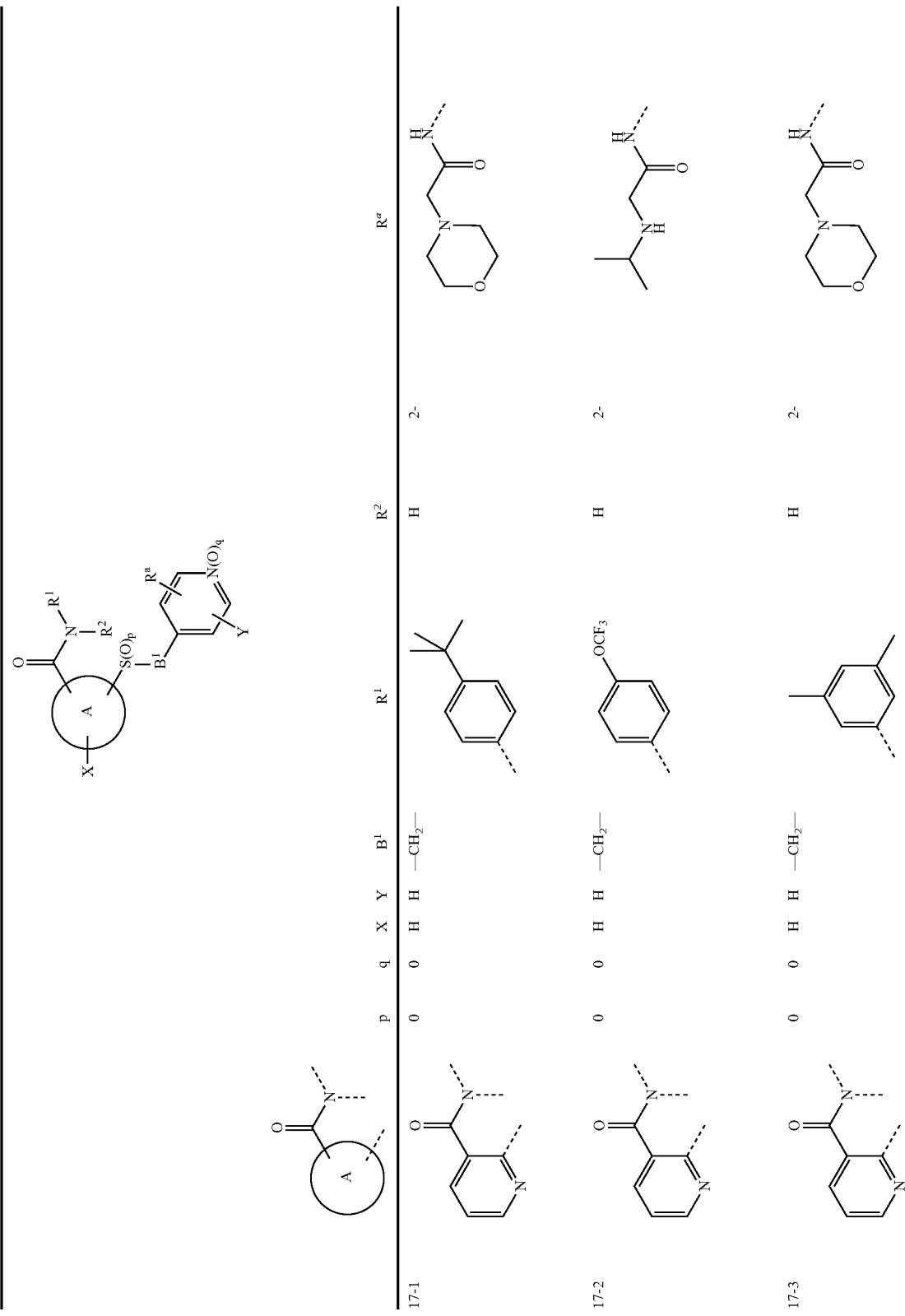

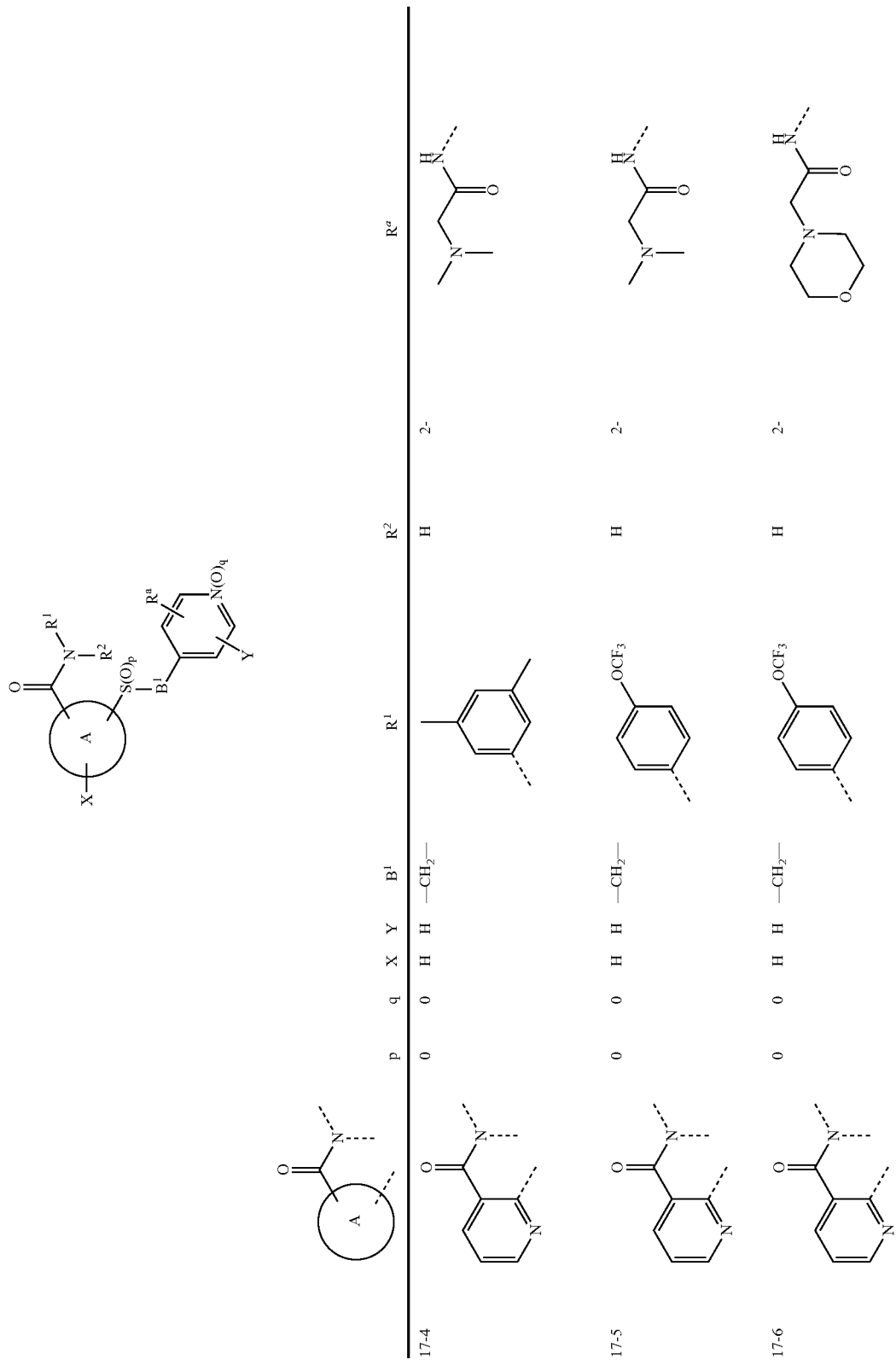

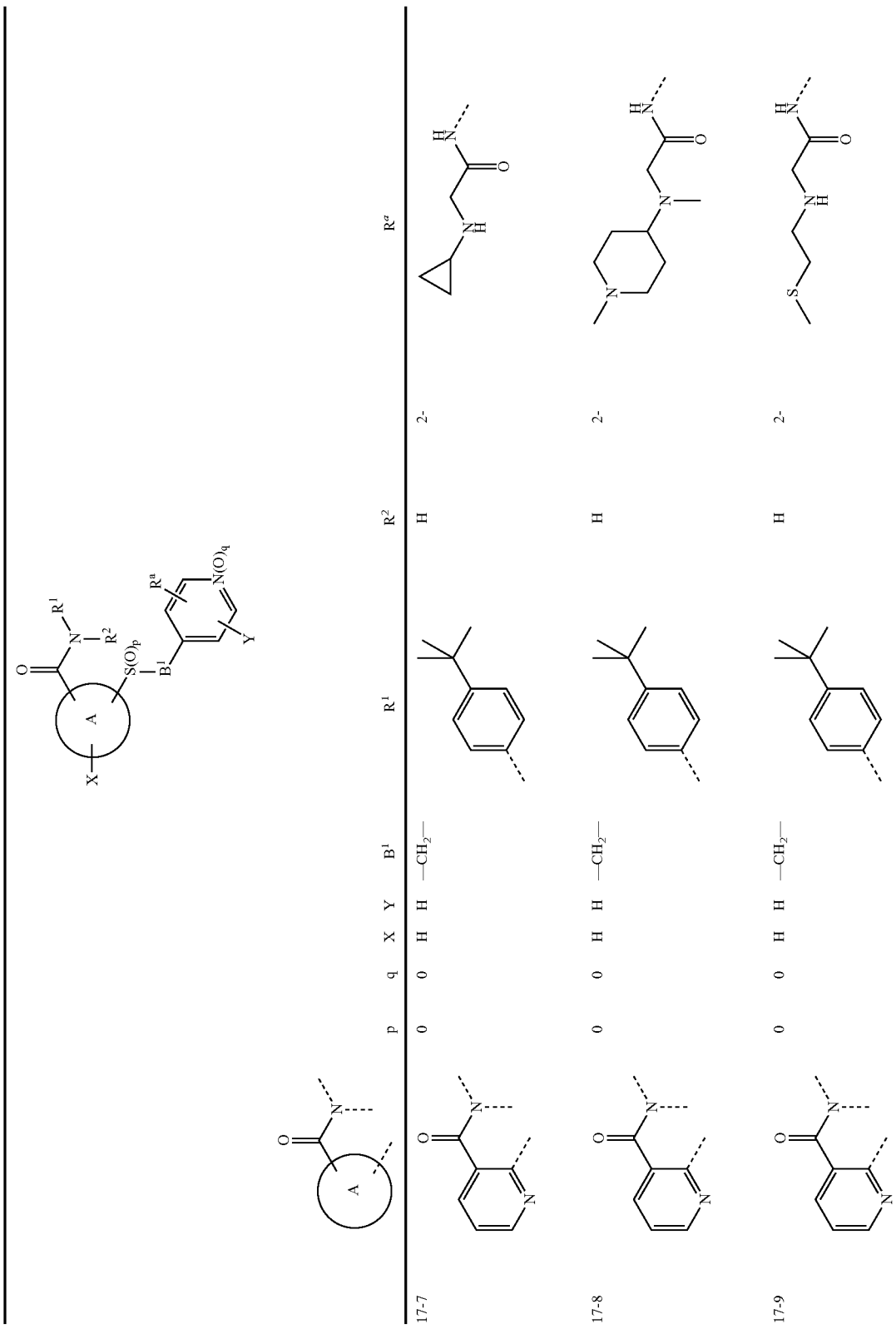

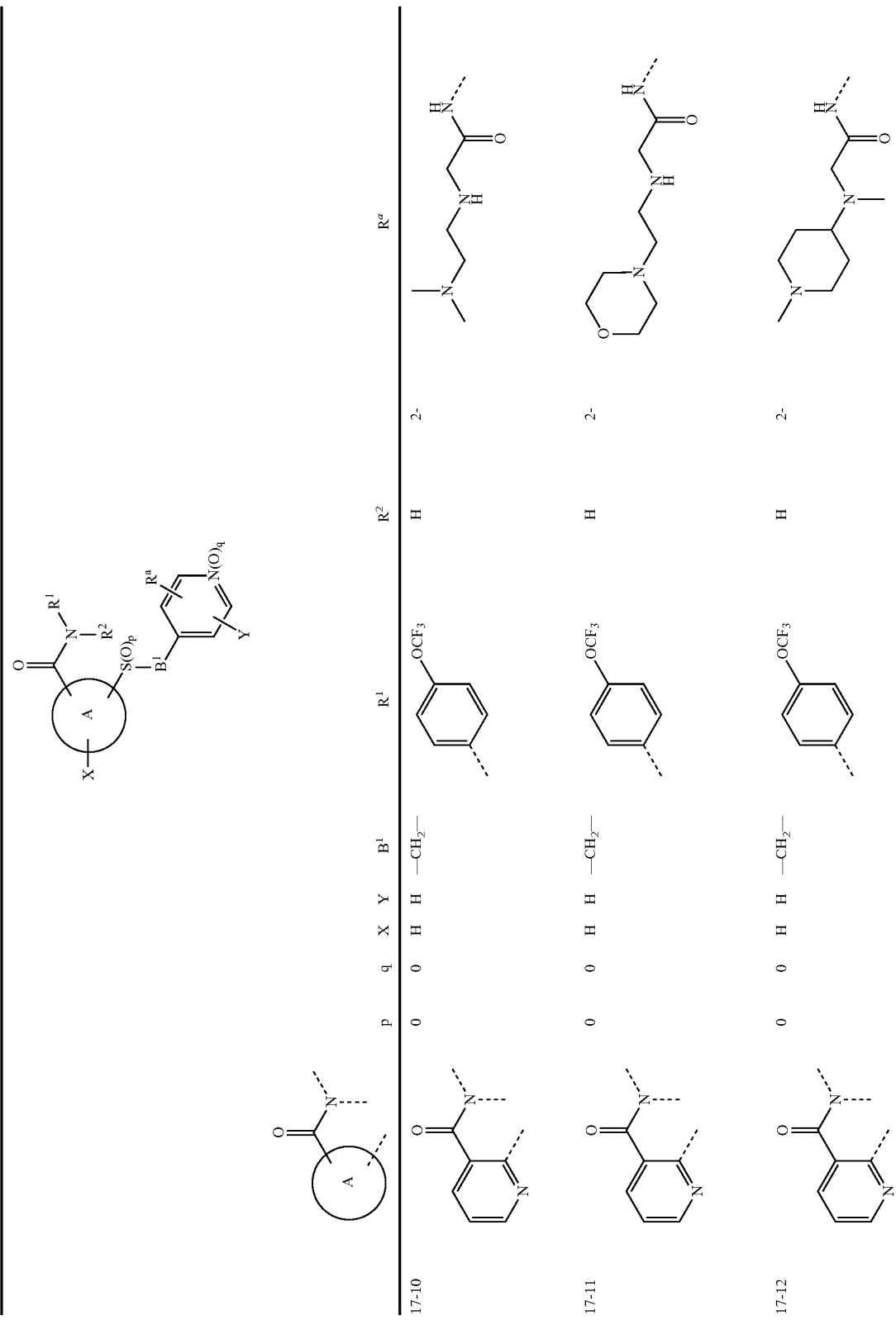

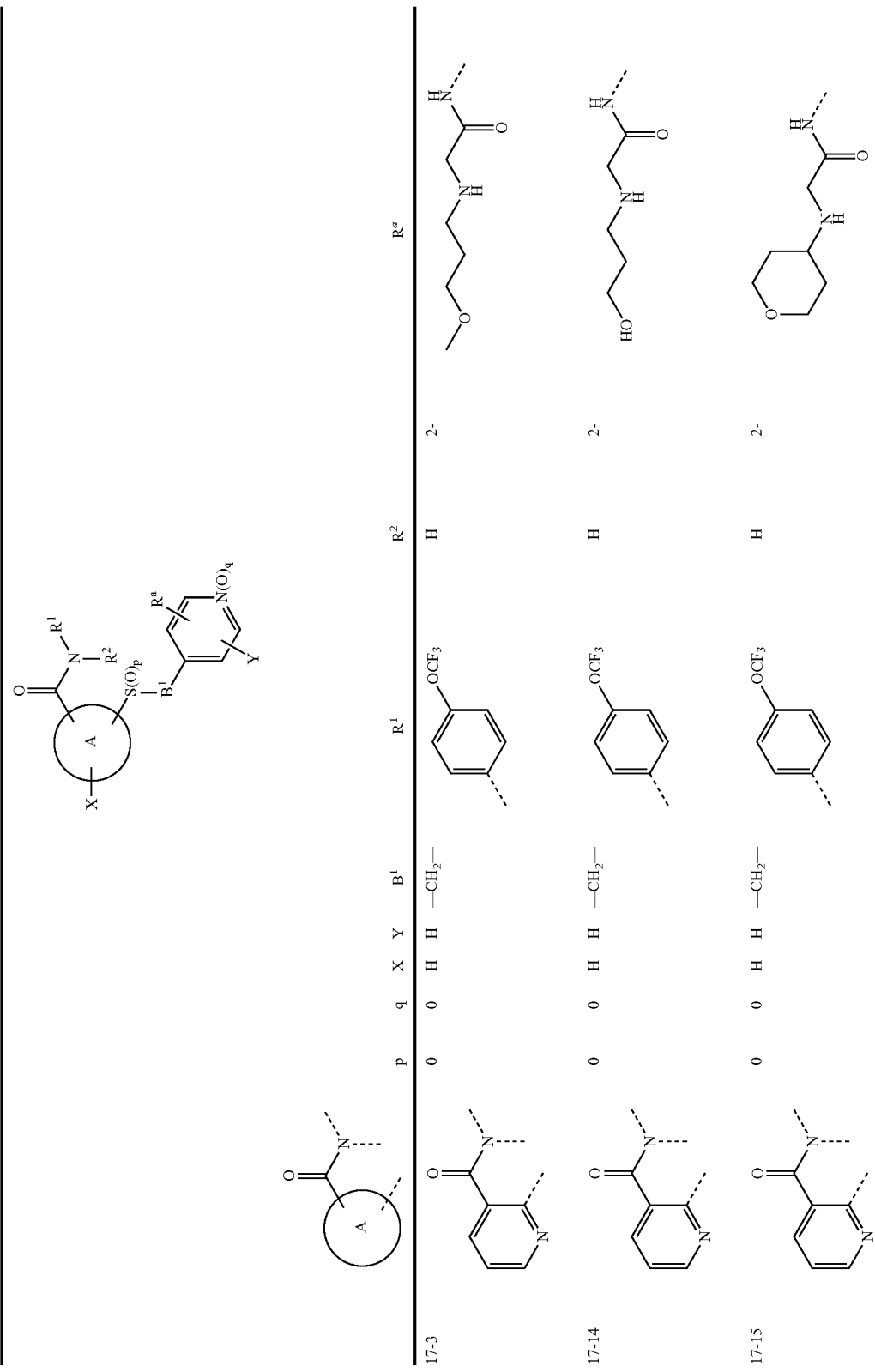

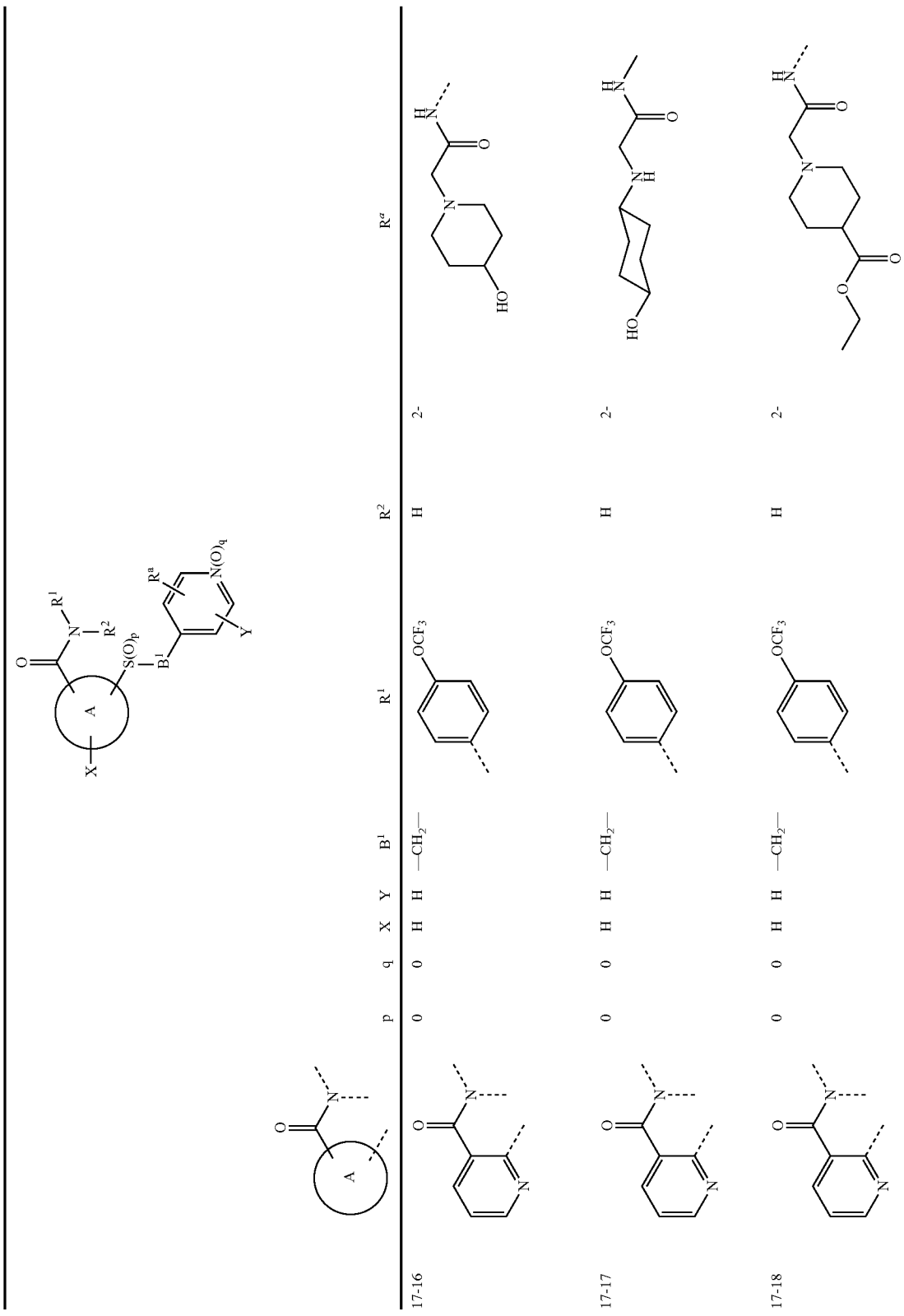

-continued

| | p | q | X | Y | B¹ | R¹ | R² | | Rᵃ |
|---|---|---|---|---|---|---|---|---|---|
| 17-19 | 0 | 0 | H | H | —CH₂— | 4-OCF₃-phenyl | H | 2- | N,N-diethylaminoacetamide |
| 17-20 | 0 | 0 | H | H | —CH₂— | 4-OCF₃-phenyl | H | 2- | pyrrolidinylacetamide |
| 17-21 | 0 | 0 | H | H | —CH₂— | 4-Cl-phenyl | H | 2- | N,N-dimethylaminoacetamide |

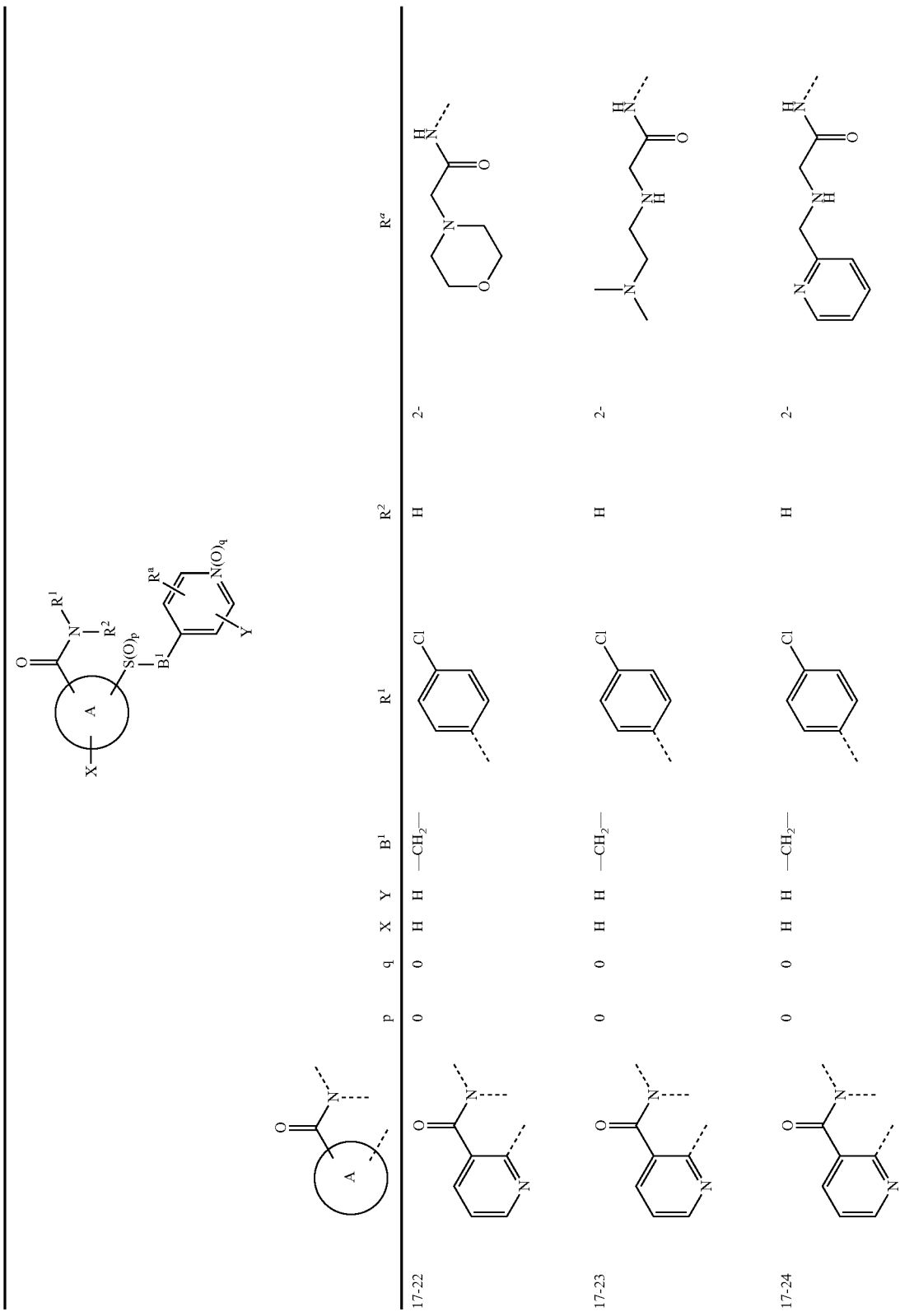

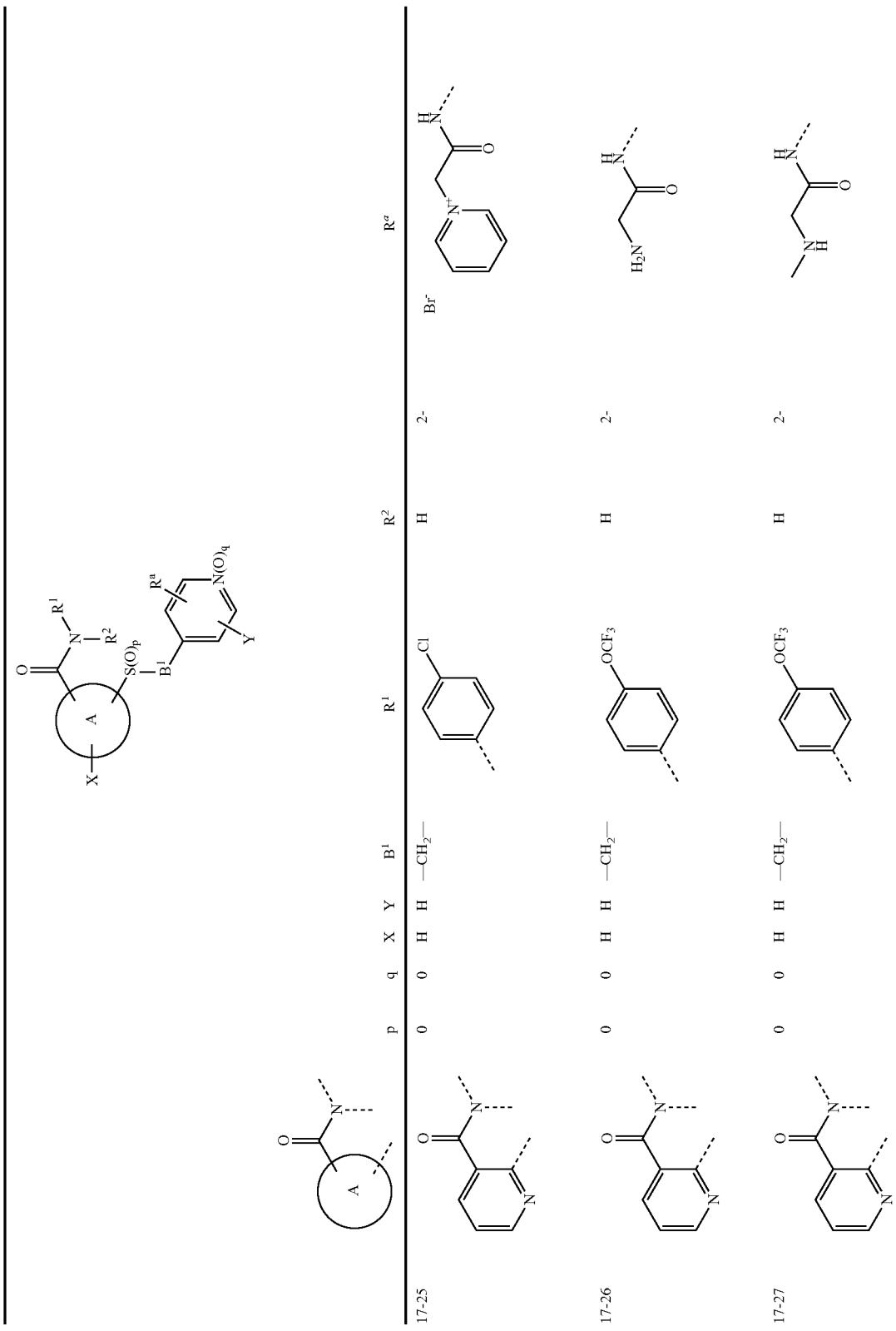

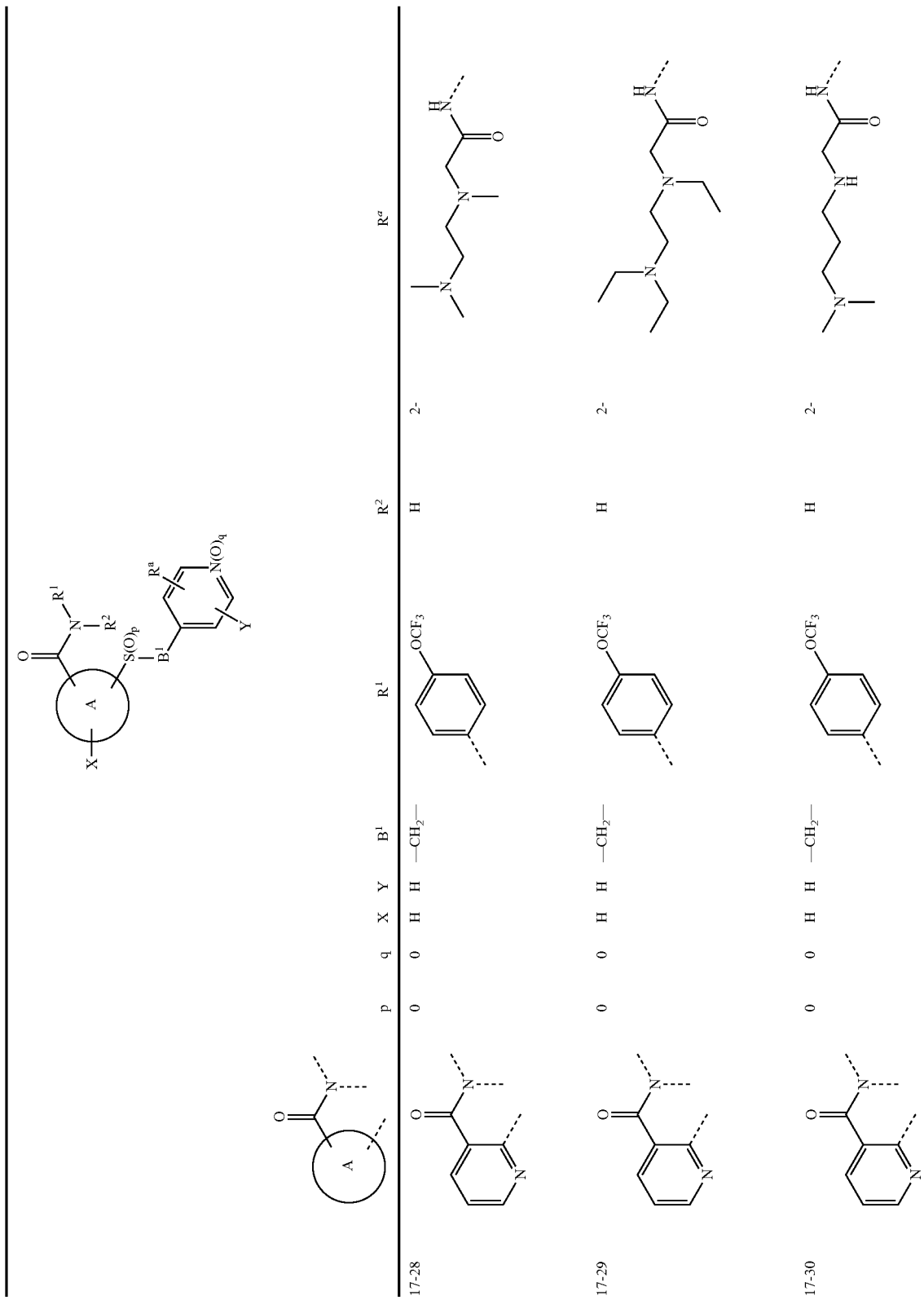

-continued

| | p | q | X | Y | B¹ | R¹ | R² | | Rᵃ |
|---|---|---|---|---|---|---|---|---|---|
| 17-31 ![A-pyridine-carboxamide] | 0 | 0 | H | H | —CH₂— | ![4-OCF₃ phenyl] | H | 2- | ![HOCH₂CH₂-NH-CH₂-C(O)-NH-] |
| 17-32 ![A-pyridine-carboxamide] | 0 | 0 | H | H | —CH₂— | ![4-OCF₃ phenyl] | H | 2- | ![EtO-CH₂CH₂-NH-CH₂-C(O)-NH-] |
| 17-33 ![A-pyridine-carboxamide] | 0 | 0 | H | H | —CH₂— | ![4-OCF₃ phenyl] | H | 2- | ![HOCH₂CH₂-O-CH₂CH₂-NH-CH₂-C(O)-NH-] |

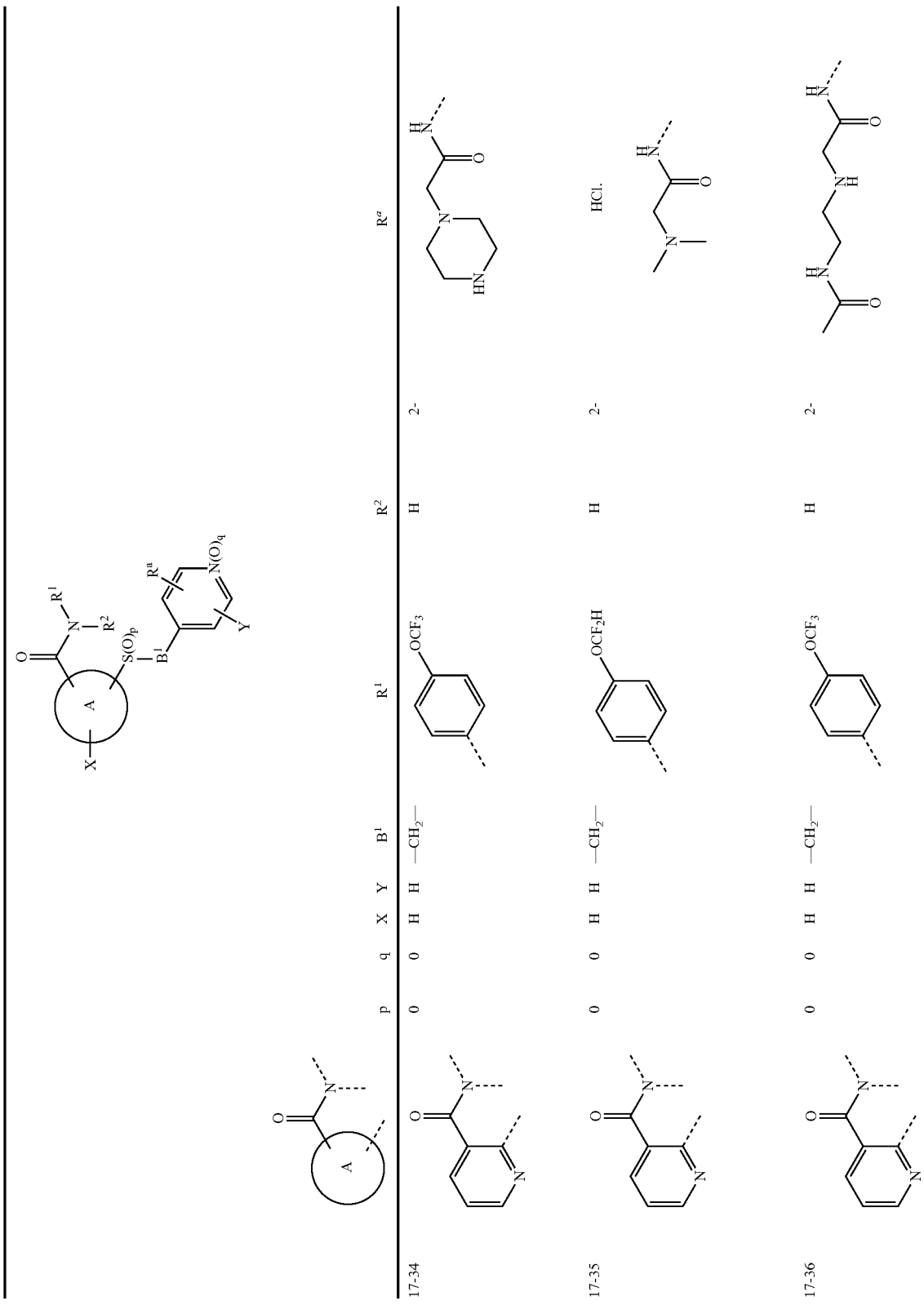

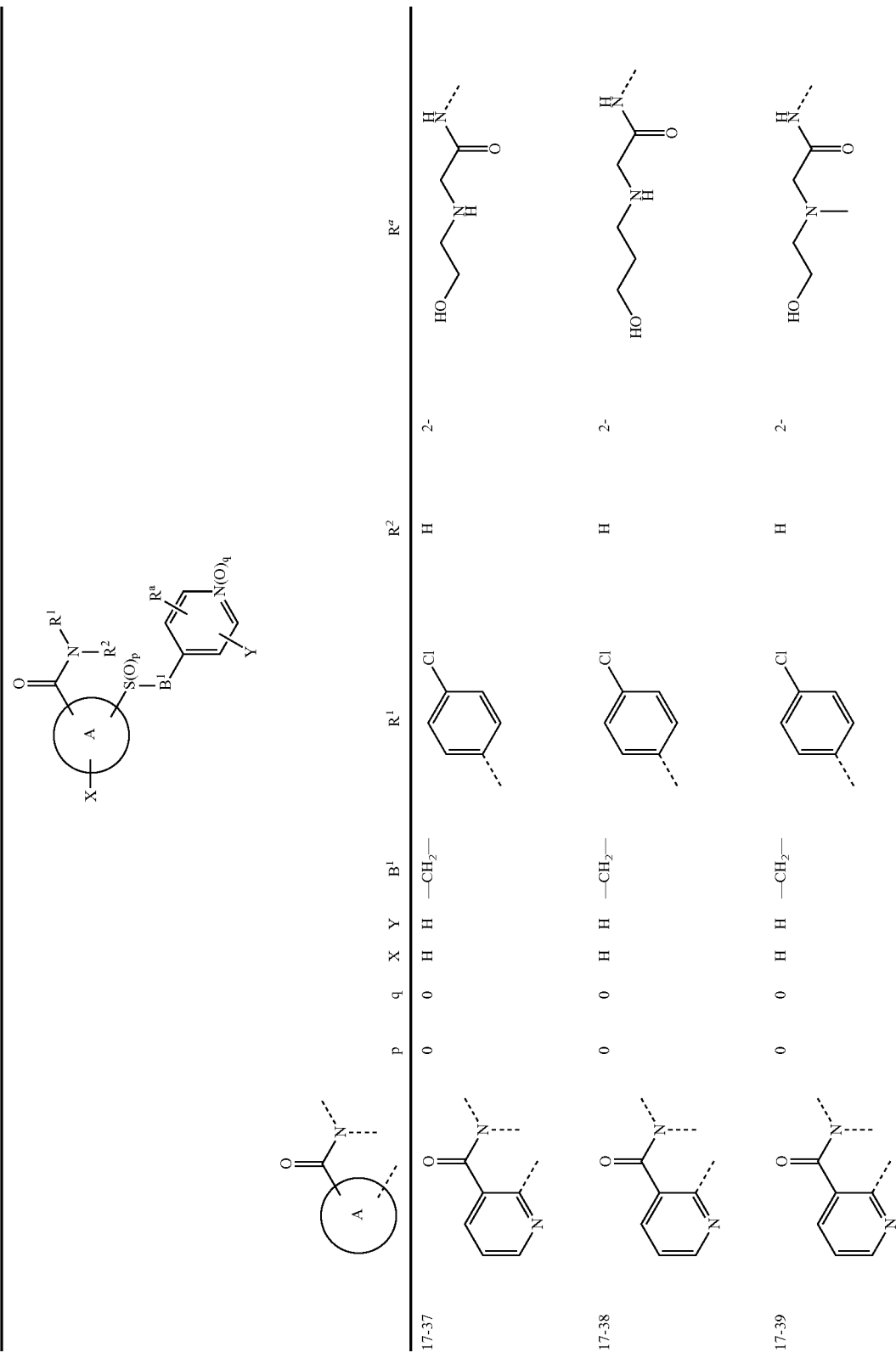

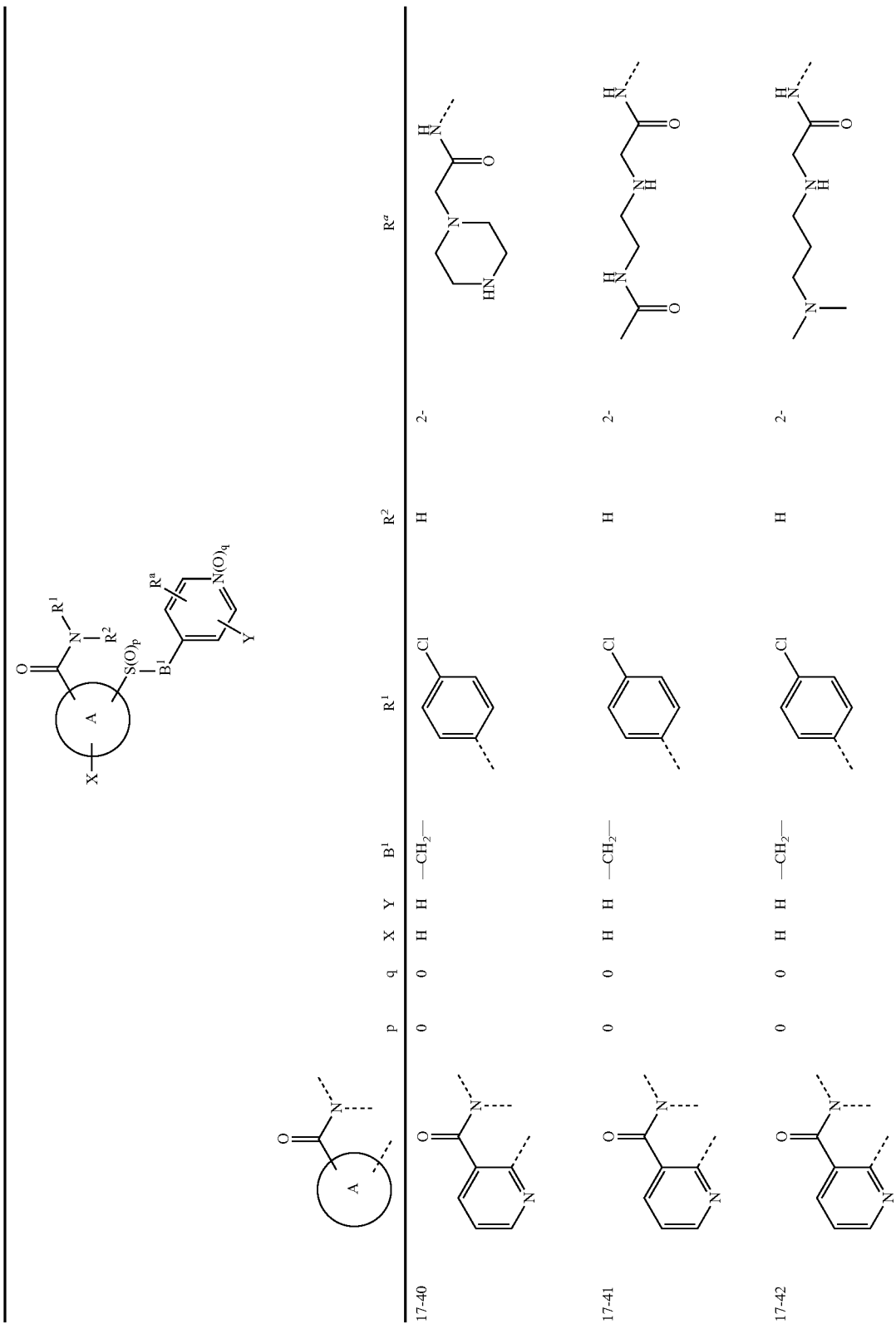

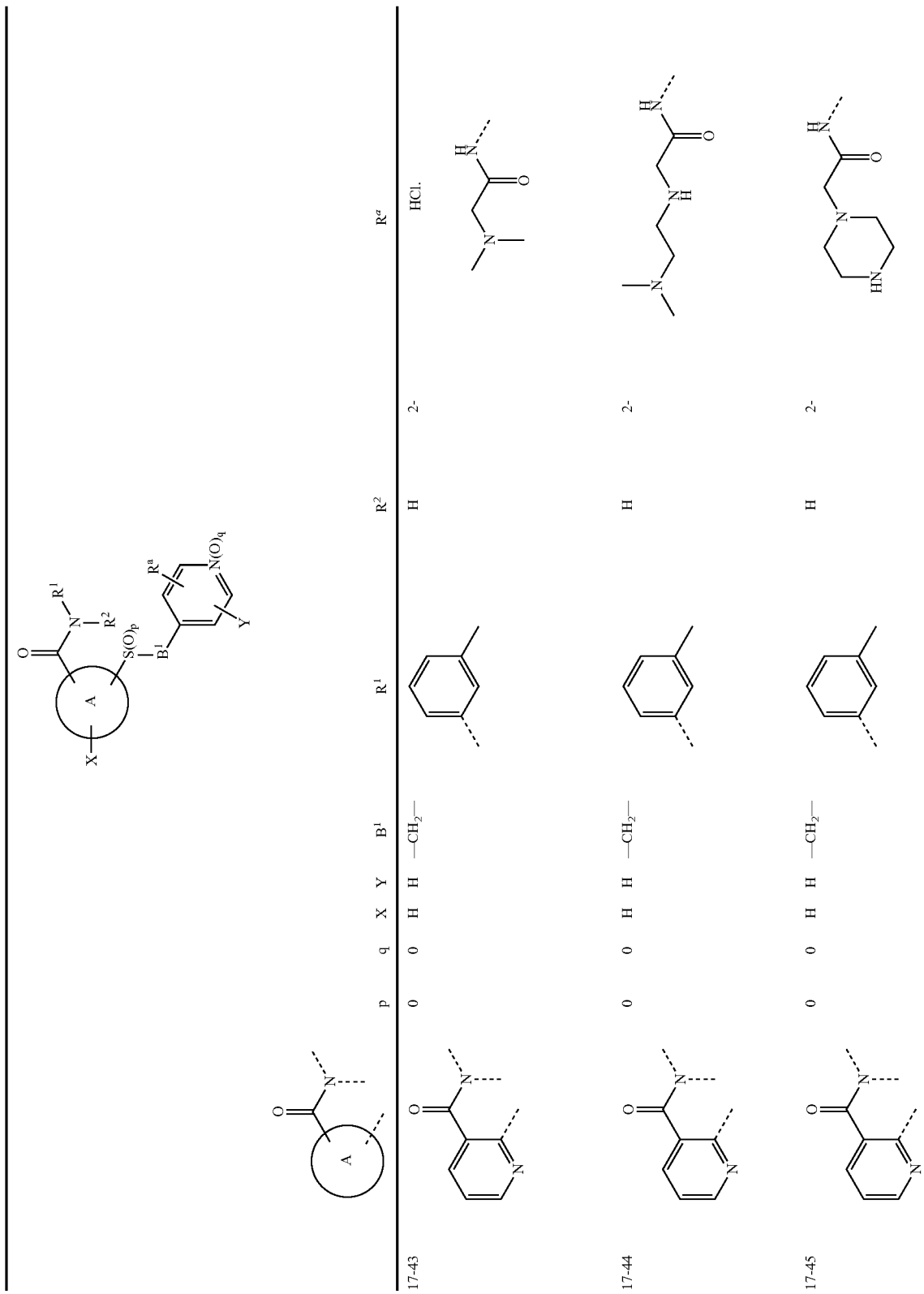

| | p | q | X | Y | B¹ | R¹ | R² | | Rᵃ |
|---|---|---|---|---|---|---|---|---|---|
| 17-46 | 0 | 0 | H | H | —CH₂— | 3-methylphenyl | H | 2- | -NH-CH₂-C(O)-NH-CH₂CH₂-OH |
| 17-47 | 0 | 0 | H | H | —CH₂— | 4-OCF₂H-phenyl | H | 2- | -NH-CH₂-C(O)-NH-CH₂CH₂-N(CH₃)₂ |
| 17-48 | 0 | 0 | H | H | —CH₂— | 4-OCF₂H-phenyl | H | 2- | -NH-CH₂-C(O)-NH-CH₂CH₂-OH |

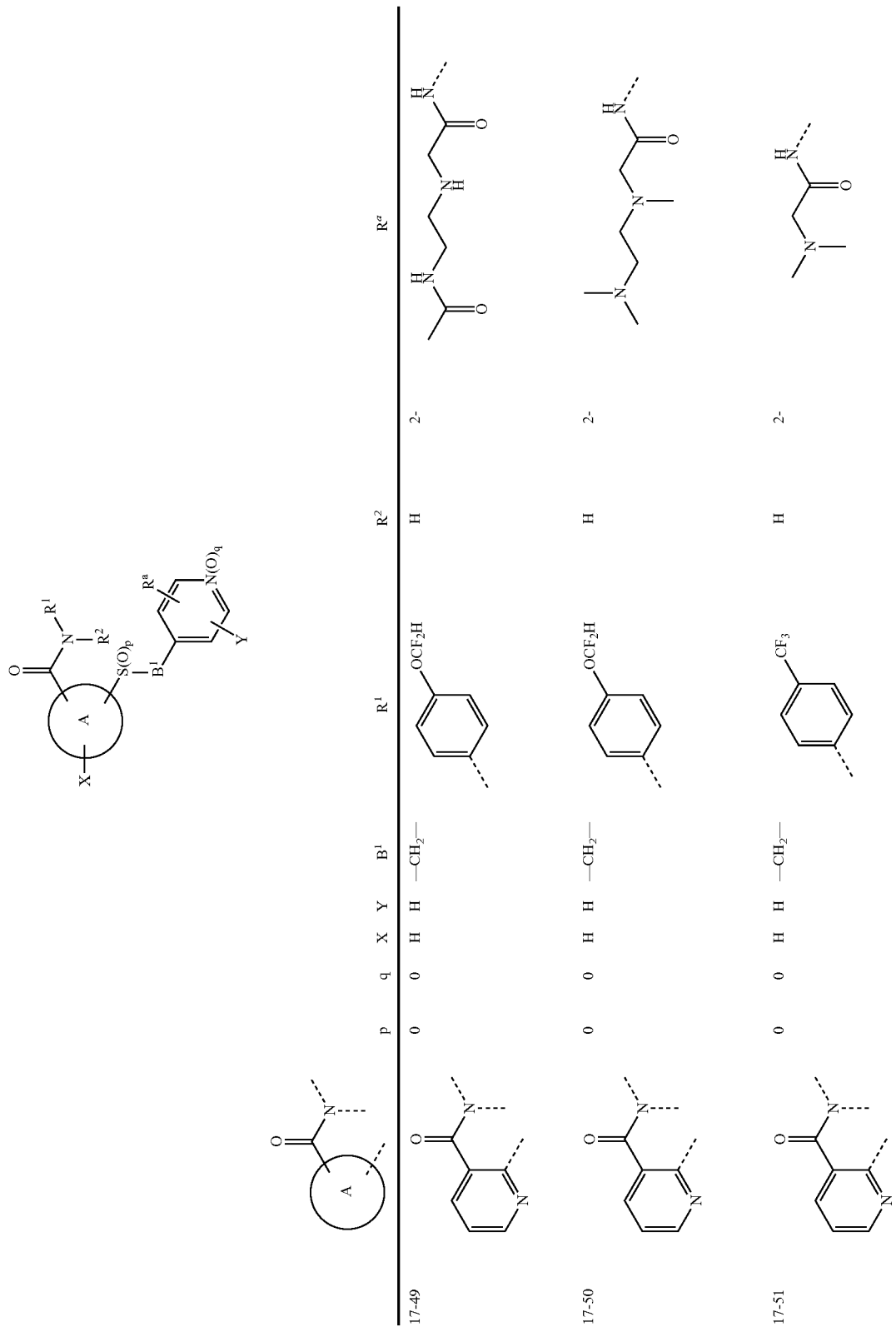

| | | p | q | X | Y | B¹ | R¹ | R² | | Rᵃ |
|---|---|---|---|---|---|---|---|---|---|---|
| 17-52 | [pyridine-C(O)N] | 0 | 0 | H | H | —CH₂— | [4-CF₃-phenyl] | H | 2- | [CH₂C(O)NH-CH₂CH₂-N(CH₃)₂] |
| 17-53 | [pyridine-C(O)N] | 0 | 0 | H | H | —CH₂— | [4-CF₃-phenyl] | H | 2- | [CH₂C(O)NH-CH₂CH₂-OH] |
| 17-54 | [pyridine-C(O)N] | 0 | 0 | H | H | —CH₂— | [4-CF₃-phenyl] | H | 2- | [CH₂C(O)-piperazine] |

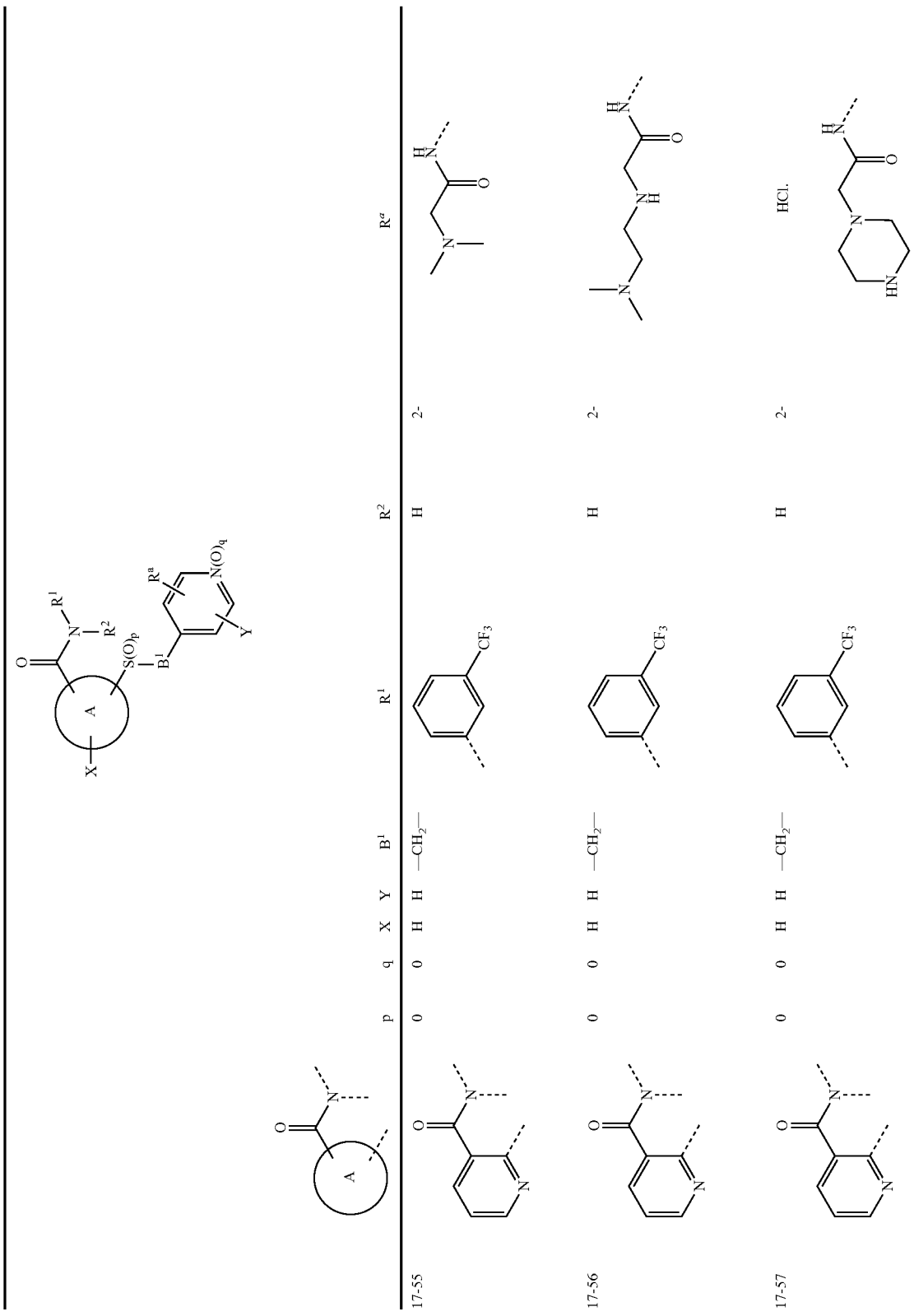

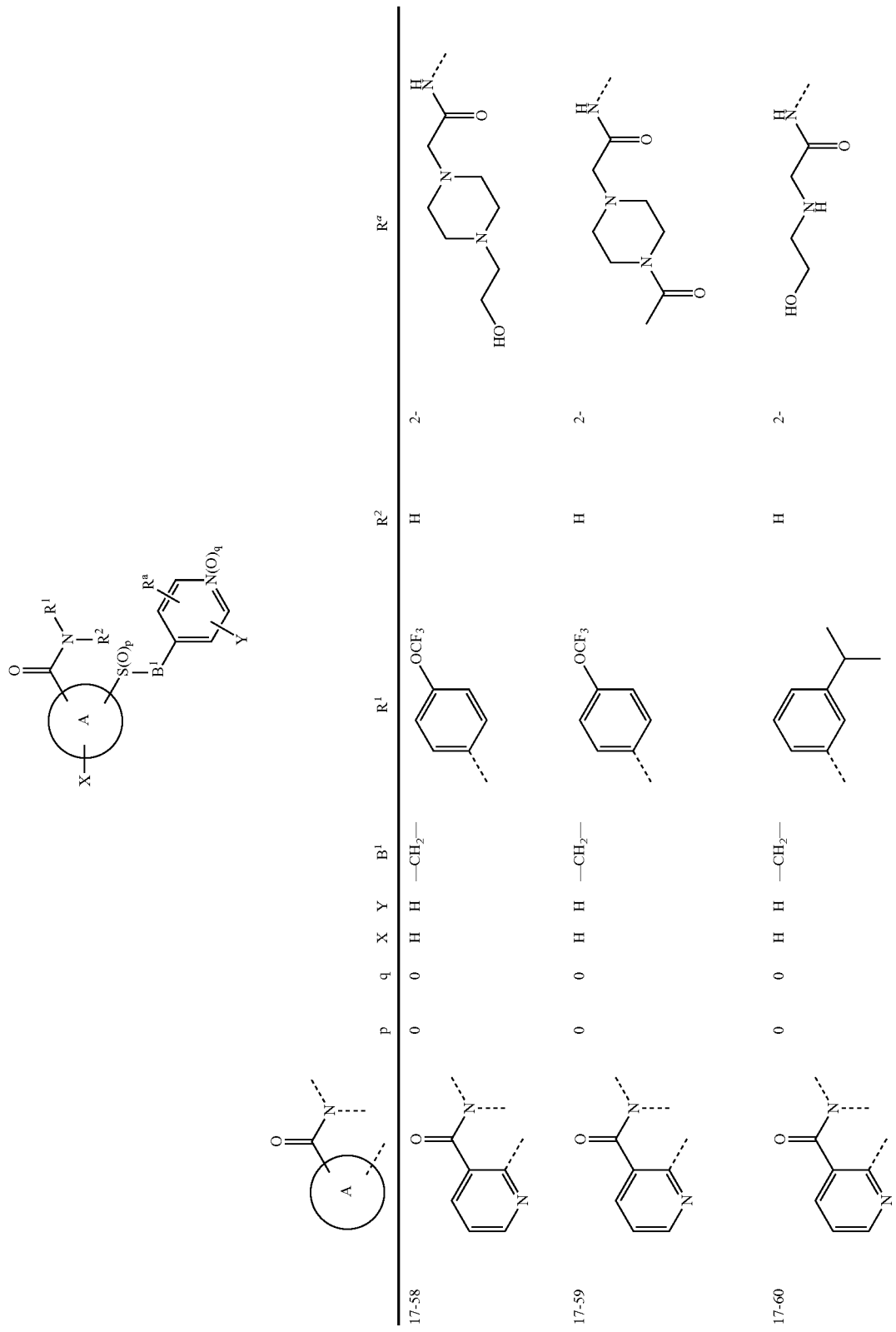

| | | p | q | X | Y | B¹ | R¹ | R² | | Rᵃ |
|---|---|---|---|---|---|---|---|---|---|---|
| 17-61 | nicotinoyl | 0 | 0 | H | H | —CH₂— | 3-isopropylphenyl | H | 2- | -NHCH₂CH₂N(CH₃)CH₂C(O)NH- |
| 17-62 | nicotinoyl | 0 | 0 | H | H | —CH₂— | 4-OCF₃-phenyl | H | 2- | 4-methylpiperazinyl-CH₂C(O)NH- |
| 17-63 | nicotinoyl | 0 | 0 | H | H | —CH₂— | 4-Cl-phenyl | H | 2- | HC≡C-CH₂-NH-CH₂C(O)NH- |

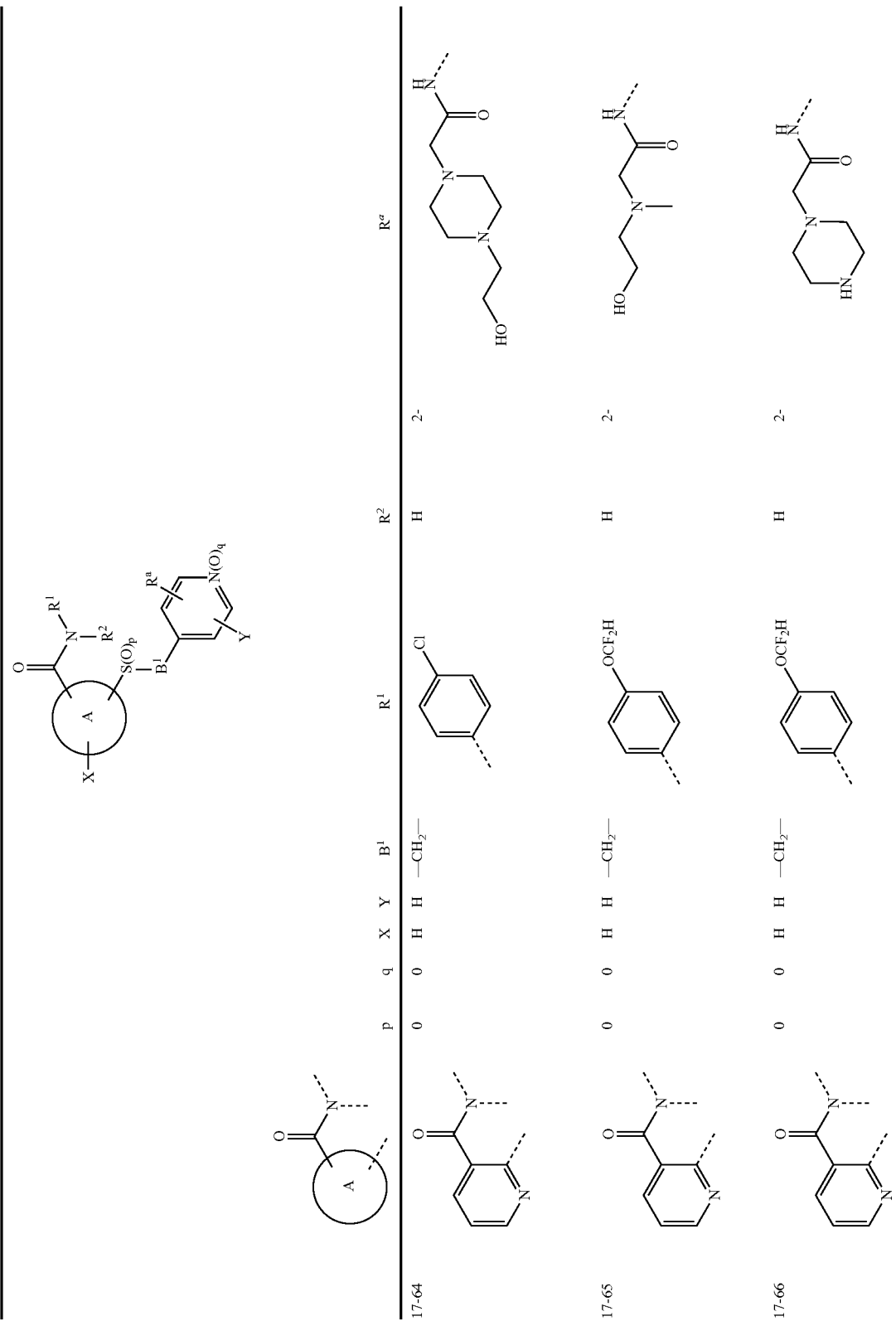

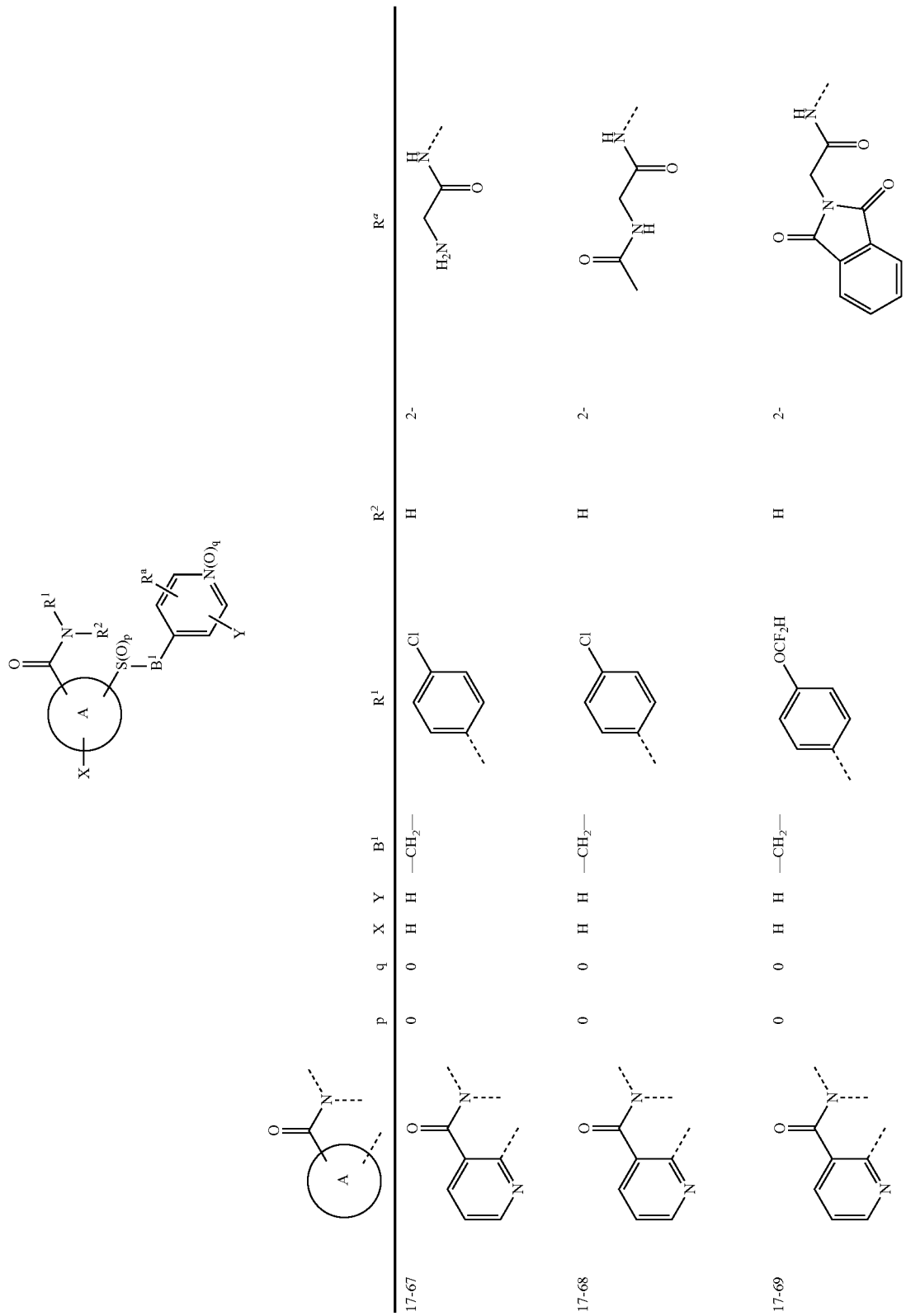

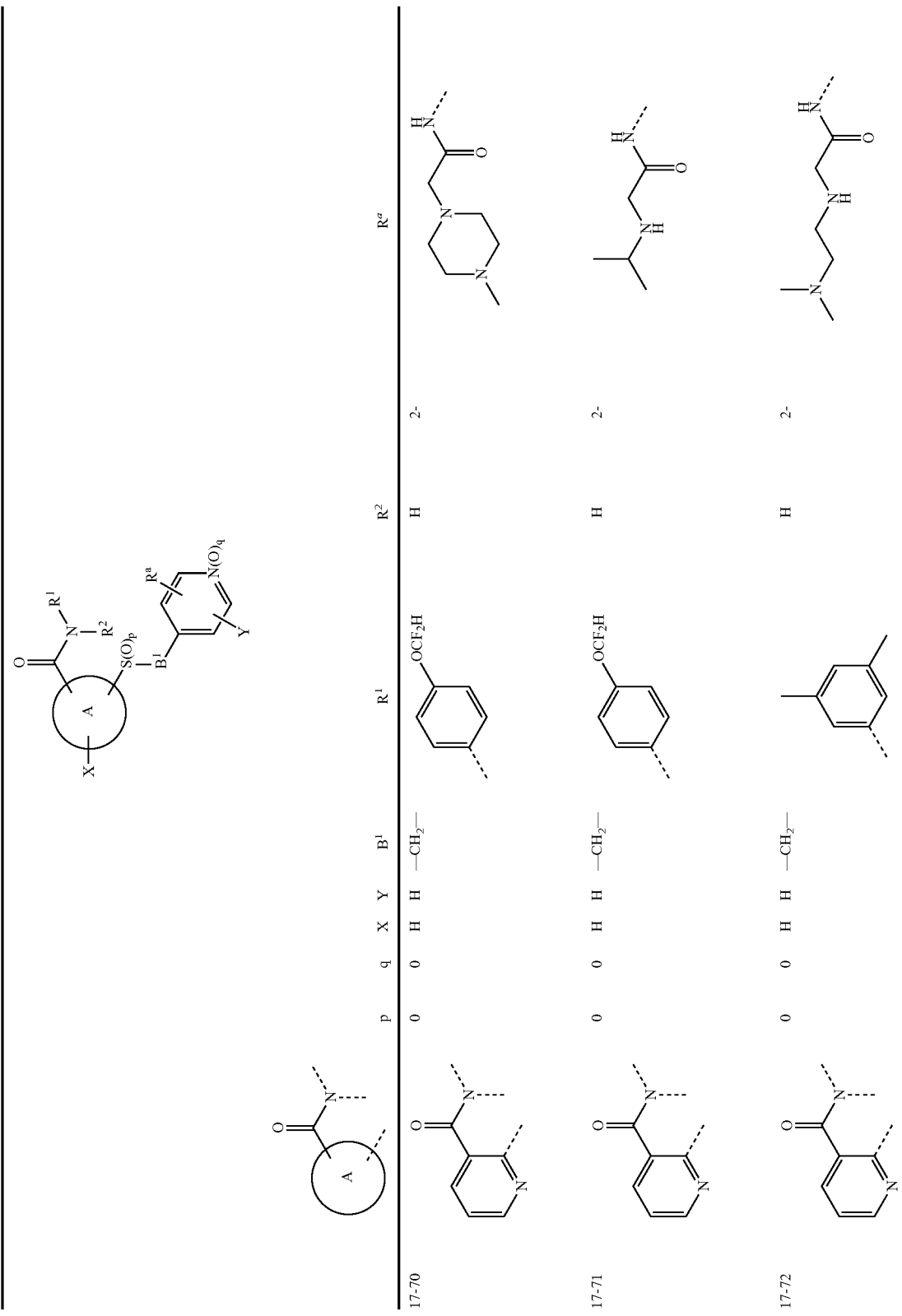

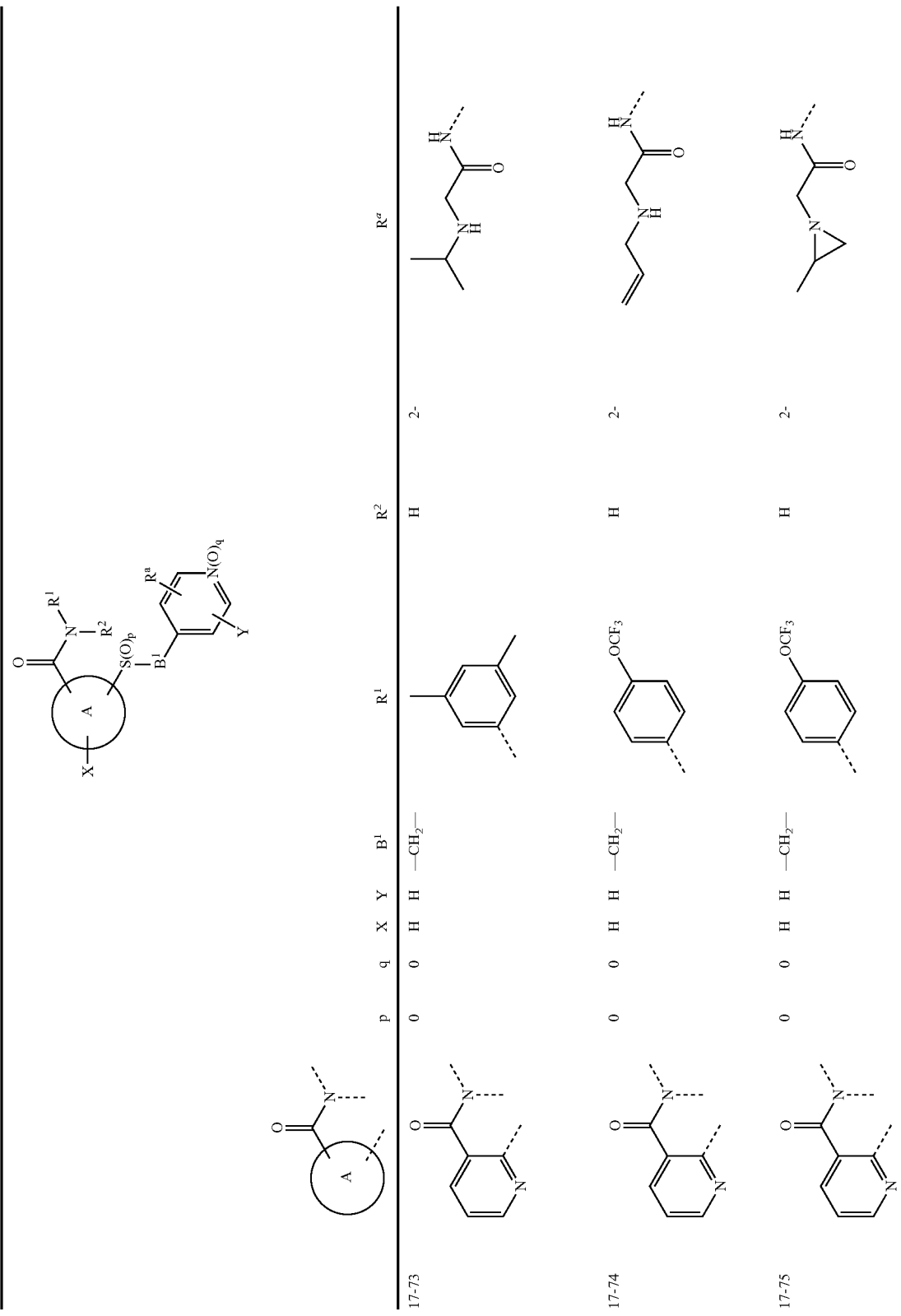

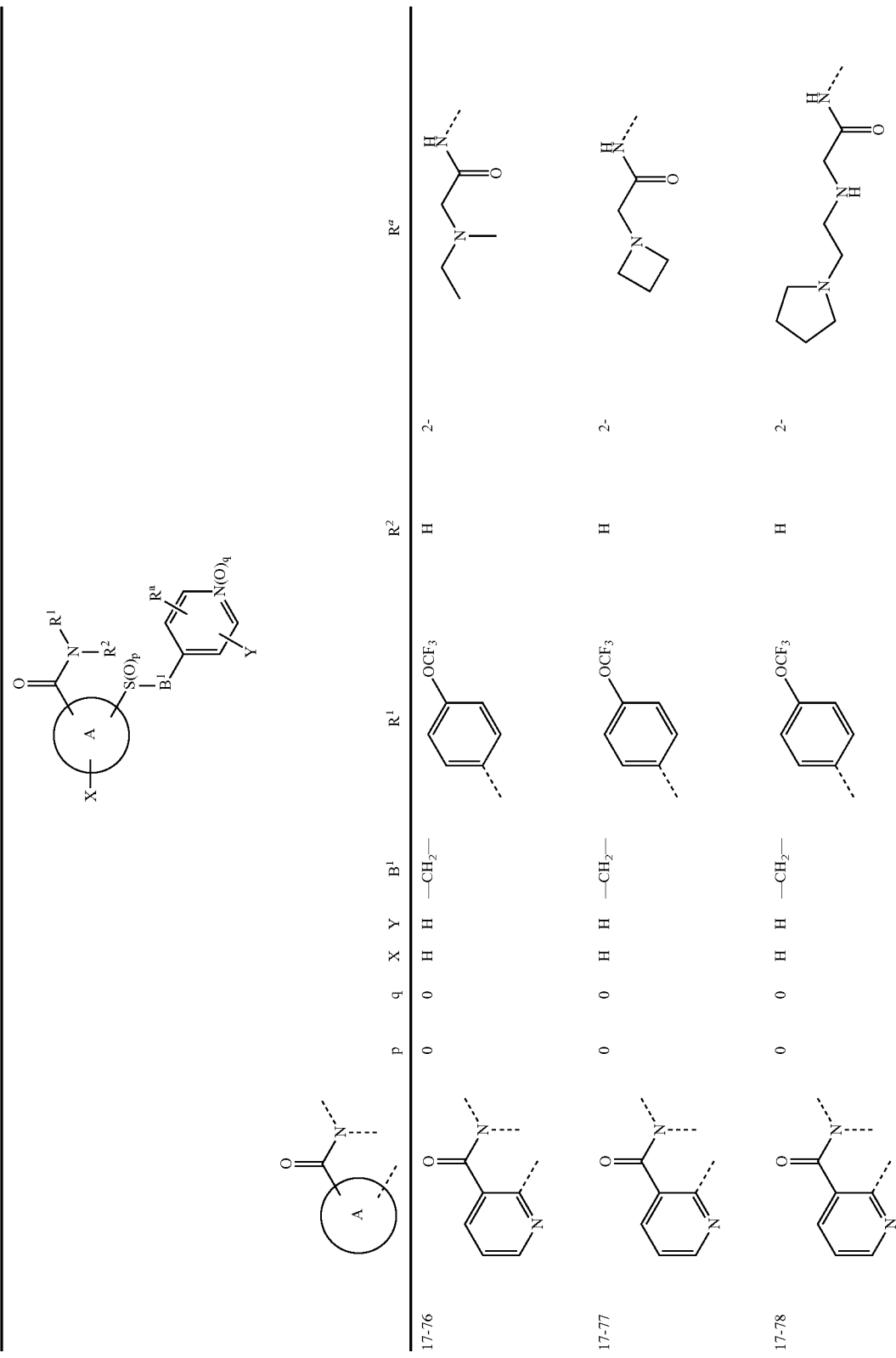

-continued

| | p | q | X | Y | B¹ | R¹ | R² | | Rᵃ |
|---|---|---|---|---|---|---|---|---|---|
| 17-79 | 0 | 0 | H | H | —CH₂— | 4-Cl-phenyl | H | 2- | pyrrolidinylethyl-NH-CH₂-C(O)NH— |
| 17-80 | 0 | 0 | H | H | —CH₂— | 4-OCF₃-phenyl | H | 2- | 4-oxopyridin-1-yl-CH₂-C(O)NH— |
| 17-81 | 0 | 0 | H | H | —CH₂— | 4-Cl-phenyl | H | 2- | 4-methylpiperazin-1-yl-CH₂-C(O)NH— |

-continued

| | p | q | X | Y | B¹ | R¹ | R² | | Rᵃ |
|---|---|---|---|---|---|---|---|---|---|
| 17-82 | 0 | 0 | H | H | —CH₂— | 4-OCF₃-phenyl | H | 2- | imidazolyl-CH₂-C(O)NH— |
| 17-83 | 0 | 0 | H | H | —CH₂— | 4-Cl-phenyl | H | 2- | azetidinyl-CH₂-C(O)NH— |
| 17-84 | 0 | 0 | H | H | —CH₂— | 3,5-dimethylphenyl | H | 2- | HO(CH₂)₃NHC(O)CH₂NH— |

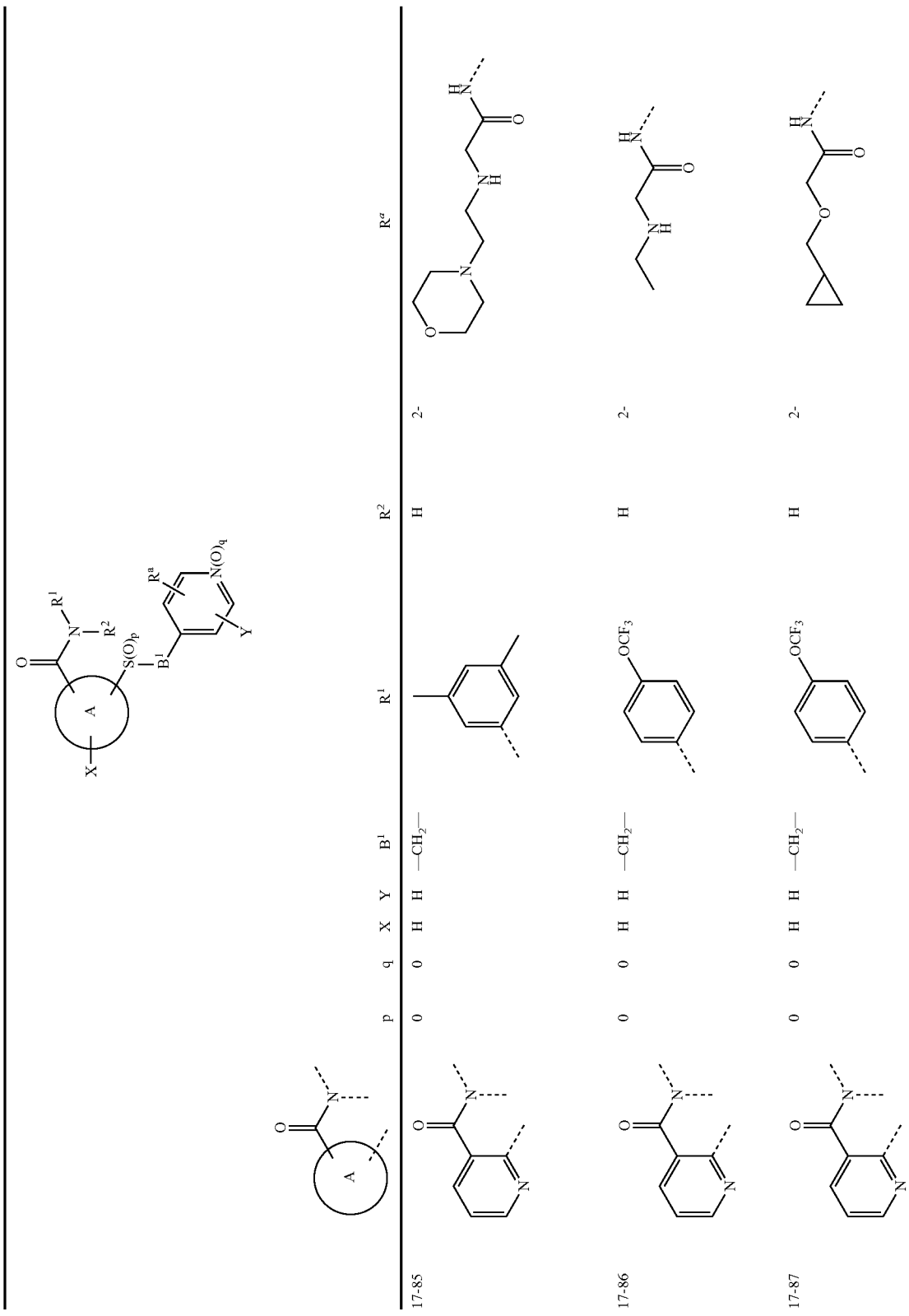

-continued
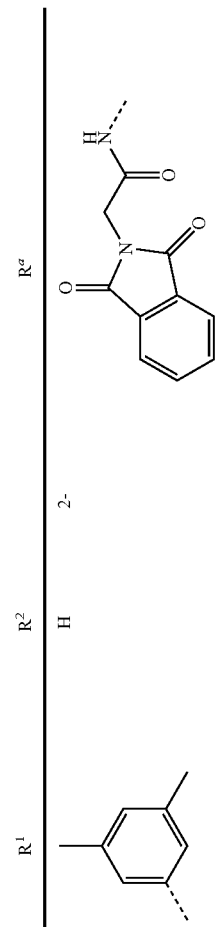
| | | p | q | X | Y | B¹ | R¹ | R² | Rᵃ |
|---|---|---|---|---|---|---|---|---|---|
| 17-88 | 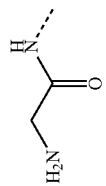 | 0 | 0 | H | H | —CH₂— | 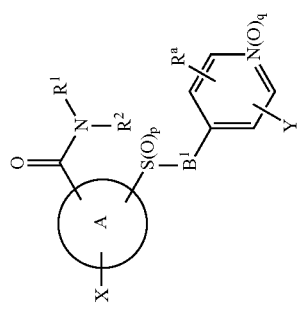 | H | 2- 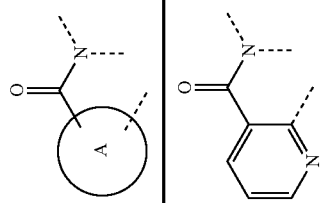 |
| 18-1 | 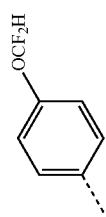 | 0 | 0 | H | H | —CH₂— | 4-OCF₂H-phenyl | H | 2- H₂N-CH₂-C(O)-NH- |

Formulation Examples

Typical formulation examples of the compound of the present invention are shown below.

| 1) Tablet (in 100 mg) | |
| --- | --- |
| Compound of the present invention | 1 mg |
| Lactose | 66.4 mg |
| Cornstarch | 20 mg |
| Calcium carboxymethyl cellulose | 6 mg |
| Hydroxypropyl cellulose | 4 mg |
| Magnesium stearate | 0.6 mg |

The tablet of the above-mentioned formulation is coated using 2 mg of a coating agent (for example, a conventional coating agent such as hydroxypropylmethyl cellulose, macrogol or a silicone resin), whereby a desired coated tablet is obtained. In addition, a desired tablet can be obtained by appropriately changing the kinds and/or the amounts of the compound of the present invention and/or the additives.

| 2) Capsule Formulation 2 (in 150 mg) | |
| --- | --- |
| Compound of the present invention | 5 mg |
| Lactose | 145 mg |

A desired capsule can be obtained by appropriately changing the mixing ratio of the compound of the present invention to lactose.

| 3) Ophthalmic solution Formulation 3 (in 100 mL) | |
| --- | --- |
| Compound of the present invention | 100 mg |
| Sodium chloride | 900 mg |
| Polysorbate 80 | 200 mg |
| Sodium hydroxide | quantum sufficient |
| Hydrochloric acid | quantum sufficient |
| Sterile purified water | quantum sufficient |

A desired ophthalmic solution can be obtained by appropriately changing the kinds and/or the amounts of the compound of the present invention and/or the additives.

[Pharmacological Tests]

1. Evaluation Test of Angiogenesis Inhibitory Effect

As one of the widely-used methods of evaluating angiogenesis inhibitory effects of drugs, a cell proliferation inhibitory action test using a VEGF-induced HUVEC proliferation reaction evaluation system has been reported in Cancer Res., 59, 99-106 (1999). According to the method described in the above-mentioned document, a cell proliferation inhibitory action test of the compounds of the present invention was performed, the cell proliferation inhibition rate was calculated, and the angiogenesis inhibitory effect of each of the compounds of the present invention was evaluated using the obtained rate as an index.

(Preparation of Test Compound Solution)

Each test compound was dissolved in dimethyl sulfoxide (hereinafter abbreviated as DMSO), and the obtained solution was diluted with a commercially available phosphoric acid buffer solution (hereinafter abbreviated as PBS), whereby a 20 μg/mL test compound solution was prepared.

(Preparation of HUVEC Suspension)

HUVEC was suspended in a 0.5% fetal bovine serum (hereinafter abbreviated as FBS)-containing F12K medium, whereby a $2 \times 10^4$ cells/mL HUVEC suspension was prepared.

(Preparation of VEGF Solution)

VEGF was dissolved in 0.1% bovine serum albumin-containing PBS, and the obtained solution was diluted with the 0.5% FBS-containing F12K medium, whereby a 400 ng/mL VEGF solution was prepared.

(Method of Test and Method of Measurement)

1) The HUVEC suspension was inoculated in an amount of 100 μL into each well of a 96-well plate coated with type I collagen ($2 \times 10^3$ cells per well).
2) One day after the inoculation, the test compound solution was added in an amount of 5 μL per well.
3) One hour after the addition of the test compound solution, the VEGF solution was added in an amount of 5 μL per well.
4) Three days after the addition of the VEGF solution, WST-8 assay kit (Dojin Chemical Co., Ltd.) was added in an amount of 10 μL per well.
5) After 3 hours, the above-mentioned plate was attached to an absorptiometer (Multilabel Counter ARVO), and an absorbance at 450 nm of each well suspension (hereinafter referred to as test compound suspension) was measured.
6) A test was carried out in the same manner as in the above 1) to 5) except that 1.0% DMSO was used instead of the test compound solution. The result was used as a control.

Incubation was carried out under conditions of 37° C., 5% carbon dioxide and 95% oxygen in an incubator throughout the above-mentioned test steps.

(Calculation of Cell Proliferation Inhibition Rate)

The cell proliferation inhibition rate (%), which was used as an index of an angiogenesis inhibitory effect, was calculated according to the following calculation equation.

Cell proliferation inhibition rate (%)=100−{(Absorbance of test compound suspension−$A$)/(absorbance of control−$A$)}×100  (Calculation Equation)

A: Absorbance of only cell suspension (cell+medium)

(Test Results and Discussion)

As an example of the test results, Table 1 shows the cell proliferation inhibition rates (%) of the test compounds (Compound 1-1, Compound 1-2, Compound 1-3, Compound 1-4, Compound 1-5, Compound 1-6, Compound 1-10, Compound 1-11, Compound 1-20, Compound 2-1, Compound 2-2, Compound 2-3, Compound 2-4, Compound 2-5, Compound 2-6, Compound 2-7, Compound 2-24, Compound 3-1, Compound 3-2, Compound 3-3, Compound 3-4, Compound 3-5, Compound 3-6, Compound 3-7, Compound 3-8, Compound 3-9, Compound 3-10, Compound 3-13, Compound 3-20, Compound 3-21, Compound 3-28, Compound 4-1, Compound 4-2, Compound 4-3, Compound 4-4, Compound 4-5, Compound 4-6, Compound 4-10, Compound 4-11, Compound 4-12, Compound 4-22, Compound 4-37, Compound 4-42, Compound 4-44, Compound 4-56, Compound 4-57, Compound 5-1, Compound 5-2, Compound 5-3, Compound 6-1, Compound 8-1, Compound 9-1, Compound 9-2, Compound 9-3, Compound 9-4, Compound 10-1, Compound 11-2, Compound 12-1, Compound 12-2, Compound 12-3, Compound 12-5, Compound 12-6, Compound 12-7, Compound 12-9, Compound 12-10, Compound 12-11, Compound 12-12, Compound 12-13, Compound 12-15, Compound 12-16, Compound 13-4, Compound 13-5, Compound 13-7, Compound 17-2, Compound 17-4, Compound 17-5, Compound 17-6, Compound 17-10, Compound 17-11, Compound 17-14, Compound 17-23, Compound 17-26, Compound 17-28, Compound 17-31, Compound 17-34, Compound 17-35, Compound 17-36, Compound 17-40, Compound 17-46, Compound 17-47, Compound 17-48, Compound 17-49, Compound 17-50, Compound 17-52, Compound 17-58, Compound 17-66, Compound 17-71, Compound 17-72, Compound 17-73, Compound 17-84, Compound 17-85, Compound 17-86 and Compound 18-1).

TABLE 1

| Compound | Cell proliferation inhibition rate (%) |
|---|---|
| 1-1 | 97 |
| 1-2 | 100 |
| 1-3 | 99 |
| 1-4 | 100 |
| 1-5 | 90 |
| 1-6 | 100 |
| 1-10 | 94 |
| 1-11 | 96 |
| 1-20 | 100 |
| 2-1 | 100 |
| 2-2 | 100 |
| 2-3 | 100 |
| 2-4 | 99 |
| 2-5 | 95 |
| 2-6 | 100 |
| 2-7 | 52 |
| 2-24 | 88 |
| 3-1 | 100 |
| 3-2 | 97 |
| 3-3 | 100 |
| 3-4 | 100 |
| 3-5 | 96 |
| 3-6 | 100 |
| 3-7 | 96 |
| 3-8 | 100 |
| 3-9 | 100 |
| 3-10 | 97 |
| 3-13 | 100 |
| 3-20 | 100 |
| 3-21 | 100 |
| 3-28 | 100 |
| 4-1 | 100 |
| 4-2 | 100 |
| 4-3 | 100 |
| 4-4 | 100 |
| 4-5 | 100 |
| 4-6 | 100 |
| 4-10 | 100 |
| 4-11 | 93 |
| 4-12 | 100 |
| 4-22 | 97 |
| 4-37 | 100 |
| 4-42 | 100 |
| 4-44 | 85 |
| 4-56 | 99 |
| 4-57 | 100 |
| 5-1 | 100 |
| 5-2 | 100 |
| 5-3 | 100 |
| 6-1 | 100 |
| 8-1 | 100 |
| 9-1 | 100 |
| 9-2 | 100 |
| 9-3 | 100 |
| 9-4 | 100 |
| 10-1 | 100 |
| 11-2 | 100 |
| 12-1 | 78 |
| 12-2 | 100 |
| 12-3 | 100 |

TABLE 1-continued

| Compound | Cell proliferation inhibition rate (%) |
|---|---|
| 12-5 | 100 |
| 12-6 | 96 |
| 12-7 | 87 |
| 12-9 | 99 |
| 12-10 | 100 |
| 12-11 | 100 |
| 12-12 | 91 |
| 12-13 | 91 |
| 12-15 | 91 |
| 12-16 | 99 |
| 13-4 | 88 |
| 13-5 | 100 |
| 13-7 | 81 |
| 17-2 | 88 |
| 17-4 | 100 |
| 17-5 | 83 |
| 17-6 | 84 |
| 17-10 | 82 |
| 17-11 | 84 |
| 17-14 | 77 |
| 17-23 | 93 |
| 17-26 | 87 |
| 17-28 | 100 |
| 17-31 | 92 |
| 17-34 | 81 |
| 17-35 | 95 |
| 17-36 | 81 |
| 17-40 | 92 |
| 17-46 | 100 |
| 17-47 | 89 |
| 17-48 | 100 |
| 17-49 | 95 |
| 17-50 | 100 |
| 17-52 | 94 |
| 17-58 | 76 |
| 17-66 | 91 |
| 17-71 | 95 |
| 17-72 | 100 |
| 17-73 | 100 |
| 17-84 | 100 |
| 17-85 | 100 |
| 17-86 | 86 |
| 18-1 | 88 |

As shown in Table 1, the compounds of the present invention exhibited an excellent cell proliferation inhibitory action. Accordingly, the compounds of the present invention have an excellent angiogenesis inhibitory effect.

2. Evaluation Test of Anticancer Effect

As one of the widely-used methods of evaluating anticancer effects of drugs, a tumor growth inhibitory action test using cancer models in mice has been reported in Cancer Res., 59, 5209-5218 (1999). According to the method described in the above-mentioned document, a tumor growth inhibitory action test of the compounds of the present invention was performed, the tumor tissue weight inhibition rate was calculated, and the anticancer effect of each of the compounds of the present invention was evaluated using the obtained rate as an index.

(Preparation of Test Compound Suspension)

A 1% aqueous methyl cellulose solution was added to each test compound to suspend it with a sonicator, whereby a 10 mg/mL test compound suspension was prepared.

(Preparation of B16 Cell Suspension)

Physiological saline was added to B16 cells, whereby a $3.3 \times 10^7$ cells/mL B16 cell suspension was prepared.

(Method of Test and Method of Measurement)
1) The back of each mouse (female, 6 weeks of age, C57BL/6N mouse) was depilated using a depilatory under Nembutal anesthesia.
2) Several days after the depilation, the B16 cell suspension (300 μL) was injected intradermally into the back of the mouse under Nembutal anesthesia.
3) From the B16 cell injection day (i.e. on day 0) to day 10, the test compound suspension (100 mg/kg/day) was orally administered once a day consecutively.
4) Ten days after the injection of the cells, the mouse was euthanized with $CO_2$ gas.
5) A tumor tissue was enucleated from the mouse, and the weight of the tumor tissue was measured with an electronic balance.
6) A test was performed in the same manner as in 1) to 5) except that the 1% aqueous methyl cellulose solution was used instead of the test compound suspension, and the result was used as a control.

(Calculation of Tumor Tissue Weight Inhibition Rate)

A tumor tissue weight inhibition rate (the average of 9 mice per group), which was used as an index of anticancer effect, was calculated according to the following calculation equation.

Tumor tissue weight inhibition rate (%)=100−(Mx/Mo)×100 (Calculation Equation)

Mo: Tumor tissue weight of control group

Mx: Tumor tissue weight of test compound solution administration group (Test Results and Discussion)

As an example of the test results, Table 2 shows the tumor tissue weight inhibition rates (%) of the test compounds (Compound 1-4, Compound 1-6, Compound 3-1, Compound 3-2, Compound 3-6, Compound 3-8, Compound 3-10, Compound 3-20, Compound 4-1, Compound 4-2, Compound 4-10, Compound 4-11, Compound 4-14, Compound 4-16, Compound 4-20, Compound 4-43, Compound 4-56, Compound 4-59, Compound 9-1, Compound 10-1, Compound 10-2, Compound 11-2, Compound 12-1, Compound 12-2, Compound 12-3, Compound 12-5, Compound 12-7, Compound 12-9, Compound 12-11, Compound 12-12, Compound 12-15, Compound 13-7, Compound 17-2, Compound 17-5, Compound 17-10, Compound 17-11, Compound 17-14, Compound 17-23 and Compound 17-35).

TABLE 2

| Compound | Tumor tissue weight inhibition rate (%) |
|---|---|
| 1-4 | 68 |
| 1-6 | 42 |
| 3-1 | 70 |
| 3-2 | 61 |
| 3-6 | 71 |
| 3-8 | 80 |
| 3-10 | 85 |
| 3-20 | 42 |
| 4-1 | 75 |
| 4-2 | 51 |
| 4-10 | 75 |
| 4-11 | 86 |
| 4-14 | 44 |
| 4-16 | 74 |
| 4-20 | 84 |
| 4-43 | 47 |

TABLE 2-continued

| Compound | Tumor tissue weight inhibition rate (%) |
|---|---|
| 4-56 | 42 |
| 4-59 | 80 |
| 9-1 | 43 |
| 10-1 | 54 |
| 10-2 | 83 |
| 11-2 | 64 |
| 12-1 | 85 |
| 12-2 | 71 |
| 12-3 | 41 |
| 12-5 | 67 |
| 12-7 | 59 |
| 12-9 | 47 |
| 12-11 | 52 |
| 12-12 | 60 |
| 12-15 | 69 |
| 13-7 | 75 |
| 17-2 | 83 |
| 17-5 | 69 |
| 17-10 | 79 |
| 17-11 | 81 |
| 17-14 | 79 |
| 17-23 | 56 |
| 17-35 | 72 |

As shown in Table 2, the compounds of the present invention exhibited an excellent tumor growth inhibitory action. Accordingly, the compounds of the present invention have an excellent anticancer effect.

3. Evaluation Test of Antiarthritic Effect

As one of the widely-used methods of evaluating antiarthritic effects of drugs, a paw edema inhibitory action test using adjuvant arthritis models in rats is known. Accordingly, a paw edema inhibitory action test of the compounds of the present invention was performed, the paw edema inhibition rate was calculated, and the antiarthritic effect of each of the compounds of the present invention was evaluated using the obtained rate as an index.

(Preparation of Test Compound Suspension)

A 1% aqueous methyl cellulose solution was added to each test compound to suspend it, whereby a 2 mg/mL test compound suspension was prepared.

(Preparation of Adjuvant)

Liquid paraffin was added to Mycobacterium butyricum to suspend it, whereby 6 mg/mL adjuvant was prepared.

(Method of Experiment)
1) The adjuvant (0.1 mL) was injected subcutaneously into a left hind paw sole of each rat (male, 9 weeks of age, Lewis rat) to induce arthritis.
2) From the adjuvant injection day (i.e. on day 0) to day 20, the test compound suspension (10 mg/kg/day) was orally administered once a day consecutively.
3) On the adjuvant injection day, day 1, day 4, day 7, day 11, day 14, day 18 and day 21, each paw volume of both hind paws was measured with a plethysmometer.
4) A test was performed in the same manner as in 1) to 3) except that the 1% aqueous methyl cellulose solution was used instead of the test compound suspension, and the result was used as a control.

(Method of Evaluation)

Each paw edema inhibition rate of paw edema in an adjuvant-untreated paw (secondary inflammation paw) in each test compound administration group to paw edema in a secondary inflammation paw in a control group was calculated, and the antiarthritic effect of each of the compounds of the present invention was evaluated using the obtained rate as an index.

(Calculation of Paw Edema Inhibition Rate)

The paw edema rate was calculated according to the following calculation equation 1, and then the paw edema inhibition rate (the average of 8 rats per group), which was used as an index of the antiarthritic effect, was calculated according to the calculation equation 2.

Paw edema rate (%)=(Paw volume after adjuvant treatment/paw volume before adjuvant treatment)×100     (Calculation Equation 1)

Paw edema inhibition rate (%)=100−{($Sx$−100)/($So$−100)}×100     (Calculation Equation 2)

$So$: Paw edema rate of control group $Sx$: Paw edema rate of test compound suspension administration group (Test Results and Discussion)

As an example of the test results, Table 3 shows the paw edema inhibition rates (%) on day 21 of the test compounds (Compound 3-1, Compound 3-6, Compound 3-8, Compound 3-10, Compound 4-1, Compound 4-10, Compound 4-11, Compound 9-1, Compound 10-1, Compound 10-2, Compound 12-1 and Compound 12-2).

TABLE 3

| Compound | Paw edema inhibition rate (%) |
|---|---|
| 3-1 | 48 |
| 3-6 | 33 |
| 3-8 | 30 |
| 3-10 | 35 |
| 4-1 | 90 |
| 4-10 | 71 |
| 4-11 | 65 |
| 9-1 | 55 |
| 10-1 | 59 |
| 10-2 | 57 |
| 12-1 | 48 |
| 12-2 | 44 |

As shown in Table 3, the compounds of the present invention exhibited an excellent paw edema inhibitory action. Accordingly, the compounds of the present invention have an excellent antiarthritic effect.

4. Evaluation Test of Choroidal Neovascularization Inhibitory Effect

As one of the widely-used methods of evaluating choroidal neovascularization inhibitory effects of drugs, a neovascularization incidence test using choroidal neovascularization models in rats was reported in Graefe's Arch. Cli. Exp. Ophthalmol., 235, 313-319 (1997). According to the method described in the above-mentioned document, a neovascularization incidence test of the compounds of the present invention was performed, the ratio of neovascularization incidence rate of each of the compounds of the present invention administration groups to a neovascularization incidence rate of vehicle administration group (control group) was calculated, and the choroidal neovascularization inhibitory effect of each of the compounds of the present invention was evaluated using the obtained ratio as an index.

(Preparation of Test Compound Solution)

A 1% aqueous methyl cellulose solution was added to each test compound to suspend it, whereby a 6 mg/10 mL test compound suspension was prepared.

(Preparation of Laser-induced Choroidal Neovascularization Model in Rats)

1) A 7:1 mixed solution (1 mL/kg) of a 5% ketamine hydrochloride injection and a 2% xylazine hydrochloride injection was administered intramuscularly to rats (Brown Norway male rat, 8 weeks of age, weight: 200 to 250 g) to anesthetize them systemically.

2) A tropicamide-phenylephrine hydrochloride ophthalmic solution (trade name: Mydrin-P) was instilled into eyes to cause mydriasis, and then photocoagulation was performed in a Bruch's membrane of each rat using a krypton laser photocoagulation apparatus.

The laser photocoagulation was performed at 8 spots per eye sparsely avoiding thick retinal vessels in a posterior section of ocular fundus and focusing on the deep layer of the retina. Photocoagulation conditions were adjusted to 100 μm of spot size, 100 mW of intensity and 0.1 sec. dulation.

3) After the photocoagulation, the ocular fundus was photographed to confirm photocoagulation (laser irradiation) sites.

(Method of Test and Method of Measurement)

1) From the laser photocoagulation day (i.e. on day 0) to day 6, the test compound suspension (30 mg/kg/day) was administered orally once a day for 7 consecutive days.

2) As the vehicle administration group (control group), a test was performed in the same manner as in 1) except that the 1% aqueous methyl cellulose solution was used instead of the test compound suspension, and the result was used as a control.

(Method of Evaluation)

1) On day 7 after the photocoagulation, 0.1 mL of a 10% aqueous fluorescein solution was injected into a tail vein of the rat, and fluorescein fundus photography was performed.

2) Next, in the fluorescein fundus photography, a spot where fluorescence leak was not observed was judged as negative, and a spot where fluorescence leak was observed was judged as positive. Photocoagulation sites where a little fluorescence leak was observed were judged as positive when two such sites are present.

3) The neovascularization incidence rate was calculated according to the calculation equation 1. The ratio of the neovascularization incidence rate of the test compound administration group to that of the vehicle administration group was calculated according to the calculation equation 2 using the neovascularization incidence rate of the respective administration groups.

Neovascularization incidence rate (%)=(Positive photocoagulation site number/total photocoagulation site number)×100     (Calculation Equation 1)

Ratio of neovascularization incidence rate of test compound administration group to that of vehicle administration group (control group)(% of control)=$Ax/Ao$×100     (Calculation Equation 2)

$Ao$: Neovascularization incidence rate of vehicle administration group (control group)

$Ax$: Neovascularization incidence rate of test compound administration group (Test Results and Discussion)

As an example of the test results, Table 4 shows the ratios (% of control) of the neovascularization incidence rates of the test compound (Compound 1-6, Compound 3-1, Compound 3-8, Compound 3-10, Compound 4-1, Compound 4-10, Compound 4-11, Compound 4-20, Compound 9-1, Compound 10-1, Compound 10-2, Compound 11-2, Compound 12-1, Compound 12-2, Compound 12-5, Compound 12-10 and Compound 17-5) administration groups to that of the vehicle administration group (control group).

TABLE 4

| Compound | Ratio of neovascularization incidence rate (% of Control) |
| --- | --- |
| 1-6 | 38 |
| 3-1 | 12 |
| 3-8 | 6 |
| 3-10 | 7 |
| 4-1 | 3 |
| 4-10 | 9 |
| 4-11 | 0 |
| 4-20 | 22 |
| 9-1 | 8 |
| 10-1 | 11 |
| 10-2 | 0 |
| 11-2 | 16 |
| 12-1 | 6 |
| 12-2 | 0 |
| 12-5 | 5 |
| 12-10 | 37 |
| 17-5 | 8 |

(The values are the average of 3 to 4 rats and 6 to 8 eyes.)

As shown in Table 4, the compounds of the present invention exhibited a lower neovascularization incidence rate than that of the vehicle and have a choroidal neovascularization inhibitory effect.

INDUSTRIAL APPLICABILITY

The novel cyclic compound according to the present invention has an excellent cell proliferation inhibitory effect, a tumor growth inhibitory effect, a paw edema inhibitory effect and/or a choroidal neovascularization inhibitory effect, and is useful as a therapeutic agent for a disease in which angiogenesis and/or vascular hyperpermeability are/is involved, for example, cancer, rheumatoid arthritis, age-related macular degeneration, diabetic retinopathy, retinopathy of prematurity, retinal vein occlusion, polypoid choroidal angiopathy, diabetic macular edema, psoriasis vulgaris, atherosclerosis or the like.

The invention claimed is:
1. A compound represented by the formula (1):

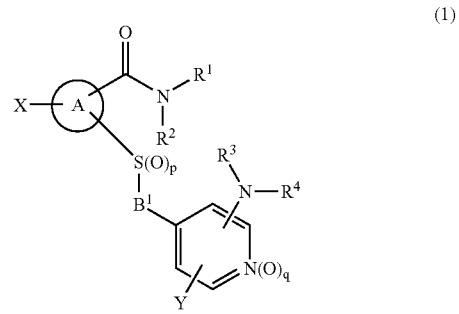

wherein the ring A represents a benzene ring, a thiophene ring or a pyridine ring;
$R^1$ represents a phenyl group which is unsubstituted or substituted by one or plural substituents selected from the group consisting of a halogen atom, a hydroxy group, an alkoxy group, a halogenoalkoxy group, an alkylcarbonyloxy group, an alkyl group and a halogenoalkyl group;
$R^2$ represents a hydrogen atom or an alkyl group;
in the case where $R^2$ is an alkyl group, the alkyl group is unsubstituted or substituted by one or plural substituents selected from the group consisting of a carboxy group and an alkoxycarbonyl group;
$R^3$ represents a hydrogen atom, an alkyl group, a cycloalkyl group, an aryl group, a heterocyclic ring or Z-$R^5$;
in the case where $R^3$ is an alkyl group, the alkyl group is unsubstituted or substituted by one or plural substituents selected from the group consisting of a hydroxy group and an alkylamino group;
in the case where $R^3$ is a heterocyclic ring, the heterocyclic ring is unsubstituted or substituted by one or plural cyano groups;
$R^3$ and $R^4$ may join together to form a heterocyclic ring;
in the case where $R^3$ and $R^4$ join together to form a heterocyclic ring, the heterocyclic ring is unsubstituted or substituted by one or plural substituents selected from the group consisting of a hydroxy group, an alkyl group, a hydroxyalkyl group, an alkylamino group, an alkoxycarbonyl group, an alkylcarbonyl group and an alkylaminocarbonyl group, further, the heterocyclic ring may have a carbonyl group in the ring;
$R^4$ represents a hydrogen atom, an alkyl group or an alkylcarbonyl group;
in the case where $R^4$ is an alkylcarbonyl group, the alkylcarbonyl group is unsubstituted or substituted by one or plural alkylcarbonyloxy groups;
Z represents CO, CO—$B^2$—O, CO—$B^2$—$NR^6$, CS—$B^2$—$NR^6$, CO—$B^2$—$NR^6SO_2$ or $SO_2$;
$R^5$ represents a hydrogen atom, an alkyl group, an alkenyl group, an alkynyl group, a cycloalkyl group, an aryl group, a heterocyclic ring, an alkoxycarbonyl group, an alkylcarbonyl group, a heterocyclic carbonyl group or an alkylaminocarbonyl group;
in the case where $R^5$ is an alkyl group, the alkyl group is unsubstituted or substituted by one or plural substituents selected from the group consisting of a halogen atom, a hydroxy group, an alkoxy group, a hydroxyalkoxy group, an alkoxyalkoxy group, a cycloalkyl group, a heterocyclic ring, a carboxy group, an alkoxycarbonyl group, an amino group, an alkylamino group, an alkoxycarbonylamino group, an alkylcarbonylamino group, an alkylthio group and a cyano group;

in the case where $R^5$ is an aryl group, the aryl group is unsubstituted or substituted by one or plural halogen atoms;

in the case where $R^5$ is a heterocyclic ring, the heterocyclic ring is unsubstituted or substituted by one or plural alkyl groups;

in the case where $R^5$ is an alkylcarbonyl group, the alkylcarbonyl group is unsubstituted or substituted by one or plural substituents selected from the group consisting of a carboxy group, an alkylcarbonyloxy group and an alkylamino group;

$R^5$ and $R^6$ may join together to form a heterocyclic ring;

in the case where $R^5$ and $R^6$ join together to form a heterocyclic ring, the heterocyclic ring is unsubstituted or substituted by one or plural substituents selected from the group consisting of a hydroxy group, an alkyl group, a hydroxyalkyl group, an alkoxycarbonyl group and an alkylcarbonyl group, further, the heterocyclic ring may have a carbonyl group in the ring;

$R^6$ represents a hydrogen atom or an alkyl group;

X and Y represent a hydrogen atom;

$B^1$ represents an alkylene group;

$B^2$ represents a single bond or an alkylene group;

p represents 0 or 1; and q represents 0, or a salt thereof.

2. The compound according to claim 1, wherein in the formula (1), the ring A represents a benzene ring, a thiophene ring or a pyridine ring;

$R^1$ represents a phenyl group which is unsubstituted or substituted by one or plural substituents selected from the group consisting of a halogen atom, a halogenoalkoxy group, an alkyl group and a halogenoalkyl group;

$R^2$ represents a hydrogen atom;

$R^3$ represents a hydrogen atom, an alkyl group, a cycloalkyl group, an aryl group, a heterocyclic ring or Z-$R^5$;

in the case where $R^3$ is an alkyl group, the alkyl group is unsubstituted or substituted by one or plural alkylamino groups;

in the case where $R^3$ is a heterocyclic ring, the heterocyclic ring is unsubstituted or substituted by one or plural cyano groups;

$R^3$ and $R^4$ may join together to form a heterocyclic ring;

in the case where $R^3$ and $R^4$ join together to form a heterocyclic ring, the heterocyclic ring is unsubstituted or substituted by one or plural substituents selected from the group consisting of an alkyl group and an alkylcarbonyl group;

$R^4$ represents a hydrogen atom or an alkyl group;

Z represents CO, CO—$B^2$—O, CO—$B^2$—$NR^6$, CO—$B^2$—$NR^6SO_2$ or $SO_2$;

$R^5$ represents a hydrogen atom, an alkyl group, an aryl group, an alkylcarbonyl group or an alkylaminocarbonyl group;

in the case where $R^5$ is an alkyl group, the alkyl group is unsubstituted or substituted by one or plural substituents selected from the group consisting of a halogen atom, a hydroxy group, a heterocyclic ring, an alkylamino group and an alkylcarbonylamino group;

in the case where $R^5$ is an aryl group, the aryl group is unsubstituted or substituted by one or plural halogen atoms;

in the case where $R^5$ is an alkylcarbonyl group, the alkylcarbonyl group is unsubstituted or substituted by one or plural carboxy groups;

$R^5$ and $R^6$ may join together to form a heterocyclic ring;

in the case where $R^5$ and $R^6$ join together to form a heterocyclic ring, the heterocyclic ring is unsubstituted or substituted by one or plural hydroxyalkyl groups;

$R^6$ represents a hydrogen atom or an alkyl group;

X and Y represent a hydrogen atom;

$B^1$ represents an alkylene group;

$B^2$ represents a single bond or an alkylene group;

p represents 0; and q represents 0, or a salt thereof.

3. The compound according to claims 1 or 2, wherein in the formula (1), the ring A represents a pyridine ring or a thiophene ring, or a salt thereof.

4. The compound according to claim 3, wherein in the formula (1), the ring A represents a pyridine ring, or a salt thereof.

5. The compound according to claims 1 or 2, wherein in the formula (1), a partial structure (C):

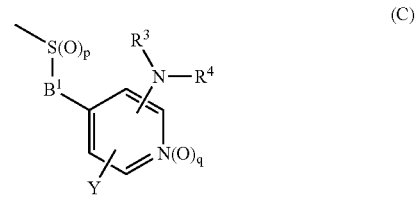

and a partial structure (D):

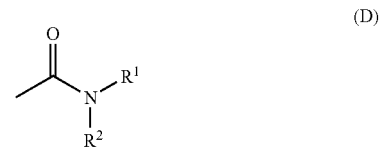

are bonded to adjacent carbon atoms on the ring A, or a salt thereof.

6. The compound according to claim 3, wherein in the formula (1), the partial structure (C) and the partial structure (D) are bonded to adjacent carbon atoms on the ring A, and the positions of the carbon atoms are an α-position and a β-position to a heteroatom on the ring A, or a salt thereof.

7. The compound according to claims 1 or 2, wherein in the formula (1), $R^3$ represents Z-$R^5$;

Z represents CO, CO—$B^2$—O, CO—$B^2$—$NR^6$ or CO—$B^2$—NR6$SO_2$;

$R^5$ represents a hydrogen atom, an alkyl group, an aryl group, an alkylcarbonyl group or an alkylaminocarbonyl group;

in the case where $R^5$ is an alkyl group, the alkyl group is unsubstituted or substituted by one or plural substituents selected from the group consisting of a halogen atom, a hydroxy group, a heterocyclic ring, an alkylamino group and an alkylcarbonylamino group;

in the case where R⁵ is an aryl group, the aryl group is unsubstituted or substituted by one or plural halogen atoms;

in the case where R⁵ is an alkylcarbonyl group, the alkylcarbonyl group is unsubstituted or substituted by one or plural carboxy groups;

R⁵ and R⁶ may join together to form a heterocyclic ring;

in the case where R⁵ and R⁶ join together to form a heterocyclic ring, the heterocyclic ring is unsubstituted or substituted by one or plural hydroxyalkyl groups;

R⁶ represents a hydrogen atom or an alkyl group;

B² represents a single bond or an alkylene group, or a salt thereof.

8. A compound selected from the group consisting of
N-(3,5-Dimethylphenyl)-2-[2-(4-methylpiperazin-1-yl)pyridin-4-ylmethylthio]pyridine-3-carboxamide,
2-(2-Cyclopropylaminopyridin-4-ylmethylthio)-N-(3,5-dimethylphenyl)pyridine-3-carboxamide,
2-[2-(N-(2-Dimethylaminoethyl)-N-methylamino)pyridin-4-ylmethylthio]-N-(3,5-dimethylphenyl)pyridine-3-carboxamide,
N-(3,5-Dimethylphenyl)-2-(2-morpholinopyridin-4-ylmethylthio)pyridine-3-carboxamide,
N-(3,5-Dimethylphenyl)-2-[2-(piperidin-1-yl)pyridin-4-ylmethylthio]pyridine-3-carboxamide,
2-[2-(4-Acetylpiperazin-1-yl)pyridin-4-ylmethylthio]-N-(3,5-dimethylphenyl)pyridine-3-carboxamide,
N-(3,5-Dimethylphenyl)-2-(2-n-pentylaminopyridin-4-ylmethylthio)pyridine-3-carboxamide,
2-(2-tert-Butoxycarbonylaminopyridin-4-ylmethylthio)-N-(3,5-dimethylphenyl)pyridine-3-carboxamide,
2-(2-tert-Butoxycarbonylaminopyridin-4-ylmethylthio)-N-(3-isopropylphenyl)pyridine-3-carboxamide,
2-(2-tert-Butoxycarbonylaminopyridin-4-ylmethylthio)-N-(4-trifluoromethoxyphenyl)pyridine-3-carboxamide,
2-(2-tert-Butoxycarbonylaminopyridin-4-ylmethylthio)-N-(4-tert-butylphenyl)pyridine-3-carboxamide,
2-[2-(N-tert-Butoxycarbonyl-N-methylamino)pyridin-4-ylmethylthio]-N-(3,5-dimethylphenyl)pyridine-3-carboxamide,
2-[2-(5-Cyanothiazol-2-ylamino)pyridin-4-ylmethylthio]-N-(3,5-dimethylphenyl)pyridine-3-carboxamide,
2-(2-Aminopyridin-4-ylmethylthio)-N-(3,5-dimethylphenyl)pyridine-3-carboxamide,
2-(2-Aminopyridin-4-ylmethylthio)-N-(3-isopropylphenyl)pyridine-3-carboxamide,
2-(2-Aminopyridin-4-ylmethylthio)-N-(4-tert-butylphenyl)pyridine-3-carboxamide,
N-(3,5-Dimethylphenyl)-2-(2-methylaminopyridin-4-ylmethylthio)pyridine-3-carboxamide,
2-(2-Methylaminopyridin-4-ylmethylthio)-N-(4-trifluoromethoxyphenyl)pyridine-3-carboxamide,
2-(2-Aminopyridin-4-ylmethylthio)-N-(4-chlorophenyl)pyridine-3-carboxamide,
2-(2-Aminopyridin-4-ylmethylthio)-N-(4-trifluoromethoxyphenyl)pyridine-3-carboxamide,
2-(2-Aminopyridin-4-ylmethylthio)-N-(3,5-dimethylphenyl)benzamide,
2-(2-Aminopyridin-4-ylmethylthio)-N-(4-chlorophenyl)benzamide,
3-(2-Aminopyridin-4-ylmethylthio)-N-(3,5-dimethylphenyl)thiophene-2-carboxamide,
2-(2-Acetylaminopyridin-4-ylmethylthio)-N-(3,5-dimethylphenyl)pyridine-3-carboxamide,
N-(3,5-Dimethylphenyl)-2-(2-propionylaminopyridin-4-ylmethylthio)pyridine-3-carboxamide,
N-(3,5-Dimethylphenyl)-2-(2-trifluoroacetylaminopyridin-4-ylmethylthio)pyridine-3-carboxamide,
N-(3,5-Dimethylphenyl)-2-(2-isobutyrylaminopyridin-4-ylmethylthio)pyridine-3-carboxamide,
N-(3,5-Dimethylphenyl)-2-(2-pivaloylaminopyridin-4-ylmethylthio)pyridine-3-carboxamide,
N-(3,5-Dimethylphenyl)-2-(2-trifluoromethanesulfonylaminopyridin-4-ylmethylthio)pyridine-3-carboxamide,
2-(2-Acetylaminopyridin-4-ylmethylthio)-N-(4-chlorophenyl)pyridine-3-carboxamide,
2-(2-Acetylaminopyridin-4-ylmethylthio)-N-(4-trifluoromethoxyphenyl)pyridine-3-carboxamide,
2-[2-(N-Acetyl-N-methylamino)pyridin-4-ylmethylthio]-N-(3,5-dimethylphenyl)pyridine-3-carboxamide,
2-(2-Acetylaminopyridin-4-ylmethylthio)-N-(3,5-dimethyl-4-hydroxyphenyl)pyridine-3-carboxamide,
2-(2-Acetylaminopyridin-4-ylmethylthio)-N-(4-chlorophenyl)benzamide,
2-(2-Acetylaminopyridin-4-ylmethylthio)-N-(4-tert-butylphenyl)benzamide,
3-(2-Acetylaminopyridin-4-ylmethylthio)-N-(3,5-dimethylphenyl)thiophene-2-carboxamide,
3-(2-Acetylaminopyridin-4-ylmethylthio-N-(4-chlorophenyl)thiophene-2-carboxamide,
N-(3,5-Dimethylphenyl)-2-[2-(N'-n-propylureido)pyridin-4-ylmethylthiol]pyridine-3-carboxamide,
2-[2-(N'-tert-Butylureido)pyridin-4-ylmethylthio]-N-(3,5-dimethylphenyl)pyridine-3-carboxamide,
2-[2-(N'-4-Chlorophenylureido)pyridin-4-ylmethylthio]-N-(3,5-dimethylphenyl)pyridine-3-carboxamide,
N-(3,5-Dimethylphenyl)-2-(2-formylaminopyridin-4-ylmethylthio)pyridine-3-carboxamide,
N-(3,5-Dimethylphenyl)-2-(2-phenylaminopyridin-4-ylmethylthio)pyridine-3-carboxamide,
N-(3,5-Dimethylphenyl)-2-[2-(N'-methylureido)pyridin-4-ylmethylthio]pyridine-3-carboxamide,
2-[2-(N'-Methylureido)pyridin-4-ylmethylthiol]-N-(4-trifluoromethoxyphenyl)pyridine-3-carboxamide,
N-(4-Chlorophenyl)-2-[2-(N'-methylureido)pyridin-4-ylmethylthio]pyridine-3-carboxamide,
N-(4-Difluoromethoxyphenyl)-2-[2-(N'-methylureido)pyridin-4-ylmethylthio]pyridine-3-carboxamide,
2-(2-Acetoxyacetylaminopyridin-4-ylmethylthio)-N-(3,5-dimethylphenyl)pyridine-3-carboxamide,
2-(2-Acetoxyacetylaminopyridin-4-ylmethylthio)-N-(4-trifluoromethoxyphenyl)pyridine-3-carboxamide,
2-(2-Aminoacetylaminopyridin-4-ylmethylthio)-N-(3,5-dimethylphenyl)pyridine-3-carboxamide,
2-(2-Hydroxyacetylaminopyridin-4-ylmethylthio)-N-(4-trifluoromethoxyphenyl)pyridine-3-carboxamide,
N-(3,5-Dimethylphenyl)-2-(2-hydroxyacetylaminopyridin-4-ylmethylthio)pyridine-3-carboxamide,
N-(4-Chlorophenyl)-2-(2-hydroxyacetylaminopyridin-4-ylmethylthio)pyridine-3-carboxamide,
N-(3,5-Dimethyl-4-hydroxyphenyl)-2-(2-hydroxyacetylaminopyridin-4-ylmethylthio)pyridine-3-carboxamide,
2-(2-Hydroxyacetylaminopyridin-4-ylmethylthio)-N-(3-methylphenyl)pyridine-3-carboxamide,
2-(2-Hydroxyacetylaminopyridin-4-ylmethylthio)-N-(4-trifluoromethylphenyl)pyridine-3-carboxamide,
N-(3-Chlorophenyl)-2-(2-hydroxyacetylaminopyridin-4-ylmethylthio)pyridine-3-carboxamide,
N-(3-Chloro-4-trifluoromethoxyphenyl)-2-(2-hydroxyacetylaminopyridin-4-ylmethylthio)pyridine-3-carboxamide, 2-(2-Hydroxyacetylaminopyridin-4-ylmethylthio)-N-(3-isopropylphenyl)pyridine-3-carboxamide, N-(4-Difluoromethoxyphenyl)-2-(2-hydroxyacetylaminopyridin-4-ylmethylthio)pyridine-3-carboxamide, 2-(2-Hydroxyacetylaminopyridin-4-ylmethylthio)-N-(3-trifluoromethylphenyl)pyridine-3-carboxamide, 2-[2-(3-Hydroxycarbonylpropionyloxy)acetylaminopyridin-4-ylmethylthio]-N-(4-trifluoromethoxyphenyl)pyridine-3-carboxamide, N-(3,5-Dimethylphenyl)-2-(2-methanesulfonylaminoacetylaminopyridin-4-ylmethylthio)pyridine-3-carboxamide, 2-(2-Dimethylaminocarbonyloxyacetylaminopyridin-4-ylmethylthio)-N-(4-trifluoromethoxyphenyl)pyridine-3-carboxamide, 2-(2-Isopropylaminoacetylaminopyridin-4-ylmethylthio)-N-(4-trifluoromethoxyphenyl)pyridine-3-carboxamide, 2-(2-Dimethylaminoacetylaminopyridin-4-ylmethylthio)-N-(3,5-dimethylphenyl)pyridine-3-carboxamide, 2-(2-Dimethylaminoacetylaminopyridin-4-ylmethylthio)-N-(4-trifluoromethoxyphenyl)pyridine-3-carboxamide, 2-(2-Morpholinoacetylaminopyridin-4-ylmethylthio)-N-(4-trifluoromethoxyphenyl)pyridine-3-carboxamide, 2-[2-(2-Dimethylaminoethyl)aminoacetylaminopyridin-4-ylmethylthio]-N-(4-trifluoromethoxyphenyl)pyridine-3-carboxamide, 2-[2-(2-Morpholinoethyl)aminoacetylaminopyridin-4-ylmethylthio]N-(4-trifluoromethoxyphenyl)pyridine-3-carboxamide, 2-[2-(3-Hydroxypropyl)aminoacetylaminopyridin-4-ylmethylthio]-N-(4-trifluoromethoxyphenyl)pyridine-3-carboxamide, N-(4-Chlorophenyl)-2-[2-(2-dimethylaminoethyl)aminoacetylaminopyridin-4-ylmethylthio]pyridine-3-carboxamide, 2-(2-Aminoacetylaminopyridin-4-ylmethylthio)-N-(4-trifluoromethoxyphenyl)pyridine-3-carboxamide, 2-[2-(N-(2-Dimethylaminoethyl)-N-methylamino)acetylaminopyridin-4-ylmethylthio]-N-(4-trifluoromethoxyphenyl)pyridine-3-carboxamide, 2-[2-(2-Hydroxyethyl)aminoacetylaminopyridin-4-ylmethylthio]-N-(4-trifluoromethoxyphenyl)pyridine-3-carboxamide, 2-[2-(Piperazin-1-yl)acetylaminopyridin-4-ylmethylthio]-N-(4-trifluoromethoxyphenyl)pyridine-3-carboxamide, N-(4-Difluoromethoxyphenyl)-2-(2-dimethylaminoacetylaminopyridin-4-ylmethylthio)pyridine-3-carboxamide, 2-[2-(2-Acetylaminoethyl)aminoacetylaminopyridin-4-ylmethylthio]-N-(4-trifluoromethoxyphenyl)pyridine-3-carboxamide, N-(4-Chlorophenyl)-2-[2-(piperazin-1-yl)acetylaminopyridin-4-ylmethylthio]pyridine-3-carboxamide, 2-[2-(2-Hydroxyethyl)aminoacetylaminopyridin-4-ylmethylthio]-N-(3-methylphenyl)pyridine-3-carboxamide, N-(4-Difluoromethoxyphenyl)-2-[2-(2-dimethylaminoethyl)aminoacetylaminopyridin-4-ylmethylthio]pyridine-3-carboxamide, N-(4-Difluoromethoxyphenyl)-2-[2-(2-hydroxyethyl)aminoacetylaminopyridin-4-ylmethylthio]pyridine-3-carboxamide, 2-[2-(2-Acetylaminoethyl)aminoacetylaminopyridin-4-ylmethylthio]-N-(4-difluoromethoxyphenyl)pyridine-3-carboxamide, N-(4-Difluoromethoxyphenyl)-2-[2-(N-(2-dimethylaminoethyl)-N-methylamino)acetylaminopyridin-4-ylmethylthio]pyridine-3-carboxamide, 2-[2-(2-Dimethylaminoethyl)aminoacetylaminopyridin-4-ylmethylthio]-N-(4-trifluoromethylphenyl)pyridine-3-carboxamide, 2-[2-(4-(2-Hydroxyethyl)piperazin-1-yl)acetylaminopyridin-4-ylmethylthio]-N-(4-trifluoromethoxyphenyl)pyridine-3-carboxamide, N-(4-Difluoromethoxyphenyl)-2-[2-(piperazin-1-yl)acetylaminopyridin-4-ylmethylthio]pyridine-3-carboxamide, N-(4-Difluoromethoxyphenyl)-2-(2-isopropylaminoacetylaminopyridin-4-ylmethylthio)pyridine-3-carboxamide, 2-[2-(2-Dimethylaminoethyl)aminoacetylaminopyridin-4-ylmethylthio]-N-(3,5-dimethylphenyl)pyridine-3-carboxamide, N-(3,5-Dimethylphenyl)-2-(2-isopropylaminoacetylaminopyridin-4-ylmethylthio)pyridine-3-carboxamide, N-(3,5-Dimethylphenyl)-2-[2-(3-hydroxypropyl)aminoacetylaminopyridin-4-ylmethylthio]pyridine-3-carboxamide, N-(3,5-Dimethylphenyl)-2-[2-(2-morpholinoethyl)aminoacetylaminopyridin-4-ylmethylthio]pyridine-3-carboxamide, 2-(2-Ethylaminoacetylaminopyridin-4-ylmethylthio)-N-(4-trifluoromethoxyphenyl)pyridine-3-carboxamide, 2-(2-Aminoacetylaminopyridin-4-ylmethylthio)-N-(4-difluoromethoxyphenyl)pyridine-3-carboxamide, 2-(3-Aminopyridin-4-ylmethylthio)-N-(3,5-dimethylphenyl)pyridine-3-carboxamide, 2-(3-Acetylaminopyridin-4-ylmethylthio)-N-(3,5-dimethylphenyl)pyridine-3-carboxamide, N-(3,5-Dimethylphenyl)-2-(2-morpholinoacetylaminopyridin-4-ylmethylthio)pyridine-3-carboxamide, 2-[2-(3-Dimethylaminopropyl)aminoacetylaminopyridin-4-ylmethylthio]-N-(4-trifluoromethoxyphenyl)pyridine-3-carboxamide, 2-(2-Dimethylaminoacetylaminopyridin-4-ylmethylthio)-N-(3-methylphenyl)pyridine-3-carboxamide, 2-[2-(2-Dimethylaminoethyl)aminoacetylaminopyridin-4-ylmethylthio]-N-(3-methylphenyl)pyridine-3-carboxamide, N-(3-Methylphenyl)-2-[2-(piperazin-1-yl)acetylaminopyridin-4-ylmethylthio]pyridine-3-carboxamide, 2-[2-(Piperazin-1-yl)acetylaminopyridin-4-ylmethylthio]-N-(4trifluoromethylphenyl)pyridine-3-carboxamide and N-(4-Difluoromethoxyphenyl)-2-[2-(N-(2-hydroxyethyl)-N-methylamino)acetylaminopyridin-4-ylmethylthio]pyridine-3-carboxamide, or a salt thereof.

9. A pharmaceutical composition comprising a pharmaceutically effective amount of the compound or a salt thereof as claimed in claims 1 or 2 as an active ingredient and a pharmaceutically acceptable carrier.

10. A method for treating cancer, rheumatoid arthritis, age-related macular degeneration, diabetic retinopathy, retinopathy of prematurity, retinal vein occlusion, polypoid choroidal angiopathy, diabetic macular edema, psoriasis vulgaris or atherosclerosis comprising administering to a patient a pharmaceutically effective amount of the compound or a salt thereof as claimed in claims 1 or 2 as an active ingredient.

11. The compound according to claim 1, wherein the compound is 2-(2-aminopyridin-4-ylmethylthio)-N-(3,5-dimethylphenyl)pyridine-3-carboxamide or a salt thereof.

12. The compound according to claim 1, wherein the compound is N-(3,5-dimethylphenyl)-2-(2-methylaminopyridin-4-ylmethylthio)pyridine-3-carboxamide or a salt thereof.

13. The compound according to claim 1, wherein the compound is 2-(2-methylaminopyridin-4-ylmethylthio)-N-(4-trifluoromethoxyphenyl)pyridine-3-carboxamide or a salt thereof.

14. The compound according to claim 1, wherein the compound is 2-(2-aminopyridin-4-ylmethylthio)-N-(4-trifluoromethoxyphenyl)pyridine-3-carboxamide or a salt thereof.

15. The compound according to claim 1, wherein the compound is 2-(2-acetylaminopyridin-4-ylmethylthio)-N-(3,5-dimethylphenyl)pyridine-3-carboxamide or a salt thereof.

16. The compound according to claim 1, wherein the compound is 2-(2-acetylaminopyridin-4-ylmethylthio)-N-(4-chlorophenyl)pyridine-3-carboxamide or a salt thereof.

17. The compound according to claim 1, wherein the compound is 2-(2-acetylaminopyridin-4-ylmethylthio)-N-(4-trifluoromethoxyphenyl)pyridine-3-carboxamide or a salt thereof.

18. The compound according to claim 1, wherein the compound is N-(3,5-dimethylphenyl)-2-[2-(N'-methylureido)pyridine-4-ylmethylthio]pyridine-3-carboxamide or a salt thereof.

19. The compound according to claim 1, wherein the compound is 2-(2-acetoxyacetylaminopyridin-4-ylmethylthio)-N-(3,5-dimethylphenyl)pyridine-3-carboxamide or a salt thereof.

20. The compound according to claim 1, wherein the compound is 2-(2-acetoxyacetylaminopyridin-4-ylmethylthio)-N-(4-trifluoromethoxyphenyl)pyridine-3-carboxamide or a salt thereof.

21. The compound according to claim 1, wherein the compound is 2-(2-hydroxyacetylaminopyridin-4-ylmethylthio)-N-(4-trifluoromethoxyphenyl)pyridine-3-carboxamide or a salt thereof.

22. The compound according to claim 1, wherein the compound is N-(3,5-dimethylphenyl)-2-(2-hydroxyacetylaminopyridin-4-ylmethylthio)pyridine-3-carboxamide or a salt thereof.

* * * * *